(12) United States Patent
DeFrees

(10) Patent No.: US 10,874,714 B2
(45) Date of Patent: Dec. 29, 2020

(54) METHOD OF TREATING FIBROBLAST GROWTH FACTOR 21 (FGF-21) DEFICIENCY

(71) Applicant: 89bio Ltd., Herzliya (IL)

(72) Inventor: Shawn DeFrees, North Wales, PA (US)

(73) Assignee: 89BIO LTD., Herzliya (IL)

(*) Notice: Subject to any disclaimer, the term of this patent is extended or adjusted under 35 U.S.C. 154(b) by 1075 days.

(21) Appl. No.: 14/954,696

(22) Filed: Nov. 30, 2015

(65) Prior Publication Data

US 2016/0158319 A1   Jun. 9, 2016

Related U.S. Application Data

(62) Division of application No. 13/332,708, filed on Dec. 21, 2011, now Pat. No. 9,200,049, which is a division of application No. 11/665,908, filed as application No. PCT/US2005/039226 on Oct. 31, 2005, now abandoned.

(60) Provisional application No. 60/623,342, filed on Oct. 29, 2004.

(51) Int. Cl.
| | | |
|---|---|---|
| *A61K 38/18* | (2006.01) | |
| *A61K 47/54* | (2017.01) | |
| *A61K 47/60* | (2017.01) | |
| *C07K 14/50* | (2006.01) | |
| *C12P 21/00* | (2006.01) | |
| *A61K 38/00* | (2006.01) | |

(52) U.S. Cl.
CPC ........ *A61K 38/1825* (2013.01); *A61K 47/549* (2017.08); *A61K 47/60* (2017.08); *C07K 14/50* (2013.01); *C12P 21/005* (2013.01); *A61K 38/00* (2013.01)

(58) Field of Classification Search
CPC .. A61K 38/1825; A61K 47/549; A61K 47/56; A61K 47/60; A61K 47/61; C07K 14/50; C07K 14/501; C07K 14/503
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,451,566 A | 5/1984 | Spencer |
| 4,496,689 A | 1/1985 | Mitra |
| 4,565,653 A | 1/1986 | Ives et al. |
| 4,675,414 A | 6/1987 | DeFusco et al. |
| 4,704,361 A | 11/1987 | Miccoli et al. |
| 4,767,702 A | 8/1988 | Cohenford |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,918,009 A | 4/1990 | Nilsson |
| 4,925,796 A | 5/1990 | Bergh et al. |
| 4,980,502 A | 12/1990 | Felder et al. |
| 5,032,519 A | 7/1991 | Paulson et al. |
| 5,047,335 A | 9/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,164,374 A | 11/1992 | Rademacher et al. |
| 5,166,322 A | 11/1992 | Shaw et al. |
| 5,169,933 A | 12/1992 | Anderson et al. |
| 5,180,674 A | 1/1993 | Roth |
| 5,182,107 A | 1/1993 | Friden |
| 5,194,376 A | 3/1993 | Kang |
| 5,202,413 A | 4/1993 | Spinu |
| 5,206,344 A | 4/1993 | Katre et al. |
| 5,219,564 A | 6/1993 | Zalipsky et al. |
| 5,272,066 A | 12/1993 | Bergh et al. |
| 5,278,299 A | 1/1994 | Wong et al. |
| 5,281,698 A | 1/1994 | Nitecki |

(Continued)

FOREIGN PATENT DOCUMENTS

| | | |
|---|---|---|
| AU | 1991/083760 A | 3/1992 |
| AU | 1992/017052 | 12/1992 |

(Continued)

OTHER PUBLICATIONS

Ajisaka et al., "Efficient Synthesis of O-linked Gycopeptide by a Transglycosylation Using Endo α-N-Acetylgalactosaminidase from *Streptomyces* sp.," *Biosci. Biotechnol. Biochem.*, 65(5): 1240-1243 (2001).

(Continued)

*Primary Examiner* — Jeffrey E. Russel
(74) *Attorney, Agent, or Firm* — Barry Schindler; Natalie Salem; Greenberg Traurig, LLP

(57) ABSTRACT

The present invention relates to mutants of Fibroblast Growth Factor (FGF), particularly FGF-20 and FGF-21, which contain newly introduced N-linked or O-linked glycosylation site(s). The polynucleotide coding sequences for the mutants, expression cassettes comprising the coding sequences, cells expressing the mutants, and methods for producing the mutants are also disclosed. Further disclosed are pharmaceutical compositions comprising the mutants and method for using the mutants.

8 Claims, 18 Drawing Sheets

Specification includes a Sequence Listing.

(56) References Cited

U.S. PATENT DOCUMENTS

| | | | |
|---|---|---|---|
| 5,288,637 | A | 2/1994 | Roth |
| 5,308,460 | A | 5/1994 | Mazid et al. |
| 5,324,663 | A | 6/1994 | Lowe |
| 5,324,844 | A | 6/1994 | Zalipsky |
| 5,342,940 | A | 8/1994 | Ono et al. |
| 5,346,696 | A | 9/1994 | Kim et al. |
| 5,352,670 | A | 10/1994 | Venot et al. |
| 5,360,896 | A * | 11/1994 | Senoo .................. C07K 14/50 530/399 |
| 5,369,017 | A | 11/1994 | Wong et al. |
| 5,374,541 | A | 12/1994 | Wong et al. |
| 5,374,655 | A | 12/1994 | Kashem et al. |
| 5,384,249 | A | 1/1995 | Sasaki et al. |
| 5,399,345 | A | 3/1995 | Schumacher et al. |
| 5,405,753 | A | 4/1995 | Brossmer et al. |
| 5,409,817 | A | 4/1995 | Ito et al. |
| 5,410,016 | A | 4/1995 | Hubbell et al. |
| 5,432,059 | A | 7/1995 | Bean et al. |
| 5,446,090 | A | 8/1995 | Harris |
| 5,464,943 | A * | 11/1995 | Senoo .................. C07K 14/50 435/252.3 |
| 5,492,821 | A | 2/1996 | Callstrom et al. |
| 5,492,841 | A | 2/1996 | Craig |
| 5,527,527 | A | 6/1996 | Friden |
| 5,529,914 | A | 6/1996 | Hubbell et al. |
| 5,545,553 | A | 8/1996 | Gotschlich |
| 5,567,422 | A | 10/1996 | Greenwald |
| 5,583,042 | A | 12/1996 | Roth |
| 5,595,900 | A | 1/1997 | Lowe |
| 5,605,793 | A | 2/1997 | Stemmer |
| 5,614,184 | A | 3/1997 | Sytkowski et al. |
| 5,621,039 | A | 4/1997 | Hallahan et al. |
| 5,629,384 | A | 5/1997 | Veronese et al. |
| 5,635,603 | A | 6/1997 | Hansen et al. |
| 5,643,575 | A | 7/1997 | Martinez et al. |
| 5,646,113 | A | 7/1997 | Attie et al. |
| 5,672,662 | A | 9/1997 | Harris et al. |
| 5,672,683 | A | 9/1997 | Friden et al. |
| 5,705,367 | A | 1/1998 | Gotschlich |
| 5,714,166 | A | 2/1998 | Tomalia et al. |
| 5,716,812 | A | 2/1998 | Withers et al. |
| 5,723,121 | A | 3/1998 | Takenaga et al. |
| 5,728,554 | A | 3/1998 | Bayer et al. |
| 5,739,208 | A | 4/1998 | Harris |
| 5,762,920 | A | 6/1998 | Yung et al. |
| 5,770,420 | A | 6/1998 | Lowe et al. |
| 5,798,233 | A | 8/1998 | Gotschlich |
| 5,811,238 | A | 9/1998 | Stemmer et al. |
| 5,824,778 | A | 10/1998 | Ishikawa et al. |
| 5,824,864 | A | 10/1998 | Fox et al. |
| 5,830,721 | A | 11/1998 | Stemmer et al. |
| 5,833,988 | A | 11/1998 | Friden |
| 5,834,251 | A | 11/1998 | Maras et al. |
| 5,837,458 | A | 11/1998 | Minshull et al. |
| 5,849,535 | A | 12/1998 | Cunningham et al. |
| 5,858,751 | A | 1/1999 | Paulson et al. |
| 5,858,752 | A | 1/1999 | Seed et al. |
| 5,861,374 | A | 1/1999 | Berkner et al. |
| 5,874,075 | A | 2/1999 | Collins et al. |
| 5,876,980 | A | 3/1999 | DeFrees et al. |
| 5,922,577 | A | 7/1999 | DeFrees et al. |
| 5,925,739 | A | 7/1999 | Spira et al. |
| 5,932,462 | A | 8/1999 | Harris et al. |
| 5,945,314 | A | 8/1999 | Prieto et al. |
| 5,945,322 | A | 8/1999 | Gotschlich |
| 5,955,347 | A | 9/1999 | Lowe |
| 5,962,294 | A | 10/1999 | Paulson et al. |
| 5,969,040 | A | 10/1999 | Hallahan et al. |
| 5,977,307 | A | 11/1999 | Friden et al. |
| 6,010,999 | A | 1/2000 | Daley et al. |
| 6,015,555 | A | 1/2000 | Friden |
| 6,030,815 | A | 2/2000 | DeFrees et al. |
| 6,034,223 | A | 3/2000 | Maddon et al. |
| 6,037,452 | A | 3/2000 | Minamino et al. |
| 6,048,720 | A | 4/2000 | Dalborg et al. |
| 6,057,292 | A | 5/2000 | Cunningham et al. |
| 6,075,134 | A | 6/2000 | Bertozzi et al. |
| 6,087,325 | A | 7/2000 | Meers et al. |
| 6,096,512 | A | 8/2000 | Elhammer et al. |
| 6,113,906 | A | 9/2000 | Greenwald et al. |
| 6,117,651 | A | 9/2000 | Schultz et al. |
| 6,127,153 | A | 10/2000 | Johnson et al. |
| 6,156,547 | A | 12/2000 | Roth |
| 6,166,183 | A | 12/2000 | Ishikawa et al. |
| 6,183,738 | B1 | 2/2001 | Clark |
| 6,251,864 | B1 | 6/2001 | Dower et al. |
| 6,261,805 | B1 | 7/2001 | Wood |
| 6,268,193 | B1 | 7/2001 | Lowe |
| 6,319,695 | B1 | 11/2001 | Wong et al. |
| 6,340,742 | B1 | 1/2002 | Burg et al. |
| 6,342,382 | B1 | 1/2002 | Gotschlich |
| 6,348,558 | B1 | 2/2002 | Harris et al. |
| 6,361,977 | B1 | 3/2002 | Bauer et al. |
| 6,362,254 | B2 | 3/2002 | Harris et al. |
| 6,376,604 | B2 | 4/2002 | Kozlowski |
| 6,379,933 | B1 | 4/2002 | Johnson et al. |
| 6,399,336 | B1 | 6/2002 | Paulson et al. |
| 6,399,337 | B1 | 6/2002 | Taylor et al. |
| 6,440,703 | B1 | 8/2002 | DeFrees |
| 6,458,937 | B1 | 10/2002 | Bertozzi et al. |
| 6,465,220 | B1 | 10/2002 | Hassan et al. |
| 6,495,365 | B1 | 12/2002 | Saito et al. |
| 6,531,121 | B2 | 3/2003 | Brines et al. |
| 6,555,346 | B1 | 4/2003 | Kretzdorn et al. |
| 6,555,660 | B2 | 4/2003 | Nissen et al. |
| 6,586,398 | B1 | 7/2003 | Kinstler et al. |
| 6,692,931 | B1 | 2/2004 | Reutter et al. |
| 6,693,183 | B2 | 2/2004 | Natsuka et al. |
| 6,716,626 | B1 * | 4/2004 | Itoh .................. C07K 14/50 435/252.3 |
| 6,743,896 | B2 | 6/2004 | Filpula et al. |
| 6,780,624 | B2 | 8/2004 | Gotschlich |
| 6,800,740 | B1 | 10/2004 | Cunningham et al. |
| 6,949,372 | B2 | 9/2005 | Betenbaugh et al. |
| 7,094,530 | B1 | 8/2006 | Sasaki et al. |
| 7,125,843 | B2 | 10/2006 | DeFrees et al. |
| 7,138,371 | B2 | 11/2006 | DeFrees et al. |
| 7,157,277 | B2 | 1/2007 | DeFrees et al. |
| 7,173,003 | B2 | 2/2007 | DeFrees et al. |
| 7,179,617 | B2 | 2/2007 | DeFrees et al. |
| 7,199,223 | B2 | 4/2007 | Bossard et al. |
| 7,202,208 | B2 | 4/2007 | Papadimitriou |
| 7,214,660 | B2 | 5/2007 | DeFrees et al. |
| 7,226,903 | B2 | 6/2007 | DeFrees et al. |
| 7,229,962 | B2 | 6/2007 | Chung et al. |
| 7,235,638 | B2 | 6/2007 | Persson |
| 7,265,084 | B2 | 9/2007 | DeFrees et al. |
| 7,265,085 | B2 | 9/2007 | DeFrees et al. |
| 7,276,475 | B2 | 10/2007 | DeFrees et al. |
| 7,297,511 | B2 | 11/2007 | DeFrees et al. |
| 7,304,150 | B1 | 12/2007 | Egrie et al. |
| 7,338,933 | B2 | 3/2008 | DeFrees et al. |
| 7,368,108 | B2 | 5/2008 | DeFrees et al. |
| 7,399,613 | B2 | 7/2008 | DeFrees et al. |
| 7,405,198 | B2 | 7/2008 | DeFrees et al. |
| 7,416,858 | B2 | 8/2008 | DeFrees et al. |
| 7,439,043 | B2 | 10/2008 | DeFrees et al. |
| 7,473,680 | B2 | 1/2009 | DeFrees et al. |
| 7,524,813 | B2 | 4/2009 | Zundel et al. |
| 7,662,933 | B2 | 2/2010 | Kinstler et al. |
| 7,691,603 | B2 | 4/2010 | DeFrees |
| 7,696,163 | B2 | 4/2010 | DeFrees et al. |
| 7,795,210 | B2 | 9/2010 | DeFrees et al. |
| 7,803,777 | B2 | 9/2010 | DeFrees |
| 7,842,661 | B2 | 11/2010 | DeFrees et al. |
| 7,932,364 | B2 | 4/2011 | DeFrees et al. |
| 7,956,032 | B2 | 6/2011 | DeFrees et al. |
| 8,008,252 | B2 | 8/2011 | DFrees et al. |
| 8,053,410 | B2 | 11/2011 | Klausen et al. |
| 8,063,015 | B2 | 11/2011 | DeFrees et al. |
| 8,076,292 | B2 | 12/2011 | DeFrees et al. |
| 8,178,108 | B2 | 5/2012 | Buechler et al. |
| 8,207,112 | B2 | 6/2012 | Hinderer et al. |
| 8,247,381 | B2 | 8/2012 | DeFrees |

(56) References Cited

U.S. PATENT DOCUMENTS

| | | |
|---|---|---|
| 8,268,967 B2 | 9/2012 | DeFrees et al. |
| 8,361,961 B2 | 1/2013 | DeFrees et al. |
| 8,404,809 B2 | 3/2013 | DeFrees et al. |
| 8,633,157 B2 | 1/2014 | DeFrees et al. |
| 8,633,300 B2 | 1/2014 | Ostergaard et al. |
| 8,716,239 B2 | 5/2014 | DeFrees et al. |
| 8,716,240 B2 | 5/2014 | DeFrees et al. |
| 8,791,066 B2 | 7/2014 | DeFrees |
| 8,791,070 B2 | 7/2014 | DeFrees et al. |
| 8,841,439 B2 | 9/2014 | Felo et al. |
| 8,853,161 B2 | 10/2014 | DeFrees et al. |
| 8,911,967 B2 | 12/2014 | DeFrees et al. |
| 8,916,360 B2 | 12/2014 | DeFrees et al. |
| 8,969,532 B2 | 3/2015 | DeFrees et al. |
| 9,005,625 B2 | 4/2015 | DeFrees et al. |
| 9,029,331 B2 | 5/2015 | DeFrees et al. |
| 9,050,304 B2 | 6/2015 | Zopf et al. |
| 9,200,049 B2 * | 12/2015 | DeFrees ............ C07K 14/50 |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0068347 A1 | 6/2002 | Taylor et al. |
| 2002/0115833 A1 | 8/2002 | Burg et al. |
| 2002/0127682 A1 | 9/2002 | Gotschlich |
| 2002/0137134 A1 | 9/2002 | Gerngross et al. |
| 2002/0142370 A1 | 10/2002 | Paulson et al. |
| 2002/0142964 A1 | 10/2002 | Nissen et al. |
| 2002/0148791 A1 | 10/2002 | DeFrees |
| 2002/0150981 A1 | 10/2002 | Canfield |
| 2002/0168323 A1 | 11/2002 | Gonda |
| 2002/0182586 A1 | 12/2002 | Morris et al. |
| 2003/0003529 A1 | 1/2003 | Bayer |
| 2003/0027257 A1 | 2/2003 | Iatrou et al. |
| 2003/0040037 A1 | 2/2003 | Bayer |
| 2003/0044908 A1 | 3/2003 | Persson |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0043464 A1 | 3/2004 | Gotschlich |
| 2004/0063911 A1 | 4/2004 | DeFrees et al. |
| 2004/0077836 A1 | 4/2004 | DeFrees et al. |
| 2004/0082024 A1 | 4/2004 | Brandstadt et al. |
| 2004/0082026 A1 | 4/2004 | DeFrees et al. |
| 2004/0082038 A1 | 4/2004 | Lee et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0032742 A1 | 2/2005 | DeFrees et al. |
| 2005/0064540 A1 | 3/2005 | DeFrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | DeFrees |
| 2006/0182714 A1 | 8/2006 | Behrens et al. |
| 2006/0183198 A1 | 8/2006 | Buechler et al. |
| 2006/0198819 A1 | 9/2006 | Behrens et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | DeFrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |

(56) References Cited

U.S. PATENT DOCUMENTS

| | | |
|---|---|---|
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0261872 A1 | 10/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0064719 A1 | 3/2011 | Rasmussen et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |
| 2013/0344050 A1 | 12/2013 | DeFrees et al. |
| 2014/0112903 A1 | 4/2014 | DeFrees et al. |
| 2014/0294762 A1 | 10/2014 | DeFrees et al. |
| 2015/0111245 A1 | 4/2015 | DeFrees et al. |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2167521 | 10/2003 |
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 0200421 A2 | 12/1986 |
| EP | 0370205 A2 | 5/1990 |
| EP | 0459630 A2 | 12/1991 |
| EP | 0474313 A2 | 3/1992 |
| EP | 0475354 A2 | 3/1992 |
| EP | 0577580 A2 | 1/1994 |
| EP | 0585109 A2 | 3/1994 |
| EP | 0605963 A2 | 7/1994 |
| EP | 0775711 A1 | 5/1997 |
| EP | 0863154 A1 | 9/1998 |
| EP | 1260582 A1 | 11/2002 |
| EP | 1270642 A1 | 1/2003 |
| EP | 1428878 A1 | 6/2004 |
| EP | 1481985 A1 | 12/2004 |
| FI | 922515 A | 12/1992 |
| GB | 2256197 A | 12/1992 |
| JP | S59172425 A | 9/1984 |
| JP | H02-076894 A | 3/1990 |
| JP | H03-503759 A | 8/1991 |
| JP | H06-086684 A | 3/1994 |
| JP | H06-160365 A | 6/1994 |
| JP | H06-172375 A | 6/1994 |
| JP | 07-107979 A | 4/1995 |
| JP | H07-196925 A | 8/1995 |
| JP | H07-223921 A | 8/1995 |
| JP | H08-506023 A | 7/1996 |
| JP | H09-503905 A | 4/1997 |
| JP | H09-208461 A | 8/1997 |
| JP | H10-307356 A | 11/1998 |
| JP | 2000-501607 A | 2/2000 |
| JP | 2001-508783 A | 7/2001 |
| JP | 2001-519784 A | 10/2001 |
| JP | 2002-536018 A | 10/2002 |
| JP | 2003-516731 A | 5/2003 |
| JP | 2003-521930 A | 7/2003 |
| JP | 2005-521635 A | 7/2005 |
| JP | 2005-328782 A | 12/2005 |
| KR | 2002-0010363 A | 2/2002 |
| KR | 10-0396983 B1 | 8/2003 |
| NZ | 532027 A | 9/2008 |
| NZ | 539415 A | 12/2008 |
| NZ | 547554 A | 9/2009 |
| RU | 2005/101348 A | 8/2005 |
| SE | 9501285 | 10/1996 |
| WO | WO 1987/000056 A1 | 1/1987 |
| WO | WO 1987/005330 A1 | 9/1987 |
| WO | WO 1989/06546 A1 | 7/1989 |
| WO | WO 1989/010134 A1 | 11/1989 |
| WO | WO 1990/007572 A1 | 7/1990 |
| WO | WO 1990/008164 A1 | 7/1990 |
| WO | WO 1990/008823 A1 | 8/1990 |
| WO | WO 1990/012090 A1 | 10/1990 |
| WO | WO 1990/013540 A1 | 11/1990 |
| WO | WO 1991/006635 A1 | 5/1991 |
| WO | WO 1991/009122 | 6/1991 |
| WO | WO 1991/014697 A1 | 10/1991 |
| WO | WO 1992/001055 A1 | 1/1992 |
| WO | WO 1992/015686 A1 | 9/1992 |
| WO | WO 1992/016555 A1 | 10/1992 |
| WO | WO 1992/016640 A1 | 10/1992 |
| WO | WO 1992/018135 A1 | 10/1992 |
| WO | WO 1992/022310 A1 | 12/1992 |
| WO | WO 1993/008842 A1 | 5/1993 |
| WO | WO 1993/013198 A1 | 7/1993 |
| WO | WO 1993/015189 A1 | 8/1993 |
| WO | WO 1993/018787 A1 | 9/1993 |
| WO | WO 1994/004193 A1 | 3/1994 |
| WO | WO 1994/005332 A2 | 3/1994 |
| WO | WO 1994/009027 A1 | 4/1994 |
| WO | WO 1994/015625 A1 | 7/1994 |
| WO | WO 1994/017039 A1 | 8/1994 |
| WO | WO 1994/018247 A1 | 8/1994 |
| WO | WO 1994/025614 A1 | 11/1994 |
| WO | WO 1994/025615 A1 | 11/1994 |
| WO | WO 1994/026760 A1 | 11/1994 |
| WO | WO 1994/027631 A1 | 12/1994 |
| WO | WO 1994/028024 A1 | 12/1994 |
| WO | WO 1995/002421 A1 | 1/1995 |
| WO | WO 1995/004278 A1 | 2/1995 |
| WO | WO 1995/005465 A1 | 2/1995 |
| WO | WO 1996/010089 A1 | 4/1996 |
| WO | WO 1996/011953 A1 | 4/1996 |
| WO | WO 1996/012800 A1 | 5/1996 |
| WO | WO 1996/021468 A1 | 7/1996 |
| WO | WO 1996/021469 A1 | 7/1996 |
| WO | WO 1996/032491 A1 | 10/1996 |
| WO | WO 1996/032492 A1 | 10/1996 |
| WO | WO 1996/034015 A1 | 10/1996 |
| WO | WO 1996/036357 A1 | 11/1996 |
| WO | WO 1996/040731 A1 | 12/1996 |
| WO | WO 1996/040881 A1 | 12/1996 |
| WO | WO 1997/005330 A1 | 2/1997 |
| WO | WO 1997/021822 A2 | 6/1997 |
| WO | WO 1997/047651 A1 | 12/1997 |
| WO | WO 1998/005363 A2 | 2/1998 |
| WO | WO 1998/031826 A1 | 7/1998 |
| WO | WO 1998/032466 A1 | 7/1998 |
| WO | WO 1998/041562 A1 | 9/1998 |
| WO | WO 1998/051784 A1 | 11/1998 |
| WO | WO 1998/058964 A1 | 12/1998 |
| WO | WO 1999/000150 A2 | 1/1999 |

(56) References Cited

FOREIGN PATENT DOCUMENTS

| | | |
|---|---|---|
| WO | WO 1999/013063 A1 | 3/1999 |
| WO | WO 1999/014259 A1 | 3/1999 |
| WO | WO 1999/022764 A1 | 5/1999 |
| WO | WO 1999/028491 A1 | 6/1999 |
| WO | WO 1999/034833 A1 | 7/1999 |
| WO | WO 1999/037779 A1 | 7/1999 |
| WO | WO 1999/045964 A1 | 9/1999 |
| WO | WO 1999/048515 A1 | 9/1999 |
| WO | WO 1999/054342 A1 | 10/1999 |
| WO | WO 1999/055376 A1 | 11/1999 |
| WO | WO 2000/023114 A2 | 4/2000 |
| WO | WO 2000/026354 A1 | 5/2000 |
| WO | WO 2000/029558 A1 | 5/2000 |
| WO | WO 2000/029603 A2 | 5/2000 |
| WO | WO 2000/044785 A1 | 8/2000 |
| WO | WO 2000/046379 A1 | 8/2000 |
| WO | WO 2000/065087 A1 | 11/2000 |
| WO | WO 2001/002017 A2 | 1/2001 |
| WO | WO 2001/005434 A2 | 1/2001 |
| WO | WO 2001/019955 A2 | 3/2001 |
| WO | WO 2001/039788 A2 | 6/2001 |
| WO | WO 2001/049830 A2 | 7/2001 |
| WO | WO 2001/051510 A2 | 7/2001 |
| WO | WO 2001/058493 A1 | 8/2001 |
| WO | WO 2001/058935 A2 | 8/2001 |
| WO | WO 2001/060411 A1 | 8/2001 |
| WO | WO 2001/076640 A2 | 10/2001 |
| WO | WO 2001/083725 A1 | 11/2001 |
| WO | WO 2001/087329 A1 | 11/2001 |
| WO | WO 2001/087925 A2 | 11/2001 |
| WO | WO 2001/088117 A2 | 11/2001 |
| WO | WO 2002/002597 A2 | 1/2002 |
| WO | WO 2002/002764 A2 | 1/2002 |
| WO | WO 2002/013843 A2 | 2/2002 |
| WO | WO 2002/013873 A2 | 2/2002 |
| WO | WO 2002/029025 A2 | 4/2002 |
| WO | WO 2002/044196 A1 | 6/2002 |
| WO | WO 2002/049673 A2 | 6/2002 |
| WO | WO 2002/050099 A2 | 6/2002 |
| WO | WO 2002/053580 A2 | 7/2002 |
| WO | WO 2002/074806 A2 | 9/2002 |
| WO | WO 2002/077218 A1 | 10/2002 |
| WO | WO 2002/092619 A2 | 11/2002 |
| WO | WO 2003/006501 A2 | 1/2003 |
| WO | WO 2003/011879 A1 | 2/2003 |
| WO | WO 2003/017949 A2 | 3/2003 |
| WO | WO 2003/029291 A2 | 4/2003 |
| WO | WO 2003/031464 A2 | 4/2003 |
| WO | WO 2003/045980 A2 | 6/2003 |
| WO | WO 2003/046150 A2 | 6/2003 |
| WO | WO 2003/093448 A2 | 11/2003 |
| WO | WO 2004/000366 A1 | 12/2003 |
| WO | WO 2004/009838 A2 | 1/2004 |
| WO | WO 2004/010327 A1 | 1/2004 |
| WO | WO 2004/014417 A2 | 2/2004 |
| WO | WO 2004/022004 A2 | 3/2004 |
| WO | WO 2004/029090 A1 | 4/2004 |
| WO | WO 2004/029091 A2 | 4/2004 |
| WO | WO 2004/033651 A2 | 4/2004 |
| WO | WO 2004/046222 A1 | 6/2004 |
| WO | WO 2004/047858 A1 | 6/2004 |
| WO | WO 2004/067566 A1 | 8/2004 |
| WO | WO 2004/075923 A2 | 9/2004 |
| WO | WO 2004/083258 A2 | 9/2004 |
| WO | WO 2004/083259 A2 | 9/2004 |
| WO | WO 2004/091499 A2 | 10/2004 |
| WO | WO 2004/093823 A2 | 11/2004 |
| WO | WO 2004/096148 A2 | 11/2004 |
| WO | WO 2004/099231 A2 | 11/2004 |
| WO | WO 2004/101597 A2 | 11/2004 |
| WO | WO 2004/101740 A2 | 11/2004 |
| WO | WO 2004/103275 A2 | 12/2004 |
| WO | WO 2004/106373 A1 | 12/2004 |
| WO | WO 2005/001025 A2 | 1/2005 |
| WO | WO 2005/003171 A2 | 1/2005 |
| WO | WO 2005/012484 A2 | 2/2005 |
| WO | WO 2005/014024 A2 | 2/2005 |
| WO | WO 2005/014035 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/079363 A2 | 9/2005 |
| WO | WO 2005/091944 A2 | 10/2005 |
| WO | WO 2005/121331 A2 | 12/2005 |
| WO | WO 2006/005058 A2 | 1/2006 |
| WO | WO 2006/010143 A2 | 1/2006 |
| WO | WO 2006/011839 A1 | 2/2006 |
| WO | WO 2006/013202 A2 | 2/2006 |
| WO | WO 2006/014349 A2 | 2/2006 |
| WO | WO 2006/014466 A2 | 2/2006 |
| WO | WO 2006/018204 A1 | 2/2006 |
| WO | WO 2006/020372 A2 | 2/2006 |
| WO | WO 2006/031811 A2 | 3/2006 |
| WO | WO 2006/035057 A1 | 4/2006 |
| WO | WO 2006/050247 A2 | 5/2006 |
| WO | WO 2006/053299 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | WO 2006/103298 A2 | 10/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | WO 2006/134173 A2 | 12/2006 |
| WO | WO 2007/022512 A2 | 2/2007 |
| WO | WO 2007/056191 A2 | 5/2007 |
| WO | WO 2007/135182 A2 | 11/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Andree et al., "Glucosyl Transferase Activity of Bovine Galactosyl Transferase," Biochim. Biophys. Acta, 544(3): 489-495 (1978).

Apicella et al., "Phenotypic variation in epitope expression of the Neisseria gonorrhoeae lipooligosaccharide.," Infect. Immun., 55(8): 1755-1761 (1987).

Arsequell et al., "Recent advances in the synthesis of complex N-glycopeptides," Tetrahedron: Asymmetry, 10(16): 3045-3094 (1999).

ATCC Catalog of Bacteria and Bacteriophages, 17th ed., p. 150-151 (1989).

Auge et al., "The use of an immobilised cyclic multi-enzyme system to synthesise branched penta- and hexa-saccharides associated with blood-group i epitopes.," Carbohydr. Res., 151: 147-156 (1986).

Auge et al., "The use of immobilised glycosyltransferases in the synthesis of sialyloligosaccharides," Carbohydr. Res., 200: 257-268 (1990).

Avigad et al., "The d-Galactose Oxidase of Polyporus circinatus," J. Biol. Chem., 237(9): 2736-2743 (1962).

Barker et al., "Agarose Derivatives of Uridine Diphosphate and N-Acetylglucosamine for the Purification of a Galactosyltransferase," J. Biol. Chem., 247(22): 7135-7147 (1972).

Bayer et al., "Improvement of Therapeutic Glycoproteins: In Vitro Remodeling and GlycoPEGylation™," Glycobiology, 13(11): 890-891 (2003).

Bertozzi et al., "Carbon-Linked Galactosphingolipid Analogs Bind Specifically to HIV-1 gp120," J. Am. Chem. Soc., 114(26): 10639-10641 (1992).

(56) References Cited

OTHER PUBLICATIONS

Biemann et al., "Characterization by Tandem Mass Spectrometry of Structural Modifications in Proteins," *Science*, 237(4818): 992-998 (1987).
Binder et al., "Galactosylation by Use of β-Galactosidase: Chemo-Enzymatic Syntheses of Di- and Trisaccharides," *Tetrahedron*, 50(35): 10407-10418 (1994).
Bocci, "Catabolism of therapeutic proteins and peptides with implications for drug delivery," *Adv. Drug Deliv. Rev.*, 4(2): 149-169 (1989).
Borman, "Controlling personalities tame wild sugars on proteins and natural products," *Chem. Eng. News*, 84(36): 13-22 (2006).
Breton et al., "Structure/function studies of glycosyltransferases," *Curr. Opin. Struct. Biol.*, 9(5): 563-571 (1999).
Breton et al., "Structural and functional features of glycosyltransferases," *Biochimie*, 83(8): 713-718 (2001).
Brinkman-Van Der Linden et al., "A Missense Mutation in the FUT6 Gene Results in Total Absence of α3-Fucosylation of Human α1-Acid Glycoprotein," *J. Biol. Chem.*, 271(24): 14492-14495 (1996).
Broquet et al., "Substrate Specificity of Cerebral GDP-fucose: Glycoprotein Fucosyltransferase," *Eur. J. Biochem.* 123(1): 9-13 (1982).
Burczak et al., "Characterization of a CMP-sialic Acid:Lactosylceramide Sialyltransferase Activity in Cultured Hamster Cells," *Biochim. Biophys. Acta*, 804(4): 442-449 (1984).
Burns et al., "Selective Reduction of Disulfides by Tris(2-carboxyethyl)phosphine," *J. Org. Chem.*, 56(8): 2648-2650 (1991).
Calvet, "Molecular approaches for analyzing differential gene expression: differential cDNA library construction and screening," *Pediatr. Nephrol.*, 5(6): 751-757 (1991).
Carlson et al., "The Sialic Acids: XIV. Synthesis of Sialyl-Lactose by a Sialyltransferase from Rat Mammary Gland," *J. Biol. Chem.*, 248(16): 5742-5750 (1973).
Chang et al, "Analysis of Erythropoietin Glycoform Produced by Recombinant CHO Cells Using the Lectin-Blotting Technique," *Biotechnol. Bioprocess Eng.*, 3(1): 40-43 (1998).
Chang et al., "Engineered Recombinant Factor VII $Q^{217}$ Variants with Altered Inhibitor Specificities," *Biochemistry*, 38(34): 10940-10948 (1999).
Clogston et al., "Glycosidase digestion, electrophoresis and chromatographic analysis of recombinant human granulocyte colony-stimulating factor glycoforms produced in Chinese hamster ovary cells," *J. Chromatogr. A*, 637(1): 55-62 (1993).
Dabkowski et al., "Characterisation of a cDNA Clone Encoding the Pig α1,3 Galactosyltransferase: Implications for Xenotransplantation," *Transplant Proc.*, 25(5): 2921 (1993).
Danaher et al., "Genetic basis of Neisseria gonorrhoeae lipooligosaccharide antigenic variation," *J. Bacteriol.*, 177(24): 7275-7279 (1995).
Datta et al., "The Sialyltransferase "Sialylmotif" Participates in Binding the Donor Substrate CMP-NeuAc," *J. Biol. Chem.*, 270(4): 1497-1500 (1995).
David et al., Immobilized enzymes in preparative carbohydrate chemistry, *Pure Appl. Chem.*, 59(11): 1501-1508 (1987).
Davis et al., Glycoprotein Synthesis: From Glycobiological Tools to Tailor-made Catalysts, *Synlett* 1999, (9): 1495-1507 (1999).
De Rosa et al., "Aliphatic and Aromatic Glycosides from the Cell Cultures of Lycopersicon esculentum," *Phytochemistry* 42(4): 1031-1034 (1996).
Deangelis et al., "Immunochemical Confirmation of the Primary Structure of Streptococcal Hyaluronan Synthase and Synthesis of High Molecular Weight Product by the Recombinant Enzyme," *Biochemistry*, 33(31): 9033-9039 (1994).
Deluca et al., "Enzymatic Snythesis of Hyaluronic Acid with Regeneration of Sugar Nucleotides," *J. Am. Chem. Soc.*, 117(21): 5869-5870 (1995).
Dennis et al., "Albumin Binding as a General Strategy for Improving the Pharmacokinetics of Proteins," *J. Biol. Chem.*, 277(38): 35035-35043 (2002).
Dickinson et al., "Identification of surface residues mediating tissue factor binding and catalytic function of the serine protease factor VIIa," *Proc. Natl. Acad. Sci. USA*, 93(25): 14379-14384 (1996).
Dreyfus et al., "Successive Isolation and Separation of the Major Lipid Fractions Including Gangliosides from Single Biological Samples," *Anal. Biochem.*, 249(1): 67-78 (1997).
Dudas et al., "Selection and immunochemical analysis of lipooligosaccharide mutants of Neisseria gonorrhoeae," *Infect. Immun.*, 56(2): 499-504 (1988).
Dudziak et al., "Cyclodextrin-assisted Glycan Chain Extension on a Protected Glycosyl Amino Acid," *Tetrahedron*, 56(32): 5865-5869 (2000).
Edano et al., "Importance of Sialic Acid in Recombinant Thrombomodulin in Terms of Pharmacokinetics and Separation of Desialyzed Glycoprotein," *Biol. Pharm. Bull.*, 21(4): 382-385 (1998).
Ellis, "Vaccines," Plotkin et al. (eds.), Chapter 29, W.B. Saunders Co., Philadelphia, pp. 568-575 (1988).
EMBL Accession No. M80599 and M86935 (Jan. 23, 1992).
EMBL Accession No. S56361 (May 4, 1993).
EMBL Accession No. U00039 (Jun. 2, 1994).
Ernst et al., "Substrate and donor specificity of glycosyl transferases," *Glycoconj. J.*, 16(2): 161-170 (1999).
Fu et al., "Carbohydrate-Directed Conjugation of Cobra Venom Factor to Antibody by Selective Derivatization of the Terminal Galactose Residues," *Bioconjug. Chem.*, 12(2): 271-279 (2001).
Fujita et al., "A novel disaccharide substrate having 1,2-oxazoline moiety for detection of transglycosylating activity of endoglycosidases," *Biochim. Biophys. Acta*, 1528(1): 9-14 (2001).
GE Healthcare, Instructions 28-9064-05 AA, pp. 1-32 (2006).
GE Healthcare, Instructions 28-9064-05 AC, pp. 1-40 (2006).
GenBank Accession No. D49915 (Sep. 1, 1995).
GenBank Accession No. U02304 (Mar. 8, 1994).
GenBank Accession No. U18918 (Oct. 1, 1995).
Gibson et al., "Investigation of the structural heterogeneity of lipooligosaccharides from pathogenic *Haemophilus* and *Neisseria* species and of R-type lipopolysaccharides from *Salmonella typhimurium* by electrospray mass spectrometry," *J. Bacteriol.*, 175(9): 2702-2712 (1993).
Gilbert, "Thiol/Disulfide Exchange Equilibria and Disulfide Bond Stability," *Methods in Enzymology*, Packer (ed.), 2(251): 8-28, Biothiols Part A, Elsevier (1995).
Gillespie et al., "Cloning of a Sialyltransferse Involded in Biosynthesis of 0-Linked Carbohydrate Groups," *FASEB Journal*, 4(7): A2068 [Abstract No. 2173] (1990).
Gillespie et al., "Cloning and Expression of the Galβ1,3GalNAc α2,3-Sialyltransferase," *J. Biol. Chem.*, 267(29): 21004-21010 (1992).
Goodson et al., "Site-Directed Pegylation of Recombinant Interleukin-2 at its Glycosylation Site," *Biotechnology (N.Y.)*, 8(4): 343-346 (1990).
Greenwell et al., "Blood Group A Synthesising Activity of the Blood Group B Gene Specified α-3-D-Galactosyl Transferase," *Clycoconjugates*, pp. 268-269 (1979).
Greenwell et al., "UDP-N-acetyl-D-Galactosamine as a Donor Substrate for the Glycosyltransferase Encoded by the B Gene at the Human Blood Group ABO locus," *Carbohydr. Res.*, 149(1): 149-170 (1986).
Gross et al., "Activation and transfer of novel synthetic 9-substituted sialic acids," *Eur. J. Biochem.*, 168(3): 595-602 (1987).
Grundmann et al., "Complete cDNA sequence encoding human β-galactoside α-2,6-sialyltransferase," *Nucleic Acids Res.*, 18(3): 667 (1990).
Gu et al., "Purification and characterization of CMP-NeuAc:GM1 (Gal β 1-4GalNAc) α2-3 sialyltransferase from rat brain," *FEBS Lett.*, 275(1-2): 83-86 (1990).
Guivisdalsky et al., "Synthesis and Antineoplastic Properties of Ether-Linked Thioglycolipids," *J. Med. Chem.*, 33(9): 2614-2621 (1990).
Hakomori et al., "Methods in Enzymology," Fleischer et al. (eds.), 33(32): 345-367, Biomembranes Part B, Elsevier USA (1974).
Helling et al., "$G_{D3}$ Vaccines for Melanoma: Superior Immunogenicity of Keyhole Limpet Hemocyanin Conjugate Vaccines," *Cancer Res.*, 54(1): 197-203 (1994).

(56) References Cited

OTHER PUBLICATIONS

Higa et al., "Sialylation of Glycoprotein Oligosaccharides with N-acetyl-, N-glycolyl-, and N-O-Diacetylneuraminic Acids," *J. Biol. Chem.*, 260(15): 8838-8849 (1985).

Higashi et al., "Conformation of Factor VIIa Stabilized by a Labile Disulfide Bond (Cys-310-Cys-329) in the Protease Domain Is Essential for Interaction with Tissue Factor," *J. Biol. Chem.*, 272(41): 25724-25730 (1997).

High et al., "The role of a repetitive DNA motif (5'-CAAT-3') in the variable expression of the *Haemophilus influenzae* lipopolysaccharide epitope αGal(1-4)βGal," *Mol. Microbiol.*, 9(6): 1275-1282 (1993).

Hoffman et al., "A Cell-Based Model of Hemostasis," *Thromb. Haemost*, 85(6): 958-965 (2001).

Ichikawa et al., "Enzyme-Catalyzed Syntheis of Sialyl Oligosaccharide with in Situ Regeneration of CMP-Sialic Acid," *J. Am. Chem. Soc.*, 113(12): 4698-4700 (1991).

Ichikawa et al., "A Highly Efficient Multienzyne System for the One-Step Synthesis of a Sialyl Trisaccharide: In Situ Generation of Sialic Acid and N-Acetyllactosamine Coupled with Regenerationof UDP-Glucose, UDP-Galactose, and CMP-Sialic Acid," *J. Am. Chem. Soc.*, 113(16): 6300-6302 (1991).

Ito et al., "A Novel Strategy for Synthesis of Ganglioside GM3 Using an Enzymatically Produced Sialoside Glycosyl Donor," *J. Am. Chem. Soc.*, 115(4): 1603-1605 (1993).

Jennemann et al., "Specific Immunization Using Keyhole Limpet Hemocyanin-Ganglioside Conjugates," *J. Biochem.*, 115(6): 1047-1052 (1994).

Jennings et al., "Cloning and molecular analysis of the galE gene of *Neisseria meningitidis* and its role in lipopolysaccharide biosynthesis," *Mol. Microbiol.*, 10(2): 361-369 (1993).

John et al., "The Structural Basis for Pyocin Resistance in *Neisseria gonorrhoeae* Lipooligosaccharides," *J. Biol. Chem.*, 266(29): 19303-19311 (1991).

Jonsson et al., "Phase variation of gonococcal pili by frameshift mutation in pilC, a novel gene for pilus assembly," *EMBO J.*, 10(2): 477-488 (1991).

Joziasse et al., "Purification and Enzymatic Characterization of CMP-sialic Acid: β-Galactosyl1-3-N-Acetylgalactosaminide α2-3-Sialyltransferase from Human Placenta," *J. Biol. Chem.*, 260(8): 4941-4951 (1985).

Joziasse et al., "Bovine α1-3-Galactosyltransferase: Isolation and Characterization of a cDNA clone. Identification of Homologous Sequences in Human Genomic DNA," *J. Biol. Chem.*, 264(24): 14290-14297 (1989).

Kawai et al., "Structure of biologically active and inactive cerebrosides prepared from *Schizophyllum commune*," *J. Lipid Res.*, 26(3): 338-343 (1985).

Kerwood et al., "Structural Analysis of Lipooligosaccharide Produced by *Neisseria gonorrhoeae*, Strain MS11mk (Variant A): A Precursor for a Gonococcal Lipooligosaccharide Associated with Virulence," *Biochemistry*, 31(51): 12760-12768 (1992).

Khidekel et al., "A Chemoenzymatic Approach toward the Rapid and Sensitive Detection of O-GlcNAc Posttranslational Modifications," *J. Am. Chem. Soc.*, 125(52): 16162-16163 (2003).

Kitagawa et al., "Cloning and expression of Human Galβ1,3(4)GlcNAc α2,3-Sialyltransferase," *Biochem. Biophys. Res. Commun.*, 194(1): 375-382 (1993).

Kitagawa et al., "Differential Expression of Five Sialyltransferase Genes in Human Tissues," *J. Biol. Chem.*, 269(27): 17872-17878 (1994).

Knight et al., "Identification and characterization of a novel insertion sequence, IS1106, downstream of the porA gene in B15 *Neisseria meningitides*," *Mol. Microbiol.*, 6(11): 1565-1573 (1992).

Kogan, "The Synthesis of Substituted Methoxy-poly(ethyleneglycol) Derivatives Suitable for Selective Protein Modification," *Synth. Commun.*, 22(16): 2417-2424 (1992).

Koike et al., "Total Synthesis of Cerebrosides: (2S, 3R, 4E)-1-O-β-D-Galacto-pyranosyl-N-(2'R and 2'S)-2"-Hydroxytetracosanoylsphingenine," *Carbohydr. Res.*, 162(2): 237-246 (1987).

Kurosawa et al., "Molecular cloning and expression of chick embryo Galβ1,4GlcNAcα2,6-sialyltransferase. Comparison with the mammalian enzyme," *Eur. J. Biochem.*, 219(1-2): 375-381 (1994).

Larsen et al, "Isolation of a cDNA encoding a murine UDPgalactose:β-D-galactosyl-1,4-N-acetyl-D-glucosaminide α-1,3-galactosyltransferase: Expression cloning by gene transfer," *Proc. Natl. Acad. Sci. USA*, 86(21): 8227-8231 (1989).

Lee et al. "Generation of cDNA Probes Directed by Amino Acid Sequence: Cloning of Urate Oxidase," *Science*, 239(4845): 1288-1291 (1988).

Lidholt et al, "Biosynthesis of heparin. Relationship between the polymerization and sulphation processes," *Biochem. J.*, 261(3): 999-1007 (1989).

Livingston et al., "Polymerase Chain Reaction Cloning of a Developmentally Regulated Member of the Sialyltransferase Gene Family," *J. Biol. Chem.*, 268(16): 11504-11507 (1993).

Lundstrom-Ljung et al., "Glutaredoxin Accelerates Glutathione-dependent Folding of Reduced Ribonuclease A Together with Protein Disulfide-isomerase," *J. Biol. Chem.*, 270(14): 7822-7828 (1995).

Maccioni et al., "Organization of ganglioside synthesis in the Golgi apparatus," *Biochim Biophys Acta.*, 1437(2): 101-118 (1999).

MacKenzie et al., "Glycosynthases: Mutant Glycosidases for Oligosaccharide Synthesis," *J. Am. Chem. Soc.*, 120(22): 5583-5584 (1998).

Madnick et al., "Effect of Modification of Galactose Residues on the Biological Properties of Asialo Human Choriogonadotropin," *Arch. Biochem. Biophys.*, 212(2): 432-442 (1981).

Mandrell et al., "Lipooligosaccharides (LOS) of *Neisseria gonorrhoeae* and *Neisseria meningitidis* have components that are immunochemically similar to precursors of human blood group antigens. Carbohydrate Sequence Specificity of the Mouse Monoclonal Antibodies that Recognize Crossreacting Antigens on LOS and Human Erythrocytes," *J. Exp. Med.*, 168(1): 107-126 (1988).

Mandrell et al., "In vitro and in vivo modification of *Neisseria gonorrhoeae* lipooligosaccharide epitope structure by sialylation," *J. Exp. Med.*, 171(5): 1649-1664 (1990).

Mandrell et al., "Endogenous Sialylation of the lipooligosaccharides of Neisseria meningitides," *J. Bacteriol.*, 173(9): 2823-2832 (1991).

Mandrell, "Further Antigenic Similarities of *Neisseria gonorrhoeae* Lipooligosaccharides and Human Glycosphingolipids," *Infect. Immun.*, 60(7): 3017-3020 (1992).

Marinier et al., "Sulfated Galactocerebrosides as Potential Antiinflammatory Agents," *J. Med. Chem.*, 40(20): 3234-3247 (1997).

Mathews et al., "Mass Spectrometrically Derived Amino Acid Sequence of Thioredoxin from *Chlorobium*, an Evolutionarily Prominent Photosynthetic Bacterium," *J. Biol. Chem.*, 262(16): 7537-7545 (1987).

Mizuguchi et al., "Structural element of factor VIIa required for active site formation," *Thromb. Haemost.*, Abstract 1474: 466, Suppl. (Aug. 1999).

Muramatsu et al., *Comprehensive Research on Clinical Organ Xenotransplantation by Genetic Regulation*, p. 10-12. (1997).

Nemansky et al., "Human liver and human placenta both contain CMP-NeuAc:Galβ1→4GlcNAc-R α2→3- as well as α2→6-sialyltransferase activity," *FEBS Lett.*, 312(1): 31-36 (1992).

Nilsson, "Enzymatic synthesis of oligosaccharides," *Trends Biotechnol.*, 6(10): 256-264 (1988).

Nucci et al., "The therapeutic value of poly(ethylene glycol)-modified proteins," *Adv. Drug Deliv. Rev.*, 6(2): 133-151 (1991).

Nunez et al., "The Metal Ion Catalyzed Decomposition of Nucleoside Diphosphate Sugars," *Biochemistry*, 15(17): 3843-3847 (1976).

Palcic et al., "Flexibility in the donor substrate specificity of β 1,4-galactosyltransferase: application in the synthesis of complex carbohydrates," *Glycobiology*, 1(2): 205-209 (1991).

Parsons et al., "Sialylation of lipopolysaccharide and loss of absorption of bactericidal antibody during conversion of gonococci to serum resistance by cytidine 5'-monophospho-N-acetyl neuraminic acid," *Microb. Pathog.*, 7(1): 63-72 (1989).

Patra et al., "Optimization of Inclusion Body Solubilization and Renaturation of Recombinant Human Growth Hormone from *Escherichia coli*," *Protein Expr. Purif.*, 18(2): 182-192 (2000).

(56) References Cited

OTHER PUBLICATIONS

Paulson et al., "Purification of a sialyltransferase from bovine colostrum by affinity chromatography on CDP-agarose," *Chemical Abstracts*, 86(25): 213 [Abstract No. 185016b] (1977).
Paulson et al., "Purification of a sialyltransferase from bovine colostrum by affinity chromatography on CDP-agarose," *J. Biol. Chem.*, 252(7): 2356-2362 (1977).
Paulson et al., "Tissue-specific expression of sialyltransferases," *J. Biol. Chem.*, 264(19):10931-10934 (1989).
Pfaffli et al., "Thioglycosides having O-benzyl blocking groups as intermediates for the systematic, sequential synthesis of oligosaccharides. Synthesis of isomaltose," *Carbohydr. Res.*, 23(2): 195-206 (1972).
Pradel et al., "Structures of the rfaB, rfaI, rfaJ, and rfaS Genes of *Escherichia coli* K-12 and Their Roles in Assembly of the Lipopolysaccharide Core," *J. Bacteriol.*, 174(14): 4736-4745 (1992).
Preuss et al., "Purification and Characterization of CMP-N-acetylneuraminic Acid:Lactosylceramide ($\alpha$2-3) Sialyltransferase ($G_{M3}$-synthase) from Rat Brain," *J. Biol. Chem.*, 268(35): 26273-26278 (1993).
Probert et al., "Chemoenzymatic Synthesis of $GM_3$, Lewis x and Sialyl Lewis x Oligosaccharides in $^{13}$C-Enriched Form," *Tetrahedron Lett.*, 38(33): 5861-5864 (1997).
Rao et al., "Mutations of endo-$\beta$-N-acetylglucosaminidase H active site residues Asp130 and Glu132: Activities and conformations," *Protein Sci.*, 8(11): 2338-2346 (1999).
Rearick et al., "Enzymatic Characterization of $\beta$-D-Galactoside $\alpha$2-3 Sialyltransferase from Porcine Submaxillary Gland," *J. Biol. Chem.*, 254(11): 4444-4451 (1979).
Rice et al., "Modification of Triantennary Glycopeptide into Probes for the Asialoglycoprotein Receptor of Hepatocytes," *J. Biol. Chem.*, 265(30): 18423-18428 (1990).
Robertson et al., "The role of galE in the biosynthesis and function of gonococcal lipopolysaccharide," *Mol. Microbiol.*, 8(5): 891-901 (1993).
Rosevear et al., "Synthesis and Solution Conformation of the Type 2 Blood Group Oligosaccharide $\alpha$L Fuc(1-2)$\beta$D Gal(1-4)$\beta$D GlcNAc," *Biochemistry*, 21(6): 1421-1431 (1982).
Sadler et al., "Purification to Homogeneity of a $\beta$-Galactoside $\beta$2-3 Sialyltransferase and Partial Purification of an $\alpha$-N-Acetylgalactosaminide $\alpha$2-6 Sialyltransferase from Porcine Submaxillary Glands," *J. Biol. Chem.*, 254(11): 4434-4442 (1979).
Sadler et al., "Purification to Homogeneity and Enzymatic Characterization of an $\alpha$-N-Acetylgalactosaminide $\alpha$2-6 Sialyltransferase from Porcine Submaxillary Glands," *J. Biol. Chem.*, 254(13): 5934-5941 (1979).
Saenko et al., "Strategies towards a longer acting factor VIII," *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, pp. 9.50-9.51 (1989).
Sandlin et al., "Role of Phosphoglucomutase in Lipooligosaccharide Biosynthesis in Neisseria gonorrhoeae," *J. Bacteriol.*, 176(10): 2930-2937 (1994).
Schmidt et al., "Structure-Function Relationships in Factor IX and Factor IXa," *Trends Cardiovasc. Med.*, 13(1): 39-45 (2003).
Schneider et al., "Instability of Expression of Lipooligosaccharides and Their Epitopes in Neisseria gonorrhoeae," *Infect. Immun.*, 56(4): 942-946 (1988).
Schneider et al., "Expression of Paragloboside-like Lipooligosaccharides May Be a Necessary Component of Gonococcal Pathogenesis in Men," *J. Exp. Med.*, 174(6): 1601-1605 (1991).
Schram et al., "The identity of $\alpha$-galactosidase B from human liver," *Biochim. Biophys. Acta*, 482(1): 138-144 (1977).
Sears et al., "Toward Automated Synthesis of Oligosaccharides and Glycoproteins," *Science*, 291(5512): 2344-2350 (2001).
Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives," *Glycobiology*, 1(2): 187-191 (1991).
Shao et al., "O-Glycosylation of EGF repeats: identification and initial characterization of a UDP-glucose: protein O-glucosyltransferase," *Glycobiology*, 12(11): 763-770 (2002).
Simon et al., "Synthesis of CMP-NeuAc from N-Acetylglucosamine: Generation of CTP from CMP Using Adenylate Kinase," *J. Am. Chem. Soc.*, 110(21): 7159-7163 (1988).
Sogin et al., "Binding of Cytochalasin B to Human Erythrocyte Glucose Transporter," *Biochemistry* 19(23): 5417-5420 (1980).
Stamenkovic et al., "The B Cell Antigen CD75 Is a Cell Surface Sialytransferase," *J. Exp. Med.*, 172(2): 641-643 (1990).
Stennicke et al., "C-Terminal Incorporation of Fluorogenic and Affinity Labels Using Wild-Type and Mutagenized Carboxypeptidase Y," *Anal. Biochem.*, 248(1): 141-148 (1997).
Stephens et al., "Tn916-Generated, Lipooligosaccharide Mutants of Neisseria meningitidis and Neisseria gonorrhoeae," *Infect Immun.*, 62(7): 2947-2952 (1994).
Stoolmiller et al., "The Biosynthesis of Hyaluronic Acid by *Streptococcus*," *J. Biol. Chem.*, 244(2): 236-246 (1969).
Suzuki et al., "N-Acetylneuraminyllactosylceramide, $G_{M3-NeuAc}$, a New Influenza A Virus Receptor Which Mediates the Adsorption-Fusion Process of Viral Infection. Binding specificity of influenza virus A/AICHI/2/68 ($H_3N_2$) to membrane-associated $G_{M3}$ with different molecular species of sialic acid," *J. Biol. Chem.*, 260(3): 1362-1365 (1985).
SWISS-PROT Accession No. P19817 (Feb. 1, 1991).
SWISS-PROT Accession No. P25740 (May 1, 1992).
SWISS-PROT Accession No. P27129 (Aug. 1, 1992).
Takegawa et al., "Synthesis of Neoglycoproteins Using Oligosaccharide-transfer Activity with Endo-$\beta$-N-Acetylglucosaminidase," *J. Biol. Chem.*, 270(7): 3094-3099 (1995).
Takeya et al., "Bovine factor VII. Its purification and complete amino acid sequence," *J. Biol. Chem.*, 263(29): 14868-14877 (1988).
Takeya et al., "Biosynthesis of the blood group P antigen-like GalNAc$\beta$1$\rightarrow$3Gal$\beta$1$\rightarrow$4GlcNAc/Glc structure: kinetic evidence for the responsibility of N-acetylglucosaminyl-transferase," *Jpn. J. Med. Sci. Biol.*, 46(1): 1-15 (1993).
Tarui et al., "A Novel Cell-Free Translation/Glycosylation System Prepared from Insect Cells," *J. Biosci. Bioeng.*, 90(5): 508-514 (2000).
Toone et al., "Enzyme-Catalyzed Synthesis of Carbohydrates," *Tetrahedron*, 45(17): 5365-5422 (1989).
Tsai et al., "Eight Lipooligosaccharides of Neisseria Meningitidis React with a Monoclonal Antibody Which Binds Lacto-N-Neotetraose (Gal$\beta$1-4GlcNAc$\beta$1-3Gal$\beta$1-4Glc)," *Infect. Immun.*, 59(10): 3604-3609 (1991).
Tsujihara et al., "A New Class of Nitrosoureas. II. Synthesis and Antitumor Activity of 1-(2-chloroethyl)-3,3-disubstituted-1-nitrosoureas having a Gluco-pyranosyl, Mannopyranosyl or Galactopyranosyl Moiety," *Chem. Pharm. Bull.*, (Tokyo) 29(11): 3262-3273 (1981).
Van Den Eijnden et al., "Detection of $\beta$-galactosyl(1-4)N-acetylglucosaminide $\alpha$(2-3)-Sialyltransferase Activity in Fetal Calf Liver and Other Tissues," *J. Biol. Chem.*, 256(7): 3159-3162 (1981).
Van Den Eijnden et al., "Novikoff Ascites Tumor Cells Contain N-Acetyllactosaminide $\beta$1-3 and $\beta$1-6 N-Acetylglucosaminyltransferase Activity," *J. Biol. Chem.*, 258(6): 3435-3437 (1983).
Van Putten et al., "Phase variation of lipopolysaccharide directs interconversion of invasive and immuno-resistant phenotypes of Neisseria gonorrhoeae," *EMBO J.*, 12(11): 4043-4051 (1993).
Van Roey et al., "Crystal Structure of Endo-$\beta$-N-acetylglucosaminidase $F_1$, an $\alpha$/$\beta$-Barrel Enzyme Adapted for a Complex Substrate," *Biochemistry*, 33(47): 13989-13996 (1994).
Vann et al., "Purification, Properties, and Genetic Location of *Escherichia coli* Cytidine 5'-Monophosphate N-Acetylneuraminic Acid Synthetase," *J Biol Chem.*, 262(36): 17556-17562 (1987).
Verheul et al., "Meningococcal Lipopolysaccharides: Virulence Factor and Potential Vaccine Component," *Microbiol. Rev.*, 57(1): 34-49 (1993).
Vijay et al., "Properties of Membrane-associated Sialyltransferase of *Escherichia coli*," *J. Biol. Chem.*, 250(1): 164-170 (1975).
Waddling et al., "Structural Basis for the Substrate Specificity of Endo-$\beta$-N-acetylglucosaminidase F(3)," *Biochemistry*, 39(27): 7878-7885 (2000).

(56) References Cited

OTHER PUBLICATIONS

Wakarchuk et al., "Functional Relationships of the Genetic Locus Encoding the Glycosyltransferase Enzymes Involved in Expression of the Lacto-N-neotetraose Terminal Lipopolysaccharide Structure in Neisseria meningitides," *J. Biol. Chem.*, 271(32): 19166-19173 (1996).

Wang et al., "The role of the Cys191-Cys220 disulfide bond in trypsin: new targets for engineering substrate specificity," *Protein Eng.*, 10(4): 405-411 (1997).

Webster et al., "Primary structures of Both Subunits of *Escherichia coli* Glycyl-tRNA Synthetase," J. Biol. Chem., 258(17): 10637-10641 (1983).

Weinstein et al., "Purification of a Galβ1-4GlcNAc α2-6 Sialyltransferase and a Galβ1-3(4)GlcNAc α2-3 Sialyltransferase to Homogeneity from Rat Liver," *J. Biol. Chem.*, 257(22): 13835-13844 (1982).

Weinstein et al., "Sialylation of Glycoprotein Oligosaccharides N-linked to Asparagine. Enzymatic characterization of a Galβ1-3(4)GlcNAc α2-3 sialyltransferase and a Galβ1-4GlcNAc α2-6 sialyltransferase from rat liver," *J. Biol. Chem.*, 257(22): 13845-13853 (1982).

Wen et al., "Primary Structure of GALβ1, 3(4) GLCNAC α2,3-sialyltransferase reveals a conserved region in the sialyltransferase family," *FASEB Journal*, 6(1): A231 [abstract No. 1329] (1992).

Wen et al., "Primary Structure of Galβ1,3(4)GlcNAc α2,3-Sialyltransferase Determined by Mass Spectrometry Sequence Analysis and Molecular Cloning. Evidence for a protein motif in the sialyltransferase gene family," *J. Biol. Chem.*, 267(29): 21011-21019 (1992).

Whisstock et al., "Prediction of protein function from protein sequence and structure," *Q. Rev. Biophys.*, 36(3): 307-340 (2003).

Wikipedia, Image:Ceramide.svg, http://en.wikipedia.org/wiki/Ceramide, pp. 1-2 (2007).

Wong et al., "Regeneration of Sugar Nucleotide for Enzymatic Oligosaccharide Synthesis: Use of Gal-I-Phosphate Uridyltransferase in the Regeneration of UDP-Galactose, UDP 2-Deoxygalactose, and UDP-Galactosamine," *J. Org. Chem.*, 57(16): 4343-4344 (1992).

Xiao et al., "Catalysis of Thiol/Disulfide Exchange. Glutaredoxin 1 and protein-disulfide isomerase use different mechanisms to enhance oxidase and reductase activities," *J. Biol. Chem.*, 280(22): 21099-21106 (2005).

Yamamoto et al., "Sugar-nucleotide Donor Specificity of Histo-blood Group A and B Transferases Is Based on Amino Acid Substitutions," *J. Biol. Chem.*, 265(31): 19257-19262 (1990).

Yamamoto et al., "Molecular genetic basis of the histo-blood group ABO system," *Nature*, 345(6272): 229-233 (1990).

Yamasaki et al., "Neuraminic acid is α2→3 Linked in the Lipooligosaccharide of *Neisseria meningitidis* Serogroup B Strain 6275," *J. Bacteriol.*, 175(14): 4565-4568 (1993).

Yoshikawa et al., "Aroma glycosides from Hovenia dulsis," *Phytochemistry*, 34(5): 1431-1433 (1993).

Zalipsky et al., "Preparation of Polyethylene Glycol Derivatives with Two Different Functional Groups at the Termini," *Polymer Prepr.*, 27(1): 1-2 (1986).

Zalipsky et al., "A convenient general method for synthesis of $N^{\alpha}$- or $N^{\omega}$-dithiasuccinoyl (Dts) amino acids and dipeptides: application of polyethylene glycol as a carrier for functional purification," *Int. J. Pept. Protein Res.*, 30(6): 740-783 (1987).

Zapata et al., "Sequence of the Cloned *Escherichia coli* K1 CMP-N-acetylneuraminic Acid Synthetase Gene," *J. Biol. Chem.*, 264(25): 14769-14774 (1989).

Zhou et al., "Lipooligosaccharide biosynthesis in pathogenic Neisseria. Cloning, identification, and characterization of the phosphoglucomutase gene," *J. Biol. Chem.*, 269(15): 11162-11169 (1994).

Abeijon et al., "3'-0-(4-Benzoyl)benzoylcytidine 5'-Triphosphate A Substrate and Photoaffinity Label for Cmp-N-Acetylneuraminic Acid Synthetase," *J. Biol. Chem.*, 261(24): 11374-11377 (1986).

Abuchowski et al., "Alteration of Immunological Properties of Bovine Serum Albumin by Covalent Attachment of Polyethylene Glycol," *J. Biol. Chem.*, 252(11): 3578-3581 (1977).

Abuchowski et al., "Effect of Covalent Attachment of Polyethylene Glycol on Immunogenicity and Circulating Life of Bovine Liver Catalase," *J. Biol. Chem.*, 252(11): 3582-3586 (1977).

Abuchowski et al., "Cancer Therapy With Chemically Modified Enzymes. I. Antitumor . Properties of Polyethylene Glycol-Asparaginase Conjugates," *Cancer Biochem. Biophys.*, 7(2): 175-186 (1984).

Adelhorst et al.,"Structure-Activity Studies of Glucagon-like Peptide-1," *J. Biol. Chem.*, 269(9): 6275-6278 (1994).

Ailor et al., "N-Glycan Patterns of Human Transferrin Produced in *Trichoplusia ni* Insect Cells: Effects of Mammalian Galactosyltransferase," *Glycobiology*, 10(8): 837-847 (2000).

Alam et al., "Expression and Purification of a Mutant Human Growth Hormone That Is Resistant to Proteolytic Cleavage by Thrombin, Plasmin and Human Plasma In Vitro," *J. Biotechnol.*, 65(2-3): 183-190 (1998).

Allegre et al., "Cholesterol Removal by Nanofiltration: Applications in Nutraceutics and Nutritional Supplements," *J. Memb. Sci.*, 269(1-2): 109-117 (2006).

Altmann et al., "Insect Cells As Hosts for the Expression of Recombinant Glycoproteins," *Glycoconj. J.*, 16(2): 109-123 (1999).

Amersham Pharmacia Biotech, "Hydrophobic Interaction Chromatography: Principles and Methods," 104 pp. (2000).

Aplin et al., "Preparation, Properties, and Applications of Carbohydrate Conjugates of Proteins and Lipids," *CRC Crit. Rev. Biochem.*, 10(4): 259-306 (1981).

Arslan et al., "Mobilization of Peripheral Blood Stem Cells," *Transf. Apher. Sci.*, 37: 179-185 (2007).

Barrios et al., "Length of the Antibody Heavy Chain Complementarity Determining Region 3 As a Specificity~Determining Factor," *J. Mol. Recognit.*, 17(4):332-338 (2004).

Beauchamp et al., "A New Procedure for the Synthesis of Polyethylene Glycol-Protein Adducts; Effects on Function, Receptor Recognition, and Clearance of Superoxide Dismutase, Lactoferrin, and α 2-Macroglobulin," *Anal. Biochem.*, 131(1): 25-33 (1983).

Bedard et al., "Maximization of Recombinant Protein Yield in the Insect Cel/baculovirus System by One-Time Addition of Nutrients to High-Density Batch Cultures," *Cytotechnology*, 15(1-3):129-138 (1994).

Bennett et al., "Cloning of a•Human UDP-N-Acetyl-α-D-Galactosamine:Polypeptide N-Acetylgalactosaminyltransferase That Complements Other GalNAc-Transferases in Complete O-Glycosylation of the Muc1 Tandem Repeat," *J. Biol. Chem.*, 273(46): 30472-30481 (1998).

Bennett et al., "A Novel Human UDP-N-Acetyl-D-Galactosamine:Polypeptide-N-Acetylgalactosaminyltransferase, GalNAc-T7, With Specificity for Partial GalNAc-Glycosylated Acceptor Substrates," *FEBS Lett.*, 460(2): 226-230 (1999).

Berger et al., "Preparation of Polyethylene Glycol-Tissue Plasminogen Activator Adducts That Retain Functional Activity: Characteristics and Behavior in Three Animal Species." *Blood*, 71(6): 1641-1647 (1988).

Berg-Fussman et al., "Human Acid ,B-Glucosidase N-Glycosylation Site Occupancy and the Effect of Glycosylation on Enzymatic Activity," *J. Biol. Chem.*, 268(20): 14861-14866 (1993).

Bhadra et al., "Pegnology: a-Review of PEG-ylated Systems," *Pharmazie*, 57(1): 5-29 (2002).

Bhatia et al., "Use of Thiol-Terminal Silanes and Heterobifunctional Crosslinkers for Immobilization of Antibodies on Silica Surfaces," *Anal. Biochem.*, 178(2): 408-413 (1989).

Bickel et al., "Delivery of Peptides and Proteins Through the Blood-Brain Barrier," *Adv. Drug Deliv. Rev.*, 46(1-3): 247-279 (2001).

Bijsterbosch et al., "Quantitative analysis of the targeting of mannose-terminal glucocerebrosidase: Predominant uptake by liver endothelial cells," *Eur. J. Biochem.*, 237(2): 344-349 (1996).

Bishop et al., "Both of the β-Subunit Carbohydrate Residues of Follicle-Stimulating Hormone Determine the Metabolic Clearance Rate and in Vivo Potency" *Endocrinology*, 136(6): 2635-2640 (1995).

(56) References Cited

OTHER PUBLICATIONS

Bjoern et al., "Human Plasma and Recombinant Factor VII. Characterization of O-Glycosylations At Serine Residues 52 and 60 and Effects of Site-Directed Mutagenesis of Serine 52 to Alanine," *J. Biol. Chem.*, 266(17): 11051-11057 (1991).

Boccu et al., "Coupling of Monomethoxypolyethyleneglycols to Proteins Via Active Esters," *Z. Naturforsch.*, 38c: 94-99 (1983).

Boime et al., "Glycoprotein Hormone Structure-Function and Analog Design," *Recent Prog. Horm. Res.*, 54: 271-289 (1999).

Boissel et al., "Erythropoietin Structure-Function Relationships: Mutant Proteins That Test a Model of Tertiary Structure," *J. Biol. Chem.*, 268(21): 15983-15993 (1993).

Bork et al., "Go Hunting in Sequence Databases But Watch Out for the Traps," *Trends Genet.*, 12(10): 425-427 (1996).

Bork, "Powers and Pitfalls in Sequence Analysis: The 70% Hurdle," *Genome Res.*, 10(4): 398-400 (2000).

Bouizar et al., "Purification and Characterization of Calcitonin Receptors in Rat Kidney Membranes by Covalent Cross-Linking Techniques," *Eur. J. Biochem.*, 155(1): 141-147 (1986).

Boyd et al., "The Effect of the Removal of Sialic Acid, Galactose and Total Carbohydrate on the Functional Activity of Campath-1H," *Mol. Immunol.*, 32(17-18): 1311-1318 (1995).

Brenner, "Errors in Genome Annotation," *Trends Genet.*, 15(4): 132-133 (1999).

Brockhausen et al., "Glycoproteins and Their Relationship to Human Disease," *Acta Anatomica*, 161: 36-78 (1998).

Brockhausen et al., "Enzymatic Basis for Sialyl-Tn Expression in Human Colon Cancer Cells," *Glycoconj. J.*, 15: 595-603 (1998).

Broun et al., "Catalytic Plasticity of Fatty Acid Modification Enzymes Underlying Chemical Diversity of Plant Lipids," *Science*, 282(5392): 1315-1317 (1998).

Browning et al., "Studies on the Differing Effects of Tumor Necrosis Factor and Lymphotoxin on the Growth of Several Human Tumor Lines," *J. Immunol.*, 143(6): 1859-1867 (1989).

Broxmeyer et al., "Rapid Mobilization of Murine and Human Hematopoietic Stem and Progenitor Cells With AMD3100, A CXCR4 Antagonist," *J. Exp. Med.*, 201(8): 1307-1318 (2005).

Brumeanu et al., "Enzymatically Mediated, Glycosidic Conjugation of Immunoglobulins With Viral Epitopes," *J. Immunol. Meth.*, 183: 185-197 (1995).

Bückmann et al., "Functionalization of Poly(Ethylene Glycol) and Monomethoxy-Poly(Ethylene Glycol)," *Makromol. Chem.*, 182(5): 1379-1384 (1981).

Burns et al., "Purification and Characterization of the Yeast-Expressed Erythropoietin Mutant Epo (R103A), A Specific Inhibitor of Human Primary Hematopoietic Cell Erythropoiesis," *Blood*, 99(12): 4400-4405 (2002).

Butnev et al., "Hormone-Specific Inhibitory Influence of Alpha-Subunit Asn56 Oligosaccharide on In Vitro Subunit Association and Follicle-Stimulating Hormone Receptor Binding of Equine Gonadotropins," *Biol. Reprod.*, 58(2): 458-469 (1998).

Byun et al., "Binding Kinetics of Thrombin and Antithrombin III With Immobilized Heparin Using a Spacer," *ASAIO J.*, 38(3): M648-M653 (1992).

Cantin et al., "Polyethylene Glycol Conjugation At Cys232 Prolongs the Half-Life of Alpha1 Proteinase Inhibitor," *Am. J. Respir. Cell Mol. Biol.*, 27(6): 659-665 (2002).

Capoccia et al., "G-Csf and Amd3100 Mobilize Monocytes Into the Blood That Stimulate Angiogenesis In Vivo Through a Paracrine Mechanism," *Blood*, 108(7): 2438-2445 (2006).

Casares et al., "Antigen-Specific Downregulation of T Cells by Doxorubicin Delivered Through a Recombinant MHC II—Peptide Chimera," *Nat. Biotechnol.*, 19(2): 142-147 (2001).

Cashen et al., "Mobilizing Stem Cells From Normal Donors: Is It Possible to Improve Upon G-CSF," *Bone Marrow Trans.*, 39: 577-588 (2007).

Chaffee et al., "Igg Antibody Response to Polyethylene Glycol-Modified Adenosine Deaminase in Patients With Adenosine Deaminase Deficiency," *J. Clin. Invest.*, 89(5): 1643-1651 (1992).

Charter et al., "Biosynthetic Incorporation of Unnatural Sialic Acids Into Polysialic Acid on Neural Cells," *Glycobiology*, 10(10): 1049-1056 (2000).

Cheng et al., "Poly(ethylene glycol) . modification of β-glucuronidase-antibody conjugates for solid-tumor therapy by targeted activation of glucuronide prodrugs", *Cancer Immunol. Immunother.*, 44: 305-315 (1997).

Chern et al., "Structural Role of Amino Acids 99-110 In Recombinant Human Erythropoietin," *Eur. J. Biochem.*, 202(2): 225-229 (1991).

Chiba et al., "Cloning and Expression of the Carboxypeptidase Gene From Aspergillus Saitoi and Determination of the Catalytic Residues by Site-Directed Mutagenesis," *Biochem. J.*, 308(2): 405-409 (1995).

Chrisey et al., "Covalent Attachment of Synthetic DNA to Self-Assembled Monolayer Films," *Nucleic Acids Res.*, 24(15): 3031-3039 (1996).

Clark et al., "Long-Acting Growth Hormones Produced by Conjugation With Polyethylene Glycol," *J. Biol. Chem.*, 271(36): 21969-21977 (1996).

Cohn et al., "Biodegradable PEO/PLA Block Copolymers," *J. Biomed. Mater. Res,*. 22(11): 993-1009 (1988).

Cointe et al., "Unusual N-Glycosylation of a Recombinant Human Erythropoietin Expressed in a Human Lymphoblastoid Cell Line Does Not Alter Its Biological Properties," *Glycobiology*, 10(5): 511-519 (2000).

Conradt et al., "Structure of the Carbohydrate Moiety of Human Interferon-Beta Secreted by a Recombinant Chinese Hamster Ovary Cell Line," *J. Biol. Chem.*, 262(30): 14600-14605 (1987).

Cope et al., "Molecular Cloning of a Gene Involved in Lipooligosaccharide Biosynthesis and Virulence Expression by Haemophilus Influenzae Type B," *Mol. Microbiol.*, 5(5): 1113-1124 (1991).

Copeland, "Enzymes: A Practical Introduction to Structure, Mechanism and Data Analysis" 2nd ed., Wiley-VCH, New York, pp. 146-150 (2000).

Corfield, "Analysis of Sugar Sequences in Glycoproteins by Glycosidase Digestion and Gel Filtration," *Methods in Molecular Biology*, 19: 269-286 (1993).

Costa et al., "Stable Expression of the Golgi Form and Secretory Variants of Human Fucosyltransferase III From BHK-21 Cells. Purification and Characterization of an Engineered Truncated Form From the Culture Medium," *J. Biol. Chem.*, 272(17): 11613-11621 (1997).

Crout et al., "Glycosidases and Glycosyl Transferases in Glycoside and Oligosaccharide Synthesis," *Curr. Opin. Chem. Biol.*, 2(1): 98-111 (1998).

Culajay et al., "Thermodynamic Characterization of Mutants of Human Fibroblast Growth Factor 1 With an Increased Physiological Half-Life," *Biochem.*, 39: 7153-7158 (2000).

Deacon, "Therapeutic Strategies Based on Glucagon-Like Peptide 1," *Diabetes*, 54: 2181-2189 (2004).

Defrees et al., "Glycopegylation of Recombinant Therapeutic Proteins Produced in *Escherichia coli,*" *Glycobiology*, 16(9): 833-843 (2006).

Delgado et al., "Coupling of Poly(Ethylene Glycol) To Albumin Under Very Mild Conditions by Activation With Tresyl Chloride: Characterization of the Conjugate by Partitioning in Aqueous Two-Phase Systems," *Biotechnol. Appl. Biochem.*, 12(2): 119-128 (1990).

Delgado et al., "The Uses and Properties of PEG-Linked Proteins," *Crit. Rev. Ther. Drug Carrier Syst.*, 9(3-4): 249-304 (1992).

De Vries et al, "Acceptor Specificity of Different Length Constructs of Human Recombinant Alpha 1,3/4-Fucosyltransferases: Replacement of the Stem Region and the Transmembrane Domain of Fucosyltransferase V by Protein A Results in an Enzyme With GDP-Fucose Hydrolyzing Activity," *J. Biol. Chem.*, 270(15): 8712-8722 (1995).

De Vries et al., "Acceptor Specificity of GDP-Fuc:Gal Beta 1→4glcnac-R Alpha 3-Fucosyltransferase VI (Fuct VI) Expressed in Insect Cells As Soluble, Secreted Enzyme," *Glycobiology*, 7(7): 921-927 (1997).

Dinter et al., "Glycosylation Engineering in Chinese Hamster Ovary Cells Using Tricistronic Vectors," *Biotechnol. Lett.*, 22(1): 25-30 (2000).

(56) References Cited

OTHER PUBLICATIONS

Doerks et al., "Protein Annotation: Detective Work for Function Prediction," *Trends Genet.*, 14(6): 248-250 (1998).
Douglas et al., "Polymer-Supported Solution Synthesis of Oligosaccharides," *J. Am. Chem. Soc.*, 113(13): 5095-5097 (1991).
Drucker et al., "Glucagon Gene Expression in Vertebrate Brain," *J. Biol. Chem.*, 263(27): 13475-13478 (1988).
Dubé et al., "Glycosylation At Specific Sites of Erythropoietin Is Essential for Biosynthesis, Secretion, and Biological Function," *J. Biol. Chem.*, 263(33): 17516-17521 (1988).
Dumas et al., "Enzymatic Synthesis of Sialyl Le$^x$ and Derivatives Based on a Recombinant Fucosyltransferase," *Bioorg. Med. Chem. Lett.*, 1(8): 425-428 (1991).
Duncan, "The drawing era of polymer therapeutics", *Nature Reviews Drug Discovery*, 2(5): 347-360 (2003).
Dunn, "Polymeric Drugs and Drug Delivery Systems" Dunn et al. (eds.), Chapter 2 "Polymeric Matrices," pp. 11-23, ACS Symposium Series vol. 469, *American Chemical Society*, Washington D.C. (1991).
Durieux et al., "Synthesis of Biotinylated Glycosulfopeptides by Chemoselective Ligation," *Tetrahedron Lett.*, 42(12): 2297-2299 (2001).
Dwek et al., "Glycobiology: 'The Function of Sugar in the Igg Molecule'," *J. Anat.*, 187(Pt. 2): 279-292 (1995).
Eavarone et al., "Targeted Drug Delivery to C6 Glioma by Transferrin-Coupled Liposomes," *J. Biomed. Mater. Res.*, 51(1): 10-14 (2000).
Edge et al., "Deglycosylation of Glycoproteins by Trifluoromethanesulfonic Acid," *Anal. Biochem.*, 118(1): 131-137 (1981).
Eisenhaber et al., "Prediction of Posttranslational Modification of Proteins from Their Amino Acid Sequence," *Methods in Molecular Biology*, 609: 365-384 (2010).
Elhalabi et al., "Synthesis and Applications for Unnatural Sugar Nucleotides," *Curr. Med. Chem.*, 6(2): 93-116 (1999).
Espuelas et al., "Synthesis of an Amphiphilic Tetraantennary Mannosyl Conjugate and Incorporation Into Liposome Carriers," *Bioorg. Med. Chem. Lett.*, 13(15): 2557-2560 (2003).
Fairhall et al., "Growth Hormone (GH) Binding Protein and GH Interactions In Vivo in the Guinea Pig," *Endocrinology*, 131(4): 1963-1969 (1992).
Fan et al., "Detailed Studies on Substrate Structure Requirements of Glycoamidases A and F," *J. Biol. Chem.*, 272(43): 27058-27064 (1997).
Fay, "Activation of factor VIII and mechanisms of cofactor action," *Blood Reviews*, 18: 1-15 (2004).
Feldman et al., "Engineering N-Linked Protein Glycosylation with Diverse O Antigen Lipopolysaccharide Structures in *Escherichia coli*," *Proc. Natl. Acad. Sci. USA*, 102(8): 3016-3021 (2005).
Felix et al., "Synthesis of Symmetrically and Asymmetrically Branched Pegylating Reagents," *J. Peptide Res.*, 63: 85-90 (2004).
Fernandes et al., "The effect of polysialylation on the immunogenicity and antigenicity of asparaginase: implication in its pharmacokinetics", *Intl. J. of Pharmaceutics*, 217(1): 215-224 (2001).
Fibi et al., "N- and O-glycosylation Muteins of Recombinant Human Erythropoietin Secreted From BHK-21 Cells," *Blood*, 85(5): 1229-1236 (1995).
Fischer et al., "Recombinant Coagulation Factor IX: Glycosylation Analysis and In Vitro Conversion into Human-Like Sialylation Pattern," *Thromb. Res.*, 89(3): 147-150 (1998).
Flomenberg et al., "The Use of AMD3100 plus G-CSF for Autologous Hematopoietic Progenitor Cell Mobilization is Superior to G-CSF Alone," *Blood*, 106(5): 1867-1874 (2005).
Flynn et al., "Campath-1H Monoclonal Antibody Therapy," *Curr. Opin. Oncol.*, 12(6): 574-581 (2000).
Francis et al.,"PEGylation of Cytokines and other Therapeutic Protiens and Peptides: the Importance of Biological Optimisation of Coupling Techniques," *Intl. J. Hematol.*, 68(1): 1-18 (1998).

Fritz et al., "The Beginnings of Mucin Biosynthesis: the Crystal Structure of UDP-GalNAc:Polypeptide Alpha-N-Acetylgalactosaminyltransferase-T1," *Proc. Natl. Acad. Sci. USA*, 101(43): 15307-15312 (2004).
Fritz et al., "Dynamic Association Between the Catalytic and Lectin Domains of Human UDP-Galnac:Polypeptide Alpha-N-Acetylgalactosaminyltransferase-2," *J. Biol. Chem.*, 281(13): 8613-8619 (2006).
Garnett et al., "Targeted Drug Conjugates: Principles and Progress," *Adv. Drug Deliv. Rev.*, 53(2): 171-216 (2002).
Gatot et al., "Conservative Mutations in the Immunosuppressive Region of the Bovine Leukemia Virus Transmembrane Protein Affect Fusion But Not Infectivity In Vivo," *J. Biol. Chem.*, 273(21): 12870-12880 (1998).
Ge et al., "Cloning and Heterologous Expression of an Alpha1,3-Fucosyltransferase Gene from the Gastric Pathogen Helicobacter Pylori," *J. Biol. Chem.*, 272(34): 21357-21363 (1997).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
GenBank Accession No. AAA98726, "Factor IX," pp. 1-3 (Apr. 14, 2009).
GenBank Accession No. CAA01607, "Factor IX of *Homo sapiens*," pp. 1-2 (Apr. 14, 2009).
Gervais et al., "Glycosylation of Human Recombinant Gonadotrophins: Characterization and Batch-To-Batch Consistency," *Glycobiology*, 13(3): 179-189 (2003).
Gilbert et al., "Effect of Lipids on Insect Cell Growth and Expression of Recombinant Proteins in Serum-Free Medium," *Cytotechnology*, 22(1-3): 211-216 (1996).
Gilbert et al., "The Synthesis of Sialylated Oligosaccharides Using a CMP-Neu5Ac Synthetase/Sialyltransferase Fusion," *Nature Biotechnology*, 16: 769-772 (1998).
Gillis et al., "Production of Recombinant Human Colony Stimulating Factors in Yeast," *Behring Inst. Mitt.*, 83: 1-7 (1988).
Ginns, PEG Glucocerebrosidase, Internet page from www.gaucher.org.uk/peg2.prg, Nov. 1994, printed Jun. 21, 2002.
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Gotschlich, "Genetic Locus for the Biosynthesis of the Variable Portion of Neisseria Gonorrhoeae Lipooligosaccharide," *J. Exp. Med.*, 180(6): 2181-2190 (1994).
Grabenhorst et al., "Biosynthesis and Secretion of Human Interleukin 2 Glycoprotein Variants From Baculovirus-Infected Sf21 Cells. Characterization of Polypeptides and Posttranslational Modifications," *Eur. J. Biochem.*, 215(1): 189-197 (1993).
Grabenhorst et al., "The Cytoplasmic, Transmembrane, and Stem Regions of Glycosyltransferases Specify Their In Vivo Functional Sublocalization and Stability in the Golgi," *J. Biol. Chem.*, 274(51): 36107-36116 (1999).
Grodberg et al.,"Alanine Scanning Mutagenesis of Human Erythropoietin Identifies Four Amino Acids Which are Critical for Biological Activity," *Eur. J. Biochem.*, 218(2): 597-601 (1993).
Gross et al., "Enzymatic Introduction of a Fluorescent Sialic Acid Into Oligosaccharide Chains of Glycoproteins," *Eur. J. Biochem,.* 177(3): 583-589 (1988).
Gross et al., "Transfer of Synthetic Sialic Acid Analogues to N- and O-Linked Glycoprotein Glycans Using Four Different Mammalian Sialyltransferases," *Biochemistry*, 28(18): 7386-7392 (1989).
Gross, "Fluorescent CMP-Sialic Acids as a Tool to Study the Specificity of the CMP-Sialic Acid Carrier and the glycoconjugate Sialylation in Permeabilized Cells," *Eur. J. Biochem.*, 203(1-2): 269-275 (1992).
Guo et al., "Utilization of Glycosyltransferases to Change Oligosaccharide Structures," *Appl. Biochem. Biotechnol.*, 68(1-2): 1-20 (1997).
Hagen et al., "Structure-Function Analysis of the UDP-N-acetyl-D-Galactosamine:Polypeptide N-acetylgalactosaminyltransferase. Essential residues Lie in a Predicted Active Site Cleft Resembling a Lactose Repressor Fold," *J. Biol. Chem.*, 274(10): 6797-6803 (1999).

(56) References Cited

OTHER PUBLICATIONS

Hagen et al., "Cloning and Characterization of a Ninth Member of the UDP-GalNAc:Polypeptide N-acetylgalactosaminyltransferase Family, ppGaNTase-T9," *J. Biol. Chem.*, 276(20): 17395-17404 (2001).
Hall, "Immunotoxin Treatment of Brain Tumors," *Methods Mol. Biol.*, 166: 139-154 (2001).
Hällgren et al., "An Animated GDP-Fucose Analog Useful in the Fucosyltransferase Catalyzed Addition of Biologocial Probes onto Oligosaccharide Chains," *J. Carb. Chem.*, 14(4-5): 453-464 (1995).
Haneda et al., "Transglycosylation of Intact Sialo Complex-Type Oligosaccharides to the N-Acetylglucosamine Moieties of Glycopeptides by Mucor Hiemalis Endo-Beta-N-Acetylglucosaminidase," *Carbohydr. Res.*, 292: 61-70 (1996).
Hang et al., "Ketone Isosteres of 2-N-Acetamidosugars as Substrates for Metabolic Cell Surface Engineering," *J. Am. Chem. Soc.*, 123(6): 1242-1243 (2001).
Hansen et al., "Prediction of O-Glycosylation of Mammalian Proteins: Specificity Patterns of UDP-Galnac:Polypeptide N-Acetylgalactosaminyltransferase," *Biochem J.*, 308: 801-813 (1995).
Haro et al., "Glycosylated Human Growth Hormone (Hgh): A Novel 24 Kda Hgh-N Variant," *Biochem. Biophys. Res. Comm.*, 228(2): 549-556 (1996).
Harris et al., "Effect of Pegylation on Pharmaceuticals," *Nat. Rev. Drug Discov.*, 2(3): 214-221 (2003).
Harris et al., "Synthesis of Polyethylene Glycol Thiol," Abstracts of Papers of the American Chemical Society, V 201, APR, P 64-POLY, pp. 154-155 (1991).
Harris, "Laboratory Synthesis of Polyethylene Glycol Derivatives," *J. Macromol. Science, Rev. Macromol. Chem. Phys.*, C25(3): 325-373 (1985).
Harris (ed.), "Poly(Ethylene Glycol) Chemistry: Biotechnical and Biomedical Applications," Plenum Press, New York (1992) (Title Pages only).
Harris et al. (eds.), "Poly(ethylene glycol): Chemistry and Biological Applications," ACS Symposium Series, vol. 680, American Chemical Society (1997) (Title Pages only).
Hassan et al., "The Lectin Domain of UDP-N-Acetyl-D-Galactosamine: Polypeptide N-Acetylgalactosaminyltransferase-T4 Directs its Glycopeptide Specificities," *J. Biol. Chem.*, 275(49): 38197-38205 (2000).
Hassan et al., "Control of Mucin-Type O-Glycosylation: O-Glycan Occupancy is Directed by Substrate Specificities of Polypeptide GalNAc-Transferases," *Carbohydrates in Chemistry and Biology*, Part II, 3: 273-292 (2000).
Hayes et al., "The Biosynthesis of Oligosaccharides in Intact Golgi Preparations from Rat Liver. Analysis of N-linked and O-Linked Glycans Labeled by UDP-[6-3H]N-Acetylgalactosamine," *J. Biol. Chem.*, 268(22): 16170-16178 (1993).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).
Hellstrom et al., "Development and Activities of the BR96-Doxorubicin Immunoconjugate," *Methods Mol. Biol.*, 166: 3-16 (2001).
Hermanson et al., *Immobilized Affinity Ligand Techniques*, Academic Press (1992) (Table of Contents).
Hermanson, *Bioconjugate Techniques*, Academic Press, San Diego (1996) (Table of Contents).
Hermentin, et al., "The Hypothetical N-Glycan Charge: a Number That Characterizes Protein Glycosylation," *Glycobiology*, 6(2): 217-230 (1996).
Herscovics et al., "Glycoprotein Biosynthesis in Yeast," *FASEB J.*, 7(6): 540-550 (1993).
Hill et al., "Allogeneic Stem Cell Transplantation with peripheral Blood Stem Cells Mobilized by Pegylated G-CSF," *Biol. Blood Marrow Trans.*, 12: 603-607 (2006).
Hills et al., "Control of Therapeutic Monoclonal Antibody Glycosylation Through the Addition of Sugar Media Components andIn Vitro Remodling," *Am. Biotechnol. Lab.*, 20(11): 30 (2002).
Hink et al., "Expression of Three Recombinant Proteins Using Baculovirus Vectors in 23 Insect Cell Lines," *Biotechnol. Prog.*, 7(1): 9-14 (1991).
Höglund, "Glycosylated and Non-Glycosylated Recombinant Human Granulocyte Colony-Stimulating Factor (rhG-CSF)—What is the Difference?," *Med. Oncol.*, 15(4): 229-233 (1998).
Hollister et al., "Engineering Lepidopteran Insect Cells for Sialoglycoprotein Production by Genetic Transformation with Mammalian Beta 1,4-Galactosyltransferase and Alpha 2,6-Sialyltransferase Genes," *Glycobiology*, 11(1): 1-9 (2001).
Hounsell et al., "O-Linked Protein Glycosylation Structure and Function," *Glycoconj. J.*, 13(1): 19-26 (1996).
Hu et al., "FGF-18, A Novel Member of the Fibroblast Growth Factor Family, Stimulates Hepatic and Intestinal Proliferation," *Mol. Cell. Biol.*, 18(10): 6063-6074 (1998).
Hübel et al., "Clinical Applications of Granulocyte Colony-Stimulating Factor: an Update and Summary," *Ann. Hematol.*, 82: 207-213 (2003).
Ichikawa et al., ,,Chemical-Enzymatic Synthesis and Conformational Analysis of Sialyl Lewis x and Derivatives, *J. Am. Chem. Soc.*, 114(24): 9283-9298 (1992).
Ikonomou et al., "Design of an Efficient Medium for Insect Cell Growth and Recombinant Protein Production," *In Vitro Cell. Dev. Biol. Anim.*, 37(9): 549-559 (2001).
Inlow et al., "Insect Cell Culture and Baculovirus Propagation in Protein-Free Medium," *J. Tissue Cult. Methods*, 12(1): 13-16 (1989).
Inoue et al., "The Production of Recombinant Human Erythropoietin," *Biotechnol. Annu. Rev.*, 1: 297-313 (1995).
Ito et al., "Synthesis of Bioactive Sialosides," *Pure Appl. Chem.*, 65(4): 753-762 (1993).
Jackson et al., "Synthesis, Isolation, and Characterization of Conjugates of Ovalbumin with Monomethoxypolyethylene Glycol Using Cyanuric Chloride as the Coupling Agent," *Anal. Biochem.*, 165(1): 114-127 (1987).
Japanese Biochemical Society, "New Course in Biochemistry Experiments 3, Sugars I, Glycoproteins (top)," Tokyo Kagaku Dojin K.K., First Edition, p. 340 (1990).
Jarvis et al., "Engineering N-Glycosylation Pathways in the Baculovirus-Insect Cell System," *Curr. Opin. Biotechnol.*, 9(5): 528-533 (1998).
Jezek et al., "Solid Phase Synthesis of Glycopeptide Dendrimers with Tn Antigenic Structure and Their Biological Activites. Part 1," *J. Peptide Sci.*, 5: 46-55 (1999).
Joppich et al., "Peptides Flanked by Two Polymer Chains, 1," *Makromol. Chem.*, 180: 1381-1384 (1979).
Joshi et al., "ATP Synthase Complex from Bovine Heart Mitochondria. Subunit Arrangement as Revealed by Nearest Neighbor Analysis and Susceptibility to Trypsin," *J. Biol. Chem.*, 265(24): 14518-14525 (1990).
Jung et al., "Crosslinking of Platelet Glycoprotein Ib by N-Succinimidyl(4-Azidophenyldithio)Propionate and 3,3'-Dithiobis-(Sulfosuccinimidyl Propionate)," *Biochim. Biophys. Acta*, 761(2): 152-162 (1983).
Kajihara et al., "Enzymatic Synthesis of Kdn Oligosaccharides by a Bacterial Alpha-(2→6)-Sialyltransferase," *Carbohydrate Research*, 315: 137-141 (1999).
Kalsner et al., "Insertion into Aspergillus Nidulans of Functional UDP-GlcNAc: Alpha 3-D-Mannoside Beta-1,2-N-Acetylglucosaminyl-Transferase I, the Enzyme Catalysing the First Committed Step from Oligomannose to Hybrid and Complex N-Glycans," *Glycoconj. J.*, 12(3): 360-370 (1995).
Kaneko et al., "Assignment of the Human Alpha 1,3-fucosyltransferase IX Gene (FUT9) to Chromosome Band 6q16 by In Situ Hybridization," *Cytogenet. Cell Genet.*, 86(3-4): 329-330 (1999).
Kaneko et al., "Alpha1,3-fucosyltransferase IX (Fuc-TIX) is Very Highly Conserved Between Human and Mouse; Molecular Cloning, Characterization and Tissue Distribution of Human Fuc-TIX," *FEBS Lett.*, 452(3): 237-242 (1999).

(56) References Cited

OTHER PUBLICATIONS

Kasina et al., "Simplified Preformed Chelate Protein Radiolabeling with Technetium-99m Mercaptoacetamidoadipoylglycylglycine (N3S-adipate)," *Bioconjug. Chem.*, 9(1): 108-117 (1998).
Katre et al., "Chemical Modification of Recombinant Interleukin 2 by Polyethylene Glycol Increases Its Potency in the Murine Meth A Sarcoma Model," *Proc. Natl. Acad. Sci. USA*, 84(6): 1487-1491 (1987).
Kawasaki et al., "Application of Liquid Chromatography/Mass Spectrometry and Liquid Chromatography With Tandem Mass Spectrometry to the Analysis of the Site-Specific Carbohydrate Heterogeneity in Erythropoietin," *Anal. Biochem.*, 285: 82-91 (2000).
Keana et al., "New Reagents for Photoaffinity Labeling: Synthesis and Photolysis of Functionalized Perfluorophenyl Azides," *J. Org. Chem.*, 55(11): 3640-3647 (1990).
Keene et al., "Expression of Biologically Active Human Follitropin in Chinese Hamster Ovary Cells," *J. Biol. Chem.*, 264(9): 4769-4775 (1989).
Kennedy, "Hydrophobic-Interaction Chromatography," in *Current Protocols in Protein Science*, pp. 8.4.1-8.4.21, Wiley (1995).
Keppler et al., "Biochemical Engineering of the N-Acyl Side Chain of Sialic Acid: Biological Implications," *Glycobiology*, 11(2): 11R-18R (2001).
Kimura et al., "Reconstitution of Functional L-Selectin Ligands on a Cultured Human Endothelial Cell Line by Cotransfection of Alpha1→3 Fucosyltransferase VII and Newly Cloned Glcnacbeta:6-Sulfotransferase Cdna," *Proc. Natl. Acad. Sci. USA*, 96(8): 4530-4535 (1999).
Kirikoshi et al., "Molecular Cloning and Characterization of Human FGF-20 on Chromosome 8p21.3-p22," *Biochem. and Biophys. Research Comm.*, 274: 337-343 (2000).
Kisselev, "Polypeptide Release Factors in Prokaryotes and Eukaryotes: Same Function, Different Structure," *Structure*, 10(1): 8-9 (2002).
Kitamura et al., "Polyethylene Glycol Modification of the Monoclonal Antibody A7 Enhances Its Tumor Localization," *Biochem. Biophys. Res. Commun.*, 171(3): 1387-1394 (1990).
Kitamura et al., "Chemical Engineering of the Monoclonal Antibody A7 by Polyethylene Glycol for Targeting Cancer Chemotherapy," *Cancer Res.*, 51(16): 4310-4315 (1991).
Kobayashi et al., "Monoclonal Antibody-Dendrimer Conjugates Enable Radiolabeling of Antibody With Markedly High Specific Activity With Minimal Loss of Immunoreactivity," *Eur. J. Nucl. Med.*, 27(9):1334-1339 (2000).
Kodama et al., "Synthesis of UDP-6-Deoxy- and -6-Fluoro-D-Galactoses and Their Enzymatic Glycosyl Transfer to Mono- and Biantennary Carbohydrate Chains," *Tetrahedron Lett.*, 34(40): 6419-6422 (1993).
Koeller et al., "Complex Carbohydrate Synthesis Tools for Glycobiologists: Enzyme-Based Approach and Programmable One-Pot Strategies," *Glycobiology*, 10(11): 1157-1169 (2000).
Koeller et al., "Emerging Themes in Medicinal Glycoscience," *Nat. Biotechnol.*, 18(8): 835-841 (2000).
Koeller et al., "Enzymes for Chemical Synthesis," *Nature*, 409(6817): 232-240 (2001).
Koide et al., "Modification of Amino Groups in Porcine Pancreatic Elastase With Polyethylene Glycol in Relation to Binding Ability Towards Anti-Serum and to Enzymic Activity," *Biochem. Biophys. Res. Commun.*, 111(2): 659-667 (1983).
Kornfeld et al., "Assembly of Asparagine-Linked Oligosaccharides," *Ann. Rev. Biochem.*, 54: 631-664 (1985).
Kreitman, "Toxin-Labeled Monoclonal Antibodies," *Curr. Pharm. Biotechnol.*, 2(4): 313-325 (2001).
Kroschinsky et al., "The Role of Pegfilgrastim in Mobilization of Hematopoietic Stem Cells," *Trans. Apher. Sci.*, 38: 237-244 (2008).
Krystal et al., "Purification of Human Erythropoietin to Homogeneity by a Rapid Five-Step Procedure," *Blood*, 67(1): 71-99 (1986).
Kuhn et al., "Active Site and Oligosaccharide Recognition Residues of Peptide-N4-(N-Acetyl-Beta-D-Glucosaminyl)Asparagine Amidase F," *J. Biol. Chem.*, 270(49): 29493-29497 (1995).

Kukowska-Latallo et al., "A Cloned Human Cdna Determines Expression of a Mouse Stage-Specific Embryonic Antigen and the Lewis Blood Group Alpha(1,3/1,4)Fucosyltransferase," *Genes Dev.*, 4(8): 1288-1303 (1990).
Kukuruzinska et al., "Protein Glycosylation in Yeast: Transcript Heterogeneity of the ALG7 Gene," *Proc. Natl. Acad. Sci. USA*, 84(8): 2145-2149 (1987).
Kumar et al., "'Green'-enzymatic synthesis of pegylated phenolic macromer and polymer," *Chem. Commun.*, 7(7): 862-863 (2004).
Lai et al, "Structural Characterization of Human Erythropoietin," *J. Biol. Chem.*, 261(7): 3116-3121 (1986).
Langer, "New Methods of Drug Delivery," *Science*, 249(4976): 1527-1533 (1990).
Lau et al., "Quantitative Competitive Reverse Transcription-PCE As a Method to Evaluate Retrovirus Removal During Chromatography Procedures," *J. Biotechnol.*, 75(2-3): 105-115 (1999).
Lee et al., "Efficient Coupling of Glycopeptides to Proteins With a Heterobifunctional Reagent," *Biochemistry*, 28(4): 1856-1861 (1989).
Lee-Huang et al., "Cloning and Expression of Human Erythropoietin Cdna in *Escherichia coli,*" *Proc. Natl. Acad. Sci. USA*, 81(9): 2708-2712 (1984).
Legault et al., "Human Alpha(1,3/1,4)-Fucosyltransferases Discriminate Between Different Oligosaccharide Acceptor Substrates Through a Discrete Peptide Fragment," *J. Biol. Chem.*, 270(36): 20987-20996 (1995).
Leist et al., "Derivatives of Erythropoietin That Are Tissue Protective But Not Erythropoietic," *Science*, 305: 239-242 (2004).
Leiter et al., "Purification, Cdna Cloning, and Expression of GDP-L-Fuc:Asn-Linked Glcnac Alpha1,3-Fucosyltransferase From Mung Beans," *J. Biol. Chem.*, 274(31): 21830-21839 (1999).
Leung, "Engineering a Unique Glycosylation Site for Site-Specific Conjugation of Haptens to Antibody Fragments," *J. Immunol.* 154(11): 5919-5926 (1995).
Lewis et al., "Structure and Properties of Members of the Hgh Family: A Review," *Endocr. J.*, 47(Suppl.): S1-S8 (2000).
Li et al., "The Role of the Transferrin-Transferrin-Receptor System in Drug Delivery and Targeting," *Trends Pharmacol. Sci.*, 23(5): 206-209 (2002).
Li et al., "Transferrin/Transferrin Receptor-Mediated Drug Delivery," *Med. Res. Rev.*, 22(3): 225-250 (2002).
Licari et al., "Modeling the Population Dynamics of Baculovirus-Infected Insect Cells: Optimizing Infection Strategies for Enhanced Recombinant Protein Yields," *Biotechnol. Bioeng.*, 39(4): 432-441 (1992).
Licari et al., "Production of a Discrete, Heterogeneous Population of Beta-Galactosidase Polypeptides Using Baculovirus Expression Vectors," *Biotechnol. Bioeng.*, 39(9): 932-944 (1992).
Liles et al., "Augmented Mobilization and Collection of CD34+ Hematopoietic Cells From Normal Human Volunteers Stimulated With Granulocyte-Colony-Stimulating Factor by Single-Dose Administration of AMD3100, A CXCR4 Antagonist," *Transfusion*, 45: 295-300 (2005).
Lin et al., "Cloning and Expression of the Human Erythropoietin Gene," *Proc. Natl. Acad. Sci. USA*, 82: 7580-7584 (1985).
Liu et al., "A Paradigm Case for the Merging of Glycal and Enzymatic Assembly Methods in Glycoconjugate Synthesis: A Highly Efficient Chemo-Enzymatic Synthesis of $GM_3$," *Chem. Eur. J.*, 2(11): 1359-1362 (1996).
Lodish et al., "Protein Glycosylation in the ER and Golgi Complex," *Molecular Cell Biology*, Section 17.7, 4th Ed. New York, W. H. Freeman (2000).
Long et al., "Design of Homogeneous, Monopegylated Erythropoietin Analogs With Preserved In Vitro Bioactivity," *Exp. Hematol.*, 34(6): 697-704 (2006).
Lönnberg, "Solid-Supported Synthesis of Glycoconjugates," *Curr. Org. Synth.*, 6(4): 400-425 (2009).
Lord et al., "Kinetics of Neutrophil Production in Normal and Neutropenic Animals During the Response to Filgrastim (R-Methu G-CSF) Or Filgrastim SD/01 (PEG-R-Methu G-CSF)," *Clin. Cancer Res.*, 7(7): 2085-2090 (2001).
Lougheed et al., "Glycosyl Fluorides Can Function As Substrates for Nucleotide Phosphosugar-Dependent Glycosyltransferases," *J. Biol. Chem.*, 274(53): 37717-37722 (1999).

(56) References Cited

OTHER PUBLICATIONS

Luckow et al., "Baculovirus Systems for the Expression of Human Gene Products," *Curr. Opin. Biotechnol.*, 4(5): 564-572 (1993).
Lund et al., "Oligosaccharide-Protein Interactions in Igg Can Modulate Recognition by Fc Gamma Receptors," *FASEB J.*, 9(1): 115-119 (1995).
Lund et al., "Multiple Interactions of Igg With Its Core Oligosaccharide Can Modulate Recognition by Complement and Human Fc Gamma Receptor I and Influence the Synthesis of Its Oligosaccharide Chains," *J. Immunol.*, 157(11): 4963-4969 (1996).
Luo et al., "Spontaneous Calcification of Arteries and Cartilage in Mice Lacking Matrix GLA Protein," *Nature*, 386: 78-81 (1997).
Mahal et al., "Engineering Chemical Reactivity on Cell Surfaces Through Oligosaccharide Biosynthesis," *Science*, 276(5315): 1125-1128 (1997).
Malissard et al., "Expression of Functional Soluble Forms of Human Beta-1,4-Galactosyltransferase I, Alpha-2,6-Sialyltransferase, and Alpha-1, 3-Fucosyltransferase VI in the Methylotrophic Yeast Pichia Pastoris," *Biochem. Biophys. Res. Commun.*, 267(1): 169-173 (2000).
Manfioletti et al., "The Protein Encoded by a Growth Arrest-Specific Gene (gas6) Is a New Member of the Vitamin K-Dependent Proteins Related to Protein S, a Negative Coregulator in the Blood Coagulation Cascade," *Mol. Cell. Bio.*, 13(8): 4976-4985 (1993).
Maranga et al., "Virus-Like Particle Production At Low Multiplicities of Infection With the Baculovirus Insect Cell System," *Biotechnol. Bioeng.*, 84(2): 245-253 (2003).
Maras et al., "Molecular Cloning and Enzymatic Characterization of a Trichoderma Reesei 1,2-Alpha-D-Mannosidase," *J Biotechnol.*, 77(2-3): 255-263 (2000).
Markovsky et al., "Administration, distribution, metabolism and elimination of polymer therapeutics", *J. Controlled Release*, 161: 446-460 (2012).
Matsumura et al., "A New Concept for Macromolecular Therapeutics in Cancer Chemotherapy: Mechanism of Tumoritropic Accumulation of Proteins and the Antitumor Agent Smancs", *Cancer Research*, 46: 6387-6392 (1986).
Mehvar, "Modulation of the Pharmacokinetics and Pharmacodynamics of Proteins by Polyethylene Glycol Conjugation", *J. Pharm. Pharmaceut Sci.*, 3(1): 125-136 (2000).
Meynial-Salles et al., "In Vitro Glycosylation of Proteins: An Enzymatic Approach," *J. Biotechnol.*, 46(1): 1-14 (1996).
Miller, "Baculoviruses: High-Level Expression in Insect Cells," *Curr. Opin. Genet. Dev.*, 3(1): 97-101 (1993).
Min et al., "Site-Directed Mutagenesis of Recombinant Equine Chorionic Gonadotropin/Luteinizing Hormone: Differential Role of Oligosaccharides in Luteinizing Hormone- and Follicle-Stimulating Hormone-Like Activities," *Endocr. J.*, 43(5): 585-593 (1996).
Mistry et al., "Therapeutic Delivery of Proteins to Macrophages: Implications for Treatment of Gaucher's Disease," *Lancet*, 348(9041): 1555-1559 (1996).
Mollicone et al., "Acceptor Specificity and Tissue Distribution of Three Human Alpha-3-Fucosyltransferases," *Eur. J. Biochem.*, 191(1): 169-176 (1990).
Monaco et al., "Expression of Recombinant Human Granulocyte Colony-Stimulating Factor in CHO Dhfr-Cells: New Insights Into the In Vitro Amplification Expression System," *Gene*, 180: 145-150 (1996).
Monfardini et al., "A Branched Monomethoxypoly (ethylene glycol) for Protein Modification," *Bioconjug. Chem.*, 6(1): 62-69 (1995).
Morimoto et al., "Biological and Physicochemical Characterization of Recombinant Human Erythropoietins Fractionated by Mono Q Column Chromatography and Their Modification With Sialyltransferase," *Glycoconj. J.*, 13(6): 1013-1020 (1996).
Moscatelli et al., "Enzymatic Properties of a β-Glucanase from *Bacillus subtilis*," *J. Biol. Chem.*, 236(11): 2858-2862 (1961).
Müller et al., "Localization of O-Glycosylation Sites on Glycopeptide Fragments From Lactation-Associated MUC1. All Putative Sites Within the Tandem Repeat Are Glycosylation Targets In Vivo," *J. Biol. Chem.*, 272(40): 24780-24793 (1997).
Müller et al., "High Density O-Glycosylation on Tandem Repeat Peptide From Secretory MUC1 of T47D Breast Cancer Cells," *J. Biol. Chem.*, 274(26): 18165-18172 (1999).
Nagata et al, "The Chromosomal Gene Structure and Two mRNAs for Human Granulocyte Colony-Stimulating Factor," *EMBO J.*, 5(3): 575-581 (1986).
Natsuka et al., "Molecular Cloning of a cDNA Encoding a Novel Human Leukocyte Alpha-1,3-fucosyltransferase Capable of Synthesizing the Sialyl Lewis X Determinant," *J. Biol. Chem.*, 269(24): 16789-16794 (1994).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
Nelsestuen et al., "Vitamin K-Dependent Proteins," *Vitamins and Hormones*, 58: 355-389 (2000).
Ngo et al., "The Protein Folding Problem and Tertiary Structure Prediction, Chapter 14: Computational Complexity Protein Structure Prediction, and the Levinthal Paradox," pp. 433-440 and 492-495 (1994).
Nilsson et al., "Immobilization of Ligands with Organic Sulfonyl Chlorides," *Methods Enzymol.*, 104: 56-69 (1984).
Nishimura et al., "Identification of a novel FGF, FGF-21, preferentially expressed in the liver," *Biochemica et Biophysica Acta*, 1492: 203-206 (2000).
Nunez et al., "The Synthesis and Characterization of α- and β-L-Fucopyranosyl phosphates and GDP Fucose[1]," *Can. J. Chem.*, 59(14): 2086-2095 (1981).
O'Connell et al., "The Influence of Flanking Sequence on the O-Glycosylation of Threonine In Vitro," *J. Biol. Chem.*, 267(35): 25010-25018 (1992).
Oetke et al., „Versatile Biosynthetic Engineering of Sialic Acid in Living Cells Using Synthetic Sialic Acid Analogues, *J. Biol. Chem.*, 277(8): 6688-6695 (2002).
Oh-Eda et al., "O-Linked Sugar Chain of Human Granulocyte Colony-Stimulating Factor Protects it Against Polymerization and Denaturation Allowing it to Retain its Biological Activity," *J. Biol. Chem.*, 265: 11432-11435 (1990).
Ohbayashi et al., "Structure and Expression of the mRNA Encoding a Novel Fibroblast Growth Factor, FGF-18," *J. Biol. Chem.*, 273(29): 18161-18164 (1998).
Olson et al., "Structural Basis for Recognition of Phosphorylated High Mannose Oligosaccharides by the Cation-Dependent Mannose 6-Phosphate Receptor," *J. Biol. Chem.*, 274(42): 29889-29896 (1999).
Orlean, "Vol. III: The Molecular and Cellular Biology of the Yeast *Saccharomyces*: Cell Cycle and Cell Biology," in *Biogenesis of Yeast Wall and Surface Components*, Chapter 3, pp. 229-362, Cold Spring Harbor Laboratory Press (1997).
Orskov et al., "Complete Sequences of Glucagon-Like Peptide-1 from Human and Pig Small Intestine," *J. Biol. Chem.*, 264(22): 12826-12829 (1989).
O'Shannessy et al., "Specific Conjugation Reactions of the Oligosaccharide Moieties of Immunoglobulins," *J. Appl. Biochem.*, 7: 347-355 (1985).
Ottenbrite, "Polymeric Drugs and Drug Delivery Systems," Dunn et al. (eds.), Chapter 1 "Biologically Active Polymers," pp. 3-10, ACS Symposium Series vol. 469, *American Chemical Society, Washington D.C.* (1991).
Palacpac et al., "Stable Expression of Human Beta1,4-Galactosyltransferase in Plant Cells Modifies N-linked Glycosylation Patterns," *Proc. Natl. Acad. Sci. USA*, 96(8): 4692-4697 (1999).
Palcic et al., "Enzymic Synthesis of Oligosaccharides Terminating in the Tumor-Associated Sialyl-Lewis—a Determinant," *Carbohydr. Res.*, 190(1): 1-11 (1989).
Park et al., "Characterization of the Cell Surface Receptor for a Multi-Lineage Colony-Stimulating Factor (CSF-2 alpha).," *J. Biol. Chem.*, 261(1): 205-210 (1986).

(56) References Cited

OTHER PUBLICATIONS

Paulson et al., "Reactivation of Asialo-Rabbit Liver Binding Protein by Resialylation with Beta-D-Galactoside Alpha2 Leads to 6 Sialyltransferase," *J. Biol. Chem.*, 252(23): 8624-8628 (1977).
Perrin et al., "Common Physical Techniques Used in Purification," in *Purification of Laboratory Chemicals*, pp. 30-31, Pergamon (1980).
Plummer et al., "Novel, Specific O-Glycosylation of Secreted Flavobacterium Meningosepticum Proteins. Asp-Ser and Asp-Thr-Thr Consensus Sites," *J. Biol. Chem.*, 270(22): 13192-13196 (1995).
PNGase-F Amidase Sequence from F. Meningosepticum (RN 128688-70-0) (2007).
PNGase-F Amidase Sequence from F. Meningosepticum (RN 128688-71-1) (2007).
Prati et al., "Engineering of Coordinated Up- and Down-Regulation of Two Glycosyltransferases of the O-Glycosylation Pathway in Chinese Hamster Ovary (CHO) Cells," *Biotech and Bioeng.*, 79(5): 580-585 (2002).
Prieels et al., "Co-Purification of the Lewis Blood Group N-Acetylglucosaminide Alpha 1 goes to 4 Fucosyltransferase and an N-Acetylglucosaminide Alpha 1 goes to 3 Fucosyltransferase From Human Milk," *J. Biol. Chem.*, 256(20): 10456-10463 (1981).
Pyatak et al., "Preparation of a Polyethylene Glycol: Superoxide Dismutase Adduct, and an Examination of its Blood Circulation Life and Anti-Inflammatory Activity," *Res. Commun. Chem. Pathol. Pharmacol.*, 29(1): 113-127 (1980).
Quelle et al., "High-level Expression and Purification of a Recombinant Human Erythropoietin Produced Using a Baculovirus Vector," *Blood*, 74(2): 652-657 (1989).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Rabouille et al., "The Drosophila GMII Gene Encodes a Golgi Alpha-Mannosidase II," *J Cell Sci.*, 112(Pt. 19): 3319-3330 (1999).
Raju et al., "Glycoengineering of Therapeutic Glycoproteins: In Vitro Galactosylation and Sialylation of Glycoproteins with Terminal N-Acetylglucosamine and Galactose Residues," *Biochemistry*, 40(30): 8868-8876 (2001).
Rasko et al., "Cloning and Characterization of the Alpha(1,3/4) Fucosyltransferase of Helicobacter pylori," *J. Biol. Chem.*, 275(7): 4988-4994 (2000).
R & D Systems, Fibroblast Growth Factors (FGFs), Internet page from www.rndsystems.com/mini_review_detail_objectname_MR01_FGFs.aspx, 2001, printed Mar. 10, 2011.
Rathnam et al., "Conjugation of a Fetuin Glycopeptide to Human Follicle-Stimulating Hormone and its Subunits by Photoactivation," *Biochim. Biophys. Acta*, 624(2): 436-442 (1980).
Reff et al., "Future of Monoclonal Antibodies in the Treatment of Hematologic Malignancies," *Cancer Control*, 9(2): 152-166 (2002).
Rosenthal et al., "Isolation of Peptidoglycan and Soluble Peptidoglycan Fragments," *Methods Enzymol.*, 235: 253-285 (1994).
Rotondaro et al., "Purification and Characterization of Two Recombinant Human Granulocyte Colony-Stimulating Factor Glycoforms," *Mol. Biotech.*, 11: 117-128 (1999).
Rudikoff et al., "Single Amino Acid Substitution Altering Antigen-Binding Specificity," *Proc. Natl. Acad. Sci. USA*, 79(6):1979-1983 (1982).
Sadler et al., "Purification of Mammalian Glycosyltransferases," *Methods Enzymol.*, 83: 458-514 (1982).
Sandberg et al., "Structural and Functional Characterization of B-Domain Deleted Recombinant Factor VIII," *Semin. Hematol.*, 38(2 Suppl. 4): 4-12 (2001).
Saneyoshi et al., "Equine Follicle-Stimulating Hormone: Molecular Cloning of Beta Subunit and Biological Role of the Asparagine-Linked Oligosaccharide at Asparagine(56) of Alpha Subunit," *Biol. Reprod.*, 65(6): 1686-1690 (2001).
Sasaki et al., "Carbohydrate Structure of Erythropoietin Expressed in Chinese Hamster Ovary Cells by a Human Erythropoietin CdnA," *J. Biol. Chem.*, 262(25): 12059-12076 (1987).
Sasaki et al., "Expression Cloning of a Novel Alpha 1,3-Fucosyltransferase that is Involved in Biosynthesis of the Sialyl Lewis X Carbohydrate Determinants in Leukocytes," *J.Biol. Chem.*, 269(20): 14730-14737 (1994).
Satchi et al., "PDEPT: polymer-directed enzyme prodrug therapy I.HPMA copolymer-cathepsin B and PK1 as a model combination", *Brit. J. Cancer*, 85(7): 1070-1076 (2001).
Saxon et al., "Cell Surface Engineering by a Modified Staudinger Reaction," *Science*, 287(5460): 2007-2010 (2000).
Saxon et al., "Investigating Cellular Metabolism of Synthetic Azidosugars with the Staudinger Ligation," *J. Am. Chem. Soc.*, 124(50): 14893-14902 (2002).
Schlaeger, "Medium Design for Insect Cell Culture," *Cytotechnology*, 20(1-3): 57-70 (1996).
Schwarz et al., "Transfer of 131I and Fluoresceinyl Sialic Acid Derivatives into the Oligosaccharide Chains of IgG: a New Method for Site-Specific Labeling of Antibodies," *Nucl. Med. Biol.*, 26(4):383-388 (1999).
Schwientek et al., "Efficient intra- and Extracellular Production of Human Beta-1,4-Galactosyltransferase in *Saccharomyces cerevisiae* is Mediated by Yeast Secretion Leaders," *Gene*, 145(2): 299-303 (1994).
Schwientek et al., "Functional Conservation of Subfamilies of Putative UDP-N-Acetylgalactosamine:Polypeptide N-Acetylgalactosaminyltransferases in *Drosophila*, Caenorhabditis Elegans, and Mammals. One Subfamily Composed of I(2)35Aa is Essential in *Drosophila*," *J. Biol. Chem.*, 277(25): 22623-22638 (2002).
Scouten, "A Survey of Enzyme Coupling Techniques," *Methods Enzymol.*, 135: 30-65 (1987).
Seely et al., "Use of Ion-Exchange Chromatography and Hydrophobic Interaction Chromatography in the Preparation and Recovery of Polyethylene Glycol-Linked Proteins," *J. Chromatog.*, 908: 235-241 (2001).
Seffernick et al., "Melamine Deaminase and Atrazine Chlorohydrolase: 98 Percent Identical but Functionally Different," *J. Bacteriol.*, 183(8): 2405-2410 (2001).
Seitz, "Glycopeptide Synthesis and the Effects of Glycosylation on Protein Structure and Activity," *Chembiochem.*, 1(4): 214-246 (2000).
Shah et al., "Transcellular Delivery of an Insulin-Transferrin Conjugate in Enterocyte-Like Caco-2 Cells," *J. Pharm. Sci.*, 85(12): 1306-1311 (1996).
Shapiro et al., "The Safety and Efficacy of Recombinant Human Blood Coagulation Factor IX in Previously Untreated Patients with Severe or Moderately Severe Hemophilia B," *Blood*, 105(2): 518-525 (2005).
Shen et al., "Cis-Aconityl Spacer Between Daunomycin and Macromolecular Carriers: a Model of pH-Sensitive Linkage Releasing Drug from a Lysosomotropic Conjugate," *Biochem. Biophys. Res. Commun.*, 102(3): 1048-1054 (1981).
Shinkai et al., "Protein Expression and Purification," *Prot. Exp. Purif.*, 10: 379-385 (1997).
Shu et al., "Peptide-Polymer Conjugates: From Fundamental Science to Application", *Annu. Rev. Phys. Chem.*, 64: 631-657 (2013).
Sinclair et al., "Glycoengineering: the Effect of Glycosylation on the Properties of Therapeutic Proteins," *J. Pharm. Sci.*, 94: 1626-1635 (2005).
Singh et al., "Glycosidase-catalysed synthesis of oligosaccharides: a two-step synthesis of the core trisaccharide of N•linked glycoproteins using the β-N-acetylhexosaminidase and the β-mannosidase from *Aspergillus oryzae*," *Chem. Commun.*, 1996(8): 993-994 (1996).
Sinha et al., "Release of Soluble Peptidoglycan from Growing Conococci: Demonstration of Anhydro-Muramyl-Containing Fragments," *Infect. Immun.*, 29(3): 914-925 (1980).
Skolnick et al., "From Genes to Protein Structure and Function: Novel Applications of Computational Approaches in the Genomic Era," *Trends Biotechnol.*, 18(1): 34-39 (2000).
Smallwood et al., "Fibroblast growth factor (FGF) homologous factors: new members of the FGF family implicated in nervous system development," *Proc. Natl. Acad. Sci. USA*, 93: 9850-9857 (1996).

(56) References Cited

OTHER PUBLICATIONS

Smith et al., "The Challenges of Genome Sequence Annotation or the Devil is in the Details," *Nat. Biotechnol.*, 15(12): 1222-1223 (1997).
Snider et al., "Characterization of the Heterogeneity of Polyethylene Glycol-Modified Superoxide Dismutase by Chromatographic and Electrophoretic Techniques," *J. Chromatogr.*, A 599(1-2): 141-155 (1992).
Sojar et al., "A Chemical Method for the Deglycosylation of Proteins," *Arch. Biochem. Biophys.*, 259(1): 52-57 (1987).
Song et al., "Enhanced Neuroprotective Effects of Basic Fibroblast Growth Factor in Regional Brain ischemia After Conjugation to a Blood-Brain Barrier Delivery Vector," *J. Pharmacol. Exp. Ther.*, 301(2): 605-610 (2002).
Song et al., "Reassembled Biosynthetic Pathway for a Large-Scale Synthesis of CMP-Neu5Ac," *Mar. Drugs*, 1: 34-45 (2003).
Sorensen et al., "Incorporation of an Active Site Inhibitor in Factor VIIa Alters the Affinity for Tissue Factor," *J. Biol. Chem.*, 272(18): 11863-11868 (1997).
Srinivasachar et al., "New Protein Cross-Linking Reagents that are Cleaved by Mild Acid," *Biochemistry*, 28(6): 2501-2509 (1989).
Srivastava et al., "Enzymatic Transfer of a Preassembled Trisaccharide Antigen to Cell Surfaces Using a Fucosyltransferase," *J. Biol. Chem.*, 267(31): 22356-22361 (1992).
Staudacher, "α 1,3 Fucosyltransferases," *Trends Glycosci. Glycotechnol.*, 8(44): 391-408 (1996).
Stemmer, "Rapid Evolution of a Protein In Vitro by DNA Shuffling," *Nature*, 370(6488): 389-391 (1994).
Stemmer, "DNA Shuffling by Random Fragmentation and Reassembly: In Vitro Recombination for Molecular Evolution," *Proc. Natl. Acad. Sci. USA*, 91(22): 10747-10751 (1994).
Stephens et al., "The Pyruvate Dehydrogenase Complex of *Escherichia coli* K12. Nucleotide Sequence Encoding the Pyruvate Dehydrogenase Component," *Eur. J. Biochem.*, 133(1): 155-162 (1983).
Stephens et al., "The Pyruvate Dehydrogenase Complex of *Escherichia coli* K12. Nucleotide Sequence Encoding the Dihydrolipoamide Acetyltransferase Component," *Eur. J. Biochem.*, 133(3): 481-489 (1983).
Stephens et al., "Nucleotide Sequence of the Lipoamide Dehydrogenase Gene of *Escherichia coli* K12," *Eur. J. Biochem.*, 135(3): 519-527 (1983).
Strausberg et al., "Generation and Initial Analysis of More Than 15,000 Full-Length Human and Mouse cDNA Sequences," *Proc Natl Acad Sci USA*, 99(26): 16899-16903 (2002).
Takane et al., "Chronopharmacology of Antitumor Effect Induced by Interferon-Beta in Tumor-Bearing Mice," *J Pharmacol Exp Ther.*, 294(2): 746-752 (2000).
Takeda et al., "GPI-Anchor Biosynthesis," *Trends Biochem. Sci.*, 20(9): 367-371 (1995).
Takeuchi et al., "Role of Sugar Chains in the In Vitro Biological Activity of Human Erythropoietin Produced in Recombinant Chinese Hamster Ovary Cells," *J. Biol. Chem.*, 265(21): 12127-12130 (1990).
Taniguchi et al., "A Glycomic Approach to the Identification and Characterization of Glycoprotein Function in Cells Transfected with Glycosyltransferase Genes," *Proteomics*, 1(2): 239-247 (2001).
Tanner et al., "Protein Glycosylation in Yeast," *Biochim. Biophys. Acta*, 906(1): 81-99. (1987).
Taylor et al., Protein Immobilization Fundamentals and Applications, Manual (1991).
Ten Hagen et al., "Characterization of a UDP-GalNAc:Polypeptide N-Acetylgalactosaminyltransferase that Displays Glycopeptide N-Acetylgalactosaminyltransferase Activity," *J. Biol. Chem.*, 274(39): 27867-27874 (1999).
Tenno et al., "The Lectin Domain of UDP-GalNAc:Polypeptide N-Acetylgalactosaminyltransferase 1 is Involved in O-Glycosylation of a Polypeptide With Multiple Acceptor Sites," *J. Biol. Chem.*, 277(49): 47088-47096 (2002).
Thotakura et al., "Enzymatic Deglycosylation of Glycoproteins," *Meth. Enzym.*, 138: 350-359 (1987).

Tom et al., "Reproducible Production of a PEGylated Dual-Acting Peptide for Diabetes," *AAPS Journal*, 9(2): E227-E234 (2007).
Trottein et al., "Molecular Cloning of a Putative Alpha3-Fucosyltransferase from Schistosoma Mansoni," *Mol. Biochem. Parasitol.*, 107(2): 279-287 (2000).
Tsuboi et al., "6'-Sulfo Sialyl Le$^X$ but Not 6-Sulfo Sialyl Le$^X$ Expressed on the Cell Surface Supports L-selectin-mediated Adhesion," *J. Biol. Chem.*, 271(44): 27213-27216 (1996).
Tsuboi et al., "Acquisition of P-Selectin Binding Activity by En Bloc Transfer of Sulfo Le(x) Trisaccharide to the Cell Surface: Comparison to a Sialyl Le(x) Tetrasaccharide Transferred on the Cell Surface," *Arch. Biochem. Biophys.*, 374(1): 100-106 (2000).
Tsuji, "Molecular Cloning and Functional Analysis of Sialyltransferases," *J. Biochemistry*, 120: 1-13 (1996).
Tsunoda et al., "Enhanced Antitumor Potency of Polyethylene Glycolylated Tumor Necrosis Factor-α: A Novel Polymer-Conjugation Technique with a Reversible Amino-Protective Reagent[1]," *J. Pharmacol. Exp. Ther.*, 209(1): 368-372 (1999).
Tuddenham, "RNA as Drug and Antidote," *Nature*, 419(6902): 23-24 (2002).
Udenfriend et al., "How Glycosylphosphatidylinositol-Anchored Membrane Proteins are Made," *Annu. Rev. Biochem.*, 64: 563-591 (1995).
Ulloa-Aguirre et al., "Role of Glycosylation in Function of Follicle-Stimulating Hormone," *Endocrine*, 11(3): 205-215 (1999).
Uludag et al., "Targeting Systemically Administered Proteins to Bone by Bisphosphonate Conjugation," *Biotechnol. Prog.*, 18(3): 604-611 (2002).
Uptima, Detergents: Solubilization of Biomolecules, Internet page from www.interchim.com/interchim/bio/produits_uptima/product_line/p1p_detergents.htm, 2001, printed Nov. 14, 2011.
Urdal et al, "Lymphokine Purification by Reversed-Phase High-Performance Liquid Chromatography," *J. Chromatogr.*, 296: 171-179 (1984).
Van Berkel et al., "Heterogeneity in Utilization of N-Glycosylation Sites Asn624 and Asn138 in Human Lactoferrin: a Study With Glycosylation-Site Mutants," *Biochem. J.*, 319(Pt. 1): 117-122 (1996).
Van Reis et al., "Industrial Scale Harvest of Proteins From Mammalian Cell Culture by Tangential Flow Filtration," *Biotechnol. Bioeng.*, 38(4): 413-422 (1991).
Van Tetering et al., "Characterization of a Core Alpha1→3-Fucosyltransferase from the Snail Lymnaea Stagnalis that is Involved in the Synthesis of Complex-Type N-Glycans," *FEBS Lett.*, 461(3): 311-314 (1999).
Vasey et al., "Phase I Clinical and Pharmacokinetic Study of PK1 [N-(2-Hydroxypropyl)methacrylamide Copolymer Doxorubicin]: First Member of a New Class of Chemotherapeutic Agents—Drug-Polymer Conjugates", *Clinical Cancer Research*, 5(1): 83-94 (1999).
Veronese et al., "Surface Modification of Proteins. Activation of monomethoxy-Polyethylene Glycols by Phenylchloroformates and Modification of ribonuclease and Superoxide Dismutase," *Appl. Biochem. Biotechnol.*, 11(2): 141-152 (1985).
Veronese, "Peptide and Protein PEGylation: a Review of Problems and Solutions," *Biomaterials*, 22(5): 405-417 (2001).
Vitetta et al., "Immunology. Considering Therapeutic Antibodies," *Science*, 313: 308-309 (2006).
Vocadlo et al., "Glycosidase-Catalysed Oligosaccharide Synthesis" in *Carbohydrate Chemistry and Biology*, vol. 2, Chapter 29, pp. 723-844 (2000).
Vyas et al., "Ligand-Receptor-Mediated Drug Delivery: An Emerging Paradigm in Cellular Drug Targeting," *Crit. Rev. Ther. Drug Carrier Syst.*, 18(1): 1-76 (2001).
Wang et al., "Identification of a GDP-L-Fucose:Polypeptide Fucosyltransferase and Enzymatic Addition of O-Linked Fucose to EGF Domains," *Glycobiology*, 6(8): 837-842 (1996).
Wang et al., "Chemoenzymatic Synthesis of a High-Mannose-Type N-Glycopeptide Analog With C-Glycosidic Linkage," *Tetrahedron Lett.*, 37(12): 1975-1978 (1996).
Wang et al., "Single-Chain Fv With Manifold N-Glycans As Bifunctional Scaffolds for Immunomolecules," *Protein Eng.*, 11(12): 1277-1283 (1998).

(56) References Cited

OTHER PUBLICATIONS

Wang et al., "Novel Helicobacter Pylori Alpha1,2-Fucosyltransferase, A Key Enzyme in the Synthesis of Lewis Antigens," *Microbiol.*, 145(Pt. 11): 3245-3253 (1999).
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).
Wellhöner et al., "Uptake and Concentration of Bioactive Macromolecules by K562 Cells Via the Transferrin Cycle Utilizing an Acid-Labile Transferrin Conjugate," *J. Biol. Chem.*, 266(7): 4309-4314 (1991).
Wells, "Additivity of Mutational Effects in Proteins," *Biochemistry*, 29(37): 8509-8517 (1990).
Weston et al., "Isolation of a Novel Human Alpha (1,3)Fucosyltransferase Gene and Molecular Comparison to the Human Lewis Blood Group Alpha (1,3/1,4)Fucosyltransferase Gene. Syntenic, Homologous, Nonallelic Genes Encoding Enzymes With Distinct Acceptor Substrate Specificities," *J. Biol. Chem.*, 267(6): 4152-4160 (1992).
Weston et al., "Molecular Cloning of a Fourth Member of a Human Alpha (1,3)Fucosyltransferase Gene Family," *J. Biol. Chem.*, 267(34): 24575-24584 (1992).
White et al., "Purification and Cdna Cloning of a Human UDP-N-Acetyl-Alpha-D-Galactosamine:Polypeptide N-Acetylgalactosaminyltransferase," *J. Biol. Chem.*, 270(41): 24156-24165 (1995).
Wishart et al., "A Single Mutation Converts a Novel Phosphotyrosine Binding Domain Into a Dual-Specificity Phosphatase," *J. Biol. Chem.*, 270(45): 26782-26785 (1995).
Witkowski et al., "Conversion of a Beta-Ketoacyl Synthase to a Malonyl Decarboxylase by Replacement of the Active-Site Cysteine With Glutamine," *Biochemistry*, 38(36): 11643-11650 (1999).
Witte et al., "Enzymatic Glycoprotein Synthesis: Preparation of Ribonuclease Glycoforms Via Enzymatic Glycopeptide Condensation and Glycosylation," *J. Am. Chem. Soc.*, 119(9): 2114-2118 (1997).
Witte et al., "Monoclonal Antibodies Targeting the VEGF Receptor-2 (Flk1/KDR) As an Anti-Angiogenic Therapeutic Strategy," *Cancer and Metastasis Rev.*, 17: 155-161 (1998).
Woghiren et al., "Protected Thiol-Polyethylene Glycol: A New Activated Polymer for Reversible Protein Modification," *Bioconjug. Chem.*, 4(5): 314-318 (1993).
Wong et al., "Enzyme-Catalyzed Synthesis of N-Acetyllactosamine With In Situ Regeneration of Uridine 5'-Diphosphate Glucose and Uridine 5'-Diphosphate Galactose," *J. Org. Chem.*, 47(27): 5416-5418 (1982).
Wong et al., "Chemical Crosslinking and the Stabilization of Proteins and Enzymes," *Enzyme Microb Technol.*, 14(11): 866-874 (1992).
Wong et al., "Low Multiplicity Infection of Insect Cells With a Recombinant Baculovirus: The Cell Yield Concept," *Biotechnol. Bioeng.*, 49(6): 659-666 (1996).
Woods et al., "Transferrin Receptors and Cation-Independent Mannose-6-Phosphate Receptors Deliver Their Ligands to Two Distinct Subpopulations of Multivesicular Endosomes," *Eur. J. Cell Biol.*, 50(1): 132-143 (1989).
Wright et al., "Effect of C2-Associated Carbohydrate Structure on Ig Effector Function: Studies With Chimeric Mouse-Human Igg1 Antibodies in Glycosylation Mutants of Chinese Hamster Ovary Cells," *J. Immunol.*, 160(7): 3393-3402 (1998).
Wu et al., "Pharmacokinetics and Brain Uptake of Biotinylated Basic Fibroblast Growth Factor Conjugated to a Blood-Brain Barrier Drug Delivery System," *J. Drug Target.*, 10(3): 239-245 (2002).
Xing et al., "Design of a Transferrin-Proteinase Inhibitor Conjugate to Probe for Active Cysteine Proteinases in Endosomes," *Biochem. J.*, 336(Pt. 3): 667-673 (1998).
Yamada et al., "Selective Modification of Aspartic Acid-101 In Lysozyme by Carbodiimide Reaction," *Biochemistry*, 20(17): 4836-4842 (1981).
Yamamoto et al., "Chemoenzymatic Synthesis of a Novel Glycopeptide Using a Microbial Endoglycosidase," *Carbohydr. Res.*, 305(3-4): 415-422 (1998).
Yarema et al., "Metabolic Delivery of Ketone Groups to Sialic Acid Residues. Application to Cell Surface Glycoform Engineering," *J. Biol. Chem.*, 273(47): 31168-31179 (1998).
Yin et al., "Effects of Antioxidants on the Hydrogen Peroxide-Mediated Oxidation of Methionine Residues in Granulocyte Colony-Stimulating Factor and Human Parathyroid Hormone Fragment 13-34," *Pharm. Res.*, 21(12): 2377-2383 (2004).
Yoshida et al., "Expression and Characterization of Rat UDP-N-Acetylglucosamine: Alpha-3-D-Mannoside Beta-1,2-N-Acetylglucosaminyltransferase I in *Saccharomyces cerevisiae*," *Glycobiology*, 9(1): 53-58 (1999).
Yoshitake et al., "Nucleotide Sequence of the Gene for Human Factor IX (Antihemophilic Factor B)," *Biochemistry*, 24(14): 3736-3750 (1985).
Younes et al., "Morphological Study of Biodegradable PEO/PLA Block Copolymers," *J. Biomed. Mater. Res.*, 21(11): 1301-1316 (1987).
Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).
Zalipsky, "Functionalized Poly(Ethylene Glycol) For Preparation of Biologically Relevant Conjugates," *Bioconjug. Chem.*, 6(2): 150-165 (1995).
Zarling et al., "Mapping of Lymphocyte Surface Polypeptide Antigens by Chemical Cross-Linking With BSOCOES," *J. Immunol.*, 124(2): 913-920 (1980).
Zhang et al., "Stable Expression of Human Alpha-2,6-Sialyltransferase in Chinese Hamster Ovary Cells: Functional Consequences for Human Erythropoietin Expression and Bioactivity," *Biochim. Biophys. Acta*, 1425: 441-452 (1998).
Zheng et al., "Optimized Production of Recombinant Bluetongue Core-Like Particles Produced by the Baculovirus Expression System," *Biotechnol. Bioeng.*, 65(5): 600-604 (1999).
Zhou et al., "Lipooligosaccharide Biosynthesis in Neisseria Gonorrhoeae: Cloning, Identification and Characterization of the Alpha 1,5 Heptosyltransferase I Gene (Rfac)," *Mol. Microbiol.*, 14(4): 609-618 (1994).
U.S. Appl. No. 08/102,385, filed Aug. 4, 1993.
U.S. Appl. No. 08/215,727, filed Mar. 22, 1994.
U.S. Appl. No. 08/312,387, filed Sep. 26, 1994.
U.S. Appl. No. 08/446,875, filed Jul. 12, 1995.
U.S. Appl. No. 08/447,435, filed May 23, 1995.
U.S. Appl. No. 08/447,783, filed May 23, 1995.
U.S. Appl. No. 08/478,140, filed Jun. 7, 1995.
U.S. Appl. No. 08/525,058, filed Sep. 8, 1995.
U.S. Appl. No. 08/683,426, filed Jul. 18, 1996.
U.S. Appl. No. 08/683,458, filed Jul. 18, 1996.
U.S. Appl. No. 08/745,840, filed Nov. 8, 1996.
U.S. Appl. No. 08/878,360, filed Jun. 18, 1997.
U.S. Appl. No. 09/333,412, filed Jun. 15, 1999.
U.S. Appl. No. 09/338,943, filed Jun. 24, 1999.
U.S. Appl. No. 09/855,320, filed May 14, 2001.
U.S. Appl. No. 10/007,267, filed Dec. 3, 2001.
U.S. Appl. No. 10/096,129, filed Mar. 7, 2002.
U.S. Appl. No. 10/109,498, filed Mar. 22, 2002.
U.S. Appl. No. 10/198,806, filed Jul. 19, 2002.
U.S. Appl. No. 10/219,197, filed Aug. 13, 2002.
U.S. Appl. No. 10/287,994, filed Nov. 5, 2002.
U.S. Appl. No. 10/360,770, filed Jan. 6, 2003.
U.S. Appl. No. 10/360,779, filed Feb. 19, 2003.
U.S. Appl. No. 10/391,035, filed Mar. 17, 2003.
U.S. Appl. No. 10/410,897, filed Apr. 9, 2003.
U.S. Appl. No. 10/410,913, filed Apr. 9, 2003.
U.S. Appl. No. 10/410,930, filed Apr. 9, 2003.
U.S. Appl. No. 10/410,945, filed Apr. 9, 2003.
U.S. Appl. No. 10/410,962, filed Apr. 9, 2003.
U.S. Appl. No. 10/410,980, filed Apr. 9, 2003.
U.S. Appl. No. 10/410,997, filed Apr. 9, 2003.
U.S. Appl. No. 10/411,012, filed Apr. 9, 2003.

(56) References Cited

OTHER PUBLICATIONS

U.S. Appl. No. 10/411,026, filed Apr. 9, 2003.
U.S. Appl. No. 10/411,037, filed Apr. 9, 2003.
U.S. Appl. No. 10/411,043, filed Apr. 9, 2003.
U.S. Appl. No. 10/411,044, filed Apr. 9, 2003.
U.S. Appl. No. 10/411,049, filed Apr. 9, 2003.
U.S. Appl. No. 10/485,892, filed Oct. 1, 2004.
U.S. Appl. No. 10/492,261, filed Apr. 9, 2004.
U.S. Appl. No. 10/497,283, filed Nov. 5, 2004.
U.S. Appl. No. 10/497,284, filed May 28, 2004.
U.S. Appl. No. 10/530,972, filed Dec. 5, 2005.
U.S. Appl. No. 10/549,445, filed Jul. 31, 2006.
U.S. Appl. No. 10/549,520, filed Jul. 10, 2006.
U.S. Appl. No. 10/549,528, filed Sep. 19, 2005.
U.S. Appl. No. 10/552,896, filed Jun. 8, 2006.
U.S. Appl. No. 10/556,094, filed Apr. 16, 2007.
U.S. Appl. No. 10/565,331, filed Sep. 11, 2006.
U.S. Appl. No. 10/576,506, filed Apr. 18, 2006.
U.S. Appl. No. 10/579,620, filed Apr. 19, 2007.
U.S. Appl. No. 10/579,621, filed Feb. 21, 2007.
U.S. Appl. No. 10/581,538, filed Apr. 12, 2007.
U.S. Appl. No. 10/585,385, filed Aug. 12, 2008.
U.S. Appl. No. 10/586,166, filed Jul. 23, 2008.
U.S. Appl. No. 10/609,701, filed Jun. 30, 2003.
U.S. Appl. No. 10/654,528, filed Sep. 2, 2003.
U.S. Appl. No. 10/997,405, filed Nov. 24, 2004.
U.S. Appl. No. 11/033,365, filed Jan. 10, 2005.
U.S. Appl. No. 11/102,497, filed Apr. 8, 2005.
U.S. Appl. No. 11/144,223, filed Jun. 2, 2005.
U.S. Appl. No. 11/166,028, filed Jun. 23, 2005.
U.S. Appl. No. 11/166,404, filed Jun. 23, 2005.
U.S. Appl. No. 11/183,205, filed Jul. 15, 2005.
U.S. Appl. No. 11/183,218, filed Jul. 15, 2005.
U.S. Appl. No. 11/339,752, filed Jan. 25, 2006.
U.S. Appl. No. 11/344,767, filed Feb. 1, 2006.
U.S. Appl. No. 11/395,784, filed Mar. 31, 2006.
U.S. Appl. No. 11/396,215, filed Mar. 30, 2006.
U.S. Appl. No. 11/402,105, filed Apr. 10, 2006.
U.S. Appl. No. 11/404,266, filed Apr. 12, 2006.
U.S. Appl. No. 11/440,839, filed May 25, 2006.
U.S. Appl. No. 11/514,484, filed Sep. 1, 2006.
U.S. Appl. No. 11/579,401, filed Nov. 2, 2006.
U.S. Appl. No. 11/580,669, filed Oct. 13, 2006.
U.S. Appl. No. 11/584,743, filed Oct. 19, 2006.
U.S. Appl. No. 11/597,258, filed Mar. 11, 2008.
U.S. Appl. No. 11/632,005, filed Apr. 14, 2008.
U.S. Appl. No. 11/644,014, filed Dec. 21, 2006.
U.S. Appl. No. 11/645,839, filed Dec. 26, 2006.
U.S. Appl. No. 11/652,467, filed Jan. 11, 2007.
U.S. Appl. No. 11/656,643, filed Jan. 23, 2007.
U.S. Appl. No. 11/657,441, filed Jan. 24, 2007.
U.S. Appl. No. 11/658,218, filed Jun. 20, 2008.
U.S. Appl. No. 11/659,153, filed Oct. 23, 2008.
U.S. Appl. No. 11/659,942, filed May 5, 2008.
U.S. Appl. No. 11/664,199, filed Sep. 19, 2007.
U.S. Appl. No. 11/665,908, filed Nov. 26, 2007.
U.S. Appl. No. 11/701,949, filed Feb. 2, 2007.
U.S. Appl. No. 11/714,874, filed Mar. 5, 2007.
U.S. Appl. No. 11/781,885, filed Jul. 23, 2007.
U.S. Appl. No. 11/781,888, filed Jul. 23, 2007.
U.S. Appl. No. 11/781,896, filed Jul. 23, 2007.
U.S. Appl. No. 11/781,900, filed Jul. 23, 2007.
U.S. Appl. No. 11/781,902, filed Jul. 23, 2007.
U.S. Appl. No. 11/792,610, filed Apr. 21, 2008.
U.S. Appl. No. 11/794,555, filed Aug. 11, 2008.
U.S. Appl. No. 11/794,560, filed Oct. 24, 2008.
U.S. Appl. No. 11/843,588, filed Aug. 22, 2007.
U.S. Appl. No. 11/845,175, filed Aug. 27, 2007.
U.S. Appl. No. 11/866,969, filed Oct. 3, 2007.
U.S. Appl. No. 11/867,553, filed Oct. 4, 2007.
U.S. Appl. No. 11/910,958, filed May 15, 2008.
U.S. Appl. No. 11/914,104, filed Jun. 20, 2008.
U.S. Appl. No. 11/915,239, filed May 21, 2008.
U.S. Appl. No. 11/917,772, filed Dec. 17, 2007.
U.S. Appl. No. 11/934,700, filed Nov. 2, 2007.
U.S. Appl. No. 11/981,483, filed Oct. 31, 2007.
U.S. Appl. No. 11/982,273, filed Oct. 31, 2007.
U.S. Appl. No. 11/982,444, filed Oct. 31, 2007.
U.S. Appl. No. 12/060,383, filed Apr. 1, 2008.
U.S. Appl. No. 12/064,012, filed Jul. 17, 2009.
U.S. Appl. No. 12/066,619, filed Sep. 3, 2008.
U.S. Appl. No. 12/092,563, filed Jun. 18, 2008.
U.S. Appl. No. 12/101,389, filed Apr. 11, 2008.
U.S. Appl. No. 12/152,587, filed May 14, 2008.
U.S. Appl. No. 12/184,956, filed Aug. 1, 2008.
U.S. Appl. No. 12/201,705, filed Aug. 29, 2008.
U.S. Appl. No. 12/276,885, filed Nov. 24, 2008.
U.S. Appl. No. 12/302,167, filed Apr. 30, 2009.
U.S. Appl. No. 12/371,156, filed Feb. 13, 2009.
U.S. Appl. No. 12/406,267, filed Mar. 18, 2009.
U.S. Appl. No. 12/418,530, filed Apr. 3, 2009.
U.S. Appl. No. 12/439,221, filed Jul. 14, 2009.
U.S. Appl. No. 12/443,428, filed Jul. 28, 2009.
U.S. Appl. No. 12/444,380, filed Jul. 28, 2009.
U.S. Appl. No. 12/494,913, filed Jun. 30, 2009.
U.S. Appl. No. 12/496,595, filed Jul. 1, 2009.
U.S. Appl. No. 12/594,326, filed Oct. 1, 2009.
U.S. Appl. No. 12/605,028, filed Oct. 23, 2009.
U.S. Appl. No. 12/605,041, filed Oct. 23, 2009.
U.S. Appl. No. 12/663,056, filed Dec. 4, 2009.
U.S. Appl. No. 12/663,748, filed Dec. 9, 2009.
U.S. Appl. No. 12/784,323, filed May 20, 2010.
U.S. Appl. No. 12/811,963, filed Jul. 7, 2010.
U.S. Appl. No. 12/820,926, filed Jun. 22, 2010.
U.S. Appl. No. 12/851,651, filed Aug. 6, 2010.
U.S. Appl. No. 12/858,247, filed Aug. 17, 2010.
U.S. Appl. No. 12/884,927, filed Sep. 17, 2010.
U.S. Appl. No. 13/073,445, filed Mar. 28, 2011.
U.S. Appl. No. 13/088,090, filed Apr. 15, 2011.
U.S. Appl. No. 13/157,575, filed Jun. 10, 2011.
U.S. Appl. No. 13/163,473, filed Jun. 17, 2011.
U.S. Appl. No. 13/186,726, filed Jul. 20, 2011.
U.S. Appl. No. 13/215,439, filed Aug. 23, 2011.
U.S. Appl. No. 13/246,512, filed Sep. 27, 2011.
U.S. Appl. No. 13/332,708, filed Dec. 21, 2011.
U.S. Appl. No. 13/541,185, filed Jul. 3, 2012.
U.S. Appl. No. 13/837,850, filed Mar. 15, 2013.
U.S. Appl. No. 13/897,529, filed May 20, 2013.
U.S. Appl. No. 14/052,442, filed Oct. 11, 2013.
U.S. Appl. No. 14/246,519, filed Apr. 7, 2014.
U.S. Appl. No. 14/275,458, filed May 12, 2014.
U.S. Appl. No. 14/624,266, filed Feb. 17, 2015.
U.S. Appl. No. 14/675,890, filed Apr. 1, 2015.
U.S. Appl. No. 14/721,761, filed May 26, 2015.

* cited by examiner

FIG. 2A

| Protein | Organism | EC# | GenBank / GenPept | | SwissProt | PDB / 3D |
|---|---|---|---|---|---|---|
| At1g08280 | Arabidopsis thaliana | n.d. | AC011438 BT004583 NC_003070 | AAF18241.1 AAO42829.1 NP_172305.1 | Q84W00 Q9SGD2 | |
| At1g08660/F22O13.14 | Arabidopsis thaliana | n.d. | AC003981 AY064135 AY124807 NC_003070 NM_180609 | AAF99778.1 AAL36042.1 AAM70516.1 NP_172342.1 NP_850940.1 | Q8VZJ0 Q9FRR9 | |
| At3g48820/T21J18_90 | Arabidopsis thaliana | n.d. | AY080589 AY133816 AL132963 NM_114741 | AAL85966.1 AAM91750.1 CAB87910.1 NP_190451.1 | Q8RY00 Q9M301 | |
| α-2,3-sialyltransferase (ST3GAL-IV) | Bos taurus | n.d. | AJ584673 | CAE48298.1 | | |
| α-2,3-sialyltransferase (St3Gal-V) | Bos taurus | n.d. | AJ585768 | CAE51392.1 | | |
| α-2,6-sialyltransferase (Siat7b) | Bos taurus | n.d. | AJ620651 | CAF05850.1 | | |
| α-2,8-sialyltransferase (SIAT8A) | Bos taurus | 2.4.99.8 | AJ699418 | CAG27880.1 | | |
| α-2,8-sialyltransferase (Siat8D) | Bos taurus | n.d. | AJ699421 | CAG27883.1 | | |
| α-2,8-sialyltransferase ST8Siα-III (Siat8C) | Bos taurus | n.d. | AJ704563 | CAG28696.1 | | |
| CMP α-2,6-sialyltransferase (ST6Gal I) | Bos taurus | 2.4.99.1 | Y15111 NM_177517 | CAA75385.1 NP_803483.1 | O18974 | |
| sialyltransferase 8 (fragment) | Bos taurus | n.d. | AF450088 | AAL47018.1 | Q8WN13 | |
| sialyltransferase ST3Gal-II (Siat4B) | Bos taurus | n.d. | AJ748841 | CAG44450.1 | | |
| sialyltransferase ST3Gal-III (Siat6) | Bos taurus | n.d. | AJ748842 | CAG44451.1 | | |
| sialyltransferase ST3Gal-VI (Siat10) | Bos taurus | n.d. | AJ748843 | CAG44452.1 | | |
| ST3Gal I | Bos taurus | n.d. | AJ305086 | CAC24698.1 | Q9BEG4 | |
| St6GalNAc-VI | Bos taurus | n.d. | AJ620949 | CAF06586.1 | | |
| CDS4 | Branchiostoma floridae | n.d. | AF391289 | AAM18873.1 | Q8T771 | |
| polysialyltransferase (PST) (fragment) ST8Sia IV | Cercopithecus aethiops | 2.4.99.- | AF210729 | AAF17105.1 | Q9TT09 | |
| polysialyltransferase (STX) (fragment) ST8Sia II | Cercopithecus aethiops | 2.4.99.- | AF210318 | AAF17104.1 | Q9TT10 | |
| α-2,3-sialyltransferase ST3Gal I (Siat4) | Ciona intestinalis | n.d. | AJ626815 | CAF25173.1 | | |
| α-2,3-sialyltransferase ST3Gal I (Siat4) | Ciona savignyi | n.d. | AJ626814 | CAF25172.1 | | |
| α-2,8-polysialyltransferase ST8Sia IV | Cricetulus griseus | 2.4.99.- | - Z46801 | AAE28634 CAA86822.1 | Q64690 | |
| Gal β-1,3/4-GlcNAc α-2,3-sialyltransferase St3Gal I | Cricetulus griseus | n.d. | AY266675 | AAP22942.1 | Q80WL0 | |
| Gal β-1,3/4-GlcNAc α-2,3-sialyltransferase St3Gal II (fragment) | Cricetulus griseus | n.d. | AY266676 | AAP22943.1 | Q80WK9 | |
| α-2,3-sialyltransferase ST3Gal I (Siat4) | Danio rerio | n.d. | AJ783740 | CAH04017.1 | | |
| α-2,3-sialyltransferase ST3Gal II (Siat5) | Danio rerio | n.d. | AJ783741 | CAH04018.1 | | |

FIG. 2B

| Protein | Organism | EC# | GenBank / GenPept | | SwissProt | PDB / 3D |
|---|---|---|---|---|---|---|
| α-2,3-sialyltransferase ST3Gal III (Siat6) | Danio rerio | n.d. | AJ626821 | CAF25179.1 | | |
| α-2,3-sialyltransferase ST3Gal IV (Siat4c) | Danio rerio | n.d. | AJ744809 | CAG32845.1 | | |
| α-2,3-sialyltransferase ST3Gal V-r (Siat5-related) | Danio rerio | n.d. | AJ783742 | CAH04019.1 | | |
| α-2,6-sialyltransferase ST6Gal I (Siat1) | Danio rerio | n.d. | AJ744801 | CAG32837.1 | | |
| α-2,6-sialyltransferase ST6GalNAc II (Siat7B) | Danio rerio | n.d. | AJ634459 | CAG25680.1 | | |
| α-2,6-sialyltransferase ST6GalNAc V (Siat7E) (fragment) | Danio rerio | n.d. | AJ646874 | CAG26703.1 | | |
| α-2,6-sialyltransferase ST6GalNAc VI (Siat7F) (fragment) | Danio rerio | n.d. | AJ646883 | CAG26712.1 | | |
| α-2,8-sialyltransferase ST8Sia I (Siat 8A) (fragment) | Danio rerio | n.d. | AJ715535 | CAG29374.1 | | |
| α-2,8-sialyltransferase ST8Sia III (Siat 8C) (fragment) | Danio rerio | n.d. | AJ715543 | CAG29382.1 | | |
| α-2,8-sialyltransferase ST8Sia IV (Siat 8D) (fragment) | Danio rerio | n.d. | AJ715545 | CAG29384.1 | | |
| α-2,8-sialyltransferase ST8Sia V (Siat 8E) (fragment) | Danio rerio | n.d. | AJ715546 | CAG29385.1 | | |
| α-2,8-sialyltransferase ST8Sia VI (Siat 8F) (fragment) | Danio rerio | n.d. | AJ715551 | CAG29390.1 | | |
| β-galactosamide α-2,6-sialyltransferase II (ST6Gal II) | Danio rerio | n.d. | AJ627627 | CAF29495.1 | | |
| N-glycan α-2,8-sialyltransferase | Danio rerio | n.d. | BC050483 AY055462 NM_153662 | AAH50483.1 AAL17875.1 NP_705948.1 | Q7ZU51 Q8QH83 | |
| ST3Gal III-related (siat6r) | Danio rerio | n.d. | BC053179 AJ626820 NM_200355 | AAH53179.1 CAF25178.1 NP_956649.1 | Q7T3B9 | |
| St3Gal-V | Danio rerio | n.d. | AJ619960 | CAF04061.1 | | |
| st6GalNAc-VI | Danio rerio | n.d. | BC060932 AJ620947 | AAH60932.1 CAF06584.1 | | |
| α-2,6-sialyltransferase (CG4871) ST6Gal I | Drosophila melanogaster | 2.4.99.1 | AE003465 AF218237 AF397532 AE003465 NM_079129 NM_166684 | AAF47256.1 AAG13185.1 AAK92126.1 AAM70791.1 NP_523853.1 NP_726474.1 | Q9GU23 Q9W121 | |
| α-2,3-sialyltransferase (ST3Gal-VI) | Gallus gallus | n.d. | AJ585767 AJ627204 | CAE51391.1 CAF25503.1 | | |
| α-2,3-sialyltransferase ST3Gal I | Gallus gallus | 2.4.99.4 | X80503 NM_205217 | CAA56666.1 NP_990548.1 | Q11200 | |
| α-2,3-sialyltransferase ST3Gal IV (fragment) | Gallus gallus | 2.4.99.- | AF035250 | AAC14163.1 | O73724 | |
| α-2,3-sialyltransferase (ST3GAL-II) | Gallus gallus | n.d. | AJ585761 | CAE51385.2 | | |
| α-2,6-sialyltransferase (Siat7b) | Gallus gallus | n.d. | AJ620653 | CAF05852.1 | | |
| α-2,6-sialyltransferase ST6Gal I | Gallus gallus | 2.4.99.1 | X75558 NM_205241 | CAA53235.1 NP_990572.1 | Q92182 | |
| α-2,6-sialyltransferase | Gallus gallus | 2.4.99.3 | - | AAE68028.1 | Q92183 | |

FIG. 2C

| Protein | Organism | EC# | GenBank / GenPept | | SwissProt | PDB / 3D |
|---|---|---|---|---|---|---|
| ST6GalNAc I | | | - <br> X74946 <br> NM_205240 | AAE68029.1 <br> CAA52902.1 <br> NP_990571.1 | | |
| α-2,6-sialyltransferase ST6GalNAc II | Gallus gallus | 2.4.99.- | X77775 <br> NM_205233 | AAE68030.1 <br> CAA54813.1 <br> NP_990564.1 | Q92184 | |
| α-2,6-sialyltransferase ST6GalNAc III (SIAT7C) (fragment) | Gallus gallus | n.d. | AJ634455 | CAG25677.1 | | |
| α-2,6-sialyltransferase ST6GalNAc V (SIAT7E) (fragment) | Gallus gallus | n.d. | AJ646877 | CAG26706.1 | | |
| α-2,8-sialyltransferase (GD3 Synthase) ST8Sia I | Gallus gallus | 2.4.99.- | U73176 | AAC28888.1 | P79783 | |
| α-2,8-sialyltransferase (SIAT8B) | Gallus gallus | n.d. | AJ699419 | CAG27881.1 | | |
| α-2,8-sialyltransferase (SIAT8C) | Gallus gallus | n.d. | AJ699420 | CAG27882.1 | | |
| α-2,8-sialyltransferase (SIAT8F) | Gallus gallus | n.d. | AJ699424 | CAG27886.1 | | |
| α-2,8-syalyltransferase ST8Siα-V (SIAT8C) | Gallus gallus | n.d. | AJ704564 | CAG28697.1 | | |
| β-galactosamide α-2,6-sialyltransferase II (ST6Gal II) | Gallus gallus | n.d. | AJ627629 | CAF29497.1 | | |
| GM3 synthase (SIAT9) | Gallus gallus | 2.4.99.9 | AY515255 | AAS83519.1 | | |
| polysialyltransferase ST8Sia IV | Gallus gallus | 2.4.99.- | AF008194 | AAB95120.1 | O42399 | |
| α-2,3-sialyltransferase ST3Gal I | Homo sapiens | 2.4.99.4 | L29555 <br> AF059321 <br> L13972 <br> AF155238 <br> AF186191 <br> BC018357 <br> NM_003033 <br> NM_173344 | AAA36612.1 <br> AAC17874.1 <br> AAC37574.1 <br> AAD39238.1 <br> AAG29876.1 <br> AAH18357.1 <br> NP_003024.1 <br> NP_775479.1 | Q11201 <br> O60677 <br> Q9UN51 | |
| α-2,3-sialyltransferase ST3Gal II | Homo sapiens | 2.4.99.4 | U63090 <br> BC036777 <br> X96667 <br> NM_006927 | AAB40389.1 <br> AAH36777.1 <br> CAA65447.1 <br> NP_008858.1 | Q16842 <br> O00654 | |
| α-2,3-sialyltransferase ST3Gal III (SiaT6) | Homo sapiens | 2.4.99.6 | L23768 <br> BC050380 <br> AF425851 <br> AF425852 <br> AF425853 <br> AF425854 <br> AF425855 <br> AF425856 <br> AF425857 <br> AF425858 <br> AF425859 <br> AF425860 <br> AF425861 <br> AF425862 <br> AF425863 <br> AF425864 <br> AF425865 <br> AF425866 <br> AF425867 <br> AY167992 <br> AY167993 <br> AY167994 | AAA35778.1 <br> AAH50380.1 <br> AAO13859.1 <br> AAO13860.1 <br> AAO13861.1 <br> AAO13862.1 <br> AAO13863.1 <br> AAO13864.1 <br> AAO13865.1 <br> AAO13866.1 <br> AAO13867.1 <br> AAO13868.1 <br> AAO13869.1 <br> AAO13870.1 <br> AAO13871.1 <br> AAO13872.1 <br> AAO13873.1 <br> AAO13874.1 <br> AAO13875.1 <br> AAO38806.1 <br> AAO38807.1 <br> AAO38808.1 | Q11203 <br> Q86UR6 <br> Q86UR7 <br> Q86UR8 <br> Q86UR9 <br> Q86US0 <br> Q86US1 <br> Q86US2 <br> Q8IX43 <br> Q8IX44 <br> Q8IX45 <br> Q8IX46 <br> Q8IX47 <br> Q8IX48 <br> Q8IX49 <br> Q8IX50 <br> Q8IX51 <br> Q8IX52 <br> Q8IX53 <br> Q8IX54 <br> Q8IX55 <br> Q8IX56 | |

FIG. 2D

| Protein | Organism | EC# | GenBank / GenPept | | SwissProt | PDB / 3D |
|---|---|---|---|---|---|---|
| | | | AY167995 | AAO38809.1 | Q8IX57 | |
| | | | AY167996 | AAO38810.1 | Q8IX58 | |
| | | | AY167997 | AAO38811.1 | | |
| | | | AY167998 | AAO38812.1 | | |
| | | | NM_006279 | NP_006270.1 | | |
| | | | NM_174964 | NP_777624.1 | | |
| | | | NM_174965 | NP_777625.1 | | |
| | | | NM_174966 | NP_777626.1 | | |
| | | | NM_174967 | NP_777627.1 | | |
| | | | NM_174969 | NP_777629.1 | | |
| | | | NM_174970 | NP_777630.1 | | |
| | | | NM_174972 | NP_777632.1 | | |
| α-2,3-sialyltransferase ST3Gal IV | Homo sapiens | 2.4.99.- | L23767 | AAA16460.1 | Q11206 | |
| | | | AF035249 | AAC14162.1 | O60497 | |
| | | | BC010645 | AAH10645.1 | Q96QQ9 | |
| | | | AY040826 | AAK93790.1 | Q8N6A6 | |
| | | | AF516602 | AAM66431.1 | Q8N6A7 | |
| | | | AF516603 | AAM66432.1 | Q8NFD3 | |
| | | | AF516604 | AAM66433.1 | Q8NFG7 | |
| | | | AF525084 | AAM81378.1 | | |
| | | | X74570 | CAA52662.1 | | |
| | | | CR456858 | CAG33139.1 | | |
| | | | NM_006278 | NP-006269.1 | | |
| α-2,3-sialyltransferase ST3Gal VI | Homo sapiens | 2.4.99.4 | AF119391 | AAD39131.1 | Q9Y274 | |
| | | | BC023312 | AAH23312.1 | | |
| | | | AB022918 | BAA77609.1 | | |
| | | | AX877828 | CAE89895.1 | | |
| | | | AX886023 | CAF00161.1 | | |
| | | | NM_006100 | NP_006091.1 | | |
| α-2,6-sialyltransferase (ST6Gal II ; KIAA1877) | Homo sapiens | n.d. | BC008680 | AAH08680.1 | Q86Y44 | |
| | | | AB058780 | BAB47506.1 | Q8IUG7 | |
| | | | AB059555 | BAC24793.1 | Q96HE4 | |
| | | | AJ512141 | CAD54408.1 | Q96JF0 | |
| | | | AX795193 | CAE48260.1 | | |
| | | | AX795193 | CAE48261.1 | | |
| | | | NM_032528 | NP_115917.1 | | |
| α-2,6-sialyltransferase (ST6GALNAC III) | Homo sapiens | n.d. | BC059363 | AAH59363.1 | Q8N259 | |
| | | | AY358540 | AAQ88904.1 | Q8NDV1 | |
| | | | AK091215 | BAC03611.1 | | |
| | | | AJ507291 | CAD45371.1 | | |
| | | | NM_152996 | NP_694541.1 | | |
| α-2,6-sialyltransferase (ST6GalNAc V) | Homo sapiens | n.d. | BC001201 | AAH01201.1 | Q9BVH7 | |
| | | | AK056241 | BAB71127.1 | | |
| | | | AL035409 | CAB72344.1 | | |
| | | | AJ507292 | CAD45372.1 | | |
| | | | NM_030965 | NP_112227.1 | | |
| α-2,6-sialyltransferase (SThM) ST6GalNAc II | Homo sapiens | 2.4.99.- | U14550 | AAA52228.1 | Q9UJ37 | |
| | | | BC040455 | AAH40455.1 | Q12971 | |
| | | | AJ251053 | CAB61434.1 | | |
| | | | NM_006456 | NP_006447.1 | | |
| α-2,6-sialyltransferase ST6Gal I | Homo sapiens | 2.4.99.1 | BC031476 | AAH31476.1 | P15907 | |
| | | | BC040009 | AAH40009.1 | | |
| | | | A17362 | CAA01327.1 | | |
| | | | A23699 | CAA01686.1 | | |
| | | | X17247 | CAA35111.1 | | |
| | | | X54363 | CAA38246.1 | | |
| | | | X62822 | CAA44634.1 | | |
| | | | NM_003032 | NP_003023.1 | | |
| | | | NM_173216 | NP_775323.1 | | |
| α-2,6-sialyltransferase ST6GalNAc I | Homo sapiens | 2.4.99.3 | BC022462 | AAH22462.1 | Q8TBJ6 | |
| | | | AY096001 | AAM22800.1 | Q9NSC7 | |
| | | | AY358918 | AAQ89277.1 | Q9NXQ7 | |
| | | | AK000113 | BAA90953.1 | | |
| | | | Y11339 | CAA72179.2 | | |

FIG. 2E

| Protein | Organism | EC# | GenBank / GenPept | | SwissProt | PDB / 3D |
|---|---|---|---|---|---|---|
| | | | NM_018414 | NP_060884.1 | | |
| α-2,8-polysialyltransferase ST8Sia IV | Homo sapiens | 2.4.99.- | L41680 | AAC41775.1 | Q8N1F4 | |
| | | | BC027866 | AAH27866.1 | Q92187 | |
| | | | BC053657 | AAH53657.1 | Q92693 | |
| | | | NM_005668 | NP_005659.1 | | |
| α-2,8-sialyltransferase (GD3 synthase) ST8Sia I | Homo sapiens | 2.4.99.8 | L32867 | AAA62366.1 | Q86X71 | |
| | | | L43494 | AAC37586.1 | Q92185 | |
| | | | BC046158 | AAH46158.1 | Q93064 | |
| | | | - | AAQ53140.1 | | |
| | | | AY569975 | AAS75783.1 | | |
| | | | D26360 | BAA05391.1 | | |
| | | | X77922 | CAA54891.1 | | |
| | | | NM_003034 | NP_003025.1 | | |
| α-2,8-sialyltransferase ST8Sia II | Homo sapiens | 2.4.99.- | L29556 | AAA36613.1 | Q92186 | |
| | | | U82762 | AAB51242.1 | Q92470 | |
| | | | U33551 | AAC24458.1 | Q92746 | |
| | | | BC069584 | AAH69584.1 | | |
| | | | NM_006011 | NP_006002.1 | | |
| α-2,8-sialyltransferase ST8Sia III | Homo sapiens | 2.4.99.- | AF004668 | AAB87642.1 | O43173 | |
| | | | AF003092 | AAC15901.2 | Q9NS41 | |
| | | | NM_015879 | NP_056963.1 | | |
| α-2,8-sialyltransferase ST8Sia V | Homo sapiens | 2.4.99.- | U91641 | AAC51727.1 | O15466 | |
| | | | CR457037 | CAG33318.1 | | |
| | | | NM_013305 | NP_037437.1 | | |
| ENSP00000020221 (fragment) | | n.d. | AC023295 | - | | |
| lactosylceramide α-2,3-sialyltransferase (ST3Gal V) | Homo sapiens | 2.4.99.9 | AF105026 | AAD14634.1 | Q9UNP4 | |
| | | | AF119415 | AAF66146.1 | O94902 | |
| | | | BC065936 | AAH65936.1 | | |
| | | | AY152815 | AAO16866.1 | | |
| | | | AAP65066 | AAP65066.1 | | |
| | | | AY359105 | AAQ89463.1 | | |
| | | | AB018356 | BAA33950.1 | | |
| | | | AX876536 | CAE89320.1 | | |
| | | | NM_003896 | NP_003887.2 | | |
| N-acetylgalactosaminide α-2,6-sialyltransferase (ST6GalNAc VI) | Homo sapiens | 2.4.99.- | BC006564 | AAH06564.1 | Q969X2 | |
| | | | BC007802 | AAH07802.1 | Q9H8A2 | |
| | | | BC016299 | AAH16299.1 | Q9ULB8 | |
| | | | AY358672 | AAQ89035.1 | | |
| | | | AB035173 | BAA87035.1 | | |
| | | | AK023900 | BAB14715.1 | | |
| | | | AJ507293 | CAD45373.1 | | |
| | | | AX880950 | CAE91145.1 | | |
| | | | CR457318 | CAG33599.1 | | |
| | | | NM_013443 | NP_038471.2 | | |
| N-acetylgalactosaminide α-2,6-sialyltransferase IV (ST6GalNAc IV) | Homo sapiens | 2.4.99.- | AF127142 | AAF00102.1 | Q9H4F1 | |
| | | | BC036705 | AAH36705.1 | Q9NWU6 | |
| | | | - | AAP63349.1 | Q9UKU1 | |
| | | | AB035172 | BAA87034.1 | Q9ULB9 | |
| | | | AK000600 | BAA91281.1 | Q9Y3G3 | |
| | | | Y17461 | CAB44354.1 | Q9Y3G4 | |
| | | | AJ271734 | CAC07404.1 | | |
| | | | AX061620 | CAC24981.1 | | |
| | | | AX068265 | CAC27250.1 | | |
| | | | AX969252 | CAF14360.1 | | |
| | | | NM_014403 | NP_055218.3 | | |
| | | | NM_175039 | NP_778204.1 | | |
| ST8SIA-VI (fragment) | Homo sapiens | n.d. | AJ621583 | CAF21722.1 | | |
| | | | XM_291725 | XP_291725.2 | | |
| unnamed protein product | Homo sapiens | n.d. | AK021929 | BAB13940.1 | Q9HAA9 | |
| | | | AX881696 | CAE91353.1 | | |
| Gal β-1,3/4-GlcNAc α- | Mesocricetus | 2.4.99.6 | AJ245699 | CAB53394.1 | Q9QXF6 | |

FIG. 2F

| Protein | Organism | EC# | GenBank / GenPept | | SwissProt | PDB / 3D |
|---|---|---|---|---|---|---|
| 2,3-sialyltransferase (ST3Gal III) | | auratus | | | | |
| Gal β-1,3/4-GlcNAc α-2,3-sialyltransferase (ST3Gal IV) | | Mesocricetus auratus | 2.4.99.6 | AJ245700 | CAB53395.1 | Q9QXF5 |
| GD3 synthase (fragment) ST8Sia I | | Mesocricetus auratus | n.d. | AF141657 | AAD33879.1 | Q9WUL1 |
| polysialyltransferase (ST8Sia IV) | | Mesocricetus auratus | 2.4.99.- | AJ245701 | CAB53396.1 | Q9QXF4 |
| α-2,3-sialyltransferase ST3Gal I | St3gal1 | Mus musculus | 2.4.99.4 | AF214028 AK031344 AK078469 X73523 NM_009177 | AAF60973.1 BAC27356.1 BAC37290.1 CAA51919.1 NP_033203.1 | P54751 Q11202 Q9JL30 |
| α-2,3-sialyltransferase ST3Gal II | St3gal2 | Mus musculus | 2.4.99.4 | BC015264 BC066064 AK034554 AK034863 AK053827 X76989 NM_009179 NM_178048 | AAH15264.1 AAH66064.1 BAC28752.1 BAC28859.1 BAC35543.1 CAA54294.1 NP_033205.1 NP_835149.1 | Q11204 Q8BPL0 Q8BSA0 Q8BSE9 Q91WH6 |
| α-2,3-sialyltransferase ST3Gal III | St3gal3 | Mus musculus | 2.4.99.- | BC006710 AK005053 AK013016 X84234 NM_009176 | AAH06710.1 BAB23779.1 BAB28598.1 CAA59013.1 NP_033202.2 | P97325 Q922X5 Q9CZ48 Q9DBB6 |
| α-2,3-sialyltransferase ST3Gal IV | St3gal4 | Mus musculus | 2.4.99.4 | BC011121 BC050773 D28941 AK008543 AB061305 X95809 NM_009178 | AAH11121.1 AAH50773.1 BAA06068.1 BAB25732.1 BAB47508.1 CAA65076.1 NP_033204.2 | P97354 Q61325 Q91Y74 Q921R5 Q9CVE8 |
| α-2,3-sialyltransferase ST3Gal VI | St3gal6 | Mus musculus | 2.4.99.4 | AF119390 BC052338 AB063326 AK033562 AK041173 NM_018784 | AAD39130.1 AAH52338.1 BAB79494.1 BAC28360.1 BAC30851.1 NP_061254 | Q80UR7 Q8BLV1 Q8VIB3 Q9WVG2 |
| α-2,6-sialyltransferase ST6GalNAc II | St6galnac2 | Mus musculus | 2.4.99.- | NM_009180 BC010208 AB027198 AK004613 X93999 X94000 NM_009180 | 6677963 AAH10208.1 BAB00637.1 BAB23410.1 CAA63821.1 CAA63822.1 NP_033206.2 | P70277 Q9DC24 Q9JJM5 |
| α-2,6-sialyltransferase ST6Gal I | St6gal1 | Mus musculus | 2.4.99.1 | BC027833 D16106 AK034768 AK084124 NM_145933 | AAE68031.1 AAH27833.1 BAA03680.1 BAC28828.1 BAC39120.1 NP_666045.1 | Q64685 Q8BM62 Q8K1L1 |
| α-2,6-sialyltransferase ST6Gal II | St6gal2 | Mus musculus | n.d. | AK082566 AB095093 AK129462 NM_172829 | BAC38534.1 BAC87752.1 BAC98272.1 NP_766417.1 | Q8BUU4 |
| α-2,6-sialyltransferase ST6GalNAc I | St6galnac1 | Mus musculus | 2.4.99.3 | Y11274 NM_011371 | CAA72137.1 NP_035501.1 | Q9QZ39 Q9JJP5 |
| α-2,6-sialyltransferase ST6GalNAc III | St6galnac3 | Mus musculus | n.d. | BC058387 AK054804 Y11342 Y11343 | AAH58387.1 BAC28836.1 CAA72181.2 CAB95031.1 | Q9WUV2 Q9JHP5 |

FIG. 2G

| Protein | Organism | EC# | GenBank / GenPept | | SwissProt | PDB / 3D |
|---|---|---|---|---|---|---|
| | | | NM_011372 | NP_035502 | | |
| α-2,6-sialyltransferase ST6GalNAc IV | St6galnac4 | Mus musculus | 2.4.99.7 | BC056451 | AAH56451.1 | Q8C3J2 | |
| | | | AK085730 | BAC39523.1 | Q9JHP2 | |
| | | | AJ007310 | CAA07446.1 | Q9R2B6 | |
| | | | Y15779 | CAB43507.1 | O88725 | |
| | | | Y15780 | CAB43514.1 | Q9JHP0 | |
| | | | Y19055 | CAB93946.1 | Q9QUP9 | |
| | | | Y19057 | CAB93948.1 | Q9R2B5 | |
| | | | NM_011373 | NP_035503.1 | | |
| α-2,8-sialyltransferase (GD3 synthase) ST8Sia I | St8sia1 | Mus musculus | 2.4.99.8 | L38677 | AAA91869.1 | Q64468 | |
| | | | BC024821 | AAH24821.1 | Q64687 | |
| | | | AK046188 | BAC32625.1 | Q8BL76 | |
| | | | AK052444 | BAC34994.1 | Q8BWI0 | |
| | | | X84235 | CAA59014.1 | Q8K1C1 | |
| | | | AJ401102 | CAC20706.1 | Q9EPK0 | |
| | | | NM_011374 | NP_035504.1 | | |
| α-2,8-sialyltransferase (ST8Sia VI) | St8sia6 | Mus musculus | n.d. | AB059554 | BAC01265.1 | Q8BI43 | |
| | | | AK085105 | BAC39367.1 | Q8K4T1 | |
| | | | NM_145838 | NP_665837.1 | | |
| α-2,8-sialyltransferase ST8Sia II | St8sia2 | Mus musculus | 2.4.99.- | X83562 | CAA58548.1 | O35696 | |
| | | | X99646 | CAA67965.1 | | |
| | | | X99647 | CAA67965.1 | | |
| | | | X99648 | CAA67965.1 | | |
| | | | X99649 | CAA67965.1 | | |
| | | | X99650 | CAA67965.1 | | |
| | | | X99651 | CAA67965.1 | | |
| | | | NM_009181 | NP_033207.1 | | |
| α-2,8-sialyltransferase ST8Sia IV | St8sia4 | Mus musculus | 2.4.99.8 | BC060112 | AAH60112.1 | Q64692 | |
| | | | AK003690 | BAB22941.1 | Q8BY70 | |
| | | | AK041723 | BAC31044.1 | | |
| | | | AJ223956 | CAA11685.1 | | |
| | | | X86000 | CAA59992.1 | | |
| | | | Y09484 | CAA70692.1 | | |
| | | | NM_009183 | NP_033209.1 | | |
| α-2,8-sialyltransferase ST8Sia V | St8sia5 | Mus musculus | 2.4.99.- | BC034855 | AAH34855.1 | P70126 | |
| | | | AK078670 | BAC37354.1 | P70127 | |
| | | | X98014 | CAA66642.1 | P70128 | |
| | | | X98014 | CAA66643.1 | Q8BJW0 | |
| | | | X98014 | CAA66644.1 | Q8JZQ3 | |
| | | | NM_013666 | NP_038694.1 | | |
| | | | NM_153124 | NP_694764.1 | | |
| | | | NM_177416 | NP_803135.1 | | |
| α-2,8-sialyltransferase ST8Sia III | St8sia3 | Mus musculus | 2.4.99.- | BC075645 | AAH75645.1 | Q64689 | |
| | | | AK015874 | BAB30012.1 | Q9CUJ6 | |
| | | | X80502 | CAA56665.1 | | |
| | | | NM_009182 | NP_033208.1 | | |
| GD1 synthase (ST6GalNAc V) | St6galnac5 | Mus musculus | n.d. | BC055737 | AAH55737.1 | Q8CAM7 | |
| | | | AB030836 | BAA85747.1 | Q8CBX1 | |
| | | | AB028840 | BAA89292.1 | Q9QYJ1 | |
| | | | AK034387 | BAC28693.1 | Q9R0K6 | |
| | | | AK038434 | BAC29997.1 | | |
| | | | AK042683 | BAC31331.1 | | |
| | | | NM_012028 | NP_036158.2 | | |
| GM3 synthase (α-2,3-sialyltransferase) ST3Gal V | St3gal5 | Mus musculus | 2.4.99.9 | AF119416 | AAF66147.1 | O88829 | |
| | | | - | AAP65063.1 | Q9CZ65 | |
| | | | AB018048 | BAA33491.1 | Q9QWF9 | |
| | | | AB013302 | BAA76467.1 | | |
| | | | AK012961 | BAB28571.1 | | |
| | | | Y15003 | CAA75235.1 | | |
| | | | NM_011375 | NP_035505.1 | | |
| N-acetylgalactosaminide α-2,6-sialyltransferase (ST6GalNAc VI) | St6galnac6 | Mus musculus | 2.4.99.- | BC036985 | AAH36985.1 | Q8CDC3 | |
| | | | AB035174 | BAA87036.1 | Q8JZW3 | |
| | | | AB035123 | BAA95940.1 | Q9JM95 | |
| | | | AK030648 | BAC27064.1 | Q9R0G9 | |

FIG. 2H

| Protein | Organism | EC# | GenBank / GenPept | | SwissProt | PDB / 3D |
|---|---|---|---|---|---|---|
| | | | NM_016973 | NP_058669.1 | | |
| M138L | Myxoma virus | n.d. | U46578 | AAD00069.1 | | |
| | | | AF170726 | AAE61323.1 | | |
| | | | NC_001132 | AAE61326.1 | | |
| | | | | AAF15026.1 | | |
| | | | | NP_051852.1 | | |
| α-2,3-sialyltransferase (St3Gal-I) | Oncorhynchus mykiss | n.d. | AJ585760 | CAE51384.1 | | |
| α-2,6-sialyltransferase (Siat1) | Oncorhynchus mykiss | n.d. | AJ620649 | CAF05848.1 | | |
| α-2,8-polysialyltransferase IV (ST8Sia IV) | Oncorhynchus mykiss | n.d. | AB094402 | BAC77411.1 | Q7T2X5 | |
| GalNAc α-2,6-sialyltransferase (RtST6GalNAc) | Oncorhynchus mykiss | n.d. | AB097943 | BAC77520.1 | Q7T2X4 | |
| α-2,3-sialyltransferase ST3Gal IV | Oryctolagus cuniculus | 2.4.99.- | AF121967 | AAF28871.1 | Q9N257 | |
| OJ1217_F02.7 | Oryza sativa (japonica cultivar-group) | n.d. | AP004084 | BAD07616.1 | | |
| OSJNBa0043L24.2 or OSJNBb0002J11.9 | Oryza sativa (japonica cultivar-group) | n.d. | AL731626 | CAD41185.1 | | |
| | | | AL662969 | CAE04714.1 | | |
| P0683f02.18 or P0489B03.1 | Oryza sativa (japonica cultivar-group) | n.d. | AP003289 | BAB63715.1 | | |
| | | | AP003794 | BAB90552.1 | | |
| α-2,6-sialyltransferase ST6GalNAc V (Siat7E) (fragment) | Oryzias latipes | n.d. | AJ646876 | CAG26705.1 | | |
| α-2,3-sialyltransferase ST3Gal I (Siat4) | Pan troglodytes | n.d. | AJ744803 | CAG32839.1 | | |
| α-2,3-sialyltransferase ST3Gal II (Siat5) | Pan troglodytes | n.d. | AJ744804 | CAG32840.1 | | |
| α-2,3-sialyltransferase ST3Gal III (Siat6) | Pan troglodytes | n.d. | AJ626819 | CAF25177.1 | | |
| α-2,3-sialyltransferase ST3Gal IV (Siat4c) | Pan troglodytes | n.d. | AJ626824 | CAF25182.1 | | |
| α-2,3-sialyltransferase ST3Gal VI (Siat10) | Pan troglodytes | n.d. | AJ744808 | CAG32844.1 | | |
| α-2,6-sialyltransferase (Sia7A) | Pan troglodytes | n.d. | AJ748740 | CAG38615.1 | | |
| α-2,6-sialyltransferase (Sia7B) | Pan troglodytes | n.d. | AJ748741 | CAG38616.1 | | |
| α-2,6-sialyltransferase ST6GalNAc III (Siat7C) | Pan troglodytes | n.d. | AJ634454 | CAG25676.1 | | |
| α-2,6-sialyltransferase ST6GalNAc IV (Siat7D) (fragment) | Pan troglodytes | n.d. | AJ646870 | CAG26699.1 | | |
| α-2,6-sialyltransferase ST6GalNAc V (Siat7E) | Pan troglodytes | n.d. | AJ646875 | CAG26704.1 | | |
| α-2,6-sialyltransferase ST6GalNAc VI (Siat7F) (fragment) | Pan troglodytes | n.d. | AJ646882 | CAG26711.1 | | |
| α-2,8-sialyltransferase 8A (Siat8A) | Pan troglodytes | 2.4.99.8 | AJ697658 | CAG26896.1 | | |
| α-2,8-sialyltransferase 8B (Siat8B) | Pan troglodytes | n.d. | AJ697659 | CAG26897.1 | | |
| α-2,8-sialyltransferase 8C (Siat8C) | Pan troglodytes | n.d. | AJ697660 | CAG26898.1 | | |
| α-2,8-sialyltransferase 8D (Siat8D) | Pan troglodytes | n.d. | AJ697661 | CAG26899.1 | | |
| α-2,8-sialyltransferase | Pan troglodytes | n.d. | AJ697662 | CAG26900.1 | | |

FIG. 2I

| Protein | Organism | EC# | GenBank / GenPept | | SwissProt | PDB / 3D |
|---|---|---|---|---|---|---|
| 8E (Siat8E) | | | | | | |
| α-2,8-sialyltransferase 8F (Siat8F) | Pan troglodytes | n.d. | AJ697663 | CAG26901.1 | | |
| β-galactosamide α-2,6-sialyltransferase I (ST6Gal I; Siat1) | Pan troglodytes | 2.4.99.1 | AJ627624 | CAF29492.1 | | |
| β-galactosamide α-2,6-sialyltransferase II (ST6Gal II) | Pan troglodytes | n.d. | AJ627625 | CAF29493.1 | | |
| GM3 synthase ST3Gal V (Siat9) | Pan troglodytes | n.d. | AJ744807 | CAG32843.1 | | |
| S138L | Rabbit fibroma virus Kasza | n.d. | NC_001266 | NP_052025 | | |
| α-2,3-sialyltransferase ST3Gal III | Rattus norvegicus | 2.4.99.6 | M97754 NM_031697 | AAA42146.1 NP_113885.1 | Q02734 | |
| α-2,3-sialyltransferase ST3Gal IV (Siat4c) | Rattus norvegicus | n.d. | AJ626825 | CAF25183.1 | | |
| α-2,3-sialyltransferase ST3Gal VI | Rattus norvegicus | n.d. | AJ626743 | CAF25053.1 | | |
| α-2,6-sialyltransferase ST3Gal II | Rattus norvegicus | 2.4.99.- | X76988 NM_031695 | CAA54293.1 NP_113883.1 | Q11205 | |
| α-2,6-sialyltransferase ST6Gal I | Rattus norvegicus | 2.4.99.1 | M18769 M83143 | AAA41196.1 AAB07233.1 | P13721 | |
| α-2,6-sialyltransferase ST6GalNAc I (Siat7A) | Rattus norvegicus | n.d. | AJ634458 | CAG25684.1 | | |
| α-2,6-sialyltransferase ST6GalNAc II (Siat7B) | Rattus norvegicus | n.d. | AJ634457 | CAG25679.1 | | |
| α-2,6-sialyltransferase ST6GalNAc III | Rattus norvegicus | 2.4.99.- | L29554 BC072501 NM_019123 | AAC42086.1 AAH72501.1 NP_061996.1 | Q64686 | |
| α-2,6-sialyltransferase ST6GalNAc IV (Siat7D) (fragment) | Rattus norvegicus | n.d. | AJ646871 | CAG26700.1 | | |
| α-2,6-sialyltransferase ST6GalNAc V (Siat7E) | Rattus norvegicus | n.d. | AJ646872 | CAG26701.1 | | |
| α-2,6-sialyltransferase ST6GalNAc VI (Siat7F) (fragment) | Rattus norvegicus | n.d. | AJ646881 | CAG26710.1 | | |
| α-2,8-sialyltransferase (GD3 synthase) ST8Sia I | Rattus norvegicus | 2.4.99.- | U53883 D45255 | AAC27541.1 BAA08213.1 | P70554 P97713 | |
| α-2,8-sialyltransferase (SIAT8E) | Rattus norvegicus | n.d. | AJ699422 | CAG27884.1 | | |
| α-2,8-sialyltransferase (SIAT8F) | Rattus norvegicus | n.d. | AJ699423 | CAG27885.1 | | |
| α-2,8-sialyltransferase ST8Sia II | Rattus norvegicus | 2.4.99.- | L13445 NM_057156 | AAA42147.1 NP_476497.1 | Q07977 Q64688 | |
| α-2,8-sialyltransferase ST8Sia III | Rattus norvegicus | 2.4.99.- | U55938 NM_013029 | AAB50061.1 NP_037161.1 | P97877 | |
| α-2,8-sialyltransferase ST8Sia IV | Rattus norvegicus | 2.4.99.- | U90215 | AAB49989.1 | O08563 | |
| β-galactosamide α-2,6-sialyltransferase II (ST6Gal II) | Rattus norvegicus | n.d. | AJ627626 | CAF29494.1 | | |
| GM3 synthase ST3Gal V | Rattus norvegicus | n.d. | AB018049 NM_031337 | BAA33492.1 NP_112627.1 | O88830 | |

FIG. 2J

| Protein | Organism | EC# | GenBank / GenPept | | SwissProt | PDB / 3D |
|---|---|---|---|---|---|---|
| sialyltransferase ST3Gal-I (Siat4A) | Rattus norvegicus | n.d. | AJ748840 | CAG44449.1 | | |
| α-2,3-sialyltransferase (St3Gal-II) | Silurana tropicalis | n.d. | AJ585763 | CAE51387.1 | | |
| α-2,6-sialyltransferase (Siat7b) | Silurana tropicalis | n.d. | AJ620650 | CAF05849.1 | | |
| α-2,6-sialyltransferase (St6galnac) | Strongylocentrotus purpuratus | n.d. | AJ699425 | CAG27887.1 | | |
| α-2,3-sialyltransferase (ST3GAL-III) | Sus scrofa | n.d. | AJ585765 | CAE51389.1 | | |
| α-2,3-sialyltransferase (ST3GAL-IV) | Sus scrofa | n.d. | AJ584674 | CAE48299.1 | | |
| α-2,3-sialyltransferase ST3Gal I | Sus scrofa | 2.4.99.4 | M97753 | AAA31125.1 | Q02745 | |
| α-2,6-sialyltransferase (fragment) ST6Gal I | Sus scrofa | 2.4.99.1 | AF136746 | AAD33059.1 | Q9XSG8 | |
| β-galactosamide α-2,6-sialyltransferase (ST6GalNAc-V) | Sus scrofa | n.d. | AJ620948 | CAF06585.2 | | |
| sialyltransferase (fragment) ST6Gal I | sus scrofa | n.d. | AF041031 | AAC15633.1 | O62717 | |
| ST6GALNAC-V | Sus scrofa | n.d. | AJ620948 | CAF06585.1 | | |
| α-2,3-sialyltransferase (Siat5-r) | Takifugu rubripes | n.d. | AJ744805 | CAG32841.1 | | |
| α-2,3-sialyltransferase ST3Gal I (Siat4) | Takifugu rubripes | n.d. | AJ626816 | CAF25174.1 | | |
| α-2,3-sialyltransferase ST3Gal II (Siat5) (fragment) | Takifugu rubripes | n.d. | AJ626817 | CAF25175.1 | | |
| α-2,3-sialyltransferase ST3Gal III (Siat6) | Takifugu rubripes | n.d. | AJ626818 | CAF25176.1 | | |
| α-2,6-sialyltransferase ST6Gal I (Siat1) | Takifugu rubripes | n.d. | AJ744800 | CAG32836.1 | | |
| α-2,6-sialyltransferase ST6GalNAc II (Siat7B) | Takifugu rubripes | n.d. | AJ634460 | CAG25681.1 | | |
| α-2,6-sialyltransferase ST6GalNAc II B (Siat7B-related) | Takifugu rubripes | n.d. | AJ634461 | CAG25682.1 | | |
| α-2,6-sialyltransferase ST6GalNAc III (Siat7C) (fragment) | Takifugu rubripes | n.d. | AJ634456 | CAG25678.1 | | |
| α-2,6-sialyltransferase ST6GalNAc IV (siat7D) (fragment) | Takifugu rubripes | 2.4.99.3 | Y17466 AJ646869 | CAB44338.1 CAG26698.1 | Q9W6U6 | |
| α-2,6-sialyltransferase ST6GalNAc V (Siat7E) (fragment) | Takifugu rubripes | n.d. | AJ646873 | CAG26702.1 | | |
| α-2,6-sialyltransferase ST6GalNAc VI (Siat7F) (fragment) | Takifugu rubripes | n.d. | AJ646880 | CAG26709.1 | | |
| α-2,8-sialyltransferase ST8Sia I (Siat 8A) (fragment) | Takifugu rubripes | n.d. | AJ715534 | CAG29373.1 | | |
| α-2,8-sialyltransferase ST8Sia II (Siat 8B) (fragment) | Takifugu rubripes | n.d. | AJ715538 | CAG29377.1 | | |
| α-2,8-sialyltransferase ST8Sia III (Siat 8C) (fragment) | Takifugu rubripes | n.d. | AJ715541 | CAG29380.1 | | |
| α-2,8-sialyltransferase ST8Sia IIIr (Siat 8Cr) | Takifugu rubripes | n.d. | AJ715542 | CAG29381.1 | | |
| α-2,8-sialyltransferase ST8Sia V (Siat 8E) | Takifugu rubripes | n.d. | AJ715547 | CAG29386.1 | | |

FIG. 2K

| Protein | Organism | EC# | GenBank / GenPept | | SwissProt | PDB / 3D |
|---|---|---|---|---|---|---|
| (fragment) | | | | | | |
| α-2,8-sialyltransferase ST8Sia VI (Siat 8F) (fragment) | Takifugu rubripes | n.d. | AJ715549 | CAG29388.1 | | |
| α-2,8-sialyltransferase ST8Sia VIr (Siat 8Fr) | Takifugu rubripes | n.d. | AJ715550 | CAG29389.1 | | |
| α-2,3-sialyltransferase (Siat5-r) | Tetraodon nigroviridis | n.d. | AJ744806 | CAG32842.1 | | |
| α-2,3-sialyltransferase ST3Gal I (Siat4) | Tetraodon nigroviridis | n.d. | AJ744802 | CAG32838.1 | | |
| α-2,3-sialyltransferase ST3Gal III (Siat6) | Tetraodon nigroviridis | n.d. | AJ626822 | CAF25180.1 | | |
| α-2,6-sialyltransferase ST6GalNAc II (Siat7B) | Tetraodon nigroviridis | n.d. | AJ634462 | CAG25683.1 | | |
| α-2,6-sialyltransferase ST6GalNAc V (Siat7E) (fragment) | Tetraodon nigroviridis | n.d. | AJ646879 | CAG26708.1 | | |
| α-2,8-sialyltransferase ST8Sia I (Siat 8A) (fragment) | Tetraodon nigroviridis | n.d. | AJ715536 | CAG29375.1 | | |
| α-2,8-sialyltransferase ST8Sia II (Siat 8B) (fragment) | Tetraodon nigroviridis | n.d. | AJ715537 | CAG29376.1 | | |
| α-2,8-sialyltransferase ST8Sia III (Siat 8C) (fragment) | Tetraodon nigroviridis | n.d. | AJ715539 | CAG29378.1 | | |
| α-2,8-sialyltransferase ST8Sia IIIr (Siat 8Cr) (fragment) | Tetraodon nigroviridis | n.d. | AJ715540 | CAG29379.1 | | |
| α-2,8-sialyltransferase ST8Sia V (Siat 8E) (fragment) | Tetraodon nigroviridis | n.d. | AJ715548 | CAG29387.1 | | |
| α-2,3-sialyltransferase (St3Gal-II) | Xenopus laevis | n.d. | AJ585762 | CAE51386.1 | | |
| α-2,3-sialyltransferase (St3Gal-VI) | Xenopus laevis | n.d. | AJ585766 | CAE51390.1 | | |
| α-2,3-sialyltransferase St3Gal-III (Siat6) | Xenopus laevis | n.d. | AJ585764 AJ626823 | CAE51388.1 CAF25181.1 | | |
| α-2,8-polysialyltransferase | Xenopus laevis | 2.4.99.- | AB007468 | BAA32617.1 | O93234 | |
| α-2,8-sialyltransferase ST8Siα-I (Siat8A;GD3 synthase) | Xenopus laevis | n.d. | AY272056 AY272057 AJ704562 | AAQ16162.1 AAQ16163.1 CAG28695.1 | | |
| Unknown (protein for MGC:81265) | Xenopus laevis | n.d. | BC068760 | AAH68760.1 | | |
| α-2,3-sialyltransferase (3Gal-VI) | Xenopus tropicalis | n.d. | AJ626744 | CAF25054.1 | | |
| α-2,3-sialyltransferase (Siat4c) | Xenopus tropicalis | n.d. | AJ622908 | CAF22058.1 | | |
| α-2,6-sialyltransferase ST6GalNAc V (Siat7E) (fragment) | Xenopus tropicalis | n.d. | AJ646878 | CAG26707.1 | | |
| α-2,8-sialyltransferase ST8Sia III (Siat 8C) (fragment) | Xenopus tropicalis | n.d. | AJ715544 | CAG29383.1 | | |
| β-galactosamide α-2,6-sialyltransferase II (ST6Gal II) | Xenopus tropicalis | n.d. | AJ627628 | CAF29496.1 | | |
| sialyltransferase St8SiaI | Xenopus tropicalis | n.d. | AY652775 | AAT67042 | | |
| poly-α-2,8-sialosyl sialyltransferase (NeuS) | Escherichia coli K1 | 2.4.-.- | M76370 X60598 | AAA24213.1 CAA43053.1 | Q57269 | |
| polysialyltransferase | Escherichia coli K92 | 2.4.-.- | M88479 | AAA24215.1 | Q47404 | |

FIG. 2L

| Protein | Organism | EC# | GenBank / GenPept | | SwissProt | PDB / 3D |
|---|---|---|---|---|---|---|
| α-2,8 polysialyltransferase SiaD | Neisseria meningitidis B1940 | 2.4.-.- | M95053 X78068 | AAA20478.1 CAA54985.1 | Q51281 Q51145 | |
| SynE | Neisseria meningitidis FAM18 | n.d. | U75650 | AAB53842.1 | O06435 | |
| polysialyltransferase (SiaD)(fragment) | Neisseria meningitidis M1019 | n.d. | AY234192 | AAO85290.1 | | |
| SiaD (fragment) | Neisseria meningitidis M209 | n.d. | AY281046 | AAP34769.1 | | |
| SiaD (fragment) | Neisseria meningitidis M3045 | n.d. | AY281044 | AAP34767.1 | | |
| polysialyltransferase (SiaD)(fragment) | Neisseria meningitidis M3315 | n.d. | AY234191 | AAO85289.1 | | |
| SiaD (fragment) | Neisseria meningitidis M3515 | n.d. | AY281047 | AAP34770.1 | | |
| polysialyltransferase (SiaD)(fragment) | Neisseria meningitidis M4211 | n.d. | AY234190 | AAO85288.1 | | |
| SiaD (fragment) | Neisseria meningitidis M4642 | n.d. | AY281048 | AAP34771.1 | | |
| polysialyltransferase (SiaD)(fragment) | Neisseria meningitidis M5177 | n.d. | AY234193 | AAO85291.1 | | |
| SiaD | Neisseria meningitidis M5178 | n.d. | AY281043 | AAP34766.1 | | |
| SiaD (fragment) | Neisseria meningitidis M980 | n.d. | AY281045 | AAP34768.1 | | |
| NMB0067 | Neisseria meningitidis MC58 | n.d. | NC_003112 | NP_273131 | | |
| Lst | Aeromonas punctata Sch3 | n.d. | AF126256 | AAS66624.1 | | |
| ORF2 | Haemophilus influenzae A2 | n.d. | M94855 | AAA24979.1 | | |
| HI1699 | Haemophilus influenzae Rd | n.d. | U32842 NC_000907 | AAC23345.1 NP_439841.1 | Q48211 | |
| α-2,3-sialyltransferase | Neisseria gonorrhoeae F62 | 2.4.99.4 | U60664 | AAC44539.1 AAE67205.1 | P72074 | |
| α-2,3-sialyltransferase | Neisseria meningitidis 126E, NRCC 4010 | 2.4.99.4 | U60662 | AAC44544.2 | | |
| α-2,3-sialyltransferase | Neisseria meningitidis 406Y, NRCC 4030 | 2.4.99.4 | U60661 | AAC44543.1 | | |
| α-2,3-sialyltransferase (NMB0922) | Neisseria meningitidis MC58 | 2.4.99.4 | U60660 AE002443 NC_003112 | AAC44541.1 AAF41330.1 NP_273962.1 | P72097 | |
| NMA1118 | Neisseria meningitidis Z2491 | n.d. | AL162755 NC_003116 | CAB84380.1 NP_283887.1 | Q9JUV5 | |
| PM0508 | Pasteurella multocida PM70 | n.d. | AE006086 NC_002663 | AAK02592.1 NP_245445.1 | Q9CNC4 | |
| WaaH | Salmonella enterica SARB25 | n.d. | AF519787 | AAM82550.1 | Q8KS93 | |
| WaaH | Salmonella enterica SARB3 | n.d. | AF519788 | AAM82551.1 | Q8KS92 | |
| WaaH | Salmonella enterica SARB39 | n.d. | AF519789 | AAM82552.1 | | |
| WaaH | Salmonella enterica SARB53 | n.d. | AF519790 | AAM82553.1 | | |
| WaaH | Salmonella enterica SARB57 | n.d. | AF519791 | AAM82554.1 | Q8KS91 | |
| WaaH | Salmonella enterica SARB71 | n.d. | AF519793 | AAM82556.1 | Q8KS89 | |
| WaaH | Salmonella enterica | n.d. | AF519792 | AAM82555.1 | Q8KS90 | |

FIG. 2M

| Protein | Organism | EC# | GenBank / GenPept | | SwissProt | PDB / 3D |
|---|---|---|---|---|---|---|
| | SARB8 | | | | | |
| WaaH | Salmonella enterica SARC10V | n.d. | AF519779 | AAM88840.1 | Q8KS99 | |
| WaaH (fragment) | Salmonella enterica SARC12 | n.d. | AF519781 | AAM88842.1 | | |
| WaaH (fragment) | Salmonella enterica SARC13I | n.d. | AF519782 | AAM88843.1 | Q8KS98 | |
| WaaH (fragment) | Salmonella enterica SARC14I | n.d. | AF519783 | AAM88844.1 | Q8KS97 | |
| WaaH | Salmonella enterica SARC15II | n.d. | AF519784 | AAM88845.1 | Q8KS96 | |
| WaaH | Salmonella enterica SARC16II | n.d. | AF519785 | AAM88846.1 | Q8KS95 | |
| WaaH (fragment) | Salmonella enterica SARC3I | n.d. | AF519772 | AAM88834.1 | Q8KSA4 | |
| WaaH (fragment) | Salmonella enterica SARC4I | n.d. | AF519773 | AAM88835.1 | Q8KSA3 | |
| WaaH | Salmonella enterica SARC5IIa | n.d. | AF519774 | AAM88836.1 | | |
| WaaH | Salmonella enterica SARC6IIa | n.d. | AF519775 | AAM88837.1 | Q8KSA2 | |
| WaaH | Salmonella enterica SARC8 | n.d. | AF519777 | AAM88838.1 | Q8KSA1 | |
| WaaH | Salmonella enterica SARC9V | n.d. | AF519778 | AAM88839.1 | Q8KSA0 | |
| UDP-glucose : α-1,2-glucosyltransferase (WaaH) | Salmonella enterica subsp. arizonae SARC 5 | 2.4.1.- | AF511116 | AAM48166.1 | | |
| bifunctional α-2,3/-2,8-sialyltransferase (Cst-II) | Campylobacter jejuni ATCC 43449 | n.d. | AF401529 | AAL06004.1 | Q93CZ5 | |
| Cst | Campylobacter jejuni 81-176 | n.d. | AF305571 | AAL09368.1 | | |
| α-2,3-sialyltransferase (Cst-III) | Campylobacter jejuni ATCC 43429 | 2.4.99.- | AY044156 | AAK73183.1 | | |
| α-2,3-sialyltransferase (Cst-III) | Campylobacter jejuni ATCC 43430 | 2.4.99.- | AF400047 | AAK85419.1 | | |
| α-2,3-sialyltransferase (Cst-II) | Campylobacter jejuni ATCC 43432 | 2.4.99.- | AF215659 | AAG43979.1 | Q9F0M9 | |
| α-2,3/8-sialyltransferase (CstII) | Campylobacter jejuni ATCC 43438 | n.d. | AF400048 | AAK91725.1 | Q93MQ0 | |
| α-2,3-sialyltransferase cst-II | Campylobacter jejuni ATCC 43446 | 2.4.99.- | AF167344 | AAF34137.1 | | |
| α-2,3-sialyltransferase (Cst-II) | Campylobacter jejuni ATCC 43456 | 2.4.99.- | AF401528 | AAL05990.1 | Q93D05 | |
| α-2,3-/α-2,8-sialyltransferase (CstII) | Campylobacter jejuni ATCC 43460 | 2.4.99.- | AY044868 | AAK96001.1 | Q938X6 | |
| α-2,3/8-sialyltransferase (Cst-II) | Campylobacter jejuni ATCC 700297 | n.d. | AF216647 | AAL36462.1 | | |
| ORF | Campylobacter jejuni GB11 | n.d. | AY422197 | AAR82875.1 | | |
| α-2,3-sialyltransferase cstIII | Campylobacter jejuni MSC57360 | 2.4.99.- | AF195055 | AAG29922.1 | | |
| α-2,3-sialyltransferase cstIII Cj1140 | Campylobacter jejuni NCTC 11168 | 2.4.99.- | AL139077 NC_002163 | CAB73395.1 NP_282288.1 | Q9PNF4 | |
| α-2,3/α-2,8-sialyltransferase II (cstII) | Campylobacter jejuni O:10 | n.d. | - AX934427 | AAO96669.1 CAF04167.1 | | |
| α-2,3/α-2,8-sialyltransferase II (CstII) | Campylobacter jejuni O:19 | n.d. | AX934431 | CAF04169.1 | | |
| α-2,3/α-2,8-sialyltransferase II (CstII) | Campylobacter jejuni O:36 | n.d. | AX934436 | CAF04171.1 | | |
| α-2,3/α-2,8- | Campylobacter | n.d. | AX934434 | CAF04170.1 | | |

FIG. 2N

| Protein | Organism | EC# | GenBank / GenPept | | SwissProt | PDB / 3D | |
|---|---|---|---|---|---|---|---|
| sialyltransferase II (CstII) | jejuni O:4 | | | | | | |
| α-2,3/α-2,8-sialyltransferase II (CstII) | Campylobacter jejuni O:41 | n.d. | -<br>-<br>AX934429 | AAO96670.1<br>AAT17967.1<br>CAF04168.1 | | | |
| α-2,3-sialyltransferase cst-I | Campylobacter jejuni OH4384 | 2.4.99.- | AF130466<br>- | AAF13495.1<br>AAS36261.1 | Q9RGF1 | | |
| bifunctional α-2,3/-2,8-sialyltransferase (Cst-II) | Campylobacter jejuni OH4384 | 2.4.99.- | AF130984<br>AX934425 | AAF31771.1<br>CAF04166.1 | | 1RO7<br>1RO8 | C<br>A |
| HI0352 (fragment) | Haemophilus influenzae Rd | n.d. | U32720<br>X57315<br>NC_000907 | AAC22013.1<br>CAA40567.1<br>NP_438516.1 | P24324 | | |
| PM1174 | Pasteurella multocida PM70 | n.d. | AE006157<br>NC_002663 | AAK03258.1<br>NP_246111.1 | Q9CLP3 | | |
| Sequence 10 from patent US 6503744 | Unknown. | n.d. | - | AAO96672.1 | | | |
| Sequence 10 from patent US 6699705 | Unknown. | n.d. | - | AAT17969.1 | | | |
| Sequence 12 from patent US 6699705 | Unknown. | n.d. | - | AAT17970.1 | | | |
| Sequence 2 from patent US 6709834 | Unknown. | n.d. | - | AAT23232.1 | | | |
| Sequence 3 from patent US 6503744 | Unknown. | n.d. | - | AAO96668.1 | | | |
| Sequence 3 from patent US 6699705 | Unknown. | n.d. | - | AAT17965.1 | | | |
| Sequence 34 from patent US 6503744 | Unknown. | n.d. | - | AAO96684.1 | | | |
| Sequence 35 from patent US 6503744 (fragment) | Unknown. | n.d. | -<br>- | AAO96685.1<br>AAS36262.1 | | | |
| Sequence 48 from patent US 6699705 | Unknown. | n.d. | - | AAT17988.1 | | | |
| Sequence 5 from patent US 6699705 | Unknown. | n.d. | - | AAT17966.1 | | | |
| Sequence 9 from patent US 6503744 | Unknown. | n.d. | - | AAO96671.1 | | | |

SEQUENCE LISTING

```
<160> NUMBER OF SEQ ID NOS: 360

<210> SEQ ID NO 1
<211> LENGTH: 211
<212> TYPE: PRT
<213> ORGANISM: Homo Sapiens

<400> SEQUENCE: 1

Met Ala Pro Leu Ala Glu Val Gly Gly Phe Leu Gly Gly Leu Glu Gly
1               5                   10                  15

Leu Gly Gln Gln Val Gly Ser His Phe Leu Leu Pro Pro Ala Gly Glu
            20                  25                  30

Arg Pro Pro Leu Leu Gly Glu Arg Arg Ser Ala Ala Glu Arg Ser Ala
        35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210

<210> SEQ ID NO 2
<211> LENGTH: 7
<212> TYPE: PRT
<213> ORGANISM: Artificial Sequence
<220> FEATURE:
<223> OTHER INFORMATION: FGF mutation motif

<400> SEQUENCE: 2

Met Ala Pro Leu Ala Glu Val
1               5

<210> SEQ ID NO 3
<211> LENGTH: 23
<212> TYPE: PRT
<213> ORGANISM: Artificial Sequence
```

```
<220> FEATURE:
<223> OTHER INFORMATION: FGF mutation motif

<400> SEQUENCE: 3

Gln Val Gly Ser His Phe Leu Leu Pro Pro Ala Gly Glu Arg Pro Pro
1               5                   10                  15

Leu Leu Gly Glu Arg Arg Ser
            20

<210> SEQ ID NO 4
<211> LENGTH: 18
<212> TYPE: PRT
<213> ORGANISM: Artificial Sequence
<220> FEATURE:
<223> OTHER INFORMATION: FGF mutation motif

<400> SEQUENCE: 4

Ala Ala Glu Arg Ser Ala Arg Gly Gly Pro Gly Ala Ala Gln Leu Ala
1               5                   10                  15

His Leu

<210> SEQ ID NO 5
<211> LENGTH: 18
<212> TYPE: PRT
<213> ORGANISM: Artificial Sequence
<220> FEATURE:
<223> OTHER INFORMATION: FGF mutation motif

<400> SEQUENCE: 5

Thr Gly Phe His Leu Gln Ile Leu Pro Asp Gly Ser Val Gln Gly Thr
1               5                   10                  15

Arg Gln

<210> SEQ ID NO 6
<211> LENGTH: 16
<212> TYPE: PRT
<213> ORGANISM: Artificial Sequence
<220> FEATURE:
<223> OTHER INFORMATION: FGF mutation motif

<400> SEQUENCE: 6

Leu Asn Lys Asp Gly Thr Pro Arg Asp Gly Ala Arg Ser Lys Arg His
1               5                   10                  15

<210> SEQ ID NO 7
<211> LENGTH: 22
<212> TYPE: PRT
<213> ORGANISM: Artificial Sequence
<220> FEATURE:
<223> OTHER INFORMATION: FGF mutation motif

<400> SEQUENCE: 7

Phe Thr His Phe Leu Pro Arg Pro Val Asp Pro Glu Arg Val Pro Glu
1               5                   10                  15

Leu Tyr Lys Asp Leu Leu
            20

<210> SEQ ID NO 8
<211> LENGTH: 4
<212> TYPE: PRT
<213> ORGANISM: Artificial Sequence
<220> FEATURE:
<223> OTHER INFORMATION: FGF mutation motif

<400> SEQUENCE: 8
```

Leu Met Tyr Thr
1

<210> SEQ ID NO 9
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 9

Met Ala Pro Thr Pro Leu Ala Glu Val
1               5

<210> SEQ ID NO 10
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 10

Met Val Thr Pro Leu Ala Glu Val
1               5

<210> SEQ ID NO 11
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 11

Met Ala Pro Thr Thr Glu Val
1               5

<210> SEQ ID NO 12
<211> LENGTH: 13
<212> TYPE: PRT
<213> ORGANISM: Artificial Sequence
<220> FEATURE:
<223> OTHER INFORMATION: FGF mutation sequence

<400> SEQUENCE: 12

Met Ala Pro Thr Gln Gly Ala Met Pro Leu Ala Glu Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 13

Met Ala Pro Thr Ser Ser Leu Ala Glu Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 14

```
Met Ala Pro Thr Ala Leu Pro Leu Ala Glu Val
1               5                   10

<210> SEQ ID NO 15
<211> LENGTH: 15
<212> TYPE: PRT
<213> ORGANISM: Artificial Sequence
<220> FEATURE:
<223> OTHER INFORMATION: FGF mutation motif

<400> SEQUENCE: 15

Val Gly Ser His Phe Leu Leu Pro Pro Ala Gly Glu Arg Pro Pro
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: FGF mutation motif

<400> SEQUENCE: 16

Pro Pro Ala Gly Glu Arg Pro Pro
1               5

<210> SEQ ID NO 17
<211> LENGTH: 10
<212> TYPE: PRT
<213> ORGANISM: Artificial Sequence
<220> FEATURE:
<223> OTHER INFORMATION: FGF mutation motif

<400> SEQUENCE: 17

Pro Pro Pro Leu Leu Gly Glu Arg Arg Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 18

Thr Glu Thr Pro Pro Ala Gly Glu Arg Pro Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: FGF mutation sequence

<400> SEQUENCE: 19

Gly Thr Glu Thr Pro Pro Ala Gly Glu Arg Pro Pro
1               5                   10

<210> SEQ ID NO 20
<211> LENGTH: 13
<212> TYPE: PRT
<213> ORGANISM: Artificial Sequence
<220> FEATURE:
<223> OTHER INFORMATION: FGF mutation sequence

<400> SEQUENCE: 20

Val Gly Thr Glu Thr Pro Pro Ala Gly Glu Arg Pro Pro
```

```
<210> SEQ ID NO 21
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 21

Thr Gly Thr Pro Pro Ala Glu Glu Arg Pro Pro
1               5                   10

<210> SEQ ID NO 22
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 22

Thr Ala Thr Pro Pro Ala Glu Glu Arg Pro Pro
1               5                   10

<210> SEQ ID NO 23
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 23

Pro Pro Thr Gly Glu Ala Pro Pro
1               5

<210> SEQ ID NO 24
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 24

Pro Pro Thr Gly Glu Val Pro Pro
1               5

<210> SEQ ID NO 25
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 25

Pro Pro Thr Gln Gly Ala Pro Pro
1               5

<210> SEQ ID NO 26
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 26

Pro Pro Ala Thr Val Ala Pro Pro
1               5
```

```
<210> SEQ ID NO 27
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 27

Pro Pro Ala Thr Ile Leu Pro Pro
1               5

<210> SEQ ID NO 28
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 28

Pro Pro Ala Gly Thr Ala Pro Pro
1               5

<210> SEQ ID NO 29
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 29

Pro Pro Thr Gln Gly Ala Met Pro Pro
1               5

<210> SEQ ID NO 30
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 30

Pro Pro Gly Ser Thr Ala Pro Pro
1               5

<210> SEQ ID NO 31
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 31

Pro Pro Ala Gly Thr Ser Pro Pro
1               5

<210> SEQ ID NO 32
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 32

Pro Pro Ala Gly Glu Thr Pro Pro
1               5
```

<210> SEQ ID NO 33
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 33

Pro Pro Ala Thr Glu Thr Pro Pro
1               5

<210> SEQ ID NO 34
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 34

Pro Pro Gly Thr Glu Thr Pro Pro
1               5

<210> SEQ ID NO 35
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 35

Pro Pro Thr Gly Glu Arg Pro Pro
1               5

<210> SEQ ID NO 36
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 36

Pro Pro Thr Gln Gly Ala Met Pro
1               5

<210> SEQ ID NO 37
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 37

Pro Pro Thr Gln Gly Ala Met Arg Ser
1               5

<210> SEQ ID NO 38
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 38

Pro Pro Thr Gln Gly Ala Met Ala Ser
1               5

```
<210> SEQ ID NO 39
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 39

Pro Pro Thr Gln Gly Ala Met Phe Ser
1               5

<210> SEQ ID NO 40
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 40

Pro Pro Thr Ser Ser Ser Thr Arg Ser
1               5

<210> SEQ ID NO 41
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 41

Pro Pro Thr Ser Ser Ser Thr Lys Ser
1               5

<210> SEQ ID NO 42
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 42

Pro Pro Thr Gly Glu Arg Arg Ser
1               5

<210> SEQ ID NO 43
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 43

Pro Pro Thr Thr Gly Val Arg Arg Ser
1               5

<210> SEQ ID NO 44
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 44

Pro Pro Thr Thr Gly Glu Ala Arg Ser
1               5

<210> SEQ ID NO 45
```

```
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 45

Pro Pro Thr Ala Gly Glu Arg Arg Ser
1               5

<210> SEQ ID NO 46
<211> LENGTH: 7
<212> TYPE: PRT
<213> ORGANISM: Artificial Sequence
<220> FEATURE:
<223> OTHER INFORMATION: FGF mutation motif

<400> SEQUENCE: 46

Arg Ser Ala Arg Gly Gly Pro
1               5

<210> SEQ ID NO 47
<211> LENGTH: 7
<212> TYPE: PRT
<213> ORGANISM: Artificial Sequence
<220> FEATURE:
<223> OTHER INFORMATION: FGF mutation motif

<400> SEQUENCE: 47

Pro Gly Ala Ala Gln Leu Ala
1               5

<210> SEQ ID NO 48
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 48

Arg Ser Ala Thr Glu Thr Pro
1               5

<210> SEQ ID NO 49
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 49

Arg Ser Gly Thr Glu Thr Pro
1               5

<210> SEQ ID NO 50
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 50

Arg Ser Gly Thr Glu Thr Pro
1               5

<210> SEQ ID NO 51
<211> LENGTH: 7
```

```
<212> TYPE: PRT
<213> ORGANISM: Artificial Sequence
<220> FEATURE:
<223> OTHER INFORMATION: FGF mutation sequence

<400> SEQUENCE: 51

Arg Val Gly Thr Glu Thr Pro
1               5

<210> SEQ ID NO 52
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 52

Gly Val Gly Thr Glu Thr Pro
1               5

<210> SEQ ID NO 53
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 53

Gly Ser Ala Thr Glu Thr Pro
1               5

<210> SEQ ID NO 54
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 54

Gly Val Gly Val Thr Glu Thr Pro
1               5

<210> SEQ ID NO 55
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 55

Gly Val Thr Glu Thr Pro
1               5

<210> SEQ ID NO 56
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 56

Gln Thr Glu Leu Pro
1               5

<210> SEQ ID NO 57
<211> LENGTH: 6
<212> TYPE: PRT
```

```
<213> ORGANISM: Artificial Sequence
<220> FEATURE:
<223> OTHER INFORMATION: FGF mutation sequence

<400> SEQUENCE: 57

Gly Val Thr Ser Ala Pro
1               5

<210> SEQ ID NO 58
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 58

Ser Val Val Thr Pro
1               5

<210> SEQ ID NO 59
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 59

Pro Thr Gly Ala Gln Leu Ala
1               5

<210> SEQ ID NO 60
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 60

Pro Thr Gln Gly Ala Met Pro
1               5

<210> SEQ ID NO 61
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 61

Pro Thr Gln Gly Ala Met Ala
1               5

<210> SEQ ID NO 62
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 62

Pro Thr Thr Ala Gln Leu Ala
1               5

<210> SEQ ID NO 63
<211> LENGTH: 7
<212> TYPE: PRT
<213> ORGANISM: Artificial Sequence
```

<220> FEATURE:
<223> OTHER INFORMATION: FGF mutation sequence

<400> SEQUENCE: 63

Pro Gly Ala Thr Gln Leu Ala
1               5

<210> SEQ ID NO 64
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 64

Pro Thr Ser Ser Ser Thr Ala
1               5

<210> SEQ ID NO 65
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 65

Pro Thr Ser Ser Ser Leu Ala
1               5

<210> SEQ ID NO 66
<211> LENGTH: 6
<212> TYPE: PRT
<213> ORGANISM: Artificial Sequence
<220> FEATURE:
<223> OTHER INFORMATION: FGF mutation motif

<400> SEQUENCE: 66

His Leu Gln Ile Leu Pro
1               5

<210> SEQ ID NO 67
<211> LENGTH: 8
<212> TYPE: PRT
<213> ORGANISM: Artificial Sequence
<220> FEATURE:
<223> OTHER INFORMATION: FGF mutation motif

<400> SEQUENCE: 67

Pro Asp Gly Ser Val Gln Gly Thr
1               5

<210> SEQ ID NO 68
<211> LENGTH: 4
<212> TYPE: PRT
<213> ORGANISM: Artificial Sequence
<220> FEATURE:
<223> OTHER INFORMATION: FGF mutation motif

<400> SEQUENCE: 68

Pro Asn Gly Ser
1

<210> SEQ ID NO 69
<211> LENGTH: 5
<212> TYPE: PRT
<213> ORGANISM: Artificial Sequence
<220> FEATURE:

<223> OTHER INFORMATION: FGF mutation sequence

<400> SEQUENCE: 69

Gln Thr Glu Leu Pro
1               5

<210> SEQ ID NO 70
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 70

Leu Ile Val Thr Pro
1               5

<210> SEQ ID NO 71
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 71

Leu Thr Glu Leu Pro
1               5

<210> SEQ ID NO 72
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 72

Leu Thr Glu Leu Pro
1               5

<210> SEQ ID NO 73
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 73

Gly Val Thr Ser Ala Pro
1               5

<210> SEQ ID NO 74
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 74

His Leu Thr Glu Thr Pro
1               5

<210> SEQ ID NO 75
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 75

Val Leu Thr Glu Thr Pro
1               5

<210> SEQ ID NO 76
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 76

Val Gly Thr Glu Thr Pro
1               5

<210> SEQ ID NO 77
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 77

Val Gly Val Gly Thr Glu Thr Pro
1               5

<210> SEQ ID NO 78
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 78

Val Thr Ser Ala Pro
1               5

<210> SEQ ID NO 79
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 79

Val Ser Thr Pro
1

<210> SEQ ID NO 80
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 80

Glu Ala Thr Pro
1

<210> SEQ ID NO 81
<211> LENGTH: 7
<212> TYPE: PRT
<213> ORGANISM: Artificial Sequence
<220> FEATURE:
<223> OTHER INFORMATION: FGF mutation sequence

```
<400> SEQUENCE: 81

Pro Thr Gly Ser Val Gly Thr
1               5

<210> SEQ ID NO 82
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 82

Pro Thr Gln Gly Val Gln Gly Thr
1               5

<210> SEQ ID NO 83
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 83

Pro Thr Gly Ser Val Gly Pro Gly Thr
1               5

<210> SEQ ID NO 84
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 84

Pro Thr Gln Gly Ala Met Pro Gly Thr
1               5

<210> SEQ ID NO 85
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 85

Pro Thr Thr Ser Val Gln Gly Thr
1               5

<210> SEQ ID NO 86
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 86

Pro Thr Thr Ala Val Gln Gly Thr
1               5

<210> SEQ ID NO 87
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 87
```

```
Ile Leu Pro Asn Gly Ser Val His
1               5

<210> SEQ ID NO 88
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 88

Ile Phe Pro Asn Gly Ser Val
1               5

<210> SEQ ID NO 89
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 89

Pro Asn Gly Thr
1

<210> SEQ ID NO 90
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 90

Leu Pro Asn Gly Thr Val His
1               5

<210> SEQ ID NO 91
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 91

Pro Asn Gly Thr Val
1               5

<210> SEQ ID NO 92
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 92

Ile Leu Pro Asn Gly Thr
1               5

<210> SEQ ID NO 93
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 93
```

```
Gln Ile Leu Pro Asn Gly Thr
1               5

<210> SEQ ID NO 94
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 94

Gln Ile Leu Pro Asn Gly Thr Val His
1               5

<210> SEQ ID NO 95
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 95

Leu Asn Val Thr Glu Thr Pro Arg Asp Gly Ala Arg Ser Lys Arg His
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 96

Leu Asn Val Thr Glu Thr Pro Asp Asp Gly Ala Arg Ser Lys Arg His
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 97

Leu Asn Val Thr Glu Thr Pro Leu Asp Gly Ala Arg Ser Lys Arg His
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 98

Leu Asn Ala Ile Thr Thr Pro Arg Asp Gly Ala Arg Ser Lys Arg His
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 99

Leu Asn Ala Ile Thr Thr Pro Leu Asp Gly Ala Arg Ser Lys Arg His
```

```
<210> SEQ ID NO 100
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 100

Leu Asn Gln Glu Ala Thr Pro Leu Asp Gly Ala Arg Ser Lys Arg His
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 101

Leu Asn Gln Thr Glu Leu Pro Leu Asp Gly Ala Arg Ser Lys Arg His
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 102

Leu Asn Gln Thr Glu Leu Pro Ala Asp Gly Ala Arg Ser Lys Arg His
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 103

Leu Asn Lys Asp Gly Thr Pro Thr Asp Gly Ala Arg Ser Lys Arg His
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 104

Leu Asn Lys Asp Gly Thr Pro Thr Ser Gly Ala Arg Ser Lys Arg His
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 105

Leu Asn Lys Asp Gly Thr Pro Thr Asp Gly Ala Ala Ser Lys Arg His
1               5                   10                  15
```

```
<210> SEQ ID NO 106
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 106

Leu Asn Lys Asp Gly Thr Pro Thr Ser Gly Ala Ala Ser Lys Arg His
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 107

Leu Asn Lys Asp Gly Thr Pro Thr Gln Gly Ala Met Pro Lys Arg His
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 108

Leu Asn Lys Asp Gly Thr Pro Thr Gln Gly Ala Met Ser Lys Arg His
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 109

Leu Asn Lys Asp Gly Thr Pro Thr Thr Thr Ala Arg Ser Lys Arg His
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: FGF mutation motif

<400> SEQUENCE: 110

Leu Pro Arg Pro Val Asp Pro Glu Arg Val Pro Glu Leu Tyr Lys Asp
1               5                   10                  15

<210> SEQ ID NO 111
<211> LENGTH: 10
<212> TYPE: PRT
<213> ORGANISM: Artificial Sequence
<220> FEATURE:
<223> OTHER INFORMATION: FGF mutation motif

<400> SEQUENCE: 111

Pro Glu Arg Val Pro Glu Leu Tyr Lys Asp
1               5                   10
```

```
<210> SEQ ID NO 112
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 112

Leu Pro Ala Pro Thr Asp Pro Glu Arg Val Pro Glu Leu Tyr Lys Asp
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 113

Leu Pro Asn Pro Thr Ala Pro Glu Arg Val Pro Glu Leu Tyr Lys Asp
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 114

Leu Pro Arg Pro Thr Ala Pro Glu Arg Val Pro Glu Leu Tyr Lys Asp
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 115

Leu Pro Ala Pro Thr Gln Pro Glu Arg Val Pro Glu Leu Tyr Lys Asp
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 116

Leu Pro Thr Pro Val Asp Pro Glu Arg Val Pro Glu Leu Tyr Lys Asp
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 117

Leu Pro Thr Pro Ser Asp Pro Glu Arg Val Pro Glu Leu Tyr Lys Asp
1               5                   10                  15
```

```
<210> SEQ ID NO 118
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 118

Leu Pro Val Pro Thr Asp Pro Glu Arg Val Pro Glu Leu Tyr Lys Asp
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 119

Leu Pro Thr Pro Ala Asp Pro Glu Arg Val Pro Glu Leu Tyr Lys Asp
1               5                   10                  15

<210> SEQ ID NO 120
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 120

Pro Thr Ala Ser Pro Glu Leu Tyr Lys Asp
1               5                   10

<210> SEQ ID NO 121
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 121

Pro Thr Ala Ser Pro Ala Leu Tyr Lys Asp
1               5                   10

<210> SEQ ID NO 122
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 122

Pro Asn Thr Leu Pro Glu Leu Tyr Lys Asp
1               5                   10

<210> SEQ ID NO 123
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 123

Pro Glu Thr Val Pro Glu Leu Tyr Lys Asp
1               5                   10

<210> SEQ ID NO 124
```

```
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 124

Pro Gln Glu Thr Pro Glu Leu Tyr Lys Asp
1               5                   10

<210> SEQ ID NO 125
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 125

Pro Thr Gln Gly Pro Glu Leu Tyr Lys Asp
1               5                   10

<210> SEQ ID NO 126
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 126

Pro Thr Gln Gly Pro Ala Leu Tyr Lys Asp
1               5                   10

<210> SEQ ID NO 127
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 127

Pro Gln Gly Thr Pro Ala Leu Tyr Lys Asp
1               5                   10

<210> SEQ ID NO 128
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 128

Pro Ala Thr Glu Pro Glu Leu Tyr Lys Asp
1               5                   10

<210> SEQ ID NO 129
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 129

Pro Thr Thr Gln Pro Glu Leu Tyr Lys Asp
1               5                   10

<210> SEQ ID NO 130
<211> LENGTH: 10
```

```
<212> TYPE: PRT
<213> ORGANISM: Artificial Sequence
<220> FEATURE:
<223> OTHER INFORMATION: FGF mutation sequence

<400> SEQUENCE: 130

Pro Thr Thr Glu Pro Glu Leu Tyr Lys Asp
1               5                   10

<210> SEQ ID NO 131
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 131

Pro Glu Arg Val Pro Thr Leu Tyr Lys Asp
1               5                   10

<210> SEQ ID NO 132
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 132

Pro Glu Arg Val Pro Thr Leu Tyr Ala Asp
1               5                   10

<210> SEQ ID NO 133
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 133

Pro Glu Arg Val Pro Thr Gln Gly Ala Asp
1               5                   10

<210> SEQ ID NO 134
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 134

Pro Glu Arg Val Pro Thr Gln Gly Ala Met Pro
1               5                   10

<210> SEQ ID NO 135
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 135

Pro Glu Arg Val Pro Thr Gln Gly Ala
1               5

<210> SEQ ID NO 136
<211> LENGTH: 6
<212> TYPE: PRT
```

```
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
      leucine, and asparagine
<220> FEATURE:
<221> NAME/KEY: misc_feature
<222> LOCATION: (6)..(6)
<223> OTHER INFORMATION: Xaa can be any naturally occurring amino acid

<400> SEQUENCE: 136

Leu Met Tyr Thr Pro Xaa
1               5

<210> SEQ ID NO 137
<211> LENGTH: 6
<212> TYPE: PRT
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
      leucine, and asparagine
<220> FEATURE:
<221> NAME/KEY: misc_feature
<222> LOCATION: (6)..(6)
<223> OTHER INFORMATION: Xaa can be any naturally occurring amino acid

<400> SEQUENCE: 137

Leu Thr Glu Thr Pro Xaa
1               5

<210> SEQ ID NO 138
<211> LENGTH: 6
<212> TYPE: PRT
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
      leucine, and asparagine
<220> FEATURE:
<221> NAME/KEY: misc_feature
<222> LOCATION: (6)..(6)
<223> OTHER INFORMATION: Xaa can be any naturally occurring amino acid

<400> SEQUENCE: 138

Val Thr Glu Thr Pro Xaa
1               5

<210> SEQ ID NO 139
<211> LENGTH: 8
<212> TYPE: PRT
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
      leucine, and asparagine
<220> FEATURE:
<221> NAME/KEY: misc_feature
<222> LOCATION: (8)..(8)
<223> OTHER INFORMATION: Xaa can be any naturally occurring amino acid

<400> SEQUENCE: 139

Gly Val Thr Glu Thr Pro Leu Xaa
1               5
```

```
<210> SEQ ID NO 140
<211> LENGTH: 13
<212> TYPE: PRT
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
      leucine, and asparagine
<220> FEATURE:
<221> NAME/KEY: misc_feature
<222> LOCATION: (13)..(13)
<223> OTHER INFORMATION: Xaa can be any naturally occurring amino acid

<400> SEQUENCE: 140

Pro Glu Leu Tyr Val Gly Val Thr Cys Thr Pro Leu Xaa
1               5                   10

<210> SEQ ID NO 141
<211> LENGTH: 5
<212> TYPE: PRT
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
      leucine, and asparagine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 141

Leu Met Tyr Thr Xaa
1               5

<210> SEQ ID NO 142
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 142

Leu Met Tyr Thr Pro Thr Ala Ser Pro
1               5

<210> SEQ ID NO 143
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 143

Leu Met Tyr Thr Pro Ala Thr Glu Pro
1               5

<210> SEQ ID NO 144
<211> LENGTH: 8
<212> TYPE: PRT
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
```

```
              leucine, and asparagine
<220> FEATURE:
<221> NAME/KEY: misc_feature
<222> LOCATION: (8)..(8)
<223> OTHER INFORMATION: Xaa can be any naturally occurring amino acid

<400> SEQUENCE: 144

Leu Met Tyr Thr Pro Thr Pro Xaa
1               5

<210> SEQ ID NO 145
<211> LENGTH: 9
<212> TYPE: PRT
<213> ORGANISM: Artificial Sequence
<220> FEATURE:
<223> OTHER INFORMATION: FGF mutation sequence
<220> FEATURE:
<221> NAME/KEY: misc_feature
<223> OTHER INFORMATION: X is selected from OH, NH2, glycine, alanine,
              leucine, and asparagine
<220> FEATURE:
<221> NAME/KEY: misc_feature
<222> LOCATION: (9)..(9)
<223> OTHER INFORMATION: Xaa can be any naturally occurring amino acid

<400> SEQUENCE: 145

Leu Met Tyr Thr Pro Thr Ala Pro Xaa
1               5

<210> SEQ ID NO 146
<211> LENGTH: 182
<212> TYPE: PRT
<213> ORGANISM: Homo Sapiens

<400> SEQUENCE: 146

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 147
<211> LENGTH: 8
```

```
<212> TYPE: PRT
<213> ORGANISM: Artificial Sequence
<220> FEATURE:
<223> OTHER INFORMATION: FGF mutation motif

<400> SEQUENCE: 147

Met His Pro Ile Pro Asp Ser Ser
1               5

<210> SEQ ID NO 148
<211> LENGTH: 5
<212> TYPE: PRT
<213> ORGANISM: Artificial Sequence
<220> FEATURE:
<223> OTHER INFORMATION: FGF mutation motif

<400> SEQUENCE: 148

Pro Leu Leu Gln Phe
1               5

<210> SEQ ID NO 149
<211> LENGTH: 9
<212> TYPE: PRT
<213> ORGANISM: Artificial Sequence
<220> FEATURE:
<223> OTHER INFORMATION: FGF mutation motif

<400> SEQUENCE: 149

Ala Asp Gln Ser Pro Glu Ser Leu Leu
1               5

<210> SEQ ID NO 150
<211> LENGTH: 6
<212> TYPE: PRT
<213> ORGANISM: Artificial Sequence
<220> FEATURE:
<223> OTHER INFORMATION: FGF mutation motif

<400> SEQUENCE: 150

Lys Pro Gly Val Ile Gln
1               5

<210> SEQ ID NO 151
<211> LENGTH: 6
<212> TYPE: PRT
<213> ORGANISM: Artificial Sequence
<220> FEATURE:
<223> OTHER INFORMATION: FGF mutation motif

<400> SEQUENCE: 151

Arg Pro Asp Gly Ala Leu
1               5

<210> SEQ ID NO 152
<211> LENGTH: 6
<212> TYPE: PRT
<213> ORGANISM: Artificial Sequence
<220> FEATURE:
<223> OTHER INFORMATION: FGF mutation motif

<400> SEQUENCE: 152

Ser Leu His Phe Asp Pro
1               5

<210> SEQ ID NO 153
<211> LENGTH: 30
<212> TYPE: PRT
```

-continued

```
<213> ORGANISM: Artificial Sequence
<220> FEATURE:
<223> OTHER INFORMATION: FGF mutation motif

<400> SEQUENCE: 153

Ala His Gly Leu Pro Leu His Leu Pro Gly Asn Lys Ser Pro His Arg
1               5                   10                  15

Asp Pro Ala Pro Arg Gly Pro Ala Arg Phe Leu Pro Leu Pro
            20                  25                  30

<210> SEQ ID NO 154
<211> LENGTH: 9
<212> TYPE: PRT
<213> ORGANISM: Artificial Sequence
<220> FEATURE:
<223> OTHER INFORMATION: FGF mutation motif

<400> SEQUENCE: 154

Glu Pro Pro Gly Ile Leu Ala Pro Gln
1               5

<210> SEQ ID NO 155
<211> LENGTH: 7
<212> TYPE: PRT
<213> ORGANISM: Artificial Sequence
<220> FEATURE:
<223> OTHER INFORMATION: FGF mutation motif

<400> SEQUENCE: 155

Asp Val Gly Ser Ser Asp Pro
1               5

<210> SEQ ID NO 156
<211> LENGTH: 6
<212> TYPE: PRT
<213> ORGANISM: Artificial Sequence
<220> FEATURE:
<223> OTHER INFORMATION: FGF mutation motif

<400> SEQUENCE: 156

Leu Ser Met Val Gly Pro
1               5

<210> SEQ ID NO 157
<211> LENGTH: 10
<212> TYPE: PRT
<213> ORGANISM: Artificial Sequence
<220> FEATURE:
<223> OTHER INFORMATION: FGF mutation motif

<400> SEQUENCE: 157

Ser Gln Gly Arg Ser Pro Ser Tyr Ala Ser
1               5                   10

<210> SEQ ID NO 158
<211> LENGTH: 3
<212> TYPE: PRT
<213> ORGANISM: Artificial Sequence
<220> FEATURE:
<223> OTHER INFORMATION: FGF mutation motif

<400> SEQUENCE: 158

Met His Pro
1

<210> SEQ ID NO 159
```

```
<211> LENGTH: 5
<212> TYPE: PRT
<213> ORGANISM: Artificial Sequence
<220> FEATURE:
<223> OTHER INFORMATION: FGF mutation motif

<400> SEQUENCE: 159

Met His Pro Ile Pro
1               5

<210> SEQ ID NO 160
<211> LENGTH: 4
<212> TYPE: PRT
<213> ORGANISM: Artificial Sequence
<220> FEATURE:
<223> OTHER INFORMATION: FGF mutation motif

<400> SEQUENCE: 160

Pro Asp Ser Ser
1

<210> SEQ ID NO 161
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 161

Met Val Thr Pro
1

<210> SEQ ID NO 162
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 162

Met Gln Thr Pro
1

<210> SEQ ID NO 163
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 163

Met Ala Thr Pro
1

<210> SEQ ID NO 164
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 164

Met Ile Ala Thr Pro
1               5

<210> SEQ ID NO 165
<211> LENGTH: 5
```

```
<212> TYPE: PRT
<213> ORGANISM: Artificial Sequence
<220> FEATURE:
<223> OTHER INFORMATION: FGF mutation sequence

<400> SEQUENCE: 165

Met Phe Pro Thr Pro
1               5

<210> SEQ ID NO 166
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 166

Met His Pro Thr Pro
1               5

<210> SEQ ID NO 167
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 167

Met Ala Pro Thr Pro
1               5

<210> SEQ ID NO 168
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 168

Met Phe Pro Ser Pro
1               5

<210> SEQ ID NO 169
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 169

Met His Pro Ser Pro
1               5

<210> SEQ ID NO 170
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 170

Met Ala Pro Ser Pro
1               5

<210> SEQ ID NO 171
<211> LENGTH: 5
<212> TYPE: PRT
```

```
<213> ORGANISM: Artificial Sequence
<220> FEATURE:
<223> OTHER INFORMATION: FGF mutation sequence

<400> SEQUENCE: 171

Met Ser Pro Thr Pro
1               5

<210> SEQ ID NO 172
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 172

Pro Thr Ser Ser
1

<210> SEQ ID NO 173
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 173

Pro Thr Gln Ala
1

<210> SEQ ID NO 174
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 174

Pro Thr Ala Gln
1

<210> SEQ ID NO 175
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 175

Pro Thr Ile Glu
1

<210> SEQ ID NO 176
<211> LENGTH: 4
<212> TYPE: PRT
<213> ORGANISM: Artificial Sequence
<220> FEATURE:
<223> OTHER INFORMATION: FGF mutation sequence

<400> SEQUENCE: 176

Pro Ser Ser Ser
1

<210> SEQ ID NO 177
<211> LENGTH: 5
<212> TYPE: PRT
<213> ORGANISM: Artificial Sequence
```

```
<220> FEATURE:
<223> OTHER INFORMATION: FGF mutation sequence

<400> SEQUENCE: 177

Pro Thr Thr Gln Phe
1               5

<210> SEQ ID NO 178
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 178

Pro Thr Ile Asn Thr
1               5

<210> SEQ ID NO 179
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 179

Pro Thr Gln Gly Ala
1               5

<210> SEQ ID NO 180
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 180

Pro Thr Gln Gly Phe
1               5

<210> SEQ ID NO 181
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 181

Pro Thr Thr Val Ser
1               5

<210> SEQ ID NO 182
<211> LENGTH: 5
<212> TYPE: PRT
<213> ORGANISM: Artificial Sequence
<220> FEATURE:
<223> OTHER INFORMATION: FGF mutation sequence

<400> SEQUENCE: 182

Pro Thr Gln Ala Phe
1               5

<210> SEQ ID NO 183
<211> LENGTH: 9
<212> TYPE: PRT
<213> ORGANISM: Artificial Sequence
<220> FEATURE:
```

```
<223> OTHER INFORMATION: FGF mutation sequence

<400> SEQUENCE: 183

Ala Asp Gln Ser Pro Thr Ser Leu Leu
1               5

<210> SEQ ID NO 184
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 184

Ala Asp Gln Ser Pro Thr Thr Val Ser
1               5

<210> SEQ ID NO 185
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 185

Ala Asp Gln Ser Pro Thr Ile Asn Thr
1               5

<210> SEQ ID NO 186
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 186

Ala Asp Gln Ser Pro Thr Gln Ala Leu
1               5

<210> SEQ ID NO 187
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 187

Ala Asp Gln Ser Pro Thr Gln Gly Ala
1               5

<210> SEQ ID NO 188
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 188

Ala Asp Gln Ser Pro Thr Gln Ala Leu
1               5

<210> SEQ ID NO 189
<211> LENGTH: 9
<212> TYPE: PRT
<213> ORGANISM: Artificial Sequence
<220> FEATURE:
<223> OTHER INFORMATION: FGF mutation sequence
```

<400> SEQUENCE: 189

Ala Thr Gln Ser Pro Glu Ser Leu Leu
1               5

<210> SEQ ID NO 190
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 190

Ala Thr Glu Ser Pro Glu Ser Leu Leu
1               5

<210> SEQ ID NO 191
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 191

Ala Thr Glu Thr Pro Glu Ser Leu Leu
1               5

<210> SEQ ID NO 192
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 192

Val Thr Gln Ser Pro Glu Ser Leu Leu
1               5

<210> SEQ ID NO 193
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 193

Val Thr Glu Thr Pro Glu Ser Leu Leu
1               5

<210> SEQ ID NO 194
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 194

Ala Thr Glu Ser Pro Ala Ser Leu Leu
1               5

<210> SEQ ID NO 195
<211> LENGTH: 6
<212> TYPE: PRT
<213> ORGANISM: Artificial Sequence
<220> FEATURE:
<223> OTHER INFORMATION: FGF mutation sequence

```
<400> SEQUENCE: 195

Ser Pro Thr Val Ile Gln
1               5

<210> SEQ ID NO 196
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 196

Ala Pro Thr Val Ile Gln
1               5

<210> SEQ ID NO 197
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 197

Ser Pro Thr Thr Val Ser
1               5

<210> SEQ ID NO 198
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 198

Ser Pro Thr Ile Asn Thr
1               5

<210> SEQ ID NO 199
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 199

Ser Pro Thr Gln Ala Gln
1               5

<210> SEQ ID NO 200
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 200

Ser Pro Thr Gln Gly Ala
1               5

<210> SEQ ID NO 201
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 201
```

Ser Pro Thr Val Ile Ala
1               5

<210> SEQ ID NO 202
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 202

Ala Pro Thr Thr Val Ser
1               5

<210> SEQ ID NO 203
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 203

Ala Pro Thr Ile Asn Thr
1               5

<210> SEQ ID NO 204
<211> LENGTH: 6
<212> TYPE: PRT
<213> ORGANISM: Artificial Sequence
<220> FEATURE:
<223> OTHER INFORMATION: FGF mutation motif

<400> SEQUENCE: 204

Ser Pro Thr Gly Ala Leu
1               5

<210> SEQ ID NO 205
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 205

Ala Pro Thr Gly Ala Leu
1               5

<210> SEQ ID NO 206
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 206

Ser Pro Thr Ile Asn Thr
1               5

<210> SEQ ID NO 207
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 207

Ser Pro Thr Thr Val Ser
1               5

<210> SEQ ID NO 208
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 208

Ser Pro Thr Gln Ala Leu
1               5

<210> SEQ ID NO 209
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 209

Ala Pro Thr Gln Ala Leu
1               5

<210> SEQ ID NO 210
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 210

Ser Pro Thr Gln Gly Ala
1               5

<210> SEQ ID NO 211
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 211

Ser Pro Thr Gln Gly Ala Met
1               5

<210> SEQ ID NO 212
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 212

Ser Leu Thr Phe Thr Pro
1               5

<210> SEQ ID NO 213
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 213

Ser Leu Thr Glu Thr Pro

```
1               5

<210> SEQ ID NO 214
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 214

Ser Val Thr Glu Thr Pro
1               5

<210> SEQ ID NO 215
<211> LENGTH: 9
<212> TYPE: PRT
<213> ORGANISM: Artificial Sequence
<220> FEATURE:
<223> OTHER INFORMATION: FGF mutation motif

<400> SEQUENCE: 215

Ala His Gly Leu Pro Leu His Leu Pro
1               5

<210> SEQ ID NO 216
<211> LENGTH: 10
<212> TYPE: PRT
<213> ORGANISM: Artificial Sequence
<220> FEATURE:
<223> OTHER INFORMATION: FGF mutation motif

<400> SEQUENCE: 216

His Leu Pro Gly Asn Lys Ser Pro His Arg
1               5                   10

<210> SEQ ID NO 217
<211> LENGTH: 10
<212> TYPE: PRT
<213> ORGANISM: Artificial Sequence
<220> FEATURE:
<223> OTHER INFORMATION: FGF mutation motif

<400> SEQUENCE: 217

Lys Ser Pro His Arg Asp Pro Ala Pro Arg
1               5                   10

<210> SEQ ID NO 218
<211> LENGTH: 10
<212> TYPE: PRT
<213> ORGANISM: Artificial Sequence
<220> FEATURE:
<223> OTHER INFORMATION: FGF mutation motif

<400> SEQUENCE: 218

Arg Gly Pro Ala Arg Phe Leu Pro Leu Pro
1               5                   10

<210> SEQ ID NO 219
<211> LENGTH: 10
<212> TYPE: PRT
<213> ORGANISM: Artificial Sequence
<220> FEATURE:
<223> OTHER INFORMATION: FGF mutation motif

<400> SEQUENCE: 219

Arg Gly Pro Ala Arg Phe Leu Pro Leu Pro
1               5                   10
```

<210> SEQ ID NO 220
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 220

Ala Thr Gly Thr Pro Leu His Leu Pro
1               5

<210> SEQ ID NO 221
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 221

Ala Thr Glu Thr Pro Leu His Leu Pro
1               5

<210> SEQ ID NO 222
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 222

Val Thr Glu Thr Pro Leu His Leu Pro
1               5

<210> SEQ ID NO 223
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 223

Val Thr Gly Leu Pro Leu His Leu Pro
1               5

<210> SEQ ID NO 224
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 224

Ala Thr Gly Leu Pro Leu His Leu Pro
1               5

<210> SEQ ID NO 225
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 225

Ala His Gly Leu Pro Thr Gln Ala Pro
1               5

```
<210> SEQ ID NO 226
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 226

Ala His Gly Leu Pro Thr Ala Gln Pro
1               5

<210> SEQ ID NO 227
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 227

Ala His Gly Leu Pro Thr Glu Ile Pro
1               5

<210> SEQ ID NO 228
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 228

Ala His Gly Leu Pro Thr Ser Ser Pro
1               5

<210> SEQ ID NO 229
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 229

Ala His Gly Leu Pro Thr Ala Leu Pro
1               5

<210> SEQ ID NO 230
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 230

Ala Ser Gly Leu Pro Thr Gln Ala Pro
1               5

<210> SEQ ID NO 231
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 231

Ala Ser Gly Leu Pro Thr Glu Ile Pro
1               5
```

<210> SEQ ID NO 232
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 232

His Leu Pro Thr Thr Ala Val Pro His Arg
1               5                   10

<210> SEQ ID NO 233
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 233

His Leu Pro Thr Ser Gly Glu Pro His Arg
1               5                   10

<210> SEQ ID NO 234
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 234

His Leu Pro Gly Ser Thr Ala Pro His Arg
1               5                   10

<210> SEQ ID NO 235
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 235

His Leu Pro Gly Asn Thr Ser Pro His Arg
1               5                   10

<210> SEQ ID NO 236
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 236

His Leu Pro Gly Thr Glu Ser Pro His Arg
1               5                   10

<210> SEQ ID NO 237
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 237

His Leu Pro Leu Thr Gln Thr Pro His Arg
1               5                   10

<210> SEQ ID NO 238

```
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 238

His Leu Pro Gly Thr Gln Thr Pro His Arg
1               5                   10

<210> SEQ ID NO 239
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 239

His Leu Pro Leu Thr Gln Thr Pro Ala Arg
1               5                   10

<210> SEQ ID NO 240
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 240

His Leu Pro Thr Asn Ala Ser Pro His Arg
1               5                   10

<210> SEQ ID NO 241
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 241

His Leu Pro Thr Gln Gly Ser Pro His Arg
1               5                   10

<210> SEQ ID NO 242
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 242

His Leu Pro Val Thr Ser Gln Pro His Arg
1               5                   10

<210> SEQ ID NO 243
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 243

His Leu Pro Thr Ile Asn Thr Pro His Arg
1               5                   10

<210> SEQ ID NO 244
<211> LENGTH: 10
```

```
<212> TYPE: PRT
<213> ORGANISM: Artificial Sequence
<220> FEATURE:
<223> OTHER INFORMATION: FGF mutation sequence

<400> SEQUENCE: 244

His Leu Pro Thr Ser Val Ser Pro His Arg
1               5                   10

<210> SEQ ID NO 245
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 245

Lys Ser Pro Thr Ala Gln Pro Ala Pro Arg
1               5                   10

<210> SEQ ID NO 246
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 246

Lys Ser Pro Thr Ala Asp Pro Ala Pro Arg
1               5                   10

<210> SEQ ID NO 247
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 247

Ala Ser Pro Thr Ala Gln Pro Ala Pro Arg
1               5                   10

<210> SEQ ID NO 248
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 248

Ser Ser Pro Thr Ala Asp Pro Ala Pro Arg
1               5                   10

<210> SEQ ID NO 249
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 249

Lys Ser Pro Thr Ser Asp Pro Ala Pro Arg
1               5                   10

<210> SEQ ID NO 250
<211> LENGTH: 10
<212> TYPE: PRT
```

```
<213> ORGANISM: Artificial Sequence
<220> FEATURE:
<223> OTHER INFORMATION: FGF mutation sequence

<400> SEQUENCE: 250

Lys Ser Pro Thr Glu Ile Pro Ala Pro Arg
1               5                   10

<210> SEQ ID NO 251
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 251

Lys Ser Pro Thr Glu Ile Pro Ala Pro Arg
1               5                   10

<210> SEQ ID NO 252
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 252

Lys Ser Pro Thr Glu Asp Pro Ala Pro Arg
1               5                   10

<210> SEQ ID NO 253
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 253

Ala Ser Pro Thr Glu Asp Pro Ala Pro Arg
1               5                   10

<210> SEQ ID NO 254
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 254

Ser Ser Pro Thr Ala Asp Pro Ala Pro Arg
1               5                   10

<210> SEQ ID NO 255
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 255

Ser Ser Pro Thr Ala Gln Pro Ala Pro Arg
1               5                   10

<210> SEQ ID NO 256
<211> LENGTH: 10
<212> TYPE: PRT
<213> ORGANISM: Artificial Sequence
```

```
<220> FEATURE:
<223> OTHER INFORMATION: FGF mutation sequence

<400> SEQUENCE: 256

Lys Ser Pro Thr Gln Ala Pro Ala Pro Arg
1               5                   10

<210> SEQ ID NO 257
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 257

Ser Ser Pro Thr Gln Ala Pro Ala Pro Arg
1               5                   10

<210> SEQ ID NO 258
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 258

Ala Ser Pro Thr Glu Ile Pro Ala Pro Arg
1               5                   10

<210> SEQ ID NO 259
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 259

Lys Ser Pro His Arg Asp Pro Thr Pro Arg
1               5                   10

<210> SEQ ID NO 260
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 260

Lys Ser Pro His Arg Asp Pro Ser Pro Arg
1               5                   10

<210> SEQ ID NO 261
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 261

Lys Ser Pro His Arg Asp Pro Thr Pro Ala
1               5                   10

<210> SEQ ID NO 262
<211> LENGTH: 10
<212> TYPE: PRT
<213> ORGANISM: Artificial Sequence
<220> FEATURE:
```

```
<223> OTHER INFORMATION: FGF mutation sequence

<400> SEQUENCE: 262

Lys Ser Pro His Arg Asp Pro Thr Pro Ser
1               5                   10

<210> SEQ ID NO 263
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 263

Lys Ser Pro His Ser Asp Pro Thr Pro Ala
1               5                   10

<210> SEQ ID NO 264
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 264

Lys Ser Pro His Ala Asp Pro Thr Pro Ser
1               5                   10

<210> SEQ ID NO 265
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 265

Lys Ser Pro His Ala Asp Pro Thr Pro Ala
1               5                   10

<210> SEQ ID NO 266
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 266

Arg Gly Pro Thr Ser Phe Leu Pro Leu Pro
1               5                   10

<210> SEQ ID NO 267
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 267

Arg Gly Pro Thr Ser Gly Glu Pro Leu Pro
1               5                   10

<210> SEQ ID NO 268
<211> LENGTH: 10
<212> TYPE: PRT
<213> ORGANISM: Artificial Sequence
<220> FEATURE:
<223> OTHER INFORMATION: FGF mutation sequence
```

<400> SEQUENCE: 268

Arg Gly Pro Gly Ser Thr Ala Pro Leu Pro
1               5                   10

<210> SEQ ID NO 269
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 269

Arg Gly Pro Ala Asn Thr Ser Pro Leu Pro
1               5                   10

<210> SEQ ID NO 270
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 270

Arg Gly Pro Ala Thr Glu Ser Pro Leu Pro
1               5                   10

<210> SEQ ID NO 271
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 271

Arg Gly Pro Ala Thr Gln Thr Pro Leu Pro
1               5                   10

<210> SEQ ID NO 272
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 272

Arg Gly Pro Ala Thr Gln Thr Pro Leu Pro
1               5                   10

<210> SEQ ID NO 273
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 273

Arg Gly Pro Leu Thr Gln Thr Pro Leu Pro
1               5                   10

<210> SEQ ID NO 274
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 274

Arg Gly Pro Thr Gln Phe Leu Pro Leu Pro
1               5                   10

<210> SEQ ID NO 275
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 275

Arg Gly Pro Thr Ser Phe Leu Pro Leu Pro
1               5                   10

<210> SEQ ID NO 276
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 276

Arg Gly Pro Val Thr Ser Gln Pro Leu Pro
1               5                   10

<210> SEQ ID NO 277
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 277

Ser Gly Pro Thr Ser Phe Leu Pro Leu Pro
1               5                   10

<210> SEQ ID NO 278
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 278

Ala Gly Pro Thr Ser Gly Glu Pro Leu Pro
1               5                   10

<210> SEQ ID NO 279
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 279

Ser Gly Pro Thr Ser Ala Leu Pro Leu Pro
1               5                   10

<210> SEQ ID NO 280
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 280

```
Arg Gly Pro Ala Arg Phe Leu Pro Thr Pro
1               5                   10

<210> SEQ ID NO 281
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 281

Arg Gly Pro Ala Arg Phe Leu Pro Ser Pro
1               5                   10

<210> SEQ ID NO 282
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 282

Arg Gly Pro Ala Ser Phe Leu Pro Thr Pro
1               5                   10

<210> SEQ ID NO 283
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 283

Thr Pro Pro Gly Ile Leu Ala Pro Gln
1               5

<210> SEQ ID NO 284
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 284

Ser Pro Pro Gly Ile Leu Ala Pro Gln
1               5

<210> SEQ ID NO 285
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 285

Glu Pro Pro Thr Ile Leu Ala Pro Gln
1               5

<210> SEQ ID NO 286
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 286
```

Glu Pro Pro Thr Thr Leu Ala Pro Gln
1               5

<210> SEQ ID NO 287
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 287

Glu Pro Pro Thr Gln Leu Ala Pro Gln
1               5

<210> SEQ ID NO 288
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 288

Glu Pro Pro Thr Gln Gly Ala Pro Gln
1               5

<210> SEQ ID NO 289
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 289

Glu Pro Pro Thr Ser Gly Glu Pro Gln
1               5

<210> SEQ ID NO 290
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 290

Glu Pro Pro Gly Ser Thr Ala Pro Gln
1               5

<210> SEQ ID NO 291
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 291

Glu Pro Pro Thr Thr Ala Val Pro Gln
1               5

<210> SEQ ID NO 292
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 292

Glu Pro Pro Gly Asn Thr Ser Pro Gln

```
<210> SEQ ID NO 293
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 293

Glu Pro Pro Gly Thr Glu Ser Pro Gln
1               5

<210> SEQ ID NO 294
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 294

Glu Pro Pro Gly Thr Glu Thr Pro Gln
1               5

<210> SEQ ID NO 295
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 295

Glu Pro Pro Val Thr Ser Gln Pro Gln
1               5

<210> SEQ ID NO 296
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 296

Glu Pro Pro Ala Val Gln Thr Pro Gln
1               5

<210> SEQ ID NO 297
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 297

Glu Pro Pro Leu Thr Gln Thr Pro Gln
1               5

<210> SEQ ID NO 298
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 298

Glu Pro Pro Val Thr Ser Gln Pro Gln
1               5
```

```
<210> SEQ ID NO 299
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 299

Glu Pro Pro Ser Ser Gly Ala Pro Gln
1               5

<210> SEQ ID NO 300
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 300

Glu Pro Pro Thr Ile Asn Thr Pro Gln
1               5

<210> SEQ ID NO 301
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 301

Glu Pro Pro Thr Thr Val Ser Pro Gln
1               5

<210> SEQ ID NO 302
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 302

Glu Pro Pro Thr Gln Ala Ala Pro Gln
1               5

<210> SEQ ID NO 303
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 303

Glu Pro Pro Gly Ile Leu Ala Pro Thr
1               5

<210> SEQ ID NO 304
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 304

Glu Pro Pro Gly Ile Leu Ala Pro Ser
1               5
```

<210> SEQ ID NO 305
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 305

Thr Val Gly Ser Ser Asp Pro
1               5

<210> SEQ ID NO 306
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 306

Asp Val Gly Ser Ser Thr Pro
1               5

<210> SEQ ID NO 307
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 307

Asp Val Gly Thr Glu Thr Pro
1               5

<210> SEQ ID NO 308
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 308

Asp Ala Ala Ser Ala Ala Pro
1               5

<210> SEQ ID NO 309
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 309

Asp Ala Ala Thr Ala Ala Pro
1               5

<210> SEQ ID NO 310
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 310

Asp Val Gly Thr Ser Asp Pro
1               5

```
<210> SEQ ID NO 311
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 311

Asp Val Ala Thr Ser Asp Pro
1               5

<210> SEQ ID NO 312
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 312

Thr Gly Asp Ser Ser Asp Pro
1               5

<210> SEQ ID NO 313
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 313

Thr Asp Ala Ser Gly Ala Pro
1               5

<210> SEQ ID NO 314
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 314

Asp Val Gly Thr Ser Gly Pro
1               5

<210> SEQ ID NO 315
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 315

Thr Ser Met Val Gly Pro
1               5

<210> SEQ ID NO 316
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 316

Thr Ser Gly Val Gly Pro
1               5

<210> SEQ ID NO 317
```

```
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 317

Thr Ser Gly Ala Met Pro
1               5

<210> SEQ ID NO 318
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 318

Thr Gln Gly Ala Met Pro
1               5

<210> SEQ ID NO 319
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 319

Thr Ser Met Val Gly Pro
1               5

<210> SEQ ID NO 320
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 320

Thr Gln Gly Ala Met Pro
1               5

<210> SEQ ID NO 321
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 321

Ser Gln Gly Arg Ser Pro
1               5

<210> SEQ ID NO 322
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 322

Arg Ser Pro Ser Tyr Ala Ser
1               5

<210> SEQ ID NO 323
<211> LENGTH: 6
```

```
<212> TYPE: PRT
<213> ORGANISM: Artificial Sequence
<220> FEATURE:
<223> OTHER INFORMATION: FGF mutation sequence

<400> SEQUENCE: 323

Ser Gln Gly Ala Ser Pro
1               5

<210> SEQ ID NO 324
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 324

Thr Gln Gly Ala Ser Pro
1               5

<210> SEQ ID NO 325
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 325

Thr Gln Gly Ala Met Pro
1               5

<210> SEQ ID NO 326
<211> LENGTH: 6
<212> TYPE: PRT
<213> ORGANISM: Artificial Sequence
<220> FEATURE:
<223> OTHER INFORMATION: FGF mutation sequence

<400> SEQUENCE: 326

Thr Gln Gly Ala Met Pro
1               5

<210> SEQ ID NO 327
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 327

Ala Ser Pro Ser Tyr Ala Ser
1               5

<210> SEQ ID NO 328
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 328

Arg Ser Pro Thr Ser Ala Val Ala Ala
1               5

<210> SEQ ID NO 329
<211> LENGTH: 9
<212> TYPE: PRT
```

```
<213> ORGANISM: Artificial Sequence
<220> FEATURE:
<223> OTHER INFORMATION: FGF mutation sequence

<400> SEQUENCE: 329

Ala Ser Pro Thr Ser Ala Val Ala Ala
1               5

<210> SEQ ID NO 330
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 330

Ala Ser Pro Ser Ser Gly Ala Pro Pro Ser
1               5                   10

<210> SEQ ID NO 331
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 331

Ala Ser Pro Ser Ser Gly Ala Pro Pro
1               5

<210> SEQ ID NO 332
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 332

Ala Ser Pro Ser Ser Gly Ala Pro
1               5

<210> SEQ ID NO 333
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 333

Arg Ser Pro Ser Ser Gly Ala Pro Pro Ser
1               5                   10

<210> SEQ ID NO 334
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 334

Ala Ser Pro Thr Ile Asn Thr
1               5

<210> SEQ ID NO 335
<211> LENGTH: 7
<212> TYPE: PRT
<213> ORGANISM: Artificial Sequence
```

```
<220> FEATURE:
<223> OTHER INFORMATION: FGF mutation sequence

<400> SEQUENCE: 335

Ala Ser Pro Thr Ser Val Ser
1               5

<210> SEQ ID NO 336
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 336

Ala Ser Pro Thr Gln Ala Phe
1               5

<210> SEQ ID NO 337
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 337

Ala Ser Pro Thr Ile Asn Thr Pro
1               5

<210> SEQ ID NO 338
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 338

Met Ala Pro Thr Gln Ala Pro Leu Ala Glu Val
1               5                   10

<210> SEQ ID NO 339
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 339

Met Ala Pro Thr Glu Ile Pro Leu Ala Glu Val
1               5                   10

<210> SEQ ID NO 340
<211> LENGTH: 12
<212> TYPE: PRT
<213> ORGANISM: Artificial Sequence
<220> FEATURE:
<223> OTHER INFORMATION: FGF mutation sequence

<400> SEQUENCE: 340

Met Ala Pro Thr Ile Asn Thr Pro Leu Ala Glu Val
1               5                   10

<210> SEQ ID NO 341
<211> LENGTH: 11
<212> TYPE: PRT
<213> ORGANISM: Artificial Sequence
<220> FEATURE:
```

```
<223> OTHER INFORMATION: FGF mutation sequence

<400> SEQUENCE: 341

Met Ala Pro Thr Ile Asn Thr Leu Ala Glu Val
1               5                   10

<210> SEQ ID NO 342
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 342

Met Ala Pro Thr Thr Val Ser Leu Ala Glu Val
1               5                   10

<210> SEQ ID NO 343
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 343

Met Ala Pro Thr Gln Glu Val Leu Ala Glu Val
1               5                   10

<210> SEQ ID NO 344
<211> LENGTH: 11
<212> TYPE: PRT
<213> ORGANISM: Artificial Sequence
<220> FEATURE:
<223> OTHER INFORMATION: FGF mutation sequence

<400> SEQUENCE: 344

Met Ala Pro Thr Gln Ala Val Leu Ala Glu Val
1               5                   10

<210> SEQ ID NO 345
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 345

Pro Pro Thr Ile Asn Thr Pro Pro
1               5

<210> SEQ ID NO 346
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 346

Pro Pro Thr Thr Val Ser Pro Pro
1               5

<210> SEQ ID NO 347
<211> LENGTH: 8
<212> TYPE: PRT
<213> ORGANISM: Artificial Sequence
<220> FEATURE:
<223> OTHER INFORMATION: FGF mutation sequence
```

<400> SEQUENCE: 347

Pro Pro Thr Gln Ala Leu Pro Pro
1               5

<210> SEQ ID NO 348
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 348

Pro Pro Thr Ile Asn Thr Arg Arg Ser
1               5

<210> SEQ ID NO 349
<211> LENGTH: 9
<212> TYPE: PRT
<213> ORGANISM: Artificial Sequence
<220> FEATURE:
<223> OTHER INFORMATION: FGF mutation sequence

<400> SEQUENCE: 349

Pro Pro Thr Thr Val Ser Arg Arg Ser
1               5

<210> SEQ ID NO 350
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 350

Pro Thr Ile Asn Thr Leu Ala
1               5

<210> SEQ ID NO 351
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 351

Pro Thr Thr Val Ser Leu Ala
1               5

<210> SEQ ID NO 352
<211> LENGTH: 7
<212> TYPE: PRT
<213> ORGANISM: Artificial Sequence
<220> FEATURE:
<223> OTHER INFORMATION: FGF mutation sequence

<400> SEQUENCE: 352

Pro Thr Gln Ala Gln Leu Ala
1               5

<210> SEQ ID NO 353
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 353

Pro Thr Ile Asn Thr Gln Gly Thr
1               5

<210> SEQ ID NO 354
<211> LENGTH: 8
<212> TYPE: PRT
<213> ORGANISM: Artificial Sequence
<220> FEATURE:
<223> OTHER INFORMATION: FGF mutation sequence

<400> SEQUENCE: 354

Pro Thr Thr Val Ser Gln Gly Thr
1               5

<210> SEQ ID NO 355
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 355

Leu Asn Lys Asp Gly Thr Pro Thr Ile Asn Thr Arg Ser Lys Arg His
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 356

Leu Asn Lys Asp Gly Thr Pro Thr Ile Asn Thr Ser Ser Lys Arg His
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 357

Leu Asn Lys Asp Gly Thr Pro Thr Thr Val Ser Arg Ser Lys Arg His
1               5                   10                  15

<210> SEQ ID NO 358
<211> LENGTH: 16
<212> TYPE: PRT
<213> ORGANISM: Artificial Sequence
<220> FEATURE:
<223> OTHER INFORMATION: FGF mutation sequence

<400> SEQUENCE: 358

Leu Asn Lys Asp Gly Thr Pro Thr Thr Val Ser Ala Ser Lys Arg His
1               5                   10                  15

<210> SEQ ID NO 359
<211> LENGTH: 10
<212> TYPE: PRT
<213> ORGANISM: Artificial Sequence
<220> FEATURE:
<223> OTHER INFORMATION: FGF mutation sequence

<400> SEQUENCE: 359

```
Pro Thr Gln Ala Pro Glu Leu Tyr Lys Asp
1               5                   10

<210> SEQ ID NO 360
<211> LENGTH: 10
<212> TYPE: PRT
<213> ORGANISM: Artificial sequence
<220> FEATURE:
<223> OTHER INFORMATION: FGF mutation sequence

<400> SEQUENCE: 360

Pro Thr Glu Ile Pro Glu Leu Tyr Lys Asp
1               5                   10
```

METHOD OF TREATING FIBROBLAST GROWTH FACTOR 21 (FGF-21) DEFICIENCY

CROSS-REFERENCE TO RELATED APPLICATIONS

The present application is a divisional of U.S. patent application Ser. No. 13/332,708, filed Dec. 21, 2011, which is a divisional of U.S. patent application Ser. No. 11/665,908, filed Nov. 26, 2007, now abandoned, which is the U.S. national phase application of International Patent Application No. PCT/US2005/039226, filed Oct. 31, 2005, which claims priority to U.S. Provisional Patent Application No. 60/623,342, filed Oct. 29, 2004, each of which are incorporated herein by reference in their entireties for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 75,751 Byte ASCII (Text) file named "722587_SeqListing.TXT," created on Nov. 30, 2015.

BACKGROUND OF THE INVENTION

Fibroblast Growth Factors (FGFs) promote growth, proliferation, survival and differentiation of a wide variety of cells and tissue types. The prototypic fibroblast growth factors (FGFs), FGF-1 and FGF-2, were originally isolated from brain and pituitary as mitogens for fibroblasts. However, FGF-1 and FGF-2, and fibroblast growth factors generally, are widely expressed in developing and adult tissues, and have multiple biological activities including angiogenesis, mitogenesis, cellular differentiation and repair of tissue injury (see e.g., Baird, A. et al., *Cancer Cells* 3:239-243 (1991) and Burgess, W. H. et al., *Annu. Rev. Biochem.* 58:575-606 (1989)).

According to the published literature, the FGF family now consists of at least twenty five members, FGF-1 to FGF-25. The 25 members of the FGF family range in molecular mass from 17 to 34 kDa and share 13-71% amino acid identity. Between vertebrate species, FGFs are highly conserved in both gene structure and amino-acid sequence.

The 25 members of the mammalian FGF family are differentially expressed in many tissues. The members are divided into subfamilies that have similar, though individually unique, patterns of expression. Some FGFs are expressed exclusively during embryonic development (for example, Fgf3, 4, 8, 15, 17 and 19), whereas others are expressed in embryonic and adult tissues. For example, FGF-16mRNA is predominantly expressed in the rat heart in adult tissues. However, in rat embryos, FGF-16mRNA is predominantly expressed in the brown adipose tissue (see e.g., Miyake A, et al. *Biochem. Biophys. Res. Commun.* 1998, 243:148-152).

Although most FGFs (FGFs 3-8, 10, 15, 17-19, and 21-25) have amino-terminal signal peptides and are readily secreted from cells, FGFs 9, 16 and 20 lack an obvious amino-terminal signal peptide but are nevertheless secreted (see e.g., Miyamoto M, et al. *Mol Cell Biol* 1993, 13:4251-4259). A third subset of FGFs (FGF 11-14) lack signal sequences and are thought to remain intracellular.

As noted above, the sub-family of FGF proteins comprising FGF-9, FGF-16, and FGF-20 lack a classical signal sequence, although they contain nuclear localization signals, and are secreted. These FGFs are expressed in the developing and adult nervous systems, suggesting a role in nervous system development and function (see e.g., Smallwood P. M., et al. *Proc Natl Acad Sci USA* (1996) 93:9850-9857). Indeed, a cDNA encoding FGF-20 was isolated from rat brain (see e.g., U.S. Pat. No. 6,797,695). Among FGF family members, FGF-20 is most similar to FGF-9 and FGF-16 (70 and 62% amino acid identity, respectively).

Numerous studies of human disorders as well as gene knock-out studies in mice indicate that FGFs are neurotrophic for cells of both the peripheral and central nervous system, and are important in the development of the skeletal system in mammals. A role in nervous system development and function is supported by in situ hybridization studies that show that FGF-20 mRNA is preferentially expressed in the substantia nigra pars compacta of the brain. Further support for a nervous system function is found in studies showing that in vitro, recombinant rat FGF-20 enhanced the survival of midbrain dopaminergic neurons in culture (see e.g., Ohmachi S. *Biochem Biophys Res Commun* 2000, 277:355-360).

In other studies, high levels of FGF-21 mRNA expression has been shown to occur in the liver, and human FGF-21 may play a role in the development of and recovery from liver disease. FGF-21 is also expressed in testis and thymus, and therefore may play a role in the development or recovery from disorders of testicular function or function of cells derived from the thymus (see e.g., U.S. Pat. No. 6,716,626).

Because of their wide ranging and potent activities, FGFs are pursued as therapeutic agents for a number of different indications, including wound healing, such as musculoskeletal conditions, bone fractures, ligament and tissue repair, tendonitis, bursitis, etc.; skin conditions, for example, burns, cuts, lacerations, bed sores, slow healing ulcers, etc.; tissue protection, repair, and the induction of angiogenesis during myocardial infarction and ischemia, inflammatory conditions and diseases (e.g., intestinal inflammation, including inflammatory bowel disease see e.g., Jeffers et al. *Gastroenterology* 2002; 123:1151-1162), in the treatment of neurological conditions such as neuro-degenerative diseases (e.g., Parkinson's disease), and stroke, in the treatment of eye disease, including macular degeneration, the pathology and treatment of cancer (see e.g., Jeffers, M., et al. *Cancer Research* 61, 3131-3138, Apr. 1, (2001) and Jeffers et al. *Expert Opinion on Therapeutic Targets* (2002) 6(4):469-482) and for the treatment of diabetes. Unfortunately, the administration of therapeutic proteins such as FGF-9, FGF-18, FGF-20, and FGF-21 for the treatment of diseases and conditions can be complicated by, for example, short half life and mutagenic properties.

Poly(ethylene glycol) ("PEG") is an exemplary polymer that has been conjugated to polypeptides. The use of PEG to derivatize peptide therapeutics has been demonstrated to reduce the immunogenicity of the peptides and improve pharmacodynamics including half-life. For example, U.S. Pat. No. 4,179,337 (Davis et al.) concerns non-immunogenic polypeptides, such as enzymes and peptide hormones coupled to polyethylene glycol (PEG) or polypropylene glycol. Between 10 and 100 moles of polymer are used per mole polypeptide and at least 15% of the physiological activity is maintained. In addition, the clearance time in circulation is prolonged due to the increased size of the PEG-conjugate of the polypeptides in question. The methods disclosed by Davis et al. are chemical PEGylation methods.

The chemical modification of peptides, frequently results in an undesirable loss of peptide activity, which is attributable to the non-selective nature of the chemistries utilized to modify the peptide. For example, when the modifying group is a water-soluble peptide, e.g., PEG, the principal mode of attachment of PEG, and its derivatives, to peptides is a non-specific bonding through a peptide amino acid residue. Studies of conjugates of water-soluble polymers and interleukin-2 (Fisher et al., *Br. J. Haematol.*, 82: 654 (1992)), granulocyte colony stimulating factor (Satake-Ishikawa et al., *Cell Struct. Funct.*, 17: 157 (1992)), tumor necrosis factor (Tsutsumi et al., *Br. J. Cancer*, 71: 963 (1996)) and Fibroblast Growth Factor (Clark, et al., *J. Biol. Chem.*, 271:21969 (1996)) have revealed that chemical PEGylation of these proteins decreases the in vivo receptor binding activity of the peptides.

In many chemical PEGylation methods, poly(ethylene glycol) is added in an essentially random, non-specific manner to reactive residues on a peptide backbone. For the production of therapeutic peptides, it is clearly desirable to utilize a derivitization strategy that results in the formation of a specifically labeled, readily characterizable, essentially homogeneous product. A promising route to preparing specifically labeled peptides is through the use of enzymes, such as glycosyltransferases to append a modified sugar moiety onto a peptide.

Enzyme-based syntheses have the advantages of regioselectivity and stereoselectivity. Moreover, enzymatic syntheses are performed using unprotected substrates. Two principal classes of enzymes are used in the synthesis of carbohydrates, glycosyltransferases (e.g., sialyltransferases, oligosaccharyltransferases, N-acetylglucosaminyltransferases), and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., *Curr. Opin. Chem. Biol.* 2: 98-111 (1998).

Glycosyltransferases modify the oligosaccharide structures on glycopeptides, producing specific products with good stereochemical and regiochemical control. Glycosyltransferases are used to prepare oligosaccharides and to modify terminal N- and O-linked carbohydrate structures, particularly on glycopeptides produced in mammalian cells. For example, the terminal oligosaccharides of glycopeptides have been completely sialylated and/or fucosylated to provide more consistent sugar structures, which improves glycopeptide pharmacodynamics and a variety of other biological properties. For example, β-1,4-galactosyltransferase was used to synthesize lactosamine, an illustration of the utility of glycosyltransferases in the synthesis of carbohydrates (see, e.g., Wong et al., *J. Org. Chem.* 47: 5416-5418 (1982)). Moreover, numerous synthetic procedures have made use of α-sialyltransferases to transfer sialic acid from cytidine-5′-monophospho-N-acetylneuraminic acid to the 3-OH or 6-OH of galactose (see, e.g., Kevin et al., *Chem. Eur. J.* 2: 1359-1362 (1996)). Fucosyltransferases are used in synthetic pathways to transfer a fucose unit from guanosine-5′-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)). For a discussion of recent advances in glycoconjugate synthesis for therapeutic use see, Koeller et al., *Nature Biotechnology* 18: 835-841 (2000). See also, U.S. Pat. Nos. 5,876,980; 6,030,815; 5,728,554; 5,922,577; and WO/9831826.

Glycosidases can also be used to prepare saccharides. Glycosidases normally catalyze the hydrolysis of a glycosidic bond. Under appropriate conditions, however, they can be used to form this linkage. Most glycosidases used for carbohydrate synthesis are exoglycosidases; the glycosyl transfer occurs at the non-reducing terminus of the substrate. The glycosidase takes up a glycosyl donor in a glycosyl-enzyme intermediate that is either intercepted by water to give the hydrolysis product, or by an acceptor, to give a new glycoside or oligosaccharide. An exemplary pathway using an exoglycosidase is the synthesis of the core trisaccharide of all N-linked glycopeptides, including the difficult β-mannoside linkage, which was formed by the action of β-mannosidase (Singh et al., *Chem. Commun.* 993-994 (1996)).

In another exemplary application of the use of a glycosidase to form a glycosidic linkage, a mutant glycosidase has been prepared in which the normal nucleophilic amino acid within the active site is changed to a non-nucleophilic amino acid. The mutant enzymes do not hydrolyze glycosidic linkages, but can still form them. The mutant glycosidases are used to prepare oligosaccharides using an α-glycosyl fluoride donor and a glycoside acceptor molecule (Withers et al., U.S. Pat. No. 5,716,812). Although the mutant glycosidases are useful for forming free oligosaccharides, it has yet to be demonstrated that such enzymes are capable of appending glycosyl donors onto glycosylated or non-glycosylated peptides, nor have these enzymes been used with unactivated glycosyl donors.

Although their use is less common than that of the exoglycosidases, endoglycosidases are also utilized to prepare carbohydrates. Methods based on the use of endoglycosidases have the advantage that an oligosaccharide, rather than a monosaccharide, is transferred. Oligosaccharide fragments have been added to substrates using endo-β-N-acetylglucosamines such as endo-F, endo-M (Wang et al., *Tetrahedron Lett.* 37: 1975-1978); and Haneda et al., *Carbohydr. Res.* 292: 61-70 (1996)).

In addition to their use in preparing carbohydrates, the enzymes discussed above are applied to the synthesis of glycopeptides as well. The synthesis of a homogenous glycoform of ribonuclease B has been published (Witte K. et al., *J. Am. Chem. Soc.* 119: 2114-2118 (1997)). The high mannose core of ribonuclease B was cleaved by treating the glycopeptide with endoglycosidase H. The cleavage occurred specifically between the two core GlcNAc residues. The tetrasaccharide sialyl Lewis X was then enzymatically rebuilt on the remaining GlcNAc anchor site on the now homogenous protein by the sequential use of β-1,4-galactosyltransferase, α-2,3-sialyltransferase and α-1,3-fucosyltransferase V. Each enzymatically catalyzed step proceeded in excellent yield.

Methods combining both chemical and enzymatic synthetic elements are also known. For example, Yamamoto and coworkers (*Carbohydr. Res.* 305: 415-422 (1998)) reported the chemoenzymatic synthesis of the glycopeptide, glycosylated Peptide T, using an endoglycosidase. The N-acetylglucosaminyl peptide was synthesized by purely chemical means. The peptide was subsequently enzymatically elaborated with the oligosaccharide of human transferrin glycopeptide. The saccharide portion was added to the peptide by treating it with an endo-β-N-acetylglucosaminidase. The resulting glycosylated peptide was highly stable and resistant to proteolysis when compared to the peptide T and N-acetylglucosaminyl peptide T.

The use of glycosyltransferases to modify peptide structure with reporter groups has been explored. For example, Brossmer et al. (U.S. Pat. No. 5,405,753) discloses the formation of a fluorescent-labeled cytidine monophosphate ("CMP") derivative of sialic acid and the use of the fluorescent glycoside in an assay for sialyl transferase activity and for the fluorescent-labeling of cell surfaces, glycoproteins and gangliosides. Gross et al. (*Analyt. Biochem.* 186: 127 (1990)) describe a similar assay. Bean et al. (U.S. Pat. No. 5,432,059) discloses an assay for glycosylation deficiency disorders utilizing reglycosylation of a deficiently glycosylated protein. The deficient protein is reglycosylated with a fluorescent-labeled CMP glycoside. Each of the fluorescent sialic acid derivatives is substituted with the fluorescent moiety at either the 9-position or at the amine that is normally acetylated in sialic acid. The methods using the fluorescent sialic acid derivatives are assays for the presence of glycosyltransferases or for non-glycosylated or improperly glycosylated glycoproteins. The assays are conducted on small amounts of enzyme or glycoprotein in a sample of biological origin. The enzymatic derivatization of a glycosylated or non-glycosylated peptide on a preparative or industrial scale using a modified sialic acid was not disclosed or suggested in either of these references.

Enzymatic methods have also been used to activate glycosyl residues on a glycopeptide towards subsequent chemical elaboration. The glycosyl residues are typically activated using galactose oxidase, which converts a terminal galactose residue to the corresponding aldehyde. The aldehyde is subsequently coupled to an amine-containing modifying group. For example, Casares et al. (*Nature Biotech.* 19: 142 (2001)) have attached doxorubicin to the oxidized galactose residues of a recombinant MHC11-peptide chimera.

Glycosyl residues have also been modified to bear ketone groups. For example, Mahal and co-workers (*Science* 276: 1125 (1997)) have prepared N-levulinoyl mannosamine ("ManLev"), which has a ketone functionality at the position normally occupied by the acetyl group in the natural substrate. Cells were treated with the ManLev, thereby incorporating a ketone group onto the cell surface. See, also Saxon et al., *Science* 287: 2007 (2000); Hang et al., *J. Am. Chem. Soc.* 123: 1242 (2001); Yarema et al., *J. Biol. Chem.* 273: 31168 (1998); and Charter et al., *Glycobiology* 10: 1049 (2000).

Carbohydrates are attached to glycopeptides in several ways of which N-linked to asparagine and mucin-type O-linked to serine and threonine are the most relevant for recombinant glycoprotein therapeutics. A determining factor for initiation of glycosylation of a protein is the primary sequence context, although clearly other factors including protein region and conformation play roles. N-linked glycosylation occurs at the consensus sequence NXS/T, where X can be any amino acid but proline.

The present invention answers these needs by providing FGF mutants that contain newly introduced N-linked or O-linked glycosylation sites, providing flexibility in glycosylation and/or glycopegylation of these recombinant FGF mutants. Moreover, the invention provides an industrially practical method for the modification of N- or O-linked mutant FGF peptides with modifying groups such as water-soluble polymers, therapeutic moieties, biomolecules, and the like. Of particular interest are methods in which the modified mutant FGF has improved properties, which enhance its use as a therapeutic or diagnostic agent.

BRIEF SUMMARY OF THE INVENTION

It has now been discovered that the controlled modification of Fibroblast Growth Factor with one or more modifying groups (e.g., non-glycosidic modifying groups) affords a novel FGF peptide conjugate with pharmacokinetic properties that are improved relative to the corresponding native (un-modified) FGF. Furthermore, cost effective methods for reliable and reproducible production of the FGF peptide conjugates of the invention have been discovered and developed.

In one aspect, the invention provides an FGF conjugate comprising a FGF peptide and a glycosyl linking group—poly(ethylene glycol) cassette attached to an amino acid residue of the FGF peptide.

In an exemplary embodiment, glycoconjugated FGF molecules of the invention are produced by the enzyme mediated formation of a conjugate between a glycosylated or non-glycosylated FGF peptide and an enzymatically transferable saccharyl moiety that includes a modifying group, such as a polymeric modifying group, e.g., poly(ethylene glycol), within its structure. The modifying group is attached to the saccharyl moiety directly (i.e., through a single group formed by the reaction of two reactive groups) or through a linker moiety, e.g., substituted or unsubstituted alkyl, substituted or unsubstituted heteroalkyl, etc.

In one aspect, the present invention provides a conjugate between a PEG moiety, and a peptide that has an in vivo activity similar or otherwise analogous to art-recognized FGF. In the conjugate of the invention, the PEG moiety is covalently attached to the peptide via a glycosyl linking group or an intact glycosyl linking group. Exemplary intact glycosyl linking groups include sialic acid moieties that are derivatized with PEG.

The saccharyl moiety bearing the polymeric modifying group can be attached at any position of a glycosyl moiety of FGF. Moreover, the polymeric modifying group can be bound to a glycosyl residue at any position in the amino acid sequence of a wild type or mutant FGF peptide.

In an exemplary embodiment, the invention provides a FGF peptide that is conjugated through a glycosyl linking group to a polymeric modifying group. Exemplary FGF peptide conjugates include a glycosyl linking group having a formula selected from:

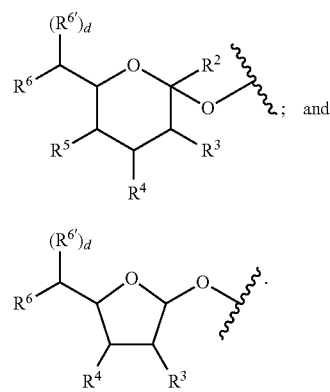

In Formulae I and II, $R^2$ is H, $CH_2OR^7$, $COOR^7$, $COO^-M^+$ or $OR^7$, in which $R^7$ represents H, substituted or unsubstituted alkyl or substituted or unsubstituted heteroalkyl. The symbols $R^3$, $R^4$, $R^5$, $R^6$ and $R^{6'}$ independently represent H, substituted or unsubstituted alkyl, $OR^8$, $NHC(O)R^9$. $M^+$ is a metal. The index d is 0 or 1. $R^8$ and $R^9$ are independently selected from H, substituted or unsubstituted alkyl, substituted or unsubstituted heteroalkyl or sialic acid. At least one of $R^3$, $R^4$, $R^5$, $R^6$ or $R^{6'}$ includes the polymeric modifying group e.g., PEG. In an exemplary embodiment, $R^6$ and $R^{6'}$, together with the carbon to which they are attached are components of the side chain of a sialyl moiety. In a further exemplary embodiment, this side chain is functionalized with the polymeric modifying group.

As discussed herein, the PEG of use in the conjugates of the invention can be linear or branched. An exemplary precursor of use to form the branched PEG containing peptide conjugates according to this embodiment of the invention has the formula:

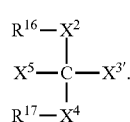

(III)

The branched polymer species according to this formula are essentially pure water-soluble polymers. $X^{3+}$ is a moiety that includes an ionizable (e.g., OH, COOH, $H_2PO_4$, $HSO_3$, $NH_2$, and salts thereof, etc.) or other reactive functional group, e.g., infra. C is carbon. $X^5$, $R^{16}$ and $R^{17}$ are independently selected from non-reactive groups (e.g., H, unsubstituted alkyl, unsubstituted heteroalkyl) and polymeric arms (e.g., PEG). $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^6$ and $R^{17}$ to C. When $X^{3'}$ is reacted with a reactive functional group of complementary reactivity on a linker, sugar or linker-sugar cassette, $X^{3'}$ is converted to a component of linkage fragment $X^3$.

In an exemplary embodiment, the polymeric modifying group is bound to the glycosyl linking group, generally through a heteroatom on the glycosyl core (e.g., N, O), through a linker, L, as shown below:

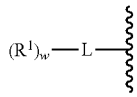

$R^1$ is the polymeric modifying group and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety. Another exemplary linking group is an amino acid residue (e.g., cysteine, serine, lysine, and short oligopeptides, e.g., Lys-Lys, Lys-Lys-Lys, Cys-Lys, Ser-Lys, etc.)

When L is a bond, it is formed by reaction of a reactive functional group on a precursor of $R^1$ and a reactive functional group of complementary reactivity on a precursor of the glycosyl linking group. When L is a non-zero order linking group, L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling of the precursors proceeds by chemistry that is well understood in the art.

In another aspect, the present invention provides an isolated nucleic acid comprising a polynucleotide sequence encoding a mutant Fibroblast Growth Factor. The mutant Fibroblast Growth Factor comprises one or more N-linked or O-linked glycosylation site that is not present in wild-type Fibroblast Growth Factor. In some embodiments, the nucleic acid encoding the mutant FGF-20 has a corresponding wild-type sequence that encodes a wild-type Fibroblast Growth Factor that has the amino acid sequence of SEQ ID NO:1. In some preferred embodiments, the mutant Fibroblast Growth Factor includes at least one amino acid sequence selected from SEQ ID NOs: 9-14, 18-45, 48-65, 69-109, and 112-145. In some other embodiments, the nucleic acid encoding the mutant FGF-21 has a corresponding wild-type sequence that encodes a wild-type Fibroblast Growth Factor that has the amino acid sequence of SEQ ID NO: 146. In some preferred embodiments, the mutant Fibroblast Growth Factor includes at least one amino acid sequence selected from SEQ ID NOs: 161-214, 220-320, and 323-360.

In another aspect, the present invention provides an expression cassette or a cell that comprises a nucleic acid, e.g., an isolated nucleic acid, including a polynucleotide sequence encoding a mutant Fibroblast Growth Factor. The mutant Fibroblast Growth Factor includes one or more N-linked or O-linked glycosylation site that is not present in the wild-type Fibroblast Growth Factor.

In another aspect, the present invention provides a mutant Fibroblast Growth Factor, that includes one or more N-linked or O-linked glycosylation site that is not present in the wild-type Fibroblast Growth Factor. In some embodiments, the wild-type Fibroblast Growth Factor has the amino acid sequence of SEQ ID NO: 1. In some preferred embodiments, the mutant Fibroblast Growth Factor comprises at least one amino acid sequence selected from SEQ ID NOs: 9-14, 18-45, 48-65, 69-109, and 112-145. In some other embodiments, the wild-type Fibroblast Growth Factor has the amino acid sequence of SEQ ID NO:146. In some preferred embodiments, the mutant Fibroblast Growth Factor comprises at least one amino acid sequence selected from SEQ ID NOs: 161-214, 220-320, and 323-360.

In another aspect, the present invention provides a method for making a mutant Fibroblast Growth Factor that includes an N-linked or O-linked glycosylation site that is not present in the wild-type Fibroblast Growth Factor. This method includes the steps of recombinantly producing the mutant Fibroblast Growth Factor, and glycosylating the mutant Fibroblast Growth Factor at the new glycosylation site. In some embodiments, the wild-type Fibroblast Growth Factor has the amino acid sequence of SEQ ID NO:1. In some preferred embodiments, the mutant Fibroblast Growth Factor comprises at least one amino acid sequence selected from SEQ ID NOs: 9-14, 18-45, 48-65, 69-109, and 112-145. In some other embodiments, the wild-type Fibroblast Growth Factor has the amino acid sequence of SEQ ID NO: 146. In some preferred embodiments, the mutant Fibroblast Growth Factor comprises at least one amino acid sequence selected from SEQ ID NOs: 161-214, 220-320, and 323-360.

In still a further aspect, the present invention provides a pharmaceutical composition having a therapeutically effective amount of a mutant Fibroblast Growth Factor that includes an N-linked or O-linked glycosylation site not present in the wild-type Fibroblast Growth Factor. In some embodiments, the wild-type Fibroblast Growth Factor has the amino acid sequence of SEQ ID NO: 1. In some preferred embodiments, the mutant Fibroblast Growth Factor comprises at least one amino acid sequence selected from SEQ ID NOs: 9-14, 18-45, 48-65, 69-109, and 112-145. In some other embodiments, the wild-type Fibroblast Growth Factor has the amino acid sequence of SEQ ID NO: 146. In some preferred embodiments, the mutant Fibroblast Growth Factor comprises at least one amino acid sequence selected from SEQ ID NOs: 161-214, 220-320, and 323-360.

In each of the aspects described above, the mutant Fibroblast Growth Factor is optionally conjugated to one or more modifying groups, preferably via glycoconjugation, giving rise to a glycosyl linking group between the glycosylation site and the modifying group. An exemplary modifying group is poly(ethylene glycol).

BRIEF DESCRIPTION OF THE DRAWINGS

FIGS. 2A-2N are a table providing exemplary sialyltransferases of use in forming the glycoconjugates of the invention, e.g., to glycoPEGylate peptides with a modified sialic acid.

DETAILED DESCRIPTION OF THE INVENTION AND THE PREFERRED EMBODIMENTS

Abbreviations

Figure 1A:
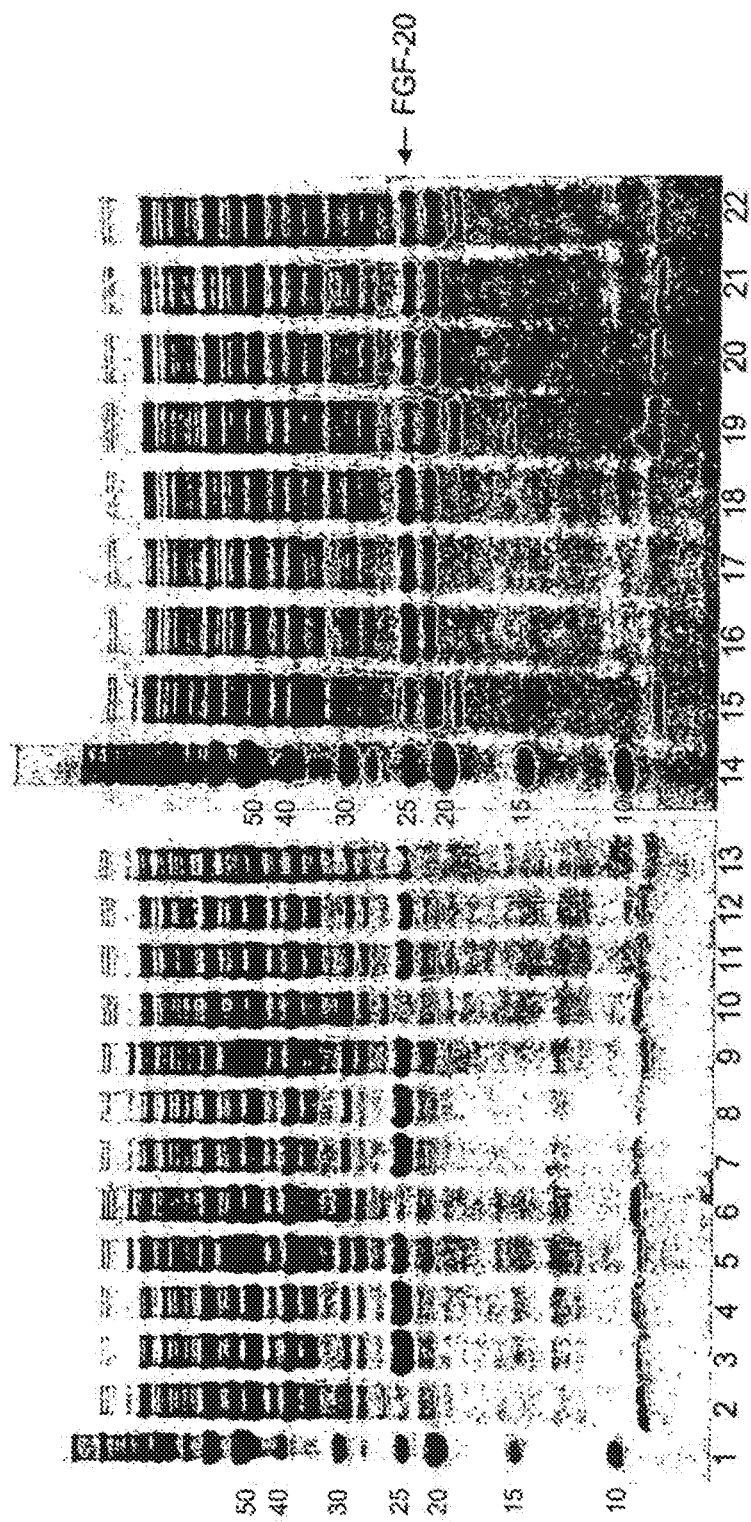
FIG. 1A displays results of an SDS-PAGE analysis of human FGF-20 induction at varied temperature, time, vector and *E. Coli* strains: lanes 1 and 14: molecular weight marker (sized in kDa), (induction temperature); lanes 2-9 and 15-18: 37° C., lanes 10-13 and 19-22: 20° C. Strain used: lanes 2-4 and 6-8 and 10-12, W3110; lanes 5, 9, and 13 BL21(DE3); lanes 15-17 and 19-21, *E. Coli*$_{(trxb, gor, supp)}$; lanes 18 and 22, *E. Coli*$_{(trxb, gor, supp)}$(DE3). Vector used: lanes 2, 6, 10, 15, 19 use vector #1; lanes 3, 7, 11, 16, 20 use vector #2; lanes 4, 8, 12, 17, 21 use vector #3; lanes 5, 9, 13, 18 and 22 use vector #4.

PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; NeuAc, sialyl or N-acetylneuraminyl; Sia, sialyl or N-acetylneuraminyl; and derivatives and analogues thereof.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid analogs described in the following patent application can be incorporated into the FGF peptide conjugates and mutant FGF sequences of the invention: U.S. patent application Ser. No. 11/094,677 (filed Mar. 29, 2005); Ser. No. 11/094,676 (filed Mar. 29, 2005); Ser. No. 11/093,798 (filed Mar. 29, 2005); Ser. No. 11/093,797 (filed Mar. 29, 2005); Ser. No. 11/093,597 (filed Mar. 29, 2005); Ser. No. 10/965,218 (filed Oct. 13, 2004); Ser. No. 11/093,797 (filed Mar. 29, 2005); Ser. No. 11/009,635 (filed Dec. 10, 2004); Ser. No. 11/016,348 (filed Dec. 16, 2004); Ser. No. 10/825,867 (filed Apr. 16, 2004); Ser. No. 10/826,919 (filed Apr. 16, 2004); and Ser. No. 10/686,944 (now U.S. Pat. No. 6,927,042, issued Aug. 9, 2005). The methods described in these applications can also be used to produce the FGF peptide conjugates and mutant FGF sequences of the invention. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the most N-terminal residue, which is numbered 1, in an unmodified wild-type polypeptide sequence.

"Proximate to a proline residue," as used herein refers to an amino acid that is less than about 10 amino acids removed from a proline residue, preferably, less than about 9, 8, 7, 6 or 5 amino acids removed from a proline residue, more preferably, less than about 4, 3, 2 or 1 residues removed from a proline residue. The amino acid "proximate a proline residue" may be on the C- or N-terminal side of the proline residue.

"Polypeptide," "peptide," and "protein" are used interchangeably herein to refer to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is conjugated with a modified sugar as set forth herein.

The term "FGF" or "Fibroblast Growth Factor" refers to any of the family of twenty-five known wild-type peptides. The term also refers to amino acid sequences with the same, fewer or additional amino acids as compared to the wild-type sequence. Additional amino acids, which can be natural or unnatural, can be inserted into the beginning, middle, or end of the amino acid sequence.

The term "mutating" or "mutation," as used in the context of introducing additional N- or O-linked glycosylation site(s) into a wild-type Fibroblast Growth Factor, refers to the deletion, insertion, or substitution of any nucleotide or amino acid residue, by chemical, enzymatic, or any other means, in a polynucleotide sequence encoding a wild-type Fibroblast Growth Factor or the amino acid sequence of a wild-type Fibroblast Growth Factor, respectively, such that the amino acid sequence of the resulting Fibroblast Growth Factor comprises at least one N- or O-linked glycosylation site that does not exist in the corresponding wild-type Fibroblast Growth Factor. In the case of amino acid substitution, both conservative and non-conservative substitutions may be used to create an FGF mutant that contains a new N- or O-linked glycosylation site.

The site for a mutation introducing a new N- or O-linked glycosylation site may be located anywhere in the polypeptide. Exemplary amino acid sequences for Fibroblast Growth Factor mutants are depicted in SEQ ID NOs: 9-14, 18-22, 23-45, 48-65, 69-109, 112-145, 161-214, 220-320, and 323-360. A "mutant Fibroblast Growth Factor" of this invention thus comprises at least one amino acid substitution, insertion, or mutated amino acid residue. On the other hand, the wild-type Fibroblast Growth Factor whose coding sequence is modified to generate a mutant Fibroblast Growth Factor can be referred to in this application as "the corresponding wild-type Fibroblast Growth Factor", or simply "wild-type peptide". For example, SEQ ID NO:1 is the amino acid sequence of the corresponding wild-type Fibroblast Growth Factor-20 for mutant Fibroblast Growth Factors having the amino acid sequences of SEQ ID NOs: 9-14, 18-22, 23-45, 48-65, 69-109, and 112-145. Likewise, SEQ ID NO:146 is the amino acid sequence of the corresponding wild-type Fibroblast Growth Factor-21 for mutant Fibroblast Growth Factors having the amino acid sequences of SEQ ID NOs: 161-214, 220-320, and 323-360.

The term "effective amount," or "an amount effective to" or a "therapeutically effective amount" or any grammatically equivalent term means the amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, water-soluble polymers (PEG moieties), therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly (ethylene imine) is an exemplary polyamine, and poly (acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly (ethylene glycol) can be represented in general form as $R(-PEG-OX)_m$ in which R represents the core moiety, such as glycerol or pentaerythritol, X represents a capping group or an end group, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly (hydroxypropylmethacrylamide), poly(α-hydroxy acid), poly(vinyl alcohol), polyphosphazene, polyoxazoline, poly (N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The term "sialic acid" or "sialyl" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius<2 nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives will vary depending upon the size, state of glycosylation, and other parameters, as is well known in the art. Further explanation of "half-life" is found in Pharmaceutical Biotechnology (1997, D F A Crommelin and R D Sindelar, eds., Harwood Publishers, Amsterdam, pp 101-120).

The term "glycoconjugation," as used herein, refers to the enzymatically mediated conjugation of a modified sugar species to an amino acid or glycosyl residue of a polypeptide, e.g., a mutant Fibroblast Growth Factor of the present invention. A subgenus of "glycoconjugation" is "glyco-PEGylation," in which the modifying group of the modified sugar is poly(ethylene glycol), an alkyl derivative of PEG (e.g., m-PEG) or a reactive derivative of PEG (e.g., $H_2N$-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term, "non-glycosidic modifying group", as used herein, refers to modifying groups which do not include a naturally occurring sugar linked directly to the glycosyl linking group.

As used herein, "a radioactive agent" includes any radioisotope that is effective in diagnosing or destroying a tumor. Examples include, but are not limited to, indium-111, cobalt-60. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, inhalation, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom (s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_u$—U—, wherein T and U are independently —NR—, —O—, —CRR'— or a single bond, and u is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_z$—X—(CR"R'")$_d$—, where z and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" is meant to include oxygen (O), nitrogen (N), sulfur (S) and silicon (Si).

Introduction

FGF-9 is a fibroblast growth factor that is expressed as a secreted protein in the brain and the uterine endometrium. The 208 amino acid heparin binding protein is thought to be unglycosylated in its wild-type state. As an autocrine/paracrine growth factor, FGF-9 plays an important role in glial cell development and in the proliferation and activation of other cells expressing FGF receptors, such as those found in the motorneurons and prostate.

FGF-18 is another member of the family of the FGF family. It is involved in stimulating hepatic and intestinal proliferation and is an essential regulator of bone and cartilage differentiation. Like FGF-9, it too is thought to be unglycosylated in its wild-type state. This 207 amino acid protein is also involved in postnatal lung development through the stimulation of myofibroblast proliferation and differentiation. Induced by calcineurin, FGF-18 has the ability to repress noggin expression and act as an effective neuroprotective agent.

FGF-20 is a novel fibroblast growth factor that is expressed as a secreted protein in the brain (e.g., cerebellum and substantia nigra pars compacta) and expressed in E. coli as a monomer of apparent molecular weight of 23 kDa. This 211 amino acid heparin binding protein is thought to be un-glycosylated in its wild-type state. Its biological activities include neurogenesis, neuroprotection, CNS regeneration, anti-inflammatory effects (e.g., bowel anti-inflammatory agent) and wound healing, making it a useful agent for treating diseases such as Parkinson's and Alzheimer's. FGF-20 can also be used as a prophylactic or mitigating agent against radiation toxicity to the GI and other parts of the body, e.g. arising from chemo- and radiation therapy, nuclear/radiological terrorism, radiation accidents, etc. In several studies, FGF-20 has also demonstrated its effectiveness in preventing and treating oral mucositis, a condition characterized by symptoms ranging from mild erythema to severe painful ulcerations.

FGF-21, another novel fibroblast growth factor, is expressed in liver, thymic and testicular tissue. The 209 amino acid protein is also thought to be unglycosylated in the wild-type state. In recent studies, FGF-21 was shown to regulate glucose uptake in human fat cells, suggesting its role as a metabolic regulator. Its effect on insulin activity and its regulation of lipidolysis make FGF-21 a useful treatment for type II diabetes and obesity. It has been implicated in various diseases characterized by complete or partial loss of cellular, tissue, or organ function as well as abnormalities in the function or number of cells and/or tissue. FGF-21 also has numerous other therapeutic applications, as will be described below.

One disease amenable to FGF-21 treatment is ischemic vascular disease. Treatment with the peptide may induce therapeutic angiogenesis or preserve function/survival of cells in patients suffering from diseases such as myocardial ischemia/infarction, peripheral vascular disease, renal artery disease, or stroke, etc.

Other diseases for which FGF-21 therapy can be useful include cardiomyopathies, which are characterized by loss of function or death of cardiac myocytes or supporting cells in the heart as occurs in, e.g. congestive heart failure, myocarditis, and musculoskeletal diseases, which are characterized by loss of function, inadequate function or death of skeletal muscle cells, bone cells or supporting cells, e.g. skeletal myopathies, bone disease, and arthritis. In addition, congenital defects in, e.g. liver, heart, lung, brain, limbs, kidney, etc., arising from the loss of FGF-21 or its function are treatable with FGF-21.

FGF-21 polypeptides and polynucleotides can also facilitate the healing of wounds originating from trauma, disease, medical or surgical treatment, and aid in cell and tissue regeneration necessitated by the above circumstances. For example, FGF-21 can effect liver regeneration, operative wound healing, re-endothelialization of injured blood vessels, healing of traumatic wounds, healing of ulcers due to vascular, metabolic disease, etc., bone fractures, loss of cells due to inflammatory disease, etc.

To improve the effectiveness of recombinant FGF used for therapeutic purposes, the present invention provides conjugates of FGF peptides with a modifying group. Some of the peptides in these FGF peptide conjugates have the same amino acid or nucleotide sequence as the wild-type FGF, while others are mutants.

The modifying groups can be selected from polymeric modifying groups such as, e.g., PEG (m-PEG), PPG (m-PPG), etc., therapeutic moieties, diagnostic moieties, targeting moieties and the like. Creation of a FGF peptide conjugate, e.g., adding a water-soluble polymeric modifying group, can improve the stability and retention time of FGF in a patient's circulation, and/or reduce the antigenicity of FGF.

The peptide conjugates of the invention can be formed by the enzymatic attachment of a modified sugar to a glycosylated or unglycosylated peptide. An amino acid glycosylation site and/or a glycosyl group provides a locus for conjugating a modified sugar bearing a modifying group to the peptide, e.g., by glycoconjugation.

The present invention also provides genetically engineered mutants of Fibroblast Growth Factor that contain N-linked or O-linked glycosylation sites not present in naturally occurring Fibroblast Growth Factor. While these FGF mutants substantially retain the biological activity of the wild-type hormone, the newly introduced glycosylation sites allow the recombinantly produced FGF mutants to be glycosylated in a large variety of patterns.

The methods of the invention also make it possible to assemble peptide conjugates and glycopeptide conjugates that have a substantially homogeneous derivatization pattern. The enzymes used in the invention are generally selective for a particular amino acid residue, combination of amino acid residues, particular glycosyl residues, or combination of glycosyl residues of the peptide. The methods are also practical for large-scale production of peptide conjugates. Thus, the methods of the invention provide a practical means for large-scale preparation of peptide conjugates having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The FGF peptide conjugates can be included in pharmaceutical formulations comprising a FGF peptide conjugate as well as a pharmaceutically acceptable carrier.

The present invention also provides conjugates of FGF peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

The Mutants

The present invention provides mutants of FGF that include one or more O- or N-linked glycosylation sites that are not found in the wild type peptide. The mutants are substrates for enzymatic glycosylation at one or more sites that would not normally be glycosylated, or would be poorly glycosylated, in the wild type peptide. Thus, the mutants allow the position of a glycosyl residue or a glycosyl linking group to be engineered to obtain a peptide having selected desirable properties. In addition to the position and number of glycosyl residues or glycosyl linking groups, other properties that can be varied using the mutants and methods of the invention include pharmacokinetics, pharmacodynamics, resistance to proteolysis, immunogenicity, recognition by the reticuloendothelial system, tissue distribution and the like.

Accordingly, in one aspect, the present invention provides an isolated nucleic acid comprising a polynucleotide sequence encoding a mutant Fibroblast Growth Factor. The mutant Fibroblast Growth Factor comprises an N-linked or O-linked glycosylation site that does not exist in the corresponding wild-type Fibroblast Growth Factor. In some embodiments, the corresponding wild-type Fibroblast Growth Factor has the amino acid sequence of SEQ ID NO: 1. In some preferred embodiments, the mutant Fibroblast Growth Factor comprises at least one amino acid sequence selected from SEQ ID NOs: 9-14, 18-45, 48-65, 69-109, and 112-145. In some other embodiments, the wild-type Fibroblast Growth Factor has the amino acid sequence of SEQ ID NO:146. In some preferred embodiments, the mutant Fibroblast Growth Factor comprises at least one amino acid sequence selected from SEQ ID NOs: 161-214, 220-320, and 323-360. In an exemplary embodiment, a peptide having Fibroblast Growth Factor activity has an amino acid sequence that is at least about 95% homologous to the amino acid sequences set forth herein. Preferably, the amino acid sequence is at least about 96%, 97%, 98% or 99% homologous to the amino acid sequences set forth herein.

In another aspect, the present invention provides an expression cassette or a cell that comprises a nucleic acid, e.g., an isolated nucleic acid, including a polynucleotide sequence encoding a mutant Fibroblast Growth Factor. The mutant Fibroblast Growth Factor includes one or more N-linked or O-linked glycosylation site that does not exist in the corresponding wild-type Fibroblast Growth Factor.

In another aspect, the present invention provides a mutant Fibroblast Growth Factor, that includes an N-linked or O-linked glycosylation site that does not exist in the corresponding wild-type Fibroblast Growth Factor. In some embodiments, the corresponding wild-type Fibroblast Growth Factor has the amino acid sequence of SEQ ID NO:1. In some preferred embodiments, the mutant Fibroblast Growth Factor comprises at least one amino acid sequence selected from SEQ ID NOs: 9-14, 18-45, 48-65, 69-109, and 112-145. In some other embodiments, the wild-type Fibroblast Growth Factor has the amino acid sequence of SEQ ID NO:146. In some preferred embodiments, the mutant Fibroblast Growth Factor comprises at least one amino acid sequence selected from SEQ ID NOs: 161-214, 220-320, and 323-360. In an exemplary embodiment, a peptide having Fibroblast Growth Factor activity has an amino acid sequence that is at least about 95% homologous to the amino acid sequences set forth herein. Preferably, the amino acid sequence is at least about 96%, 97%, 98% or 99% homologous to the amino acid sequences set forth herein.

In another aspect, the present invention provides a method for making a mutant Fibroblast Growth Factor that includes an N-linked or O-linked glycosylation site that does not exist in the corresponding wild-type Fibroblast Growth Factor. This method comprises the steps of recombinantly producing the mutant Fibroblast Growth Factor, and glycosylating the mutant Fibroblast Growth Factor at the new glycosylation site. In some embodiments, the corresponding wild-type Fibroblast Growth Factor has the amino acid sequence of SEQ ID NO: 1. In some preferred embodiments, the mutant Fibroblast Growth Factor comprises at least one amino acid sequence selected from SEQ ID NOs: 9-14, 18-45, 48-65, 69-109, and 112-145. In some other embodiments, the wild-type Fibroblast Growth Factor has the amino acid sequence of SEQ ID NO:146. In some preferred embodiments, the mutant Fibroblast Growth Factor comprises at least one amino acid sequence selected from SEQ ID NOs: 161-214, 220-320, and 323-360. In an exemplary embodiment, a peptide having Fibroblast Growth Factor activity has an amino acid sequence that is at least about 95% homologous to the amino acid sequences set forth herein. Preferably, the amino acid sequence is at least about 96%, 97%, 98% or 99% homologous to the amino acid sequences set forth herein.

Acquisition of FGF Coding Sequences
General Recombinant Technology

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type Fibroblast Growth Factor genes, polynucleotide encoding mutant Fibroblast Growth Factors, and synthetic oligonucleotides can be verified after cloning using, e.g., the chain termination method for sequencing double-stranded templates of Wallace et al., *Gene* 16: 21-26 (1981).

Cloning and Subcloning of a Wild-Type FGF Coding Sequence

A number of polynucleotide sequences encoding a wild-type Fibroblast Growth Factor-20, e.g., GenBank Accession No. NM_019851, NM_019113, have been determined and can be obtained from a commercial supplier.

The rapid progress in the studies of human genome has made possible a cloning approach where a human DNA sequence database can be searched for any gene segment that has a certain percentage of sequence homology to a known nucleotide sequence, such as one encoding a previously identified Fibroblast Growth Factor. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a Fibroblast Growth Factor can be isolated from a human cDNA or genomic DNA library using standard cloning techniques such as polymerase chain reaction (PCR), where homology-based primers can often be derived from a known nucleic acid sequence encoding a Fibroblast Growth Factor. Most commonly used techniques for this purpose are described in standard texts, e.g., Sambrook and Russell, supra.

cDNA libraries suitable for obtaining a coding sequence for a wild-type Fibroblast Growth Factor may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the wild-type Fibroblast Growth Factor from the cDNA library. A general description of appropriate procedures can be found in Sambrook and Russell, supra.

A similar procedure can be followed to obtain a full length sequence encoding a wild-type Fibroblast Growth Factor, e.g., any one of the GenBank Accession Nos. mentioned above, from a human genomic library. Human genomic libraries are commercially available or can be constructed according to various art-recognized methods. In general, to construct a genomic library, the DNA is first extracted from an tissue where a Fibroblast Growth Factor is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology*, CRC Press Inc. 1994) to amplify a segment of nucleotide sequence from a cDNA or genomic library. Using the amplified segment as a probe, the full length nucleic acid encoding a wild-type Fibroblast Growth Factor is obtained.

Upon acquiring a nucleic acid sequence encoding a wild-type Fibroblast Growth Factor, the coding sequence can be subcloned into a vector, for instance, an expression vector, so that a recombinant wild-type Fibroblast Growth Factor can be produced from the resulting construct. Further modifications to the wild-type Fibroblast Growth Factor coding sequence, e.g., nucleotide substitutions, may be subsequently made to alter the characteristics of the molecule.

Introducing Mutations into an FGF Sequence

From an encoding polynucleotide sequence, the amino acid sequence of a wild-type Fibroblast Growth Factor, e.g., SEQ ID NO:1, SEQ ID NO:146, can be determined. Subsequently, this amino acid sequence may be modified to alter the protein's glycosylation pattern, by introducing additional glycosylation site(s) at various locations in the amino acid sequence.

Several types of protein glycosylation sites are well known in the art. For instance, in eukaryotes, N-linked glycosylation occurs on the asparagine of the consensus sequence Asn-$X_{aa}$-Ser/Thr, in which $X_{aa}$ is any amino acid except proline (Kornfeld et al., *Ann Rev Biochem* 54:631-664 (1985); Kukuruzinska et al., *Proc. Natl. Acad. Sci. USA* 84:2145-2149 (1987); Herscovics et al., *FASEB J* 7:540-550 (1993); and Orlean, *Saccharomyces* Vol. 3 (1996)). O-linked glycosylation takes place at serine or threonine residues (Tanner et al., *Biochim. Biophys. Acta.* 906:81-91 (1987); and Hounsell et al., *Glycoconj. J.* 13:19-26 (1996)). Other glycosylation patterns are formed, by linking glycosylphosphatidylinositol to the carboxyl-terminal carboxyl group of the protein (Takeda et al., *Trends Biochem. Sci.* 20:367-371 (1995); and Udenfriend et al, *Ann. Rev. Biochem.* 64:593-591 (1995). Based on this knowledge, suitable mutations can thus be introduced into a wild-type Fibroblast Growth Factor sequence to form new glycosylation sites.

Although direct modification of an amino acid residue within a Fibroblast Growth Factor polypeptide sequence may be suitable to introduce a new N-linked or O-linked glycosylation site, more frequently, introduction of a new glycosylation site is accomplished by mutating the polynucleotide sequence encoding a Fibroblast Growth Factor. This can be achieved by using any of known mutagenesis methods, some of which are discussed below. Exemplary modifications to Fibroblast Growth Factor include those illustrated in SEQ ID NO:9 or SEQ ID NO:87.

A variety of mutation-generating protocols are established and described in the art. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

Modification of Nucleic Acids for Preferred Codon Usage in a Host Organism

The polynucleotide sequence encoding a mutant Fibroblast Growth Factor can be further altered to coincide with the preferred codon usage of a particular host. For example, the preferred codon usage of one strain of bacterial cells can be used to derive a polynucleotide that encodes a mutant Fibroblast Growth Factor of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the mutant Fibroblast Growth Factor coding sequences are verified by sequencing and are then subcloned into an appropriate expression vector for recombinant production in the same manner as the wild-type Fibroblast Growth Factors.

Expression and Purification of the Mutant FGF

Following sequence verification, the mutant Fibroblast Growth Factor of the present invention can be produced using routine techniques in the field of recombinant genetics, relying on the polynucleotide sequences encoding the polypeptide disclosed herein.

Expression Systems

To obtain high level expression of a nucleic acid encoding a mutant Fibroblast Growth Factor of the present invention, one typically subclones a polynucleotide encoding the mutant Fibroblast Growth Factor into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant Fibroblast Growth Factor are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the mutant Fibroblast Growth Factor in host cells. A typical expression cassette thus contains a promoter operably linked to the nucleic acid sequence encoding the mutant Fibroblast Growth Factor and signals required for efficient polyadenylation of the transcript, ribosome binding sites, and translation termination. The nucleic acid sequence encoding the Fibroblast Growth Factor is typically linked to a cleavable signal peptide sequence to promote secretion of the Fibroblast Growth Factor by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant Fibroblast Growth Factor under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a FGF mutant of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or mutant Fibroblast Growth Factor or its coding sequence while still retaining the biological activity of the Fibroblast Growth Factor. Moreover, modifications of a polynucleotide coding sequence may also be made to accommodate preferred codon usage in a particular expression host without altering the resulting amino acid sequence.

Transfection Methods

Standard transfection methods are used to produce bacterial, mammalian, yeast, insect, or plant cell lines that express large quantities of the mutant Fibroblast Growth Factor, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see. e.g., Sambrook and Russell. supra). It is only necessary that the particular genetic engineering procedure used be capable of successfully introducing at least one gene into the host cell capable of expressing the mutant Fibroblast Growth Factor.

Detection of Expression of Mutant FGF in Host Cells

After the expression vector is introduced into appropriate host cells, the transfected cells are cultured under conditions favoring expression of the mutant Fibroblast Growth Factor. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant Fibroblast Growth Factor in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant Fibroblast Growth Factor of the present invention, such as a polypeptide having the amino acid sequence of SEQ ID NO:3, 4, or 5, (e.g., Harlow and Lane, *Antibodies, A Laboratory Manual*, Chapter 14, Cold Spring Harbor, 1988; Kohler and Milstein, *Nature*, 256: 495-497 (1975)). Such techniques require antibody preparation by selecting antibodies with high specificity against the mutant Fibroblast Growth Factor or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.*, 6: 511-519 (1976). More detailed descriptions of preparing antibody against the mutant Fibroblast Growth Factor of the present invention and conducting immunological assays detecting the mutant Fibroblast Growth Factor are provided in a later section.

Purification of Recombinantly Produced Mutant FGF

Once the expression of a recombinant mutant Fibroblast Growth Factor in transfected host cells is confirmed, the host cells are then cultured in an appropriate scale for the purpose of purifying the recombinant polypeptide.

Purification of Recombinantly Produced Mutant FGF from Bacteria

When the mutant Fibroblast Growth Factors of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant Fibroblast Growth Factor from bacterial inclusion body, see. e.g., Patra et al., *Protein Expression and Purification* 18: 182-190 (2000).

Alternatively, it is possible to purify recombinant polypeptides, e.g., a mutant Fibroblast Growth Factor, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard Protein Separation Techniques for Purification

When a recombinant polypeptide, e.g., the mutant Fibroblast Growth Factor of the present invention, is expressed in host cells in a soluble form, its purification can follow the standard protein purification procedure described below.

Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant Fibroblast Growth Factor of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant Fibroblast Growth Factor. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The proteins of interest (such as the mutant Fibroblast Growth Factor of the present invention) can also be separated from other proteins on the basis of their size, net surface charge, hydrophobicity, or affinity for ligands. In addition, antibodies raised against Fibroblast Growth Factor can be conjugated to column matrices and the Fibroblast Growth Factor immunopurified. All of these methods are well known in the art.

It will be apparent to one of skill that chromatographic techniques can be performed at any scale and using equipment from many different manufacturers (e.g., Pharmacia Biotech).

Immunoassays for Detection of Mutant FGF Expression

To confirm the production of a recombinant mutant Fibroblast Growth Factor, immunological assays may be useful to detect in a sample the expression of the polypeptide. Immunological assays are also useful for quantifying the expression level of the recombinant hormone. Antibodies against a mutant Fibroblast Growth Factor are necessary for carrying out these immunological assays.

Production of Antibodies Against Mutant FGF

Methods for producing polyclonal and monoclonal antibodies that react specifically with an immunogen of interest are known to those of skill in the art (see, e.g., Coligan, *Current Protocols in Immunology* Wiley/Greene, N Y, 1991; Harlow and Lane, *Antibodies: A Laboratory Manual* Cold Spring Harbor Press, N Y, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant Fibroblast Growth Factor of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When desired, antibodies capable of specifically recognizing a mutant Fibroblast Growth Factor of the present invention can be tested for their cross-reactivity against the wild-type Fibroblast Growth Factor and thus distinguished from the antibodies against the wild-type protein. For instance, antisera obtained from an animal immunized with a mutant Fibroblast Growth Factor can be run through a column on which a wild-type Fibroblast Growth Factor is immobilized. The portion of the antisera that passes through the column recognizes only the mutant Fibroblast Growth Factor and not the wild-type Fibroblast Growth Factor. Similarly, monoclonal antibodies against a mutant Fibroblast Growth Factor can also be screened for their exclusivity in recognizing only the mutant but not the wild-type Fibroblast Growth Factor.

Polyclonal or monoclonal antibodies that specifically recognize only the mutant Fibroblast Growth Factor of the present invention but not the wild-type Fibroblast Growth Factor are useful for isolating the mutant protein from the wild-type protein, for example, by incubating a sample with a mutant Fibroblast Growth Factor-specific polyclonal or monoclonal antibody immobilized on a solid support.

Immunoassays for Detecting Mutant FGF Expression

Once antibodies specific for a mutant Fibroblast Growth Factor of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Glycosylation and Glycoconjugation of the Mutant FGF

Glycosylation and Glycoconjugation by Enzymatic Methods

Post-expression in vitro modification of peptides is an attractive strategy to remedy the deficiencies of methods that rely on controlling glycosylation by engineering expression systems; including both modification of glycan structures or introduction of glycans at novel sites. A comprehensive arsenal of enzymes that transfer saccharide donor moieties is becoming available, making in vitro enzymatic synthesis of glycoconjugates with custom designed glycosylation patterns and glycosyl structures possible. See, for example, U.S. Pat. Nos. 5,876,980; 6,030,815; 5,728,554; 5,922,577; and published patent applications WO 98/31826; WO 01/88117; WO 03/031464; WO 03/046150; WO 03/045980; WO 03/093448; WO 04/009838; US2002/142370; US2003/040037; US2003/180835; US2004/063911; US2003/207406; and US2003/124645, each of which is incorporated herein by reference.

The invention provides methods for preparing conjugates of glycosylated and unglycosylated mutant Fibroblast Growth Factors, which have glycosylation sites that do not exist in the corresponding wild-type FGF. Such conjugation may take place directly on the appropriate sugar units of a glycosylated mutant FGF, or following the removal (i.e., "trimming back") of any undesired sugar units. The conjugates are formed between peptides and diverse species such as water-soluble polymers, therapeutic moieties, diagnostic moieties, targeting moieties and the like. Also provided are conjugates that include two or more peptides linked together through a linker arm, i.e., multifunctional conjugates. The multi-functional conjugates of the invention can include two or more copies of the same peptide or a collection of diverse peptides with different structures, and/or properties.

The conjugates of the invention are formed by the enzymatic attachment of a modified sugar to the glycosylated or unglycosylated peptide. The modified sugar, when interposed between the peptide and the modifying group on the sugar becomes what is referred to herein as "an glycosyl linking group." Using the exquisite selectivity of enzymes, such as glycosyltransferases, the present method provides peptides that bear a desired group at one or more specific locations. Thus, according to the present invention, a modified sugar is attached directly to a selected locus on the peptide chain or, alternatively, the modified sugar is appended onto a carbohydrate moiety of a glycopeptide. Peptides in which modified sugars are bound to both a glycopeptide carbohydrate and directly to an amino acid residue of the peptide backbone are also within the scope of the present invention.

In contrast to known chemical and enzymatic peptide elaboration strategies, the methods of the invention, make it possible to assemble peptides and glycopeptides that have a substantially homogeneous derivatization pattern; the enzymes used in the invention are generally selective for a particular amino acid residue or combination of amino acid residues of the peptide. The methods are also practical for large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The methods of the invention also provide conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

Peptide Conjugates

In another aspect, the present invention provides a conjugate between a modified sugar and a FGF peptide. The FGF peptide in these cases may have the same sequence as a wild-type peptide, or it may be a mutant peptide. A peptide conjugate can have one of several forms. In an exemplary embodiment, a peptide conjugate can comprise a FGF peptide and a modifying group linked to an amino acid of the peptide through a glycosyl linking group.

In another exemplary embodiment, a Fibroblast Growth Factor (FGF) peptide conjugate can comprise a FGF peptide and a glycosyl group attached to an amino acid residue of the FGF peptide. In another exemplary embodiment, the FGF peptide is a member selected from FGF-1, FGF-2, FGF-9, FGF-18, FGF-20 and FGF-21. In another exemplary embodiment, the FGF peptide comprises at least one amino acid sequence which is a member selected from SEQ ID NOs: 1, 9-14, 18-45, 48-65, 69-109, 112-145 and 146.

In an exemplary embodiment, the glycosyl group is an intact glycosyl linking group. In another exemplary embodiment, the glycosyl group further comprises a modifying group. In another exemplary embodiment, the modifying group is a non-glycosidic modifying group. In another exemplary embodiment, the modifying group does not include a naturally occurring saccharide moiety.

In another exemplary embodiment, the peptide conjugate can comprise a FGF peptide and a glycosyl linking group which is bound to both a glycopeptide carbohydrate and directly to an amino acid residue of the peptide backbone. In yet another exemplary embodiment, a peptide conjugate can comprise a FGF peptide and a modifying group linked directly to an amino acid residue of the peptide. In this embodiment, the peptide conjugate may not comprise a glycosyl group. In any of these embodiments, the FGF peptide may or not be glycosylated. The present invention also encompasses a method for the modification of the glycan structure on FGF, providing a conjugate between FGF and a modifying group.

The conjugates of the invention will typically correspond to the general structure:

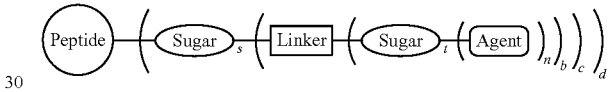

in which the symbols a, b, c, d and s represent a positive, non-zero integer; and t is either 0 or a positive integer. The "agent" is a therapeutic agent, a bioactive agent, a detectable label, water-soluble moiety (e.g., PEG, m-PEG, PPG, and m-PPG) or the like. The "agent" can be a peptide, e.g., enzyme, antibody, antigen, etc. The linker can be any of a wide array of linking groups, infra. Alternatively, the linker may be a single bond or a "zero order linker."

In the discussion that follows, the invention is illustrated by reference to the use of selected FGF peptides, such as FGF-20 and FGF-21. Those of skill in the art will recognize that the focus of the discussion is for clarity of illustration and that any FGF peptide, either wild-type or mutant, can be used to form these conjugates.

Modified Sugar

In an exemplary embodiment, the peptides of the invention are reacted with a modified sugar, thus forming a peptide conjugate. A modified sugar comprises a "sugar donor moiety" as well as a "sugar transfer moiety". The sugar donor moiety is any portion of the modified sugar that will be attached to the peptide, either through a glycosyl moiety or amino acid moiety, as a conjugate of the invention. The sugar donor moiety includes those atoms that are chemically altered during their conversion from the modified sugar to the glycosyl linking group of the peptide conjugate. The sugar transfer moiety is any portion of the modified sugar that will be not be attached to the peptide as a conjugate of the invention. For example, a modified sugar of the invention is the PEGylated sugar nucleotide, CMP-SA-PEG. For CMP-SA-PEG, the sugar donor moiety, or PEG-sialyl donor moiety, comprises PEG-sialic acid while the sugar transfer moiety, or sialyl transfer moiety, comprises CMP.

In modified sugars of use in the invention, the saccharyl moiety is preferably a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the saccharyl moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any saccharyl moiety can be utilized as the sugar donor moiety of the modified sugar. The saccharyl moiety can be a known sugar, such as mannose, galactose or glucose, or a species having the stereochemistry of a known sugar. The general formulae of these modified sugars are:

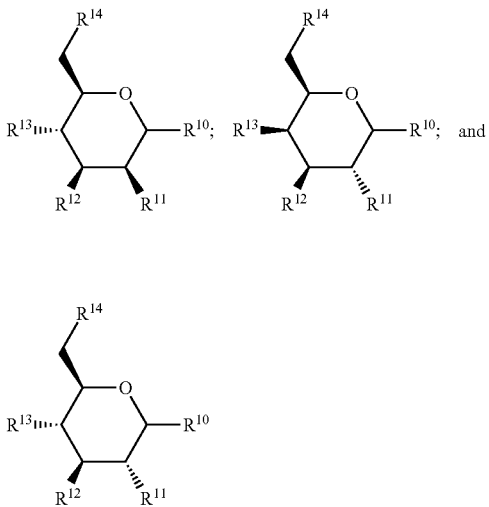

Other saccharyl moieties that are useful in forming the compositions of the invention include, but are not limited to fucose and sialic acid, as well as amino sugars such as glucosamine, galactosamine, mannosamine, the 5-amine analogue of sialic acid and the like. The saccharyl moiety can be a structure found in nature or it can be modified to provide a site for conjugating the modifying group. For example, in one embodiment, the modified sugar provides a sialic acid derivative in which the 9-hydroxy moiety is replaced with an amine. The amine is readily derivatized with an activated analogue of a selected modifying group.

Examples of modified sugars of use in the invention are described in PCT Patent Application No. PCT/US05/002522, which is herein incorporated by reference.

In a further exemplary embodiment, the invention utilizes modified sugars in which the 6-hydroxyl position is converted to the corresponding amine moiety, which bears a linker-modifying group cassette such as those set forth above. Exemplary glycosyl groups that can be used as the core of these modified sugars include Gal, GalNAc, Glc, GlcNAc, Fuc, Xyl, Man, and the like. A representative modified sugar according to this embodiment has the formula:

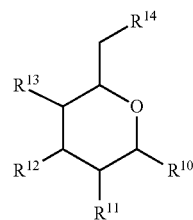

in which $R^{11}$-$R^{14}$ are members independently selected from H, OH, C(O)CH$_3$, NH, and NH C(O)CH$_3$. $R^{10}$ is a link to another glycosyl residue (—O-glycosyl) or to an amino acid of the Factor VII and/or Factor VIIa peptide (—NH-(Factor VII and/or Factor VIIa)). $R^{14}$ is OR$^1$, NHR$^1$ or NH-L-R$^1$. $R^1$ and NH-L-R$^1$ are as described above.

Glycosyl Linking Groups

In an exemplary embodiment, the invention provides a peptide conjugate formed between a modified sugar of the invention and a FGF peptide. In this embodiment, the sugar donor moiety (such as the saccharyl moiety and the modifying group) of the modified sugar becomes a "glycosyl linking group". The "glycosyl linking group" can alternatively refer to the glycosyl moiety which is interposed between the peptide and the modifying group.

Due to the versatility of the methods available for adding and/or modifying glycosyl residues on a peptide, the glycosyl linking groups can have substantially any structure. In the discussion that follows, the invention is illustrated by reference to the use of selected derivatives of furanose and pyranose. Those of skill in the art will recognize that the focus of the discussion is for clarity of illustration and that the structures and compositions set forth are generally applicable across the genus of glycosyl linking groups and modified sugars. The glycosyl linking group can comprise virtually any mono- or oligo-saccharide. The glycosyl linking groups can be attached to an amino acid either through the side chain or through the peptide backbone. Alternatively the glycosyl linking groups can be attached to the peptide through a saccharyl moiety. This saccharyl moiety can be a portion of an O-linked or N-linked glycan structure on the peptide.

In an exemplary embodiment, the invention utilizes a glycosyl linking group that has the formula:

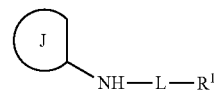

in which J is a glycosyl moiety, L is a bond or a linker and $R^1$ is a modifying group, e.g., a polymeric modifying group. Exemplary bonds are those that are formed between an NH$_2$ moiety on the glycosyl moiety and a group of complementary reactivity on the modifying group. For example, when $R^1$ includes a carboxylic acid moiety, this moiety may be activated and coupled with the NH$_2$ moiety on the glycosyl residue affording a bond having the structure NHC(O)R$^1$. J is preferably a glycosyl moiety that is "intact", not having been degraded by exposure to conditions that cleave the pyranose or furanose structure, e.g. oxidative conditions, e.g., sodium periodate.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the species of the invention, e.g., between the glycosyl moiety and the linker (L), or between the linker and the modifying group ($R^1$). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

An exemplary species of NH-L-$R^1$ has the formula: —NH{C(O)(CH$_2$)$_a$NH}$_s${C(O)(CH$_2$)$_b$(OCH$_2$CH$_2$)$_c$O(CH$_2$)$_d$NH}$_t$$R^1$, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —CH$_2$. As those of skill will appreciate one or more of the bracketed moieties corresponding to indices s and t can be replaced with a substituted or unsubstituted alkyl or heteroalkyl moiety.

More particularly, the invention utilizes compounds in which NH-L-$R^1$ is: NHC(O)(CH$_2$)$_a$NHC(O)(CH$_2$)$_b$(OCH$_2$CH$_2$)$_c$O(CH$_2$)$_d$NHR$^1$, NHC(O)(CH$_2$)$_b$(OCH$_2$CH$_2$)$_c$O(CH$_2$)$_d$NHR$^1$, NHC(O)O(CH$_2$)$_b$(OCH$_2$CH$_2$)$_c$O(CH$_2$)$_d$NHR$^1$, NH(CH$_2$)$_a$NHC(O)(CH$_2$)$_b$(OCH$_2$CH$_2$)$_c$O(CH$_2$)$_d$NHR$^1$, NHC(O)(CH$_2$)$_a$NHR$^1$, NH(CH$_2$)$_a$NHR$^1$, and NHR$^1$. In these formulae, the indices a, b and d are independently selected from the integers from 0 to 20, preferably from 1 to 5. The index c is an integer from 1 to about 2500.

In an exemplary embodiment, c is selected such that the PEG moiety is approximately 1 kD, 5 kD, 10, kD, 15 kD, 20 kD, 25 kD, 30 kD, 35 kD, 40 kD, 45 kD, 50 kD, 55 kD, 60 kD or 65 kD.

For the purposes of convenience, the glycosyl linking groups in the remainder of this section will be based on a sialyl moiety. However, one of skill in the art will recognize that another glycosyl moiety, such as mannosyl, galactosyl, glucosyl, or fucosyl, could be used in place of the sialyl moiety.

In an exemplary embodiment, the glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. In an exemplary embodiment, the invention provides a peptide conjugate comprising an intact glycosyl linking group having a formula that is selected from:

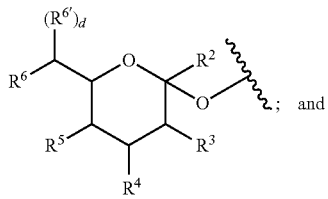

I

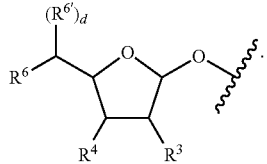

II

In Formulae I $R^2$ is H, CH$_2$OR$^7$, COOR$^7$ or OR$^7$, in which $R^7$ represents H, substituted or unsubstituted alkyl or substituted or unsubstituted heteroalkyl. When COOR$^7$ is a carboxylic acid or carboxylate, both forms are represented by the designation of the single structure COO$^-$ or COOH. In Formulae I and II, the symbols $R^3$, $R^4$, $R^5$, $R^6$ and $R^{6'}$ independently represent H, substituted or unsubstituted alkyl, OR$^8$, NHC(O)R$^9$. The index d is 0 or 1. $R^8$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes a modifying group. This modifying group can be a polymeric modifying moiety e.g., PEG, linked through a bond or a linking group. In an exemplary embodiment, $R^6$ and $R^{6'}$, together with the carbon to which they are attached are components of the pyruvyl side chain of sialic acid. In a further exemplary embodiment, the pyruvyl side chain is functionalized with the polymeric modifying group. In another exemplary embodiment, $R^6$ and $R^{6'}$, together with the carbon to which they are attached are components of the side chain of sialic acid and the polymeric modifying group is a component of $R^5$.

Exemplary modifying group-intact glycosyl linking group cassettes according to this motif are based on a sialic acid structure, such as those having the formulae:

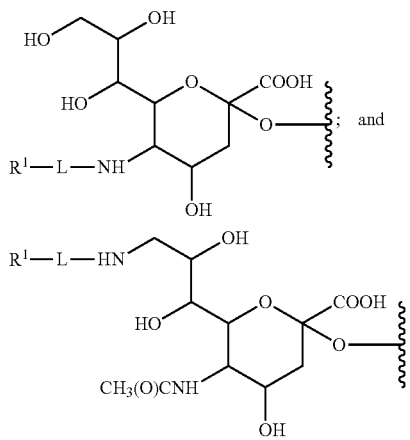

In the formulae above, $R^1$ and L are as described above. Further detail about the structure of exemplary $R^1$ groups is provided below.

In still a further exemplary embodiment, the conjugate is formed between a peptide and a modified sugar in which the modifying group is attached through a linker at the 6-carbon position of the modified sugar. Thus, illustrative glycosyl linking groups according to this embodiment have the formula:

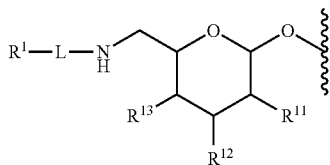

in which the radicals are as discussed above. Glycosyl linking groups include, without limitation, glucose, glucosamine, N-acetyl-glucosamine, galactose, galactosamine, N-acetylgalactosamine, mannose, mannosamine, N-acetylmannosamine, and the like.

In one embodiment, the present invention provides a peptide conjugate comprising the following glycosyl linking group:

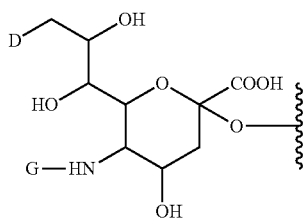

wherein D is a member selected from —OH and $R^1$-L-HN—; G is a member selected from H and $R^1$-L- and —C(O)($C_1$-$C_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is $R^1$-L-, and when G is —C(O)($C_1$-$C_6$)alkyl, D is $R^1$-L-NH—.

The invention provides a peptide conjugate that includes a glycosyl linking group having the formula:

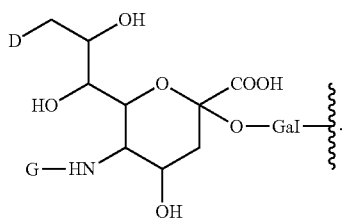

In other embodiments, the glycosyl linking group has the formula:

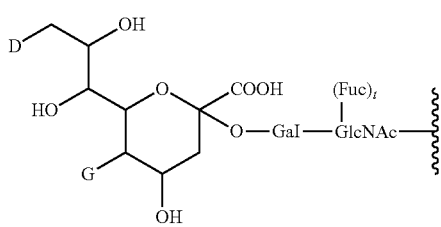

in which the index t is 0 or 1.

In a still further exemplary embodiment, the glycosyl linking group has the formula:

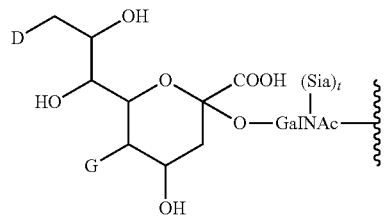

in which the index t is 0 or 1.

In yet another embodiment, the glycosyl linking group has the formula:

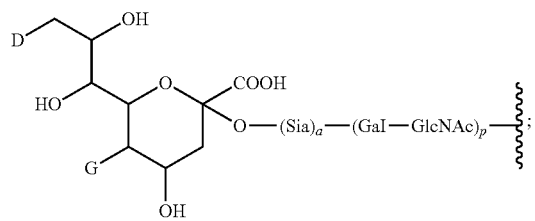

in which the index p represents and integer from 1 to 10; and a is either 0 or 1.

In an exemplary embodiment, a glycoPEGylated peptide conjugate of the invention selected from the formulae set forth below:

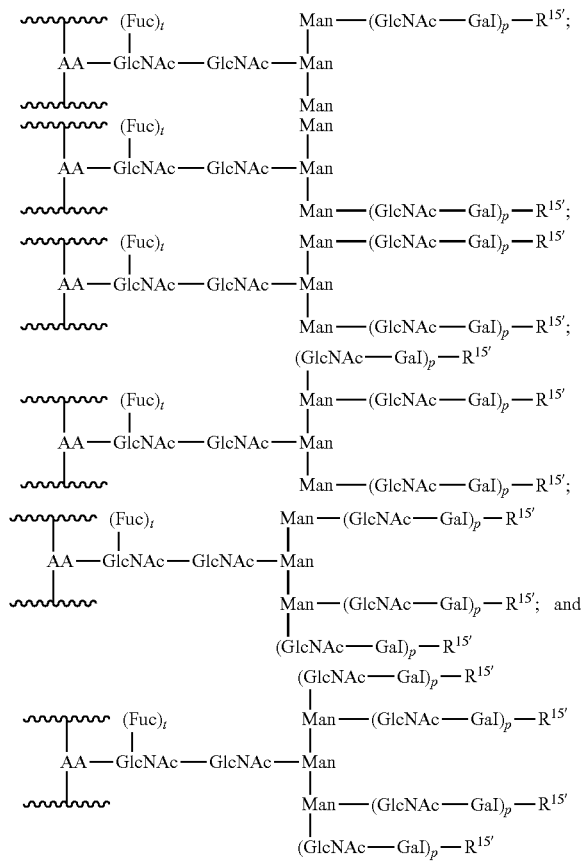

In the formulae above, the index t is an integer from 0 to 1 and the index p is an integer from 1 to 10. The symbol $R^{15'}$ represents H, OH (e.g., Gal-OH), a sialyl moiety, a sialyl linking group (i.e., sialyl linking group-polymeric modifying group (Sia-L-$R^1$), or a sialyl moiety to which is bound a polymer modified sialyl moiety (e.g., Sia-Sia-L-$R^1$) ("Sia-$Sia^{p'''}$")). Exemplary polymer modified saccharyl moieties have a structure according to Formulae I and II. An exemplary peptide conjugate of the invention will include at least one glycan having a $R^{15'}$ that includes a structure according to Formulae I or II. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3-to the galactose residue. In another exemplary embodiment, the sialic acid is linked α2,6-to the galactose residue.

In an exemplary embodiment, the sialyl linking group is a sialyl moiety to which is bound a polymer modified sialyl moiety (e.g., Sia-Sia-L-$R^1$) ("Sia-$Sia^{p'''}$"). Here, the glycosyl linking group is linked to a galactosyl moiety through a sialyl moiety:

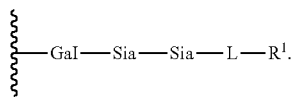

An exemplary species according to this motif is prepared by conjugating Sia-L-$R^1$ to a terminal sialic acid of a glycan using an enzyme that forms Sia-Sia bonds, e.g., CST-II, ST8Sia-II, ST8Sia-III and ST8Sia-IV.

In another exemplary embodiment, the glycans on the peptide conjugates have a formula that is selected from the group:

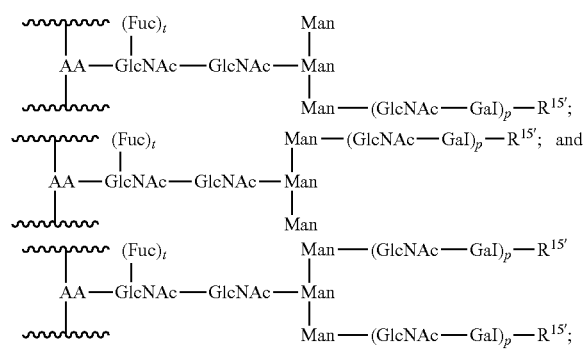

and combinations thereof.

In each of the formulae above, $R^{15'}$ is as discussed above. Moreover, an exemplary peptide conjugate of the invention will include at least one glycan with an $R^{15}$ moiety having a structure according to Formulae I or II.

In another exemplary embodiment, the glycosyl linking group comprises at least one glycosyl linking group having the formula:

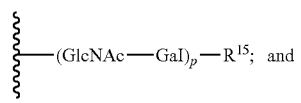

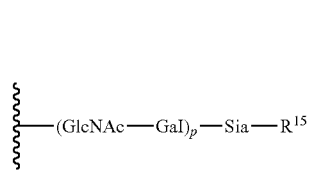

wherein $R^{15}$ is said sialyl linking group; and the index p is an integer selected from 1 to 10.

In an exemplary embodiment, the glycosyl linking moiety has the formula:

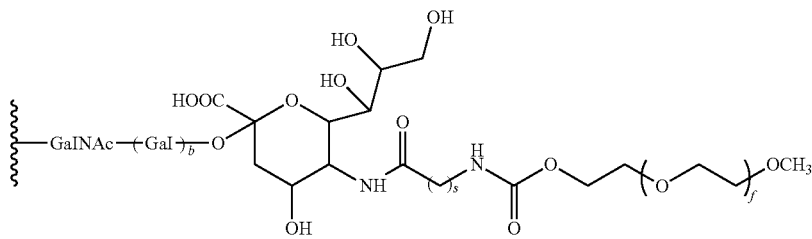

in which b is an integer from 0 to 1. The index s represents an integer from 1 to 10; and the index f represents an integer from 1 to 2500.

In an exemplary embodiment, the polymeric modifying group is PEG. In another exemplary embodiment, the PEG moiety has a molecular weight of about 20 kDa. In another exemplary embodiment, the PEG moiety has a molecular weight of about 5 kDa. In another exemplary embodiment, the PEG moiety has a molecular weight of about 10 kDa. In another exemplary embodiment, the PEG moiety has a molecular weight of about 40 kDa.

In an exemplary embodiment, the glycosyl linking group is a linear 10 kDa-PEG-sialyl, and one or two of these glycosyl linking groups are covalently attached to the peptide. In an exemplary embodiment, the glycosyl linking group is a linear 20 kDa-PEG-sialyl, and one or two of these glycosyl linking groups are covalently attached to the peptide. In an exemplary embodiment, the glycosyl linking group is a linear 5 kDa-PEG-sialyl, and one, two or three of these glycosyl linking groups are covalently attached to the peptide. In an exemplary embodiment, the glycosyl linking group is a linear 40 kDa-PEG-sialyl, and one or two of these glycosyl linking groups are covalently attached to the peptide.

Modifying Groups

The peptide conjugates of the invention comprise a modifying group. This group can be covalently attached to a FGF peptide through an amino acid or a glycosyl linking group. "Modifying groups" can encompass a variety of structures including targeting moieties, therapeutic moieties, biomolecules. Additionally, "modifying groups" include polymeric modifying groups, which are polymers which can alter a property of the peptide such as its bioavailability or its half-life in the body.

In an exemplary embodiment, the modifying group is a targeting agent that localizes selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), and lipoprotein E.

For the purposes of convenience, the modifying groups in the remainder of this section will be largely based on polymeric modifying groups such as water soluble and water insoluble polymers. However, one of skill in the art will recognize that other modifying groups, such as targeting moieties, therapeutic moieties and biomolecules, could be used in place of the polymeric modifying groups.

Linkers of the Modifying Groups

The linkers of the modifying group serve to attach the modifying group (ie polymeric modifying groups, targeting moieties, therapeutic moieties and biomolecules) to the peptide. In an exemplary embodiment, the polymeric modifying group is bound to a glycosyl linking group, generally through a heteroatom, e.g, nitrogen, on the core through a linker, L, as shown below:

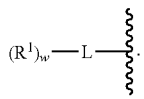

$R^1$ is the polymeric moiety and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety.

An exemplary compound according to the invention has a structure according to Formulae I or II above, in which at least one of $R^2$, $R^3$, $R^4$, $R^5$, $R^6$ or $R^{6'}$ has the formula:

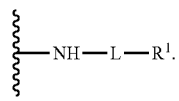

In another example according to this embodiment at least one of $R^2$, $R^3$, $R^4$, $R^5$, $R^6$ or $R^{6'}$ has the formula:

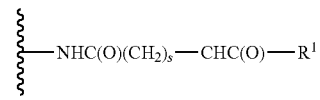

in which s is an integer from 0 to 20 and $R^1$ is a linear polymeric modifying moiety.

In an exemplary embodiment, the polymeric modifying group-linker construct is a branched structure that includes two or more polymeric chains attached to central moiety.

In this embodiment, the construct has the formula:

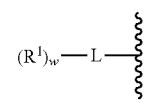

in which $R^1$ and L are as discussed above and w' is an integer from 2 to 6, preferably from 2 to 4 and more preferably from 2 to 3.

When L is a bond it is formed between a reactive functional group on a precursor of $R^1$ and a reactive functional group of complementary reactivity on the saccharyl core. When L is a non-zero order linker, a precursor of L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling the precursors proceeds by chemistry that is well understood in the art.

In an exemplary embodiment, L is a linking group that is formed from an amino acid, or small peptide (e.g., 1-4 amino acid residues) providing a modified sugar in which the polymeric modifying group is attached through a substituted alkyl linker. Exemplary linkers include glycine, lysine, serine and cysteine. The PEG moiety can be attached to the amine moiety of the linker through an amide or urethane bond. The PEG is linked to the sulfur or oxygen atoms of cysteine and serine through thioether or ether bonds, respectively.

In an exemplary embodiment, $R^5$ includes the polymeric modifying group. In another exemplary embodiment, $R^5$ includes both the polymeric modifying group and a linker, L, joining the modifying group to the remainder of the molecule. As discussed above, L can be a linear or branched structure. Similarly, the polymeric modifying group can be branched or linear.

Water-Soluble Polymers

Many water-soluble polymers are known to those of skill in the art and are useful in practicing the present invention. The term water-soluble polymer encompasses species such as saccharides (e.g., dextran, amylose, hyalouronic acid, poly(sialic acid), heparans, heparins, etc.); poly(amino acids), e.g., poly(aspartic acid) and poly(glutamic acid); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., App. Biochem. Biotech. 11: 141-45 (1985)).

Exemplary water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly(ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly(ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

An exemplary water-soluble polymer is poly(ethylene glycol), e.g., methoxy-poly(ethylene glycol). The poly(ethylene glycol) used in the present invention is not restricted to any particular form or molecular weight range. For unbranched poly(ethylene glycol) molecules the molecular weight is preferably between 500 and 100,000. A molecular weight of 2000-60,000 is preferably used and preferably of from about 5,000 to about 40,000.

In an exemplary embodiment, poly(ethylene glycol) molecules of the invention include, but are not limited to, those species set forth below.

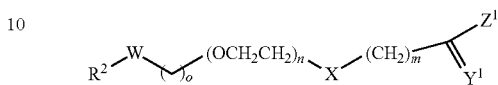

in which $R^2$ is H, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, $H_2N$—$CH_2CH_2$—, HS—$CH_2CH_2$—, and —$(CH_2)_qC(Y^1)Z^2$; -sugar-nucleotide, or protein. The index "n" represents an integer from 1 to 2500. The indeces m, o, and q independently represent integers from 0 to 20. The symbol Z represents OH, $NH_2$, halogen, S—$R^3$, the alcohol portion of activated esters, —$(CH_2)_pC(Y^2)V$, —$(CH_2)_pU(CH_2)_sC(Y^2)_v$, sugar-nucleotide, protein, and leaving groups, e.g., imidazole, p-nitrophenyl, HOBT, tetrazole, halide. The symbols X, $Y^1$, $Y^2$, W, U independently represent the moieties O, S, N—$R^4$. The symbol V represents OH, $NH_2$, halogen, S—$R^5$, the alcohol component of activated esters, the amine component of activated amides, sugar-nucleotides, and proteins. The indeces p, s and v are members independently selected from the integers from 0 to 20. The symbols $R^3$, $R^4$ and $R^5$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

In other exemplary embodiments, the poly(ethylene glycol) molecule is selected from the following:

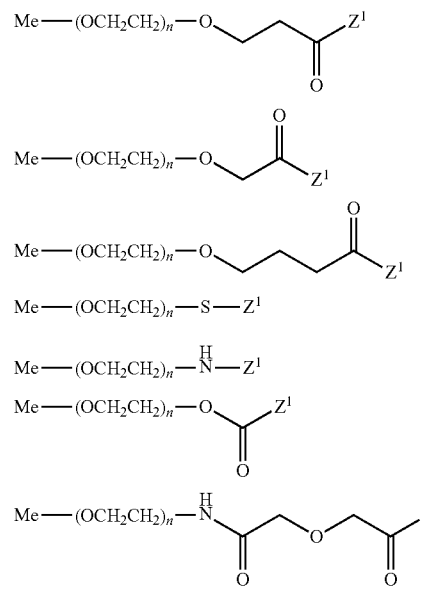

-continued

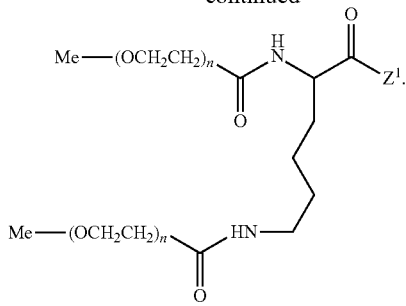

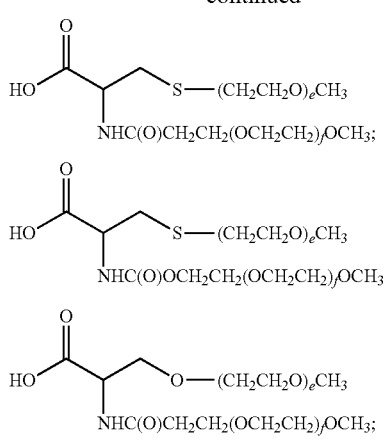

In another embodiment the poly(ethylene glycol) is a branched PEG having more than one PEG moiety attached. Examples of branched PEGs are described in U.S. Pat. Nos. 5,932,462; 5,342,940; 5,643,575; 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly (ethylene glycol) of the branched PEG is less than or equal to 40,000 daltons.

Representative polymeric modifying moieties include structures that are based on side chain-containing amino acids, e.g., serine, cysteine, lysine, and small peptides, e.g., lys-lys. Exemplary structures include:

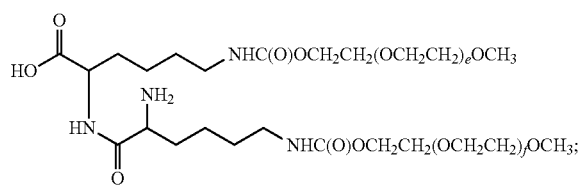

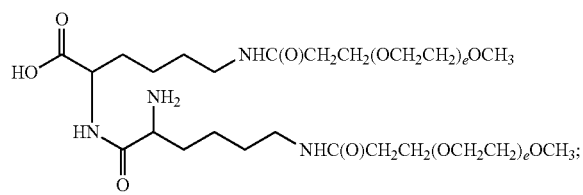

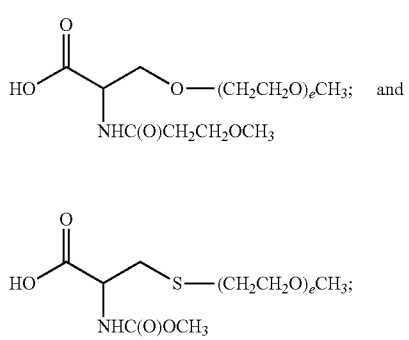

Those of skill will appreciate that the free amine in the di-lysine structures can also be pegylated through an amide or urethane bond with a PEG moiety.

In yet another embodiment, the polymeric modifying moiety is a branched PEG moiety that is based upon a tri-lysine peptide. The tri-lysine can be mono-, di-, tri-, or tetra-PEG-ylated. Exemplary species according to this embodiment have the formulae:

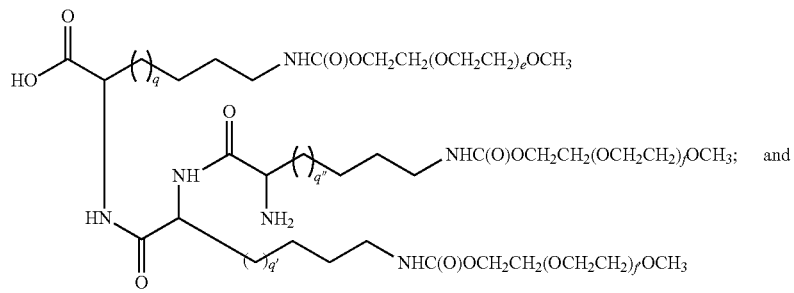

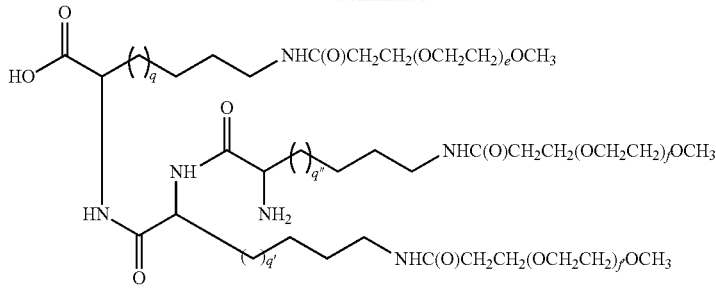

in which the indices e, f and f are, independently selected integers from 1 to 2500; and the indices q, q' and q" are independently selected integers from 1 to 20.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits labeled with the polymeric modifying moiety in a desired manner is within the scope of the invention.

As discussed herein, the PEG of use in the conjugates of the invention can be linear or branched. An exemplary precursor of use to form the branched PEG containing peptide conjugates according to this embodiment of the invention has the formula:

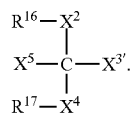

(III)

Another exemplary precursor of use to form the branched PEG containing peptide conjugates according to this embodiment of the invention has the formula:

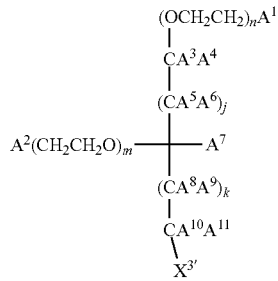

in which the indices m and n are integers independently selected from 0 to 5000. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NA^{12}A^{13}$, $-OA^{12}$ and $-SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

The branched polymer species according to this formula are essentially pure water-soluble polymers. $X^{3'}$ is a moiety that includes an ionizable (e.g., OH, COOH, $H_2PO_4$, $HSO_3$, $NH_2$, and salts thereof, etc.) or other reactive functional group, e.g., infra. C is carbon. $X^5$, $R^{16}$ and $R^{17}$ are independently selected from non-reactive groups (e.g., H, unsubstituted alkyl, unsubstituted heteroalkyl) and polymeric arms (e.g., PEG). $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^{16}$ and $R^{17}$ to C. When $X^{3'}$ is reacted with a reactive functional group of complementary reactivity on a linker, sugar or linker-sugar cassette, $X^{3'}$ is converted to a component of linkage fragment $X^3$.

Exemplary linkage fragments for $X^2$, $X^3$ and $X^4$ are independently selected and include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, the precursor (Formula III), or an activated derivative thereof, is reacted with, and thereby bound to a sugar, an activated sugar or a sugar nucleotide through a reaction between $X^{3'}$ and a group of complementary reactivity on the sugar moiety, e.g., an amine. Alternatively, $X^{3'}$ reacts with a reactive functional group on a precursor to linker, L. One or more of $R^2$, $R^3$, $R^4$, $R^3$, $R^6$ or $R^{α'}$ of Formulae I and II can include the branched polymeric modifying moiety, or this moiety bound through L.

In an exemplary embodiment, the moiety:

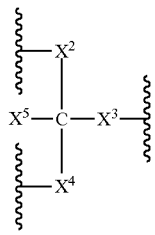

is the linker arm, L. In this embodiment, an exemplary linker is derived from a natural or unnatural amino acid, amino acid analogue or amino acid mimetic, or a small peptide formed from one or more such species. For example, certain branched polymers found in the compounds of the invention have the formula:

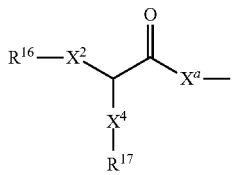
(IV)

$X^a$ is a linkage fragment that is formed by the reaction of a reactive functional group, e.g., $X^{3'}$, on a precursor of the branched polymeric modifying moiety and a reactive functional group on the sugar moiety, or a precursor to a linker. For example, when $X^{3'}$ is a carboxylic acid, it can be activated and bound directly to an amine group pendent from an amino-saccharide (e.g., Sia, GalNH$_2$, GlcNH$_2$, ManNH$_2$, etc.), forming a $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

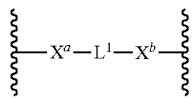

in which $X^b$ is a second linkage fragment and is independently selected from those groups set forth for $X^a$, and, similar to L, $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide (e.g., Lys-Lys) or tri-peptide (e.g., Lys-Lys-Lys) in which the alpha-amine moiety(ies) and/or side chain heteroatom(s) are modified with a polymeric modifying moiety.

In a further exemplary embodiment, the peptide conjugates of the invention include a moiety, e.g., an $R^{15}$ moiety that has a formula that is selected from:

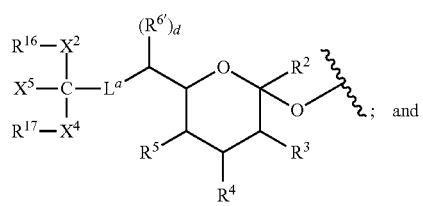
V

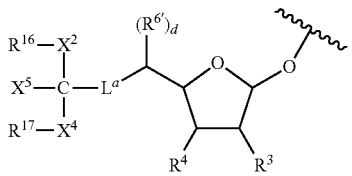
VI

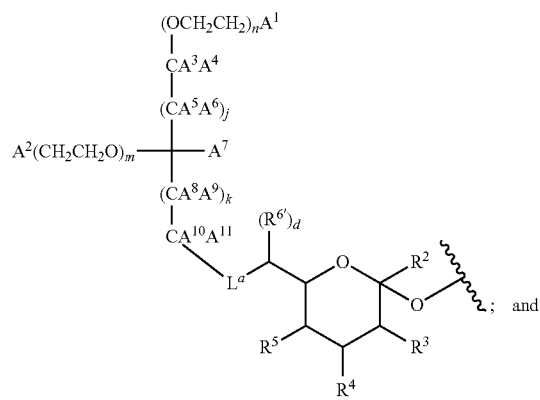
Va

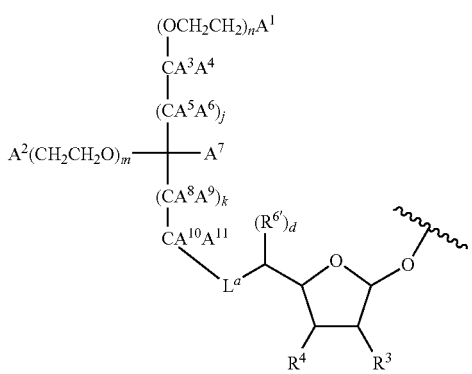
VIa in which the identity of the radicals represented by the various symbols is the same as that discussed hereinabove. $L^a$ is a bond or a linker as discussed above for L and $L^1$, e.g., substituted or unsubstituted alkyl or substituted or unsubstituted heteroalkyl moiety. In an exemplary embodiment, $L^a$ is a moiety of the side chain of sialic acid that is functionalized with the polymeric modifying moiety as shown. Exemplary $L^a$ moieties include substituted or unsubstituted alkyl chains that include one or more OH or NH$_2$.

In yet another exemplary embodiment, the invention provides peptide conjugates having a moiety, e.g., an $R^{15}$ moiety with formula:

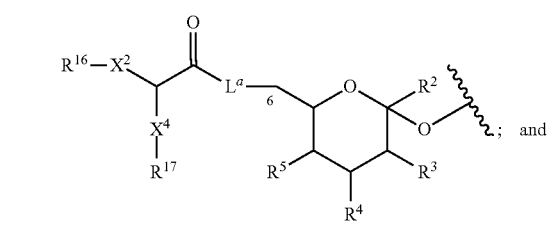
VII

-continued

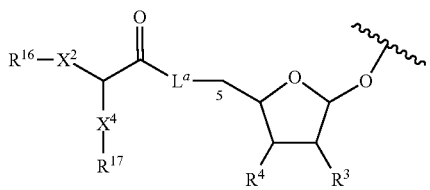

VIII

The identity of the radicals represented by the various symbols is the same as that discussed hereinabove. As those of skill will appreciate, the linker arm in Formulae VII and VIII is equally applicable to other modified sugars set forth herein. In exemplary embodiment, the species of Formulae VII and VIII are the $R^{15}$ moieties attached to the glycan structures set forth herein.

In yet another exemplary embodiment, the Factor VII or Factor VIIa peptide conjugate includes a $R^{15}$ moiety with a formula which is a member selected from:

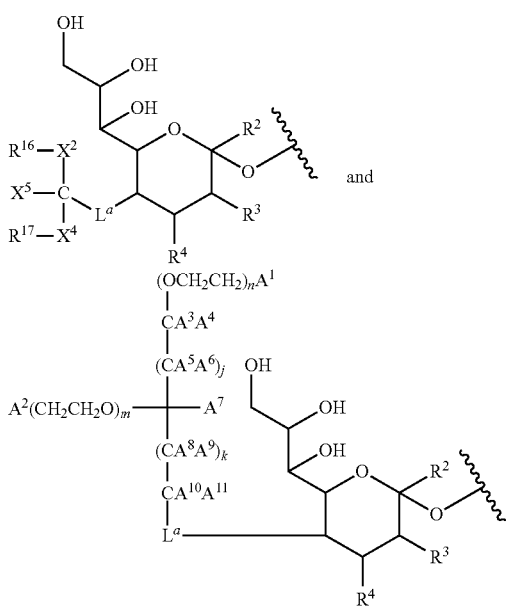

and in which the identities of the radicals are as discussed above. An exemplary species for $L^a$ is —$(CH_2)_jC(O)NH(CH_2)_hC(O)NH$—, in which the indices h and j are independently selected integers from 0 to 10. A further exemplary species is —C(O)NH—. The indices m and n are integers independently selected from 0 to 5000. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$NA^{12}A^{13}$, —$OA^{12}$ and —$SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the glycosyl linking group has a structure according to the following formula:

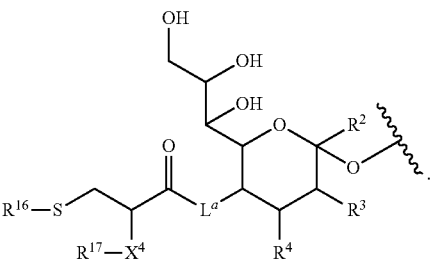

The embodiments of the invention set forth above are further exemplified by reference to species in which the polymer is a water-soluble polymer, particularly poly(ethylene glycol) ("PEG"), e.g., methoxy-poly(ethylene glycol). Those of skill will appreciate that the focus in the sections that follow is for clarity of illustration and the various motifs set forth using PEG as an exemplary polymer are equally applicable to species in which a polymer other than PEG is utilized.

PEG of any molecular weight, e.g., 1 kDa, 2 kDa, 5 kDa, 10 kDa, 15 kDa, 20 kDa, 25 kDa, 30 kDa, 35 kDa, 40 kDa and 45 kDa is of use in the present invention.

In an exemplary embodiment, the $R^{15}$ moiety has a formula that is a member selected from the group:

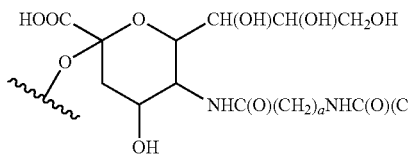
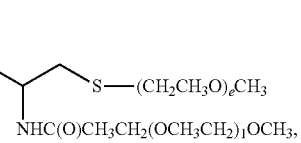

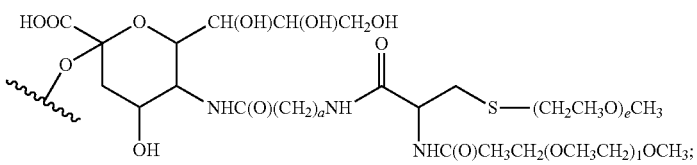

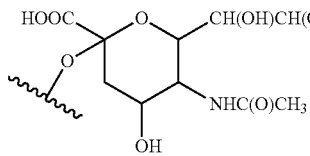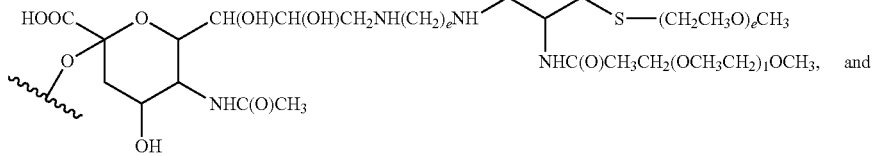
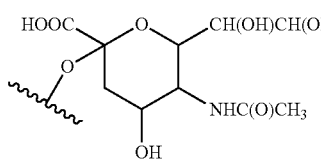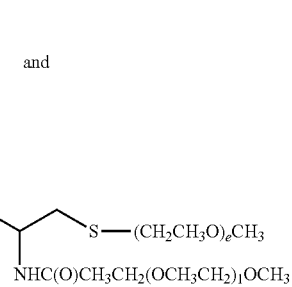
In each of the structures above, the linker fragment —NH(CH$_2$)$_a$— can be present or absent.
In other exemplary embodiments, the peptide conjugate includes an R$^{15}$ moiety selected from the group:
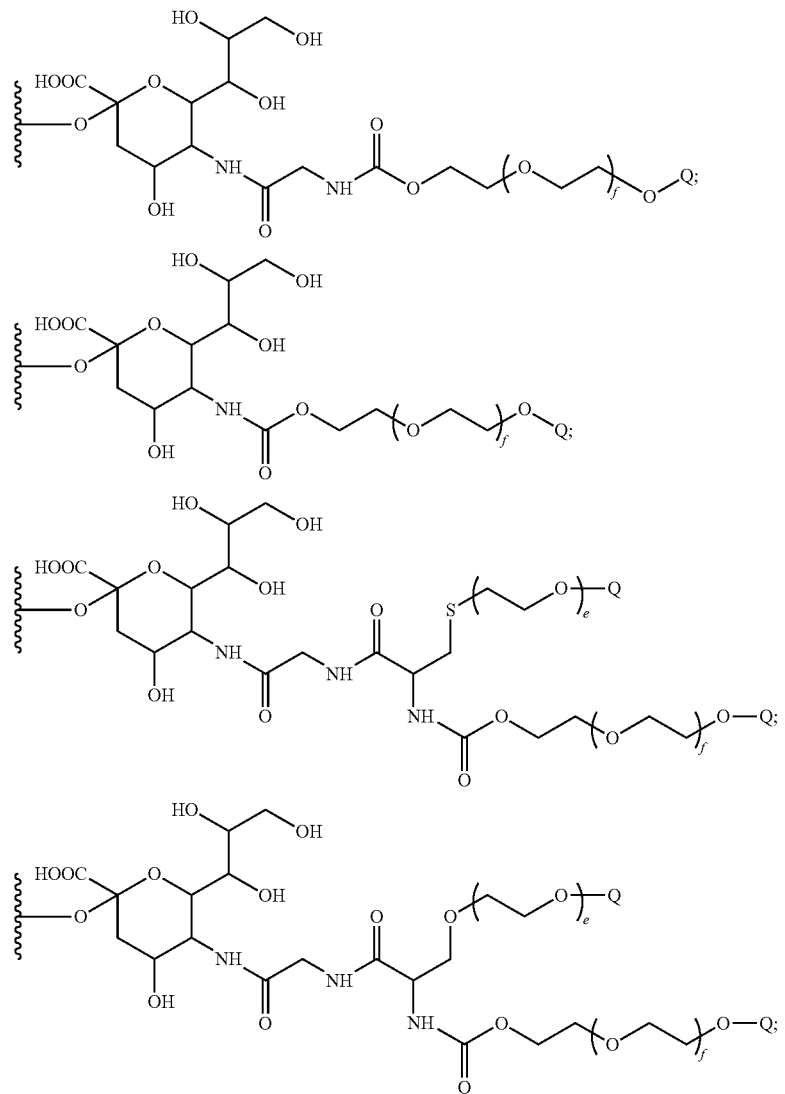

-continued

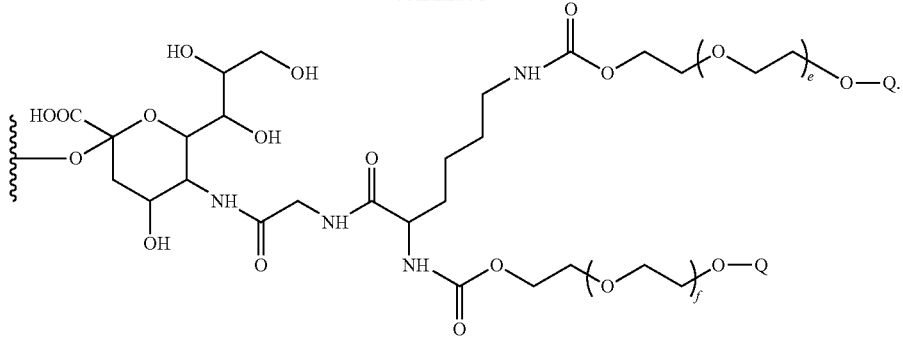

In each of the formulae above, the indices e and f are independently selected from the integers from 1 to 2500. In further exemplary embodiments, e and f are selected to provide a PEG moiety that is about 1 kDa, 2 kDa, 5 kDa, 10 kDa, 15 kDa, 20 kDa, 25 kDa, 30 kDa, 35 kDa, 40 kDa and 45 kDa. The symbol Q represents substituted or unsubstituted alkyl (e.g., $C_1$-$C_6$ alkyl, e.g., methyl), substituted or unsubstituted heteroalkyl or H.

Other branched polymers have structures based on di-lysine (Lys-Lys) peptides, e.g.:

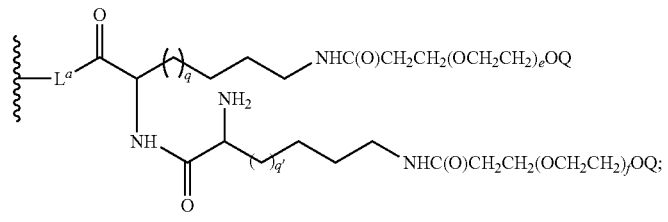

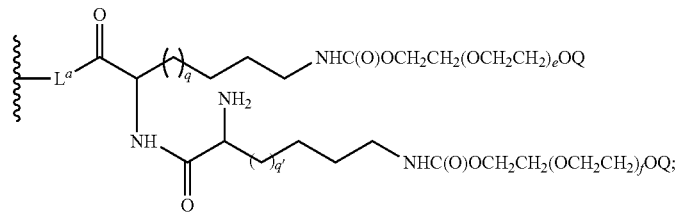

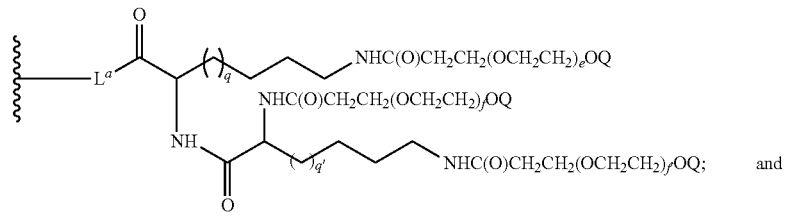

and

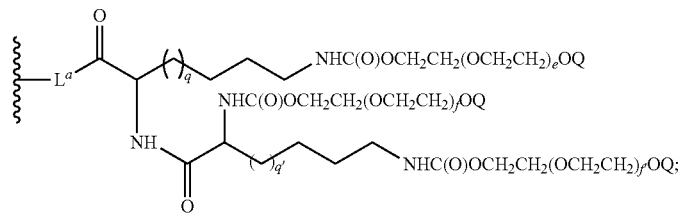

and tri-lysine peptides (Lys-Lys-Lys), e.g.:

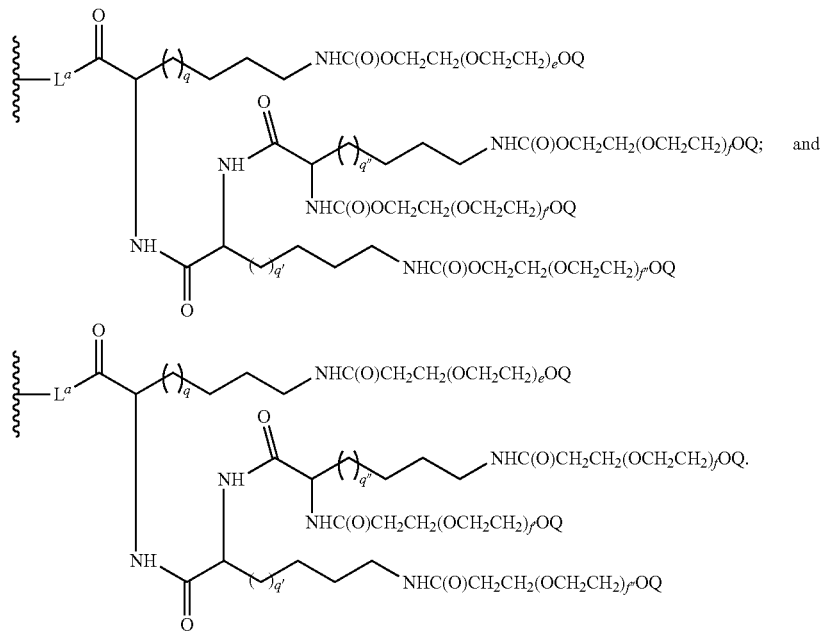

In each of the figures above, the indices e, f, f' and f" represent integers independently selected from 1 to 2500. The indices q, q' and q" represent integers independently selected from 1 to 20.

In another exemplary embodiment, the modifying group:

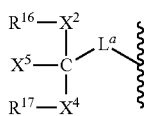

has a formula that is a member selected from:

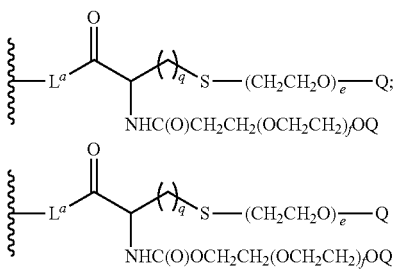

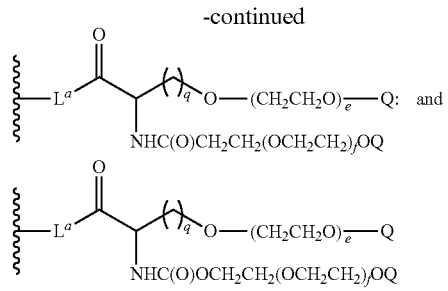

wherein Q is a member selected from H and substituted or unsubstituted $C_1$-$C_6$ alkyl. The indices e and f are integers independently selected from 1 to 2500, and the index q is an integer selected from 0 to 20.

In another exemplary embodiment, the modifying group:

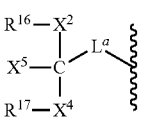

has a formula that is a member selected from:

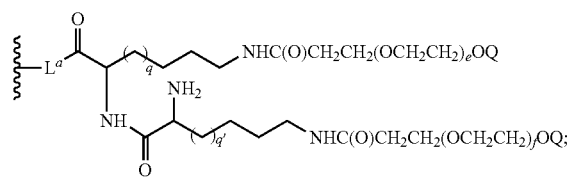

-continued

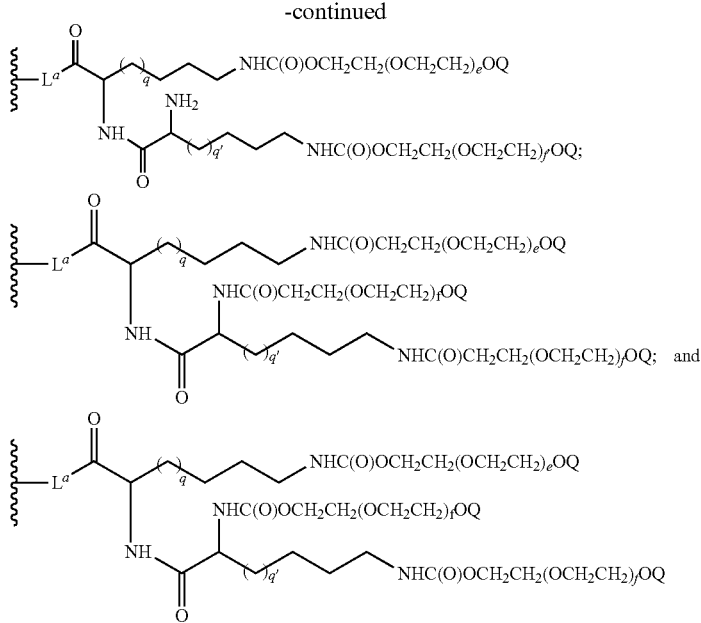

wherein Q is a member selected from H and substituted or unsubstituted $C_1$-$C_6$ alkyl. The indices e, f and f' are integers independently selected from 1 to 2500, and q and q' are integers independently selected from 1 to 20.

In another exemplary embodiment, the branched polymer has a structure according to the following formula:

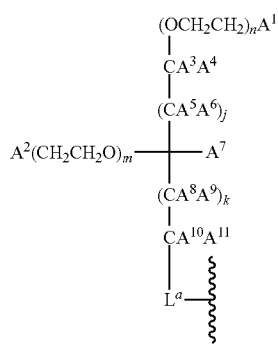

(IIIa)

in which the indices m and n are integers independently selected from 0 to 5000. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$NA^{12}A^{13}$, —$OA^{12}$ and —$SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Formula IIIa is a subset of Formula III. The structures described by Formula IIIa are also encompassed by Formula III.

In another exemplary embodiment according to the formula above, the branched polymer has a structure according to the following formula:

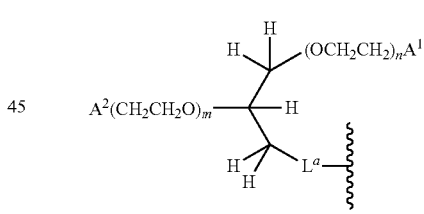

In an exemplary embodiment, $A^1$ and $A^2$ are each —$OCH_3$ or H.

In an illustrative embodiment, the modified sugar is sialic acid and selected modified sugar compounds of use in the invention have the formulae:

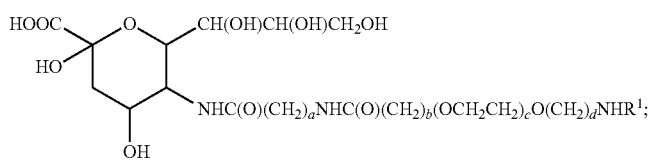 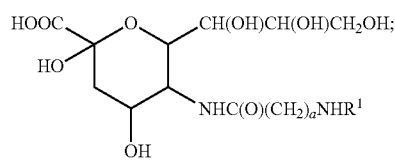

-continued

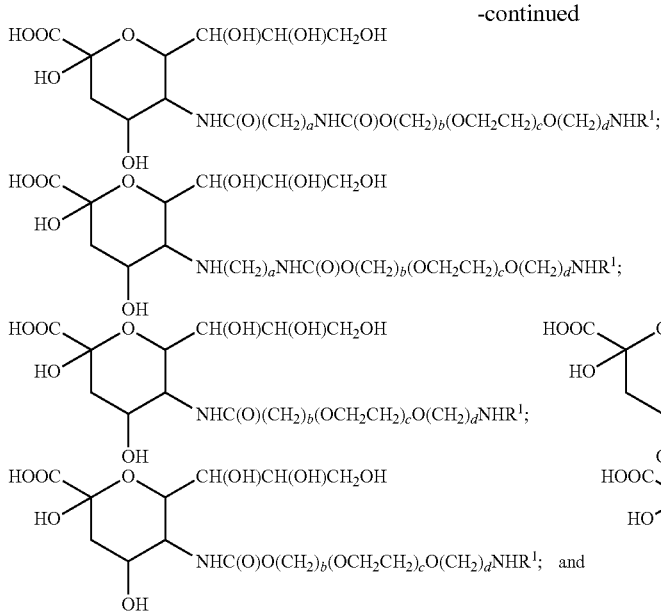
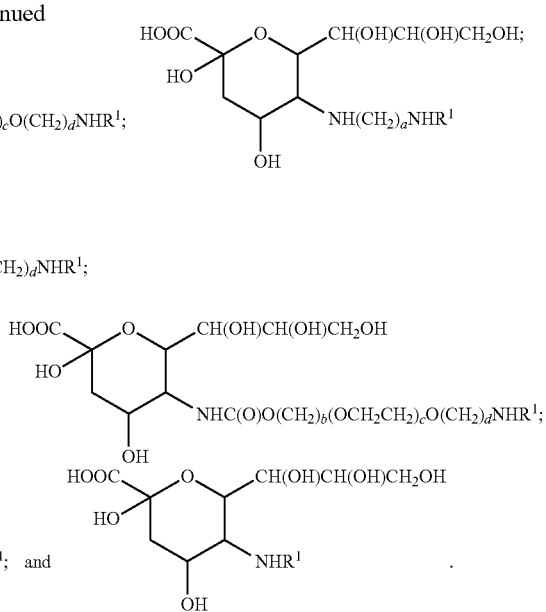

The indices a, b and d are integers from 0 to 20. The index c is an integer from 1 to 2500. The structures set forth above can be components of $R^{15}$.

In another illustrative embodiment, a primary hydroxyl moiety of the sugar is functionalized with the modifying group. For example, the 9-hydroxyl of sialic acid can be converted to the corresponding amine and functionalized to provide a compound according to the invention. Formulae according to this embodiment include:

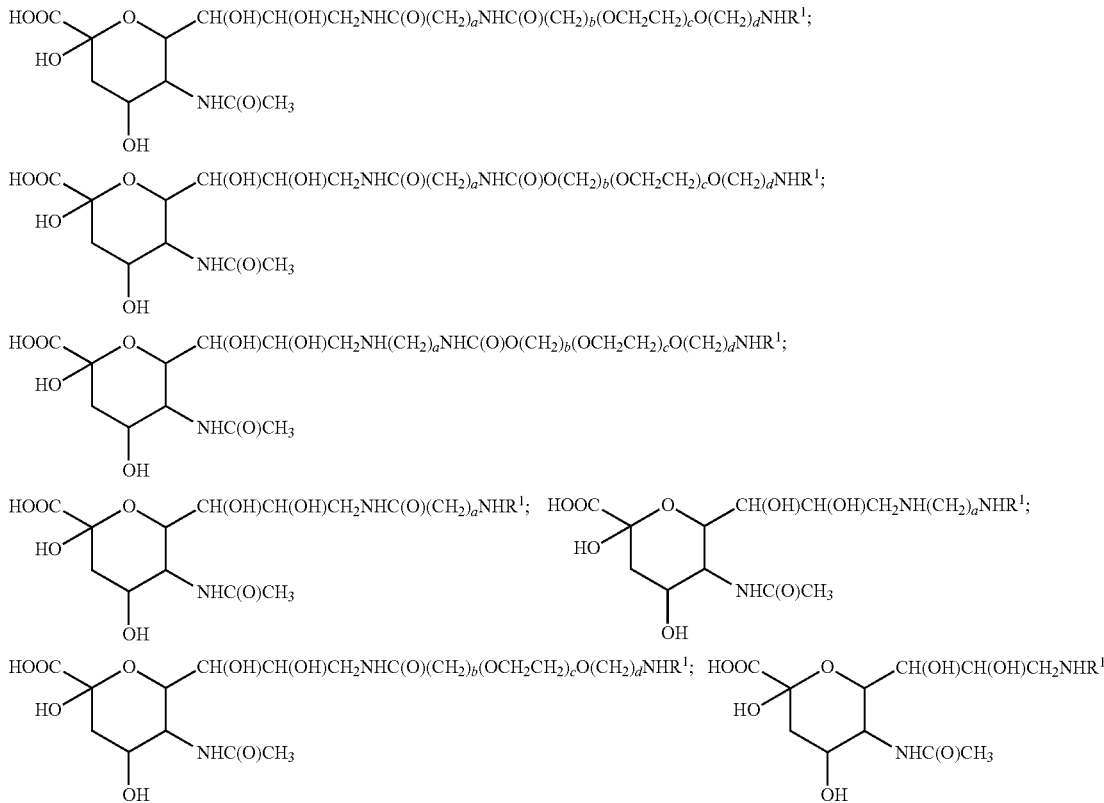

-continued

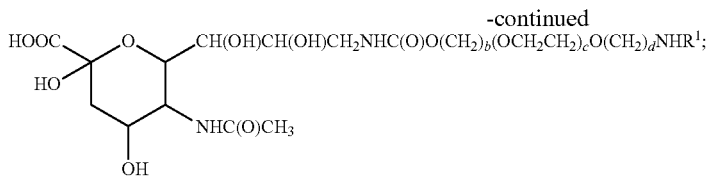

The structures set forth above can be components of $R^{15}$.

Although the present invention is exemplified in the preceding sections by reference to PEG, as those of skill will appreciate, an array of polymeric modifying moieties is of use in the compounds and methods set forth herein.

In selected embodiments, $R^1$ or L-$R^1$ is a branched PEG, for example, one of the species set forth above. In an exemplary embodiment, the branched PEG structure is based on a cysteine peptide. Illustrative modified sugars according to this embodiment include:

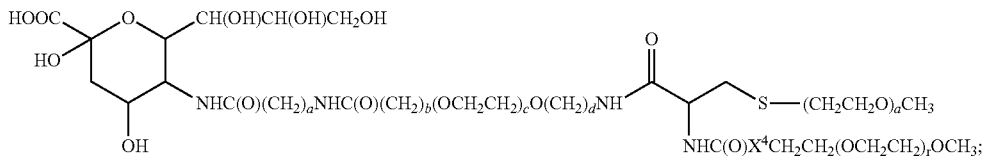

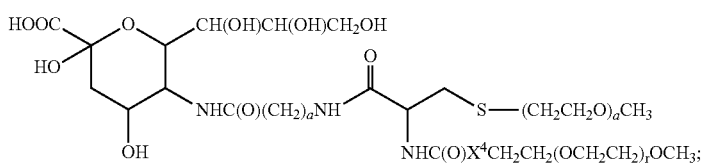

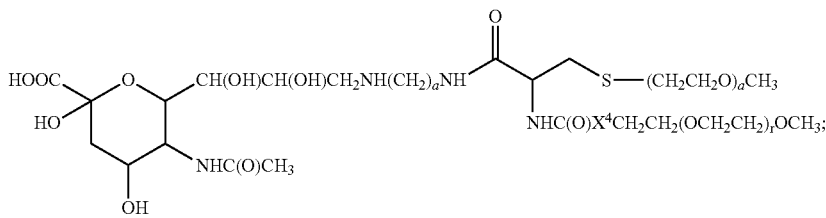

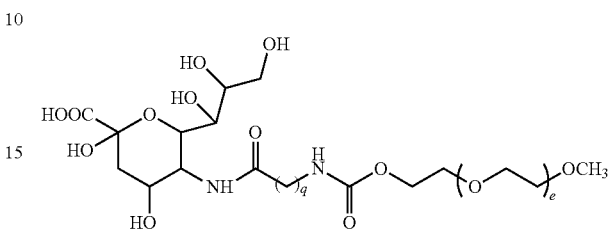

in which the indices q and e are as discussed above.

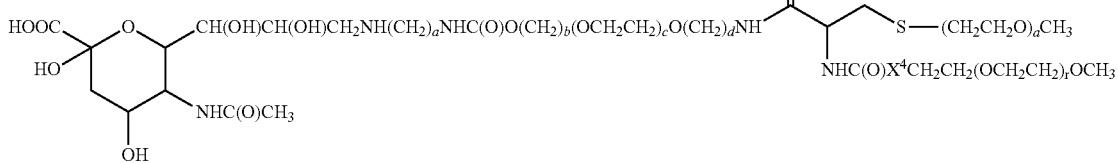

in which $X^4$ is a bond or O. In each of the structures above, the alkylamine linker —$(CH_2)_a$NH— can be present or absent. The structures set forth above can be components of $R^{15}/R^{15'}$.

As discussed herein, the polymer-modified sialic acids of use in the invention may also be linear structures. Thus, the invention provides for conjugates that include a sialic acid moiety derived from a structure such as:

Exemplary modified sugars are modified with water-soluble or water-insoluble polymers. Examples of useful polymer are further exemplified below.

In another exemplary embodiment, the peptide is derived from insect cells, remodeled by adding GlcNAc and Gal to the mannose core and glycopegylated using a sialic acid bearing a linear PEG moiety, affording a Factor VII or Factor VIIa peptide that comprises at least one moiety having the formula:

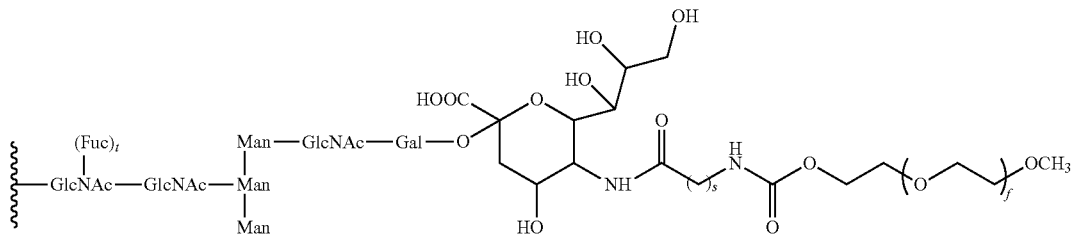

in which the index t is an integer from 0 to 1; the index s represents an integer from 1 to 10; and the index f represents an integer from 1 to 2500.

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

The motifs forth above for $R^1$, $L-R^1$, $R^{15}$, $R^{15'}$ and other radicals are equally applicable to water-insoluble polymers, which may be incorporated into the linear and branched structures without limitation utilizing chemistry readily accessible to those of skill in the art. Similarly, the incorporation of these species into any of the modified sugars discussed herein is within the scope of the present invention. Accordingly, the invention provides conjugates containing, and for the use of to prepare such conjugates, sialic acid and other sugar moieties modified with a linear or branched water-insoluble polymers, and activated analogues of the modified sialic acid species (e.g., CMP-Sia-(water insoluble polymer)).

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinyl pyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate)polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid' polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly(α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J Biomed. Mater. Res.* 21: 1301-1316 (1987); and Cohn et al., *J Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly(amino acids), poly(anhydrides), poly(orthoesters), poly (carbonates), poly(phosphazines), poly(phosphoesters), poly(thioesters), polysaccharides and mixtures thereof. More preferably still, the bioresorbable polymer includes a poly(hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438, 253, which issued on Mar. 20, 1984, discloses tri-block copolymers produced from the transesterification of poly (glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202, 413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a difunctional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly (vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly(propylene) oxide and mixtures and copolymers thereof. Polymers that are components of hydrogels are also useful in the present invention.

Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyaluronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, is of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

Biomolecules

In another preferred embodiment, the modified sugar bears a biomolecule. In still further preferred embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Preferred biomolecules are essentially non-fluorescent, or emit such a minimal amount of fluorescence that they are inappropriate for use as a fluorescent marker in an assay. Moreover, it is generally preferred to use biomolecules that are not sugars. An exception to this preference is the use of an otherwise naturally occurring sugar that is modified by covalent attachment of another entity (e.g., PEG, biomolecule, therapeutic moiety, diagnostic moiety, etc.). In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution.

Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided as conjugate with biotin. Thus, for example, a selectively biotinylated peptide is elaborated by the attachment of an avidin or streptavidin moiety bearing one or more modifying groups.

The Methods

In addition to the conjugates discussed above, the present invention provides methods for preparing these and other conjugates. Thus, in a further aspect, the invention provides a method of forming a covalent conjugate between a selected moiety and a peptide. Additionally, the invention provides methods for targeting conjugates of the invention to a particular tissue or region of the body. Furthermore, the present invention provides a method for preventing, curing, or ameliorating a disease state by administering a conjugate of the invention to a subject at risk of developing the disease or a subject that has the disease.

In exemplary embodiments, the conjugate is formed between a water-soluble polymer, a therapeutic moiety, targeting moiety or a biomolecule, and a glycosylated or non-glycosylated peptide. The polymer, therapeutic moiety or biomolecule is conjugated to the peptide via an intact glycosyl linking group, which is interposed between, and covalently linked to both the peptide and the modifying group (e.g., water-soluble polymer).

In an exemplary embodiment, the conjugate is formed through a chemical process sometimes referred to as chemoPEGylation. Further discussion of the synthesis chemoPEGylated peptide conjugates is provided in PCT/US02/3226, filed Oct. 9, 2002 and U.S. patent application Ser. No. 10/287,994, filed Nov. 5, 2002, each of which are herein incorporated by reference in their entirety.

The method includes contacting the peptide with a mixture containing a modified sugar and a glycosyltransferase for which the modified sugar is a substrate. The reaction is conducted under conditions sufficient to form a covalent bond between the modified sugar and the peptide. The sugar moiety of the modified sugar is preferably selected from nucleotide sugars, activated sugars, and sugars that are neither nucleotides nor activated.

The acceptor peptide (glycosylated or non-glycosylated) is typically synthesized de novo, or recombinantly expressed in a prokaryotic cell (e.g., bacterial cell, such as *E. coli*) or in a eukaryotic cell such as a mammalian cell (e.g., CHO cells), yeast (e.g., *Saccharomyces*), insect, or plant cell. The peptide can be either a full-length protein or a fragment. Moreover, the peptide can be a wild type or mutated peptide. In an exemplary embodiment, the peptide includes a mutation that adds one or more consensus glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-aceylgalactosamine, galactose, mannose, GlcNAc, glucose, fucose or xylose) to a the hydroxy side chain of a hydroxyamino acid, preferably serine or threonine, although 5-hydroxyproline or 5-hydroxylysine may also be used.

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation and O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC Crit. Rev. Biochem., pp. 259-306 (1981).

In one embodiment, the invention provides a method for linking FGF-21 and one or more peptide through a linking group. The linking group is of any useful structure and may be selected from straight-chain and branched chain structures. Preferably, each terminus of the linker, which is attached to a peptide, includes a modified sugar (i.e., a nascent intact glycosyl linking group).

In an exemplary method of the invention, two peptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosyl units, respectively. In practice, the $(glycosyl)^1$-PEG-$(glycosyl)^2$ linker is contacted with the first peptide and a first transferase for which the first glycosyl unit is a substrate, thereby forming $(peptide)^1$-$(glycosyl)^1$-PEG-$(glycosyl)^2$. Glycosyltransferase and/or unreacted peptide is then optionally removed from the reaction mixture. The second peptide and a second transferase for which the second glycosyl unit is a substrate are added to the (peptide)$^1$-$(glycosyl)^1$-PEG-$(glycosyl)^2$ conjugate, forming (peptide)$^1$-$(glycosyl)^1$-PEG-$(glycosyl)^2$-$(peptide)^2$. Those of skill in the art will appreciate that the method outlined above is also applicable to forming conjugates between more than two peptides by, for example, the use of a branched PEG, dendrimer, poly(amino acid), polysaccharide or the like.

Another exemplary embodiment is set forth in Scheme 3. Scheme 3 shows a method of preparing a conjugate comprising a polymer. The polymer increases the circulatory half-life of the FGF protein.

Scheme 3

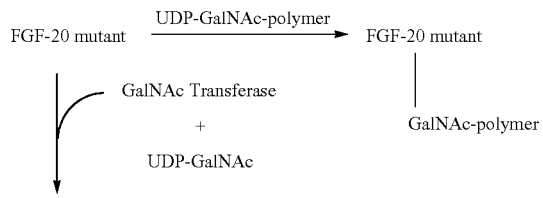

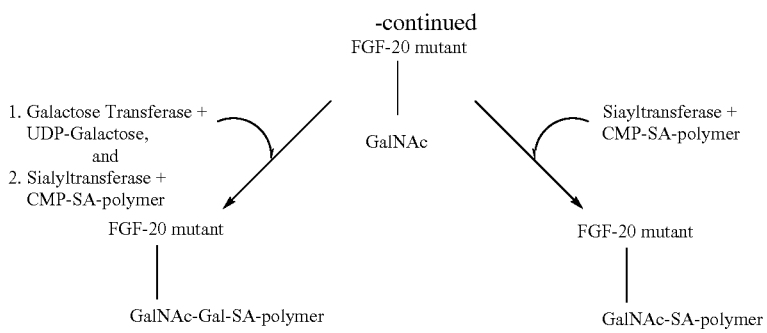

in which SA is sialic acid, and polymer is PEG, mPEG, poly sialic acid, a water soluble or water insoluble polymer. Though the method is exemplified by reference to FGF-20 and FGF-21, those of skill will appreciate it is equally applicable to other FGF peptides, e.g., FGF-9 and FGF-18.

The use of reactive derivatives of PEG (or other linkers) to attach one or more peptide moieties to the linker is within the scope of the present invention. The invention is not limited by the identity of the reactive PEG analogue. Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al, *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

Preparation of Modified Sugars

In general, the sugar moiety and the modifying group are linked together through the use of reactive groups, which are typically transformed by the linking process into a new organic functional group or species that is unreactive under physiologically relevant conditions. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., Curr. Med. Chem. 6: 93 (1999); and Schafer et al., J. Org. Chem. 65: 24 (2000)).

In an exemplary embodiment, the peptide that is modified by a method of the invention is a glycopeptide that is produced in prokaryotic cells (e.g., E. coli), eukaryotic cells including yeast and mammalian cells (e.g., CHO cells), or in a transgenic animal and thus, contains N- and/or O-linked oligosaccharide chains, which are incompletely sialylated. The oligosaccharide chains of the glycopeptide lacking a sialic acid and containing a terminal galactose residue can be PEG-ylated, PPG-ylated or otherwise modified with a modified sialic acid.

Exemplary PEG-sialic acid derivative include:

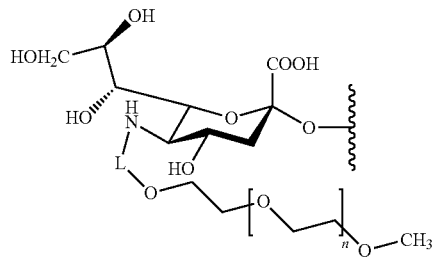

in which L is a substituted or unsubstituted alkyl or substituted or unsubstituted heteroalkyl linker moiety joining the sialic acid moiety and the PEG moiety, and "n" is 1 or greater; and

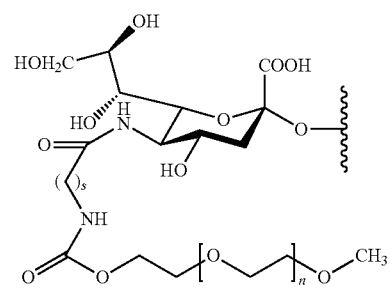

in which the index "s" represents an integer from 0 to 20, and "n" is 1 or greater.

In Scheme 4, the amino glycoside 1, is treated with the active ester of a protected amino acid (e.g., glycine) derivative, converting the sugar amine residue into the corresponding protected amino acid amide adduct. The adduct is treated with an aldolase to form z-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG attachment by reacting compound 3 with an activated PEG or PPG derivative (e.g., PEG-C(O)NHS, PEG-OC(O)O-p-nitrophenyl), producing species such as 4 or 5, respectively.

Scheme 4

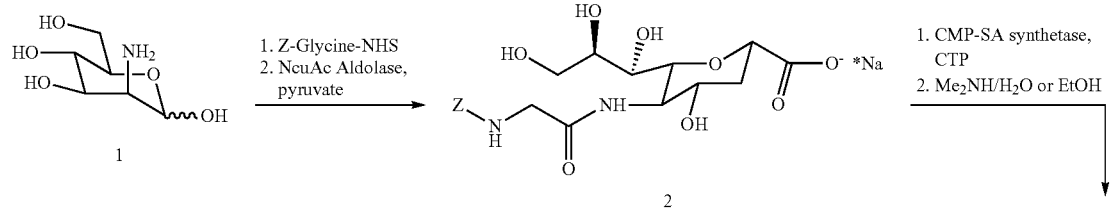

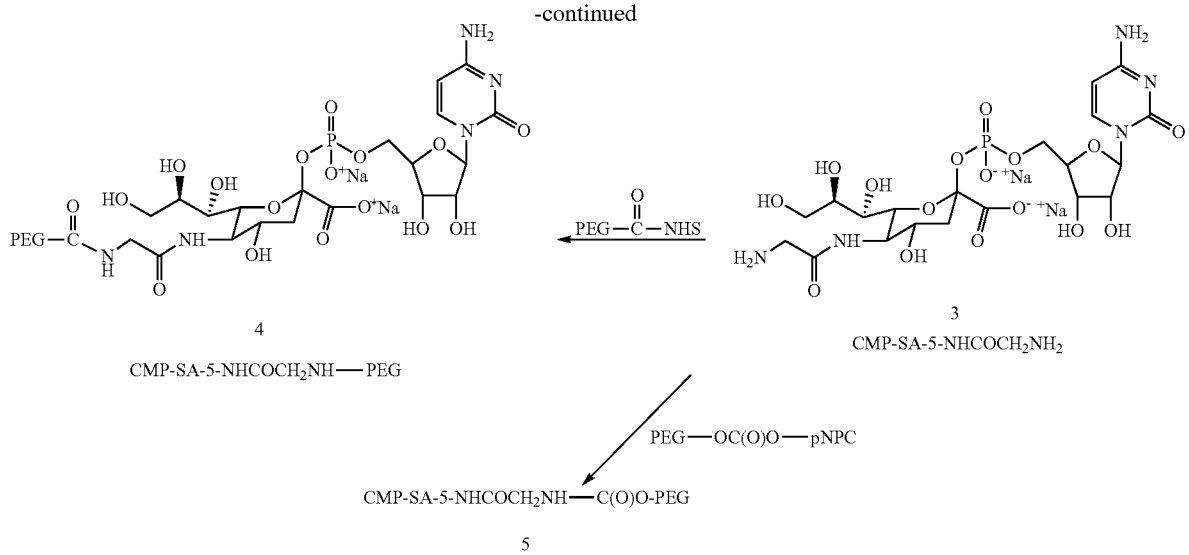

Table 1 sets forth representative examples of sugar monophosphates that are derivatized with a modifying group, such as a PEG or PPG moiety. Fibroblast Growth Factor peptides can be modified by the method of Scheme 1. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 1

TABLE 1-continued

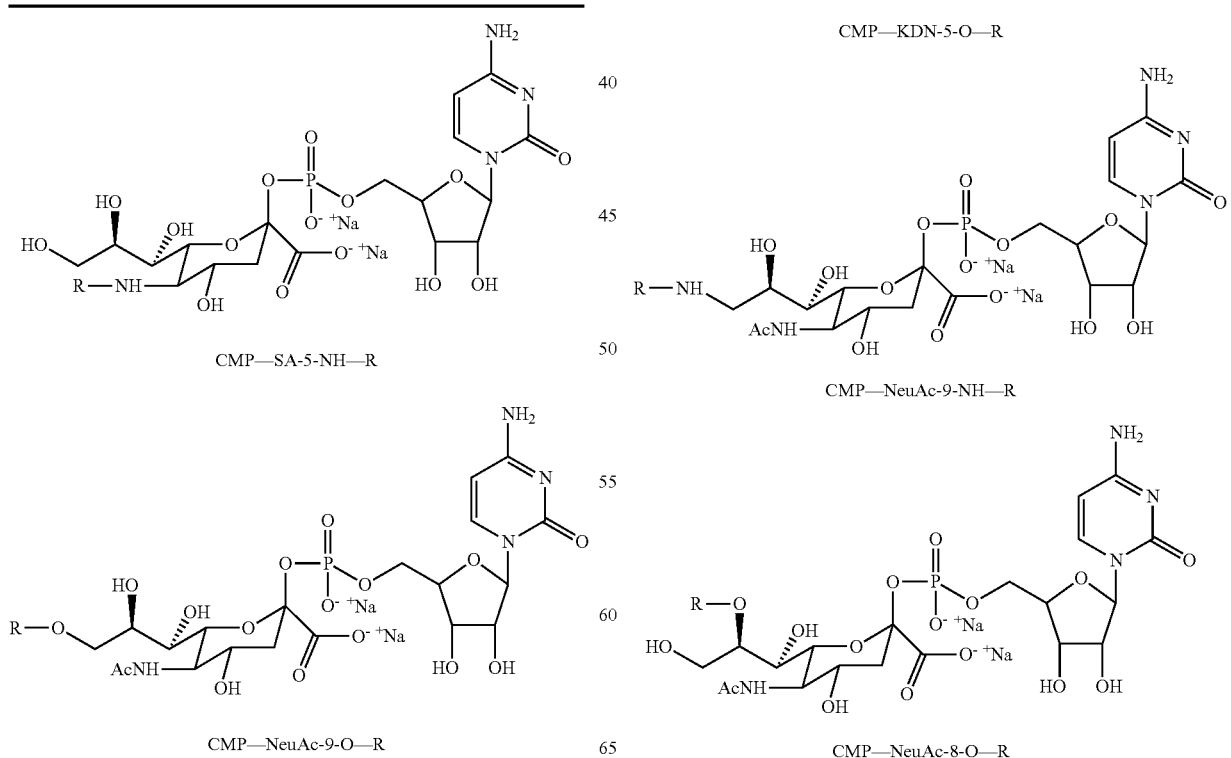

TABLE 1-continued

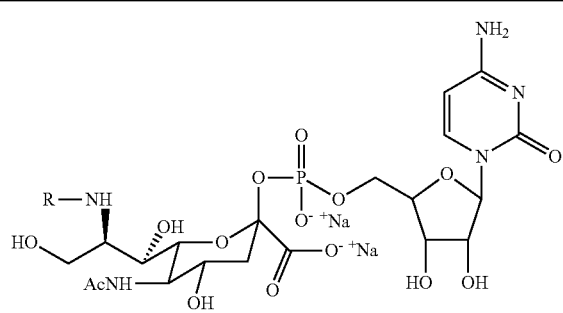

CMP—NeuAc-8-NH—R

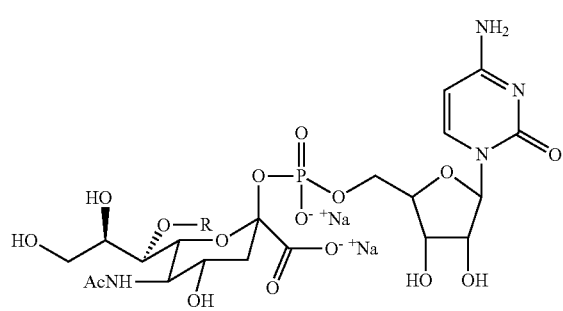

CMP—NeuAc-7-O—R

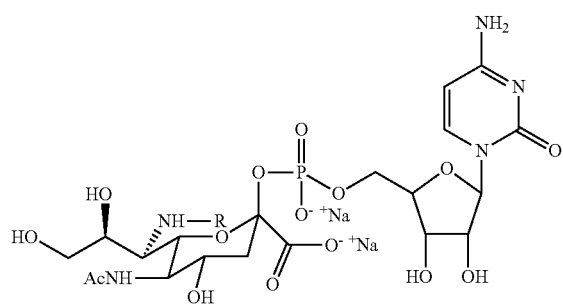

CMP—NeuAc-7-NH—R

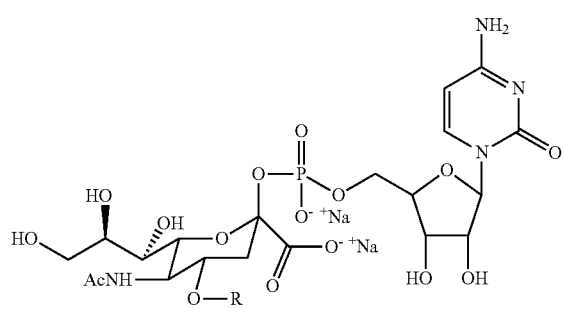

CMP—NeuAc-4-O—R

TABLE 1-continued

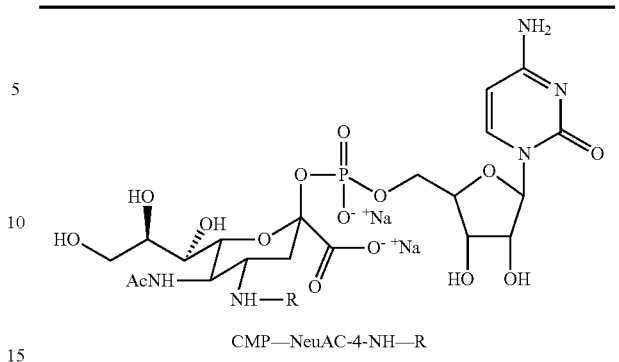

CMP—NeuAC-4-NH—R wherein R represents a modifying group, e.g., linear or branched PEG or -$L^x$-$R^x$ in which $L^x$ is a linker selected from a bond (zero-order), substituted or unsubstituted alkyl and substituted or unsubstituted heteroalkyl, and $R^x$ is the modifying group.

The modified sugar phosphates of use in practicing the present invention can be substituted in other positions as well as those set forth above. Presently preferred substitutions of sialic acid are set forth in Formula I:

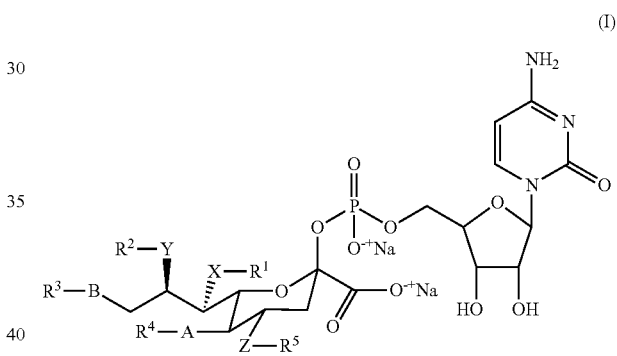

(I)

in which X is a linking group, which is preferably selected from —O—, —N(H)—, —S, $CH_2$—, and —N(R)$_2$, in which each R is a member independently selected from $R^1$-$R^5$. The symbols Y, Z, A and B each represent a group that is selected from the group set forth above for the identity of X. X, Y, Z, A and B are each independently selected and, therefore, they can be the same or different. The symbols $R^1$, $R^2$, $R^3$, $R^4$ and $R^5$ represent H, a water-soluble polymer, therapeutic moiety, biomolecule or other moiety. Alternatively, these symbols represent a linker that is bound to a water-soluble polymer, therapeutic moiety, biomolecule or other moiety.

Exemplary moieties attached to the conjugates disclosed herein include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, $SLe_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (POLY (ETHYLENE GLYCOL CHEMISTRY: BIOTECHNICAL AND BIOMEDICAL APPLICATIONS, J. Milton Harris, Ed., Plenum Pub. Corp., 1992; POLY (ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

Cross-Linking Groups

Preparation of the modified sugar for use in the methods of the present invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

A variety of reagents are used to modify the components of the modified sugar with intramolecular chemical cross-links (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length cross-linking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see. Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Conjugation of Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide (s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352,670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

In another embodiment, the method makes use of one or more exo- or endoglycosidase. The glycosidase is typically a mutant, which is engineered to form glycosyl bonds rather than cleave them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g, enzyme concentration, donor concentration, acceptor concentration, temperature, solvent volume), which are optimized for a selected system.

The present invention also provides for the industrial-scale production of modified peptides. As used herein, an industrial scale generally produces at least about 250 mg, preferably at least about 500 mg, and more preferably at least about 1 gram of finished, purified conjugate, preferably after a single reaction cycle, i.e., the conjugate is not a combination the reaction products from identical, consecutively iterated synthesis cycles.

In the discussion that follows, the invention is exemplified by the conjugation of modified sialic acid moieties to a glycosylated peptide. The exemplary modified sialic acid is labeled with m-PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than m-PEG including other water-soluble polymers, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, GalNAc, Galβ1, 3GalNAc, Galβ1,6GlcNAc, Galβ3,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GalNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In the discussion that follows, the method of the invention is exemplified by the use of modified sugars having a water-soluble polymer attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment, an O-linked carbohydrate residue is "trimmed" prior to the addition of the modified sugar. For example a GalNAc-Gal residue is trimmed back to GalNAc. A modified sugar bearing a water-soluble polymer is conjugated to one or more of the sugar residues exposed by the "trimming." In one example, a glycopeptide is "trimmed" and a water-soluble polymer is added to the resulting O-side chain amino acid or glycopeptide glycan via a saccharyl moiety, e.g., Sia, Gal, or GalNAc moiety conjugated to the water-soluble polymer. The modified saccharyl moiety is attached to an acceptor site on the "trimmed" glycopeptide. Alternatively, an unmodified saccharyl moiety, e.g., Gal can be added the terminus of the O-linked glycan.

In another exemplary embodiment, a water-soluble polymer is added to a GalNAc residue via a modified sugar having a galactose residue. Alternatively, an unmodified Gal can be added to the terminal GalNAc residue.

In yet a further example, a water-soluble polymer is added onto a Gal residue using a modified sialic acid.

In another exemplary embodiment, an O-linked glycosyl residue is "trimmed back" to the GalNAc attached to the amino acid. In one example, a water-soluble polymer is added via a Gal modified with the polymer. Alternatively, an unmodified Gal is added to the GalNAc, followed by a Gal with an attached water-soluble polymer. In yet another embodiment, one or more unmodified Gal residue is added to the GalNAc, followed by a sialic acid moiety modified with a water-soluble polymer.

Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, the water-soluble polymer is added to a terminal Gal residue using a polymer modified sialic acid. An appropriate sialyltransferase is used to add a modified sialic acid. The approach is summarized in Scheme 5.

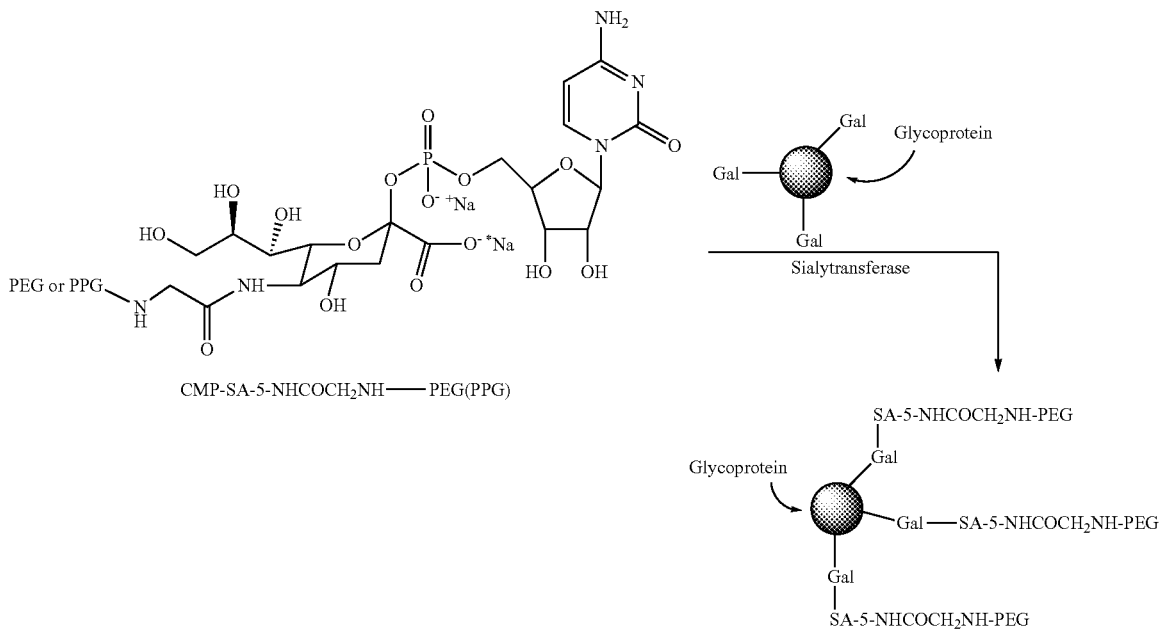

In yet a further approach, summarized in Scheme 6, a masked reactive functionality is present on the sialic acid. The masked reactive group is preferably unaffected by the conditions used to attach the modified sialic acid to the peptide. After the covalent attachment of the modified sialic acid to the peptide, the mask is removed and the peptide is conjugated with an agent such as PEG, PPG, a therapeutic moiety, biomolecule or other agent. The agent is conjugated to the peptide in a specific manner by its reaction with the unmasked reactive group on the modified sugar residue.

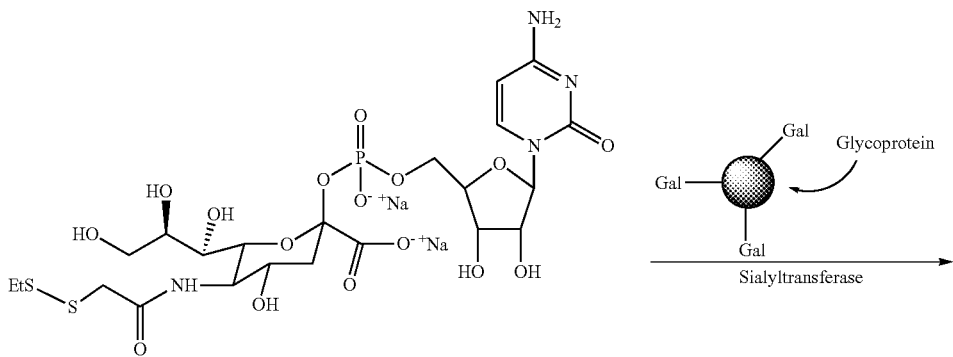

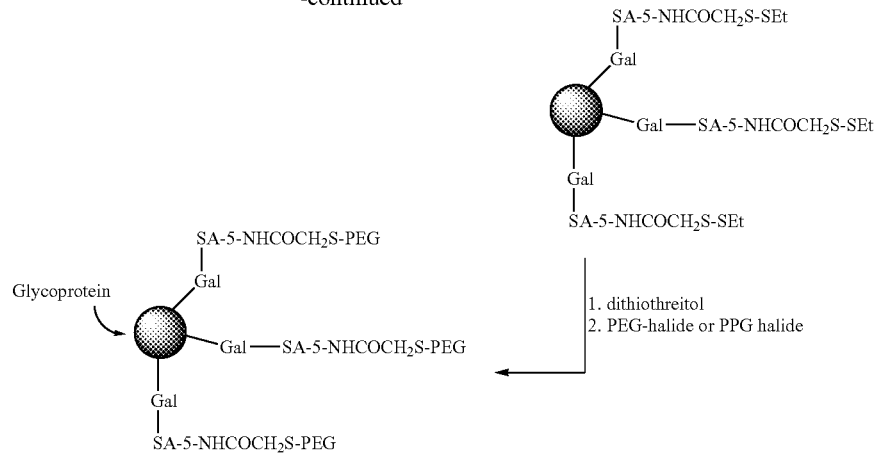

Any modified sugar can be used with its appropriate glycosyltransferase, depending on the terminal sugars of the oligosaccharide side chains of the glycopeptide (Table 2). As discussed above, the terminal sugar of the glycopeptide required for introduction of the PEG-ylated or PPG-ylated structure can be introduced naturally during expression or it can be produced post expression using the appropriate glycosidase(s), glycosyltransferase(s) or mix of glycosidase(s) and glycosyltransferase(s).

TABLE 2

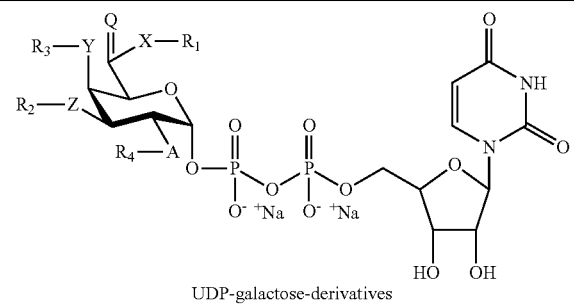

UDP-galactose-derivatives

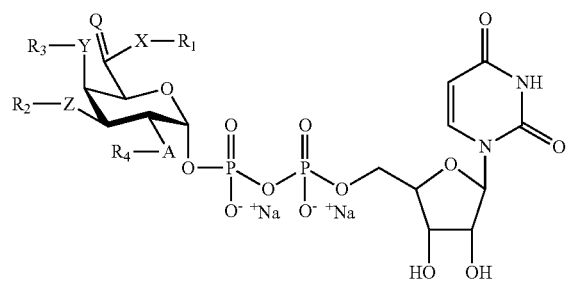

UDP-galactosamine-derivatives
(when A = NH, $R_4$ may be acetyl)

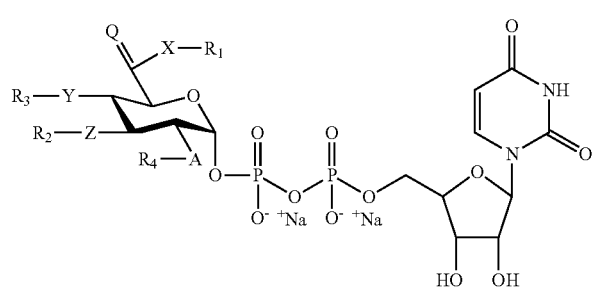

UDP-Glucose-derivatives

TABLE 2-continued

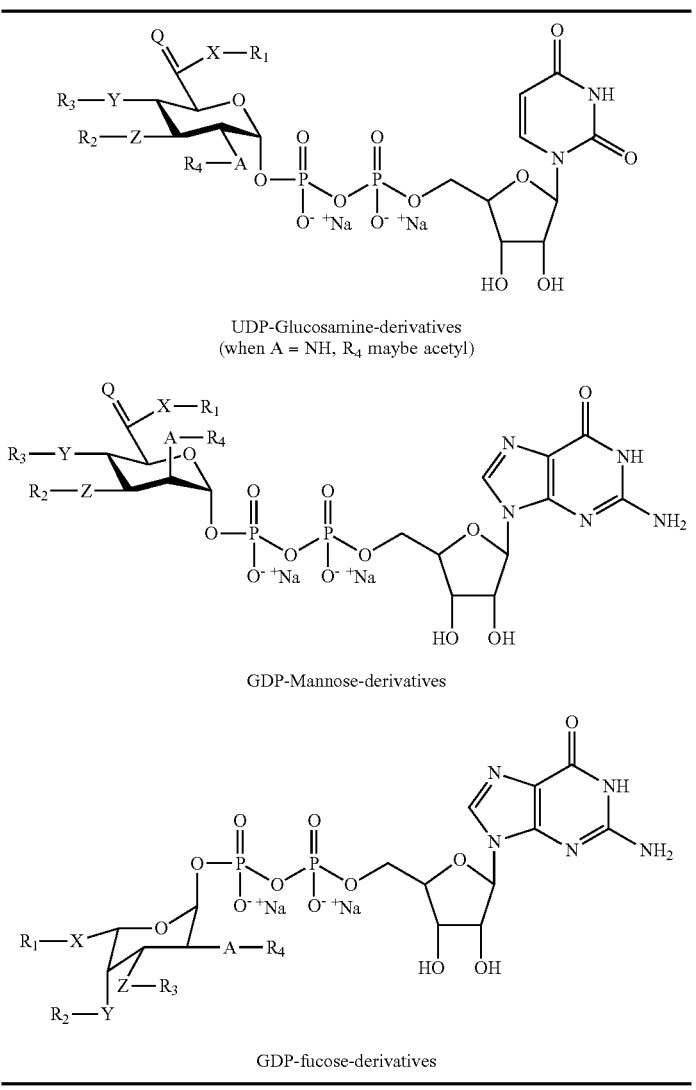

UDP-Glucosamine-derivatives
(when A = NH, R$_4$ maybe acetyl)

GDP-Mannose-derivatives

GDP-fucose-derivatives

X = O, NH, S, CH$_2$, N—(R$_{1-5}$)$_2$.
Y = X; Z = X; A = X; B = X.
Q = H$_2$, O, S, NH, N—R.
R, R$_{1-4}$ = H, Linker-M, M.
M = Ligand of interest
Ligand of interest = acyl-PEG, acyl-PPG, alkyl-PEG, acyl-alkyl-PEG, acyl-alkyl-PEG, carbamoyl-PEG, carbamoyl-PPG, PEG, PPG, acyl-aryl-PEG, acyl-aryl-PPG, aryl-PEG, aryl-PPG, Mannose-$_6$-phosphate, heparin, heparan, SLex, Mannose, FGF VFGF, protein, chondroitin, keratan, dermatan, albumin, integrins, peptides, etc.

In a further exemplary embodiment, UDP-galactose-PEG is reacted with bovine milk β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GNT1-5, is utilized to transfer PEGylated-GlcN to a terminal mannose residue on a glycopeptide. In a still further exemplary embodiment, an the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG- or PPG-galactose functionality onto the exposed GlcNAc.

In an alternative embodiment, the modified sugar is added directly to the peptide backbone using a glycosyltransferase known to transfer sugar residues to the peptide backbone. This exemplary embodiment is set forth in Scheme 7. Exemplary glycosyltransferases useful in practicing the present invention include, but are not limited to, GalNAc transferases (GalNAc T1-20), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

Scheme 7

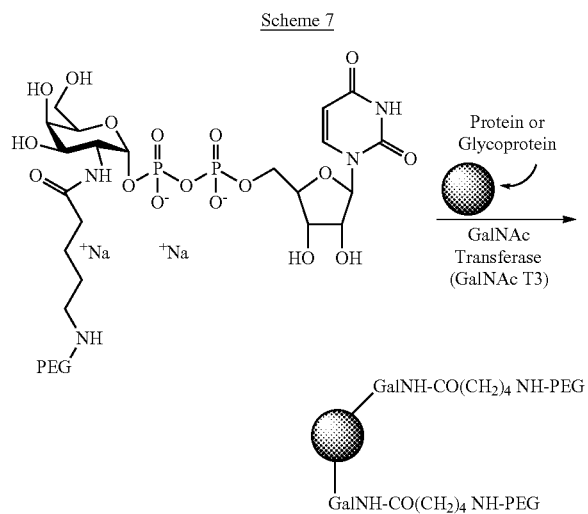

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" (e.g., sialylate) sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

Enzyme Classes

Aspects of the present invention make use of enzymes that form a bond between an activated acyl moiety and a heteroatom found on a sugar nucleus. The enzymes useful in practicing the present invention include, but are not limited to, wild-type and mutant proteases, lipases, esterases, acylases, acyltransferases, glycosyltransferases, sulfotransferases, glycosidases, and the like. An exemplary mutant is one in which one or more amino acid residues in the active site are altered to provide an enzyme with synthetic activity that is improved relative to the activity in the corresponding wild-type enzyme.

Acyl Transfer

The discovery that some enzymes are catalytically active in organic solvents has greatly expanded their use as biocatalysts. In this medium these enzymes show a new catalytic behavior. For example lipases catalyse esterification and transesterification reactions in organic media. These properties enable the production of compounds which are difficult to obtain using chemical methods.

Proteases

A protease is employed in some embodiments of the invention. Proteases are known in the art to catalyze the attachment of amino acids to sugars through esterification. (Davis, (WO 03/014371, published Feb. 20, 2003). In this publication, a vinyl ester amino acid group was reacted with a carbohydrate acyl acceptor in the presence of the serine protease subtilisin derived from *Bacillus lentus*. Wild-type proteases can be additionally be isolated from *Bacillus amyloliquefaciens*. Mutant proteases can be made according to the teachings of, for example, PCT Publication Nos. WO 95/10615 and WO 91/06637, which are hereby incorporated by reference. Other proteases of use in this invention include serine proteases (such as chymotrypsin, plasmin, and thrombin), cysteine proteases (such as cathepsin B and papain), and aspartic endopeptidases (such as pepsin A, chymosin, cathepsin D, asparagenase).

In an exemplary embodiment, utilizing a protease, the link between the sugar moiety and the modifying group is an amino acid that is derivatized with the modifying group. The sugar and amino acid are linked through an amide moiety formed by the protease.

Lipases

A lipase is used in some embodiments of the invention. The use of lipases in the acylation of saccharides has been previously reported. For example, regioselective acylations of alkyl β-D-xylopyranosides using lipase PS in organic solvents was reported by Lopez. (Lopez et al., *J. Org. Chem.*, 59, 7027-7032 (1994). Another group also utilized lipase PS in order to catalyze the transfer of acetyl groups onto sialic acids in vinyl acetate. (Lo et al., *Bioorg. Med. Chem. Lett.*, 9, 709-712 (1999)). Regioselective disaccharide acylation in tert-butyl alcohol catalyzed by *Candida antarctica* lipase has also been reported. (Woudenberg van-Oosterom et al., *Biotechnol. Bioeng.*, 49, 328-333 (1996)). Immobilized versions of the *Candida antarctica* lipase have also been used to acylate hydroxypropyl cellulose in tort-butanol. (Sereti et al., *Biotechnol Bioeng.*, 72(4), 495-500 (2001)). Other lipases of use in this invention include lipoprotein lipase, triacylglycerol lipase, diglyceride lipase, and postheparin lipase.

Esterases

Esterases can also be used in some embodiments of the invention. Acetylation of cellobiose and cellulose was shown to be catalyzed in aqueous medium in the presence of isopropenyl acetate by an intracellular carboxylesterase from *Arthrobacter viscosus*. (Cui et al., *Enzyme Microb. Technol.*, 24, 200-208 (1999)). Another group acetylated the amino groups of chitobiose and chitotetraose in an aqueous solution of 3M sodium acetate using a chitin deacetylase from *Colletotrichum lindemuthianum* (Tokuyasu et al., *Carbohydr. Res.*, 322, 26-31 (1999)). A third group utilized acetylxylan esterase (AcXE) from *Schizophyllum commune* to catalyze acetyl group transfer to methyl β-D-xylopyranoside, methyl β-D-cellobioside, methyl β-D-glucopyranoside, cellotetraose, 2-deoxy-D-glucose, D-mannose, β-1,4-mannobiose, β-1,4-mannopentaose, β-1,4-mannohexaose, β-1,4-xylobiose, and β-1,4-xylopentaose. (Biely et al., *Biochimica et Biophysica Acta*, 1623, 62-71 (2003)). Acetylation of secondary alcohols was also achieved by transesterification from vinyl acetate by a feruloyl esterase from *Humicola insolens*. (Hatzakis et al., J. Mol. Catal., B Enzym.

21, 309-311 (2003). Other esterases of use in this invention include choline esterase, sterol esterase, hydroxycinnamoyl esterase, acetylsalicyclic acid esterase, and polyneuridine esterase.

Acylases

Acylases can also be used in some embodiments of the invention. Exemplary acylases of use in this invention include aminoacylase 1, L-amino-acid acylase, penicillin acylase, acetyl-CoA acylase, acyl-lysine deacylase, aculeacin A acylase, succinyl-CoA acylase, and acetyl-aspartic deaminase.

Acetyltransferases

In another embodiment of the invention, acyl transfer is accomplished by an acetyltransferase. The use of acetyltransferases in the acylation of saccharides has been previously reported. O-acetylation at the 9 position of sialic acid has been shown to occur from the product of several genes in the COS cell system (Shi et al., *Glycobiology*, 8(2), 199-205 (1998)). Maltose O-acetyltransferase (MAT) from *Escherichia coli* is known to catalyze acetyl group transfer to the C6 positions of glucose and maltose. (Leggio et al., *Biochemistry*, 42, 5225-5235 (2003)). This same group also utilized galactoside acetyltransferase (GAT) to catalyze acetyl group transfer to galactosyl units. Other acetyltransferases of use in this invention include spermidine acetyltransferase, diamine N-acetyltransferase, and sialate O-acetyltransferase.

Sugar Transfer

In addition to the enzymes discussed above in the context of forming the acyl-linked conjugate, the glycosylation pattern of the conjugate and the starting substrates (e.g., peptides, lipids) can be elaborated, trimmed back or otherwise modified by methods utilizing other enzymes. The methods of remodeling peptides and lipids using enzymes that transfer a sugar donor to an acceptor are discussed in great detail in DeFrees, WO 03/031464 A2, published Apr. 17, 2003. A brief summary of selected enzymes of use in the present method is set forth below.

Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," (http://www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases.

Suitable glycosyltransferases include those obtained from eukaryotes, as well as from prokaryotes.

Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., *Carbohydrate Res.* 190: 1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ((1→3)GlcNAcβ fucosyltransferase, has also been characterized. A recombinant form of the Galβ(1→3,4) GlcNAcβ-α(1→3,4)fucosyltransferase has also been characterized (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include, for example, a 1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)). Yet a further exemplary galactosyltransferase is core Gal-T1.

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., *J. Biochem.* 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see. Table 3).

TABLE 3

Sialyltransferases which use the Galβ1,
4GlcNAc sequence as an acceptor substrate

| Sialyltransferase | Source | Sequence(s) formed | Ref. |
|---|---|---|---|
| ST6Gal I | Mammalian | NeuAcα2,6Galβ1,4GlcNAc- | 1 |
| ST3Gal III | Mammalian | NeuAcα2,3Galβ1,4GlcNAc-<br>NeuAcα2,3Galβ1,3GlcNAc- | 1 |
| ST3Gal IV | Mammalian | NeuAcα2,3Galβ1,4GlcNAc-<br>NeuAcα2,3Galβ1,3GlcNAc- | 1 |
| ST6Gal II | Mammalian | NeuAcα2,6Galβ1,4GlcNAc- | |
| ST6Gal II | photobacterium | NeuAcα2,6Galβ1,4GlcNAc- | 2 |
| ST3Gal V | *N. meningitides*<br>*N. gonorrhoeae* | NeuAcα2,3Galβ1,4GlcNAc- | 3 |

1) Goochee el al., *Bio/Technology* 9: 1347-1355 (1991)
2) Yamamoto et al., *J. Biochem.* 120: 104-110 (1996)
3) Gilbert et al., *J. Biol. Chem.* 271: 28271-28276 (1996)

An example of a sialyltransfcrase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see. e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other exemplary sialyltransferases of use in the present invention include those isolated from *Campylobacter jejuni*, including the α(2,3). See, e.g, WO99/49051.

Sialyltransferases other those listed in Table 3, are also useful in an economic and efficient large-scale process for sialylation of commercially important glycopeptides. As a simple test to find out the utility of these other enzymes, various amounts of each enzyme (1-100 mU/mg protein) are reacted with asialo-$\alpha_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-$\alpha_1$ AGP for this evaluation. Sialyltransferases with the ability to sialylate N-linked oligosaccharides of glycopeptides more efficiently than ST6Gal I are useful in a practical large-scale process for peptide sialylation.

FIG. 2 provides a listing of exemplary sialyltransferases of use in the present invention.

GalNAc Transferases

N-acetylgalactosaminyltransferases are of use in practicing the present invention, particularly for binding a GalNAc moiety to an amino acid of the O-linked glycosylation site of the peptide. Suitable N-acetylgalactosaminyltransferases include, but are not limited to, α(1,3)N-acetylgalactosaminyltransferase, β(1,4)N-acetylgalactosaminyltransferases (Nagata et al., *J. Biol. Chem.* 267: 12082-12089 (1992) and Smith et al., *J. Biol Chem.* 269: 15162 (1994)) and polypeptide N-acetylgalactosaminyltransferase (Homa et al., *J. Biol. Chem.* 268: 12609 (1993)).

Production of proteins such as the enzyme GalNAc $T_{1-XX}$ from cloned genes by genetic engineering is well known. See, e.g., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are over-represented in glycosylated peptide segments and that residues in specific positions surrounding glycosylated serine and threonine residues may have a more marked influence on acceptor efficiency than other amino acid moieties.

Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES TO SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β.-D-galactosyl-1,4-N-acetyl-D-glucosaminide α-1,3-galactosyltransferase was transfected into COS-1 cells. The transfected cells were then cultured and assayed for α 1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270: 18575-18580 (1995); GenBank Accession No. D49915), glycosaminoglycan N-acetylglucosamine N-deacetylase/N-sulphotransferase 1 (Dixon et al., *Genomics* 26: 239-241 (1995); UL18918), and glycosaminoglycan N-acetylglucosamine N-deacetylase/N-sulphotransferase 2 (murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

Glycosidases

This invention also encompasses the use of wild-type and mutant glycosidases. Mutant β-galactosidase enzymes have been demonstrated to catalyze the formation of disaccharides through the coupling of an α-glycosyl fluoride to a galactosyl acceptor molecule. (Withers, U.S. Pat. No. 6,284, 494; issued Sep. 4, 2001). Other glycosidases of use in this invention include, for example, β-glucosidases, β-galactosidases, β-mannosidases, β-acetyl glucosaminidases, β-N-acetyl galactosaminidases, β-xylosidases, β-fucosidases, cellulases, xylanases, galactanases, mannanases, hemicellulases, amylases, glucoamylases, α-glucosidases, α-galactosidases, α-mannosidases, α-N-acetyl glucosaminidases, α-N-acetyl galactose-aminidases, α-xylosidases, α-fucosidases, and neuraminidases/sialidases.

Immobilized Enzymes

The present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Glycosylation by Recombinant Methods

FGF peptide conjugates may also be prepared intracellularly by recombinant means. A polynucleotide sequence encoding a FGF, which comprises at least one newly introduced N- or O-linked glycosylation site, may be transfected into a suitable host cell line, e.g., a eukaryotic cell line derived from yeast, insect, or mammalian origin. The Fibroblast Growth Factor recombinantly produced from such a cell line is glycosylated by the host cell glycosylation machinery.

Purification of FGF Peptide Conjugates

The FGF peptide conjugate produced by the above processes is preferably purified before use. Standard, well known techniques such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein.

If the FGF peptide conjugate is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, SP-Sepharose, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

A FGF peptide conjugate produced in culture is usually isolated by initial extraction from cells, cell lysate, culture media, etc., followed by one or more concentration, salting-out, aqueous ion-exchange, or size-exclusion chromatography steps. Additionally, the glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics may be included to prevent the growth of adventitious contaminants.

In some cases, supernatants from systems that produce the FGF peptide conjugates of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Also, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a FGF peptide conjugate. Some or all of the foregoing purification steps, in various combinations, can also be employed to provide a glycoprotein.

The FGF peptide conjugate of the invention resulting from a large-scale fermentation may be purified by methods analogous to those disclosed by Urdal et al., *J. Chromalog.* 296: 171 (1984). This reference describes two sequential, RP-HPLC steps for purification of recombinant human IL-2 on a preparative HPLC column. Alternatively, techniques such as affinity chromatography, may be utilized to purify the glycoprotein.

Following the production and, preferably, purification of a glycosylated mutant Fibroblast Growth Factor, the biological functions of the glycoprotein are tested using several methods known in the art. The functional assays are based on various characteristics of Fibroblast Growth Factor.

Pharmaceutical Composition and Administration

The FGF peptide conjugates having desired oligosaccharide determinants described above can be used as therapeutics for treating a variety of diseases and conditions related to deficiency in growth hormone. Growth-related conditions that can be treated with the FGF peptide conjugates of the present invention include: dwarfism, short-stature in children and adults, cachexia/muscle wasting, general muscular atrophy, and sex chromosome abnormality (e.g., Turner's Syndrome). Other conditions may be treated using the FGF peptide conjugates of the present invention include: short-bowel syndrome, lipodystrophy, osteoporosis, uraemaia, burns, female infertility, bone regeneration, general diabetes, type II diabetes, osteo-arthritis, chronic obstructive pulmonary disease (COPD), and insomia. The FGF peptide conjugates of the invention may also be used to promote various healing processes, e.g., general tissue regeneration, bone regeneration, and wound healing, or as a vaccine adjunct. Thus, the present invention also provides pharmaceutical compositions comprising an effective amount of FGF peptide conjugate, which is produced according to the methods described above.

Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions are intended for parenteral, intranasal, topical, oral, or local administration, such as by subcutaneous injection, aerosol inhalation, or transdermal adsorption, for prophylactic and/or therapeutic treatment. Commonly, the pharmaceutical compositions are administered parenterally, e.g., subcutaneously or intravenously. Thus, the invention provides compositions for parenteral administration which comprise the FGF peptide conjugate dissolved or suspended in an acceptable carrier, preferably an aqueous carrier, e.g., water, buffered water, saline, PBS and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 and 8.

The compositions containing the FGF peptide conjugates can be administered for prophylactic and/or therapeutic treatments. In therapeutic applications, compositions are administered to a patient already suffering from a disease or condition related to growth hormone deficiency, in an amount sufficient to cure or at least partially arrest the symptoms of the disease and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of FGF peptide conjugates per day for a 70 kg patient, with dosages of from about 5 mg to about 200 mg of the compounds per day being more commonly used.

In prophylactic applications, compositions containing the FGF peptide conjugate of the invention are administered to a patient susceptible to or otherwise at risk of a particular disease. Such an amount is defined to be a "prophylactically effective dose." In this use, the precise amounts again depend on the patient's state of health and weight, but generally range from about 0.1 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the FGF peptide conjugate of this invention sufficient to effectively treat the patient.

EXAMPLES

The following examples are provided by way of illustration only and not by way of limitation. Those of skill in the art will readily recognize a variety of non-critical parameters that could be changed or modified to yield essentially similar results. Though the method is exemplified by reference to FGF-20 and FGF-21, those of skill will appreciate that glycosylation sites can be incorporated into the peptide sequences of other FGFs, e.g. FGF-9 and FGF-18, in the manner set forth below.

Fibroblast Growth Factor-20 Sequence Information

A Fibroblast Growth Factor-20 sequence displaying the different regions of the protein is shown in Table 5. The wild-type FGF-20 is thought to be un-glycosylated and may be produced in *Escherichia coli* as a therapeutic. The amino acid sequence is shown in Table 4, below.

TABLE 4

| Human Fibroblast Growth Factor-20, (SEQ ID NO: 1) |
|---|
| MAPLAEVGGE LGGLEGLGQQ VGSHFLLPPA GERPPLLGER |
| RSAAERSARG GPGAAQLAHL HGILRRRQLY CRTGFHLQIL |
| PDGSVQGTRQ DHSLFGILEF ISVAVGLVSI RGVDSGLYLG |
| MNDKGELYGS EKLTSECIFR EQFEENWYNT YSSNIYKHGD |
| TGRRYFVALN KDGTPRDGAR SKRHQKFTHF LPRPVDPERV |
| PELYKDLLMY T |

Regions of FGF-20 that are suited to mutation for the purpose of creating glycosylation sites are shown in Table 5.

These regions are indicated either in bold, or in italics when one region is contiguous to another.

WO 03/31464, incorporated herein by reference). GlycoPEGylation of the FGF is expected to result in improved

TABLE 5

Wild-type Human FGF-20 Sequence Showing Different Protein Regions (SEQ ID NO: 1)

```
MAPLAEVGGF LGGLEGLGQQ VGSHFLLPPA GERPPLLGER RSAAERSARG GPGRAAQLAHL
region 1                  region 2                  region 3
1.............10.............20.............30.............40.............50.............60

HGILRRRQLY CRTGFHLQIL PDGSVQGTRQ DHSLFGILEF ISVAVGLVSI RGVDSGLYLGMN
                region 4
61...........70.............80.............90.............100............110............120...

DKGELYGSEKLTSECIFR EQFEENWYNTYSSNIYKHGD TGRRYFVALN KDGTPRDGAR SKRH
                                                              region 5
123... 130............140............150...........160............170............180...

QKFTHF LPRPVDPERV PELYKDLLMY T
        region 6          region 7
185...190............200............210.211
```

Fibroblast Growth Factor-21 Sequence Information

A Fibroblast Growth Factor-21 sequence displaying the different regions of the protein is shown in Table 7. The wild-type FGF-21 is thought to be un-glycosylated and may be produced in *Escherichia coli* as a therapeutic. The amino acid sequence is shown in Table 6, below.

TABLE 6

Human Fibroblast Growth Factor-21, (SEQ ID NO: 146)

MHP IPDSSPLLQF GGQVRQRYLY TDDAQQTEAH

LEIREDGTVG GAADQSPESL LQLKALKPGV IQILGVKTSR

FLCQRPDGAL YGSLHFDPEA CSFRELLLED GYNVYQSEAH

GLPLHLPGNK SPHRDPAPRG PARFLPLPGL PPALPEPPGI

LAPQPPDVGS SDPLSMVGPS QGRSPSYAS

Regions of FGF-21 that are suited to mutation for the purpose of creating glycosylation sites are shown in Table 7. These regions are indicated either in bold, or in italics when one region is contiguous to another.

biophysical properties that may include but are not limited to improved half-life, improved area under the curve (AUC) values, reduced clearance, and reduced immunogenicity.

Example 1

Exemplary regions on FGF-20 that are suited for the introduction of glycosylation sites by mutation are shown in Table 5, above. In all cases, the N-terminal Met may be present or absent on any FGF mutant. The numbering of the amino acid residues is based on the initial unmodified sequence in which the left most residue, methionine, is numbered as position 1. To highlight how the mutant sequence differs in respect to the unmodified sequence, the numbering of unmodified amino acids as they appear in the sequences below remains unchanged following the modification. More than one of the described sequence modifications may be present in an FGF mutant of the present invention. Specifically, the preferred regions for introduction of mutations to create a glycosylation site(s) not present in the wild-type peptide are the nucleotide sequences that encode: amino acids 1-7 (REGION 1; SEQ ID NO:2), amino acids 20-42 (REGION 2; SEQ ID NO:3), amino acids 43-60 (REGION 3; SEQ ID NO:4), amino acids 73-90 (REGION 4; SEQ ID NO:5), amino acids 159-174 (REGION 5; SEQ ID NO:6), amino acids 177-198 (REGION 6; SEQ ID NO:7) or amino acids 199-201 (REGION 7; SEQ ID NO:8) of the wild-type FGF amino acid sequence (see Table 5) can be

TABLE 7

Wild-type Human FGF-21 Sequence Showing Different Protein Regions (SEQ ID NO: 146)

```
MHPIPDSSPLLQFGGQVRQRYLYTDDAQQTEAHLEIREDGTVGGAADQSPESLL
 region 1    region 2                                                         region 3
1............10.............20.............30.............40.............50.......

QLKALKPGVIQILGVKTSRFLCQRPDGALYGSLHFDPEACSFRELLLEDGYNVYQS
         region 4              region 5     region 6
55.....60.............70.............80.............90.............100............110

EAHGLPLHLPGNKSPHRDPAPRGPARFLPLPGLPPALPEPPGILAPQPP
 region 7                                                   region 8
111.........120............130............140............150..........159

DVGSSDPLSMVGPSQGRSPSYAS
region 9  region 10   region 11
160............170............180.182
```

FGF or mutated FGF can be glycosylated or glycoconjugated (see WO 03/31464, incorporated herein by reference). Preferably, a mutated FGF is glycoPEGylated, wherein a polyethylene glycol (PEG) moiety is conjugated to the mutated FGF polypeptide via a glycosyl linkage (see mutated so that either an N-linked or an O-linked glycosylation site is introduced into the resulting mutated FGF-20 polypeptide.

The following example describes amino acid sequence mutations introducing N-linked e.g., asparagine residues, and O-linked glycosylation sites, e.g., serine or threonine residues, into a preferably proline-containing site of a wild-type Fibroblast Growth Factor-20 sequence or any modified version thereof.

1. Region 1

In the Region 1 mutants, the N-terminus of a wild-type FGF-20, MAP$^3$LAEV; SEQ ID NO:2, is replaced with MXY$_a$Z$_b$P$^3$BJO1234, wherein 1, 2, 3, 4, X, Y, Z, B, J and O are independently selected from any uncharged amino acid, or glutamic acid (E), and wherein at least one is threonine (T) or serine (S), and is a substrate for GalNAc transferase where GalNAc is added to at least threonine or serine to create an O-linked glycosylation site. The symbols a and b independently represent 0 or 1. To clarify, sequences designated as SEQ ID NO:12-14, 338-344 contain amino acid insertions between P$^3$ and L$^4$ of the native FGF-20 sequence. Preferred examples include:

| | |
|---|---|
| MAPTP$^3$LAEV; | SEQ ID NO: 9 |
| MVTP$^3$LAEV; | SEQ ID NO: 10 |
| MAP$^3$TTEV; | SEQ ID NO: 11 |
| MAP$^3$TQGAMPL$^4$AEV; | SEQ ID NO: 12 |
| MAP$^3$TSSL$^4$AEV; | SEQ ID NO: 13 |
| MAP$^3$TALPL$^4$AEV; | SEQ ID NO: 14 |
| MAP$^3$TQAPL$^4$AEV; | SEQ ID NO: 338 |
| MAP$^3$TEIPL$^4$AEV; | SEQ ID NO: 339 |
| MAP$^3$TINTPL$^4$AEV; | SEQ ID NO: 340 |
| MAP$^3$TINTL$^4$AEV; | SEQ ID NO: 341 |
| MAP$^3$TTVSL$^4$AEV; | SEQ ID NO: 342 |
| MAP$^3$TQEVL$^4$AEV; | SEQ ID NO: 343 |
| MAP$^3$TQAVL$^4$AEV; | SEQ ID NO: 344 |

2. Region 2

In these mutants, the wild-type QVGSHFLLP$^{28}$P$^{29}$A$^{30}$GERPPLLGERRS; SEQ ID NO:3, is subdivided into three regions: Region 2(a) VGSHFLLP$^{28}$P$^{29}$A$^{30}$GERPP, SEQ ID NO: 15; Region 2(b) P$^{28}$P$^{29}$AGERPP, SEQ ID NO: 16; and Region 2(c) P$^{34}$P$^{35}$PLLGERRS, SEQ ID NO: 17. Mutations in each region are considered separately below.

Region 2(a): in these mutants the wild-type VGSHFLLP$^{28}$P$^{29}$A$^{30}$GERPP (SEQ ID NO:15) is replaced with 1234XYZ P$^{28}$P$^{29}$A$^{30}$ wherein 1, 2, 3, 4, X, Y, Z, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. The symbols a and b independently represent 0 or 1. Preferred mutations include:

| | |
|---|---|
| TET P$^{28}$P$^{29}$A$^{30}$GERPP; | SEQ ID NO: 18 |
| GTET P$^{28}$P$^{29}$A$^{30}$GERPP; | SEQ ID NO: 19 |
| VGTET P$^{28}$P$^{29}$A$^{30}$GERPP; | SEQ ID NO: 20 |
| TGT P$^{28}$P$^{29}$AEERPP; | SEQ ID NO: 21 |
| TAT P$^{28}$P$^{29}$ AEERPP; | SEQ ID NO: 22 |

Region 2(b): in these mutants the wild-type P$^{28}$P$^{29}$A$^{30}$GERPP (SEQ ID NO: 16) is replaced with P$^{28}$P$^{29}$1234(5)$_a$PP wherein 1, 2, 3, 4, X, Y, Z, are as described for Region 2(a). Preferred mutations include:

| | |
|---|---|
| P$^{28}$ P$^{29}$TGEAPP; | SEQ ID NO: 23 |
| P$^{28}$ P$^{29}$TGEVPP; | SEQ ID NO: 24 |
| P$^{28}$ P$^{29}$TQGAPP; | SEQ ID NO: 25 |
| P$^{28}$ P$^{29}$ATVAPP; | SEQ ID NO: 26 |
| P$^{28}$ P$^{29}$ATILPP; | SEQ ID NO: 27 |
| P$^{28}$ P$^{29}$AGTAPP; | SEQ ID NO: 28 |
| P$^{28}$ P$^{29}$TQGAMPP; | SEQ ID NO: 29 |
| P$^{28}$ P$^{29}$GSTAPP; | SEQ ID NO: 30 |
| P$^{28}$ P$^{29}$AGTSPP; | SEQ ID NO: 31 |
| P$^{28}$ P$^{29}$AGETPP; | SEQ ID NO: 32 |
| P$^{28}$ P$^{29}$ATETPP; | SEQ ID NO: 33 |
| P$^{28}$ P$^{29}$GTETPP; | SEQ ID NO: 34 |
| P$^{28}$ P$^{29}$TGERPP; | SEQ ID NO: 35 |
| P$^{28}$ P$^{29}$TINTPP; | SEQ ID NO: 345 |
| P$^{28}$ P$^{29}$TTVSPP; | SEQ ID NO: 346 |
| P$^{28}$ P$^{29}$TQALPP; | SEQ ID NO: 347 |

Region 2(c): in these mutants the wild-type P$^{34}$P$^{35}$PLLGERRS (SEQ ID NO:17) is replaced with P$^{24}$P$^{25}$123456 wherein 1, 2, 3, 4, 5, 6, are independently selected from any uncharged amino acid, or glutamic acid (E), and wherein at least one is threonine (T) or serine (S), and is a substrate for GalNAc transferase where GalNAc is added to at least threonine or serine to create an O-linked glycosylation site. Preferred mutations include:

| | |
|---|---|
| $P^{34}P^{35}$TQGAMP; | SEQ ID NO: 36 |
| $P^{34}P^{35}$TQGAMRS; | SEQ ID NO: 37 |
| $P^{34}P^{35}$TQGAMAS; | SEQ ID NO: 38 |
| $P^{34}P^{35}$TQGAMFS; | SEQ ID NO: 39 |
| | SEQ ID NO: 40 |
| $P^{34}P^{35}$TSSSTKS; | SEQ ID NO: 41 |
| $P^{34}P^{35}$TGERRS; | SEQ ID NO: 42 |
| $P^{34}P^{35}$TTGVRRS; | SEQ ID NO: 43 |
| $P^{34}P^{35}$TTGEARS; | SEQ ID NO: 44 |
| $P^{34}P^{35}$TAGERRS; | SEQ ID NO: 45 |
| | SEQ ID NO: 348 |
| $P^{34}P^{35}$TTVSRRS; | SEQ ID NO: 349 |

3. Region 3

In these mutants, the amino acid sequence surrounding $P^{52}$, AAERSARGGP$^{52}$GAAQLAHL; SEQ ID NO:4, is subdivided into two regions; Region 3(a) RSARGGP$^{52}$; SEQ ID NO:46 and Region 3(b) P$^{52}$GAAQLA, SEQ ID NO:47. Mutations in each region are considered separately, below. Region 3(a): in these mutants the wild-type RSARGG P$^{52}$ (SEQ ID NO:46) is replaced with 123456P$^{52}$ wherein 1, 2, 3, 4, 5, 6, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. Preferred examples include:

| | |
|---|---|
| RSATETP$^{52}$; | SEQ ID NO: 48 |
| RSGTETP$^{52}$; | SEQ ID NO: 49 |
| RSGTETP$^{52}$; | SEQ ID NO: 50 |
| RVGTETP$^{52}$; | SEQ ID NO: 51 |
| GVGTETP$^{52}$; | SEQ ID NO: 52 |
| GSATETP$^{52}$; | SEQ ID NO: 53 |
| GVGVTETP$^{52}$; | SEQ ID NO: 54 |
| GVTETP$^{52}$; | SEQ ID NO: 55 |
| QTELP$^{52}$; | SEQ ID NO: 56 |
| GVTSAP$^{52}$; | SEQ ID NO: 57 |
| SVVTP$^{52}$; | SEQ ID NO: 58 |

Region 3(b): in these mutants the wild-type P$^{52}$GAAQLA (SEQ ID NO:47) is replaced with P$^{52}$123456 wherein 1, 2, 3, 4, 5, 6, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. Preferred examples include:

| | |
|---|---|
| P$^{52}$TGAQLA; | SEQ ID NO: 59 |
| P$^{52}$TQGAMP; | SEQ ID NO: 60 |
| P$^{52}$TQGAMA; | SEQ ID NO: 61 |
| P$^{52}$TTAQLA; | SEQ ID NO: 62 |
| P$^{52}$GATQLA; | SEQ ID NO: 63 |
| P$^{52}$TSSSTA; | SEQ ID NO: 64 |
| P$^{52}$TSSSLA; | SEQ ID NO: 65 |
| P$^{52}$TINTLA; | SEQ ID NO: 350 |
| P$^{52}$TTVSLA; | SEQ ID NO: 351 |
| P$^{52}$TQAQLA; | SEQ ID NO: 352 |

4. Region 4

In these mutants, the wild-type TGFHLQIL P$^{81}$DGSVQGTRQ; SEQ ID NO:5, is subdivided into three regions; Region 4(a) HLQILP$^{81}$; SEQ ID NO:66; Region 4(b) P$^{81}$DGSVQGT; SEQ ID NO:67; and Region 4(c) P$^{81}$NGS SEQ ID NO:68. Mutations in each region are considered separately below.

Region 4(a): in these mutants the wild-type HLQILP$^{81}$ (SEQ ID NO:66) is replaced with 12345 P$^{81}$ wherein 1, 2, 3, 4, 5, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. Preferred examples include:

| | |
|---|---|
| QTELP$^{81}$; | SEQ ID NO: 69 |
| LIVTP$^{81}$; | SEQ ID NO: 70 |

-continued

| | |
|---|---|
| LTELP$^{81}$; | SEQ ID NO: 71 |
| LTELP$^{81}$; | SEQ ID NO: 72 |
| GVTSAP$^{81}$; | SEQ ID NO: 73 |
| HLTETP$^{81}$; | SEQ ID NO: 74 |
| VLTETP$^{81}$; | SEQ ID NO: 75 |
| VGTETP$^{81}$; | SEQ ID NO: 76 |
| VGVGTETP$^{81}$; | SEQ ID NO: 77 |
| VTSAP$^{81}$; | SEQ ID NO: 78 |
| VSTP$^{81}$; | SEQ ID NO: 79 |
| EATP$^{81}$; | SEQ ID NO: 80 |

Region 4(b): in these mutants the wild-type P$^{81}$DGSVQGT (SEQ ID NO:67) is replaced with P$^{81}$12345GT wherein 1, 2, 3, 4 and 5 are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. Preferred examples include:

| | |
|---|---|
| P$^{81}$TGSVGT; | SEQ ID NO: 81 |
| P$^{81}$TQGVQGT; | SEQ ID NO: 82 |
| P$^{81}$TGSVGPGT; | SEQ ID NO: 83 |
| P$^{81}$TQGAMPGT; | SEQ ID NO: 84 |
| P$^{81}$TTSVQGT; | SEQ ID NO: 85 |
| P$^{81}$TTAVQGT; | SEQ ID NO: 86 |
| P$^{81}$TINTQGT; | SEQ ID NO: 353 |
| P$^{81}$TTVSQGT; | SEQ ID NO: 354 |

Region 4(c): in these mutants the wild-type P$^{81}$DGS (SEQ ID NO:68) is mutated to create an N-linked glycosylation site. Preferred examples include:

| | |
|---|---|
| IL P$^{81}$NGSVH; | SEQ ID NO: 87 |
| IF P$^{81}$NGSV; | SEQ ID NO: 88 |
| P$^{81}$NGT; | SEQ ID NO: 89 |
| L P$^{81}$NGTVH; | SEQ ID NO: 90 |
| P$^{81}$NGTV; | SEQ ID NO: 91 |
| IL P$^{81}$NGT; | SEQ ID NO: 92 |
| QIL P$^{81}$NGT; | SEQ ID NO: 93 |
| QIL P$^{81}$NGTVH; | SEQ ID NO: 94 |

5. Region 5

In these mutants the wild-type LN KDGTP$^{175}$RDGAR SKRH, SEQ ID NO:6 is replaced with 12345 P$^{175}$67891011 wherein 1, 2, 3, 4, 5, 6, 7, 8, 9, 10, 11, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. Preferred examples include:

| | |
|---|---|
| LNVTETP$^{175}$RDGARSKRH; | SEQ ID NO: 95 |
| LNVTET P$^{175}$DDGARSKRH; | SEQ ID NO: 96 |
| LNVTET P$^{175}$LDGARSKRH; | SEQ ID NO: 97 |
| LNAITT P$^{175}$RDGARSKRH; | SEQ ID NO: 98 |
| LNAITT P$^{175}$LDGARSKRH; | SEQ ID NO: 99 |
| LNQEAT P$^{175}$LDGARSKRH; | SEQ ID NO: 100 |
| LNQTEL P$^{175}$LDGARSKRH; | SEQ ID NO: 101 |
| LNQTEL P$^{175}$ADGARSKRH; | SEQ ID NO: 102 |
| LNKDGT P$^{175}$TDGARSKRH; | SEQ ID NO: 103 |
| LNKDGT P$^{175}$TSGARSKRH; | SEQ ID NO: 104 |
| LNKDGT P$^{175}$TDGAASKRH; | SEQ ID NO: 105 |
| LNKDGT P$^{175}$TSGAASKRH; | SEQ ID NO: 106 |
| LNKDGT P$^{175}$TQGAMPKRH; | SEQ ID NO: 107 |
| LNKDGT P$^{175}$TQGAMSKRH; | SEQ ID NO: 108 |
| LNKDGT P$^{175}$TTTARSKRH; | SEQ ID NO: 109 |
| LN KDGTP$^{175}$TINTRSKRH; | SEQ ID NO: 355 |
| LN KDGTP$^{175}$TINTSSKRH; | SEQ ID NO: 356 |

LN KDGTP$^{175}$TTVSRSKRH; SEQ ID NO: 357

LN KDGTP$^{175}$TTVSASKRH; SEQ ID NO: 358

6. Region 6

In these mutants, the wild-type sequence, FTHFL P$^{192}$RPVD P$^{197}$ERVP$^{201}$ELYKDLL; SEQ ID NO:7, is subdivided into two regions; Region 6(a) LP$^{192}$RPVD P$^{197}$ERV P$^{201}$ELYKD; SEQ ID NO:110 and Region 6(b) P$^{197}$ERVP$^{201}$ELYKD, SEQ ID NO:111. Mutations in each region are considered separately, below.

Region 6(a): Region 6(a) in these mutants the wild-type LP$^{192}$RPVD P$^{197}$ERVP$^{201}$ELYKD (SEQ ID NO: 110) is replaced with P$^{192}$1P23 P$^{197}$ wherein 1, 2, 3, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. Preferred examples include:

LP$^{192}$APTD P$^{197}$ERVP$^{201}$ELYKD; SEQ ID NO: 112

LP$^{192}$NPTA P$^{197}$ERVP$^{201}$ELYKD; SEQ ID NO: 113

LP$^{192}$RPTA P$^{197}$ERVP$^{201}$ELYKD; SEQ ID NO: 114

LP$^{192}$APTQ P$^{197}$ERVP$^{201}$ELYKD; SEQ ID NO: 115

LP$^{192}$TPVD P$^{197}$ERVP$^{201}$ELYKD; SEQ ID NO: 116

LP$^{192}$TPSD P$^{197}$ERVP$^{201}$ELYKD; SEQ ID NO: 117

LP$^{192}$VPTD P$^{197}$ERVP$^{201}$ELYKD; SEQ ID NO: 118

LP$^{192}$TPAD P$^{197}$ERVP$^{201}$ELYKD; SEQ ID NO: 119

Region 6(b): Region 6(b) in these mutants the wild-type P$^{197}$ERVP$^{201}$ELYKD (SEQ ID NO:111) is replaced with P$^{197}$123P$^{201}$45678 wherein 1, 2, 3, 4, 5, 6, 7, 8, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. Preferred examples include:

P$^{197}$TAS P$^{201}$ELYKD; SEQ ID NO: 120

P$^{197}$TAS P$^{201}$ALYKD; SEQ ID NO: 121

P$^{197}$NTL P$^{201}$ELYKD; SEQ ID NO: 122

P$^{197}$ETV P$^{201}$ELYKD; SEQ ID NO: 123

P$^{197}$QET P$^{201}$ELYKD; SEQ ID NO: 124

P$^{197}$TQG P$^{201}$ELYKD; SEQ ID NO: 125

P$^{197}$TQG P$^{201}$ALYKD; SEQ ID NO: 126

P$^{197}$QGT P$^{201}$ALYKD; SEQ ID NO: 127

P$^{197}$ATE P$^{201}$ELYKD; SEQ ID NO: 128

P$^{197}$TTQ P$^{201}$ELYKD; SEQ ID NO: 129

P$^{197}$TTE P$^{201}$ELYKD; SEQ ID NO: 130

P$^{197}$ERVP$^{201}$TLYKD; SEQ ID NO: 131

P$^{197}$ERVP$^{201}$TLYAD; SEQ ID NO: 132

P$^{197}$ERVP$^{201}$TQGAD; SEQ ID NO: 133

P$^{197}$ERVP$^{201}$TQGAMP; SEQ ID NO: 134

P$^{197}$ERVP$^{201}$TQGA; SEQ ID NO: 135

P$^{197}$TQAP$^{201}$ELYKD; SEQ ID NO: 359

P$^{197}$TEIP$^{201}$ELYKD; SEQ ID NO: 360

7. Region 7

In these mutants the wild-type L$^{208}$MY T$^{211}$ (SEQ ID NO: 8) is replaced with 123(4)$_a$(5)$_b$(6)$_c$(x) wherein 1, 2, 3, 4, 5, are independently selected from any uncharged amino acid, or glutamic acid (E), wherein at least one is threonine (T) or serine (S), and is a substrate for GalNAc transferase where GalNAc is added to at least threonine or serine to create an O-linked glycosylation site. The symbols a, b, and c independently represent 0 or 1, and (x) is selected from OH, NH$_2$, glycine, alanine, leucine, and asparagine. Preferred examples include:

L$^{208}$MY T$^{211}$P(x); SEQ ID NO: 136

L$^{208}$TE T$^{211}$P(x); SEQ ID NO: 137

VTE T$^{211}$P(x); SEQ ID NO: 138

GVTE T$^{211}$PL(x); SEQ ID NO: 139

PELYVGVTC T$^{211}$PL(x); SEQ ID NO: 140

L$^{208}$MY T$^{211}$ (x); SEQ ID NO: 141

L$^{208}$MY T$^{211}$PTASP; SEQ ID NO: 142

L$^{208}$MY T$^{211}$PATEP; SEQ ID NO: 143

L$^{208}$MY T$^{211}$PTP(x); SEQ ID NO: 144

-continued $L^{208}MY\ T^{211}PTAP(x);$     SEQ ID NO: 145

The numbering of the amino acid residues is based on the initial unmodified sequence in which the most N-terminal residue is numbered 1. The numbering of unmodified amino acids remains unchanged following the modification. More than one of the above described sequence modifications may be present in a FGF mutant of the present invention.

Example 2

A library of FGF-20 peptides each with one potential O-linked glycosylation site as disclosed in Example 1, is expressed in E. coli or by using in vitro translation methods. Protein is purified using either a heparin binding or IMAC capture method and tested by for in vitro biological activity. Those protein sequences that retain in vitro activity are tested as acceptors for GlycoPEGylation. GlycoPEGylated FGF-20's (40 kDa branched) are purified for further biological evaluation as outlined above.

Example 3

Exemplary regions on FGF-21 that are suited for the introduction of glycosylation sites by mutation are shown in Table 7, above. In all cases, the N-terminal Met may be present or absent on any FGF mutant. The numbering of the amino acid residues is based on the initial unmodified sequence in which the left most residue, methionine, is numbered as position 1. To highlight how the mutant sequence differs in respect to the unmodified sequence, the numbering of unmodified amino acids as they appear in the mutant sequences below remains unchanged following the modification. More than one of the described sequence modifications may be present in an FGF mutant of the present invention. Specifically, the preferred regions for introduction of mutations to create a glycosylation site(s) not present in the wild-type peptide are the nucleotide sequences that encode: amino acids 1-8 (REGION 1; SEQ ID NO:147), amino acids 9-13 (REGION 2; SEQ ID NO:148), amino acids 46-54 (REGION 3; SEQ ID NO:149), amino acids 60-65 (REGION 4; SEQ ID NO: 150), amino acids 78-83 (REGION 5; SEQ ID NO: 151), amino acids 86-91 (REGION 6; SEQ ID NO: 152) or amino acids 112-141 (REGION 7; SEQ ID NO: 153), amino acids 149-157 (REGION 8; SEQ ID NO:154), amino acids 160-166 (REGION 9; SEQ ID NO:155), amino acids 167-172 (REGION 10; SEQ ID NO:156), amino acids 173-182 (REGION 11; SEQ ID NO:157) of the wild-type FGF-121 amino acid sequence (see Table 7) can be mutated so that either an N-linked or an O-linked glycosylation site is introduced into the resulting mutated FGF-21 polypeptide.

The following example describes amino acid sequence mutations introducing N-linked e.g., asparagine residues, and O-linked glycosylation sites, e.g., serine or threonine residues, into a preferably proline-containing site of a wild-type Fibroblast Growth Factor-21 sequence or any modified version thereof.

1. Region 1

In the Region 1 mutants, the N-terminus of a wild-type FGF-21, $M^1HPIPDSS$ (SEQ ID NO:147), is subdivided into three regions; Region 1(a) $M^1HP^3$ (SEQ ID NO:158); Region 1(b) $M^1HPIP$ (SEQ ID NO:159); and Region 1(c) $P^5DSS$ (SEQ ID NO:160). Mutations in each region are considered separately, below.

Region 1(a): In these mutants, the wild-type $M^1HP^3$ (SEQ ID NO:158) is replaced with $M^1X_nB_oO_rJ_qP^3$ wherein B, O, J are independently selected from any uncharged amino acid, and where X is any uncharged amino acid, or histidine (H), and where at least one is T or S, and is a substrate for GalNAc transferase where GalNAc is added to at least T or S. The symbols n, o, q, r independently represent 0-3. Preferred mutations include:

$M^1VTP^3$     SEQ ID NO: 161

$M^1QTP^3;$     SEQ ID NO: 162

$M^1ATP^3;$     SEQ ID NO: 163

$M^1IATP^3;$     SEQ ID NO: 164

Region 1(b): in these mutants the wild-type $M^1HPIP$ (SEQ ID NO:159) is replaced with $M^1X_nPB_oP$ wherein B is independently selected from any uncharged amino acid, and where X is any uncharged amino acid, or histidine (H), and whereat least one is T or S, and is a substrate for GalNAc transferase where GalNAc is added to at least T or S. The symbols n, o independently represent 0-3. Preferred mutations include:

$M^1FPTP;$     SEQ ID NO: 165

$M^1HPTP;$     SEQ ID NO: 166

$M^1APTP;$     SEQ ID NO: 167

$M^1FPSP;$     SEQ ID NO: 168

$M^1HPSP;$     SEQ ID NO: 169

$M^1APSP;$     SEQ ID NO: 170

$M^1SPTP;$     SEQ ID NO: 171

Region 1(c): in these mutants the wild-type $P^5DSS$ (SEQ ID NO: 160) is replaced with $P^5B_oO_rJ_q$ wherein B, O, J are independently selected from any uncharged amino acid, and where at least one is T or S, and is a substrate for GalNAc transferase where GalNAc is added to at least T or S. The symbols o, q, r independently represent 0-3. Preferred mutations include:

$P^5TSS;$     SEQ ID NO: 172

$P^5TQA;$     SEQ ID NO: 173

$P^5TAQ;$     SEQ ID NO: 174

$P^5TIE$;  SEQ ID NO: 175

$P^5SSS$;  SEQ ID NO: 176

2. Region 2

In these mutants, the wild-type $P^9L^{10}LQF$ (SEQ ID NO:148) is replaced with $P^9J_qX_nO_rU_s$ wherein X, J, O, U are independently selected from any uncharged amino acid, and where at least one is T or S, and is a substrate for GalNAc transferase where GalNAc is added to at least T or S. The symbols q, n, r, s independently represent 0-3. Preferred examples include:

$P^9T^{10}TQF$;  SEQ ID NO: 177

$P^9T^{10}INT$;  SEQ ID NO: 178

$P^9T^{10}QGA$;  SEQ ID NO: 179

$P^9T^{10}QGF$;  SEQ ID NO: 180

$P^9T^{10}TVS$;  SEQ ID NO: 181

$P^9T^{10}QAF$;  SEQ ID NO: 182

3. Region 3

In these mutants, the wild-type $ADQSP^{50}ESLL$ (SEQ ID NO:149) is replaced with $1_t\emptyset Z_mB_oP^{50}J_qX_nO_rU_s$ wherein Ø, Z, X, B, J, O, U, 1, 2, 3 are independently selected from any uncharged amino acid, where Z or J is independently selected as glutamic acid (E), where 2 and X may be independently selected as lysine (K) or arginine (R), and where at least one is T or S, and is a substrate for GalNAc transferase where GalNAc is added to at least T or S. The symbols t, m, n, o, q, r, s, t independently represent 0-3. Preferred examples include:

$ADQSP^{50}TSLL$;  SEQ ID NO: 183

$ADQSP^{50}TTVS$;  SEQ ID NO: 184

$ADQSP^{50}TINT$;  SEQ ID NO: 185

$ADQSP^{50}TQAL$;  SEQ ID NO: 186

$ADQSP^{50}TQGA$;  SEQ ID NO: 187

$ADQSP^{50}TQAL$;  SEQ ID NO: 188

$ATQSP^{50}ESLL$;  SEQ ID NO: 189

$ATESP^{50}ESLL$;  SEQ ID NO: 190

$ATETP^{50}ESLL$;  SEQ ID NO: 191

$VTQSP^{50}ESLL$;  SEQ ID NO: 192

$VTETP^{50}ESLL$;  SEQ ID NO: 193

$ATESP^{50}ASLL$;  SEQ ID NO: 194

4. Region 4

In these mutants, the wild-type $KP^{61}6GVIQ$ (SEQ ID NO: 150) is replaced with $B_oP^{61}J_qX_nO_rU_s$ wherein B is selected from lysine (K) or any uncharged amino acid, where X, J, O, U are independently selected from any uncharged amino acid, and where at least one is T or S, and is a substrate for GalNAc transferase where GalNAc is added to at least T or S. The symbols n, o, q, r, s independently represent 0-3. Preferred examples include:

$SP^{61}TVIQ$;  SEQ ID NO: 195

$AP^{61}TVIQ$;  SEQ ID NO: 196

$SP^{61}TTVS$;  SEQ ID NO: 197

$SP^{61}TINT$;  SEQ ID NO: 198

$SP^{61}TQAQ$;  SEQ ID NO: 199

$SP^{61}TQGA$;  SEQ ID NO: 200

$SP^{61}TVIA$;  SEQ ID NO: 201

$AP^{61}TTVS$;  SEQ ID NO: 202

$AP^{61}TINT$;  SEQ ID NO: 203

5. Region 5

In these mutants, the wild-type $RP^{19}DGAL$ (SEQ ID NO:151) is replaced with $B_oP^7J_qX_nO_rU_s$ wherein X, B, J, O, U are independently selected from any uncharged amino acid, where B may be independently selected as lysine (K) or arginine (R), and where at least one is T or S, and is a substrate for GalNAc transferase where GalNAc is added to at least T or S. The symbols n, o, q, r, s independently represent 0-3. Preferred examples include:

$SP^{79}TGAL$;  SEQ ID NO: 204

$AP^{79}TGAL$;  SEQ ID NO: 205

$SP^{79}TINT$;  SEQ ID NO: 206

$SP^{79}TTVS$;  SEQ ID NO: 207

$SP^{79}TQAL$;  SEQ ID NO: 208

AP$^{79}$TQAL;  SEQ ID NO: 209

SP$^{79}$TQGA;  SEQ ID NO: 210

SP$^{79}$TQGAM;  SEQ ID NO: 211

6. Region 6

In these mutants, the wild-type SLHFDP$^{91}$ (SEQ ID NO:152) is replaced with $21_t\mathit{\emptyset} Z_m B_o P^{91}$ wherein Ø, Z, B, 1, 2 are independently selected from any uncharged amino acid, and where at least one is T or S, and is a substrate for GalNAc transferase where GalNAc is added to at least T or S. The symbols t, m, o independently represent 0-3. Preferred examples include:

SLTFTP$^{91}$;  SEQ ID NO: 212

SLTETP$^{91}$;  SEQ ID NO: 213

SVTETP$^{91}$;  SEQ ID NO: 214

7. Region 7

In these mutants, the wild-type A$^{112}$HGLPLHLPGNKSPHRDPAPRGPARFLPLP (SEQ ID NO: 153) is subdivided into five regions; Region 7(a) AHGLP$^{116}$LHLP$^{120}$ (SEQ ID NO:215); Region 7(b) HLP$^{120}$GNKSP$^{125}$HR(SEQ ID NO:216); Region 7(c) KSP$^{125}$HRDP$^{129}$APR (SEQ ID NO:217); Region 7(d) RGP$^{134}$ARFLP$^{139}$LP (SEQ ID NO:218); and Region 7(e) RGP$^{134}$ARFLP$^{139}$LP (SEQ ID NO:219). Mutations in each region are considered separately, below.

Region 7(a): In these mutants, the wild-type AHGLP$^{116}$LHLP$^{120}$ (SEQ ID NO:215) is replaced with $1_t\mathit{\emptyset} Z_m B_o P^{116} J_q X_n O_r P^{120}$ wherein 1, Ø, Z, X, B, J, O are independently selected from any uncharged amino acid, and where at least one is T or S, and is a substrate for GalNAc transferase where GalNAc is added to at least T or S. The symbols t, m, o, q, n, r independently represent 0-3. Preferred mutations include:

ATGTP$^{116}$LHLP$^{120}$;  SEQ ID NO: 220

ATETP$^{116}$LHLP$^{120}$;  SEQ ID NO: 221

VTETP$^{116}$LHLP$^{120}$;  SEQ ID NO: 222

VTGLP$^{116}$LHLP$^{120}$;  SEQ ID NO: 223

ATGLP$^{116}$LHLP$^{120}$;  SEQ ID NO: 224

AHGLP$^{116}$TQAP$^{120}$;  SEQ ID NO: 225

AHGLP$^{116}$TAQP$^{120}$;  SEQ ID NO: 226

AHGLP$^{116}$TEIP$^{120}$;  SEQ ID NO: 227

AHGLP$^{116}$TSSP$^{120}$;  SEQ ID NO: 228

AHGLP$^{116}$TALP$^{120}$;  SEQ ID NO: 229

ASGLP$^{116}$TQAP$^{120}$;  SEQ ID NO: 230

ASGLP$^{116}$TEIP$^{120}$;  SEQ ID NO: 231

Region 7(b): In these mutants, the wild-type HLP$^{120}$GNKSP$^{125}$HR (SEQ ID NO:216) is replaced with $1_t LP^{120} X_n O_r U_s 2_a P^{125} B_o J_q$ wherein X, B, J, O, U, 1, 2 are independently selected from any uncharged amino acid, where B, J, 1 are independently selected as histidine (H), lysine (K), or arginine (R), and where at least one is T or S, and is a substrate for GalNAc transferase where GalNAc is added to at least T or S. The symbols t, n, r, s, a, o, q independently represent 0-3. Preferred mutations include:

HLP$^{120}$TTAVP$^{125}$HR;  SEQ ID NO: 232

HLP$^{120}$TSGEP$^{125}$HR;  SEQ ID NO: 233

HLP$^{120}$GSTAP$^{125}$HR;  SEQ ID NO: 234

HLP$^{120}$GNTSP$^{125}$HR;  SEQ ID NO: 235

HLP$^{120}$GTESP$^{125}$HR;  SEQ ID NO: 236

HLP$^{120}$LTQTP$^{125}$HR;  SEQ ID NO: 237

HLP$^{120}$GTQTP$^{125}$HR;  SEQ ID NO: 238

HLP$^{120}$LTQTP$^{125}$AR;  SEQ ID NO: 239

HLP$^{120}$TNASP$^{125}$HR;  SEQ ID NO: 240

HLP$^{120}$TQGSP$^{125}$HR;  SEQ ID NO: 241

HLP$^{120}$VTSQP$^{125}$HR  SEQ ID NO: 242

HLP$^{120}$TINTP$^{125}$HR;  SEQ ID NO: 243

HLP$^{120}$TSVSP$^{125}$HR;  SEQ ID NO: 244

Region 7(c): In these mutants, the wild-type KSP$^{125}$HRDP$^{29}$APR (SEQ ID NO:217) is replaced with $1_t SP^{125} X_n O_r U_s P^{129} B_o PJ_q$ wherein B, U, 1 are independently selected from any uncharged amino acid, where X, O, J are independently selected from any uncharged amino acid or histine (H), lysine (K), or arginine (R), and where at least one is T or S, and is a substrate for GalNAc transferase where GalNAc is added to at least T or S. The symbols t, n, r, s, o, q independently represent 0-3. Preferred mutations include:

KSP$^{125}$TAQP$^{129}$APR;  SEQ ID NO: 245

KSP$^{125}$TADP$^{129}$APR; SEQ ID NO: 246

ASP$^{125}$TAQP$^{129}$APR; SEQ ID NO: 247

SSP$^{125}$TADP$^{129}$APR; SEQ ID NO: 248

KSP$^{125}$TSDP$^{129}$APR; SEQ ID NO: 249

KSP$^{125}$TEIP$^{129}$APR; SEQ ID NO: 250

KSP$^{125}$TEIP$^{129}$APR; SEQ ID NO: 251

KSP$^{125}$TEDP$^{129}$APR; SEQ ID NO: 252

ASP$^{125}$TEDP$^{129}$APR; SEQ ID NO: 253

SSP$^{125}$TADP$^{129}$APR; SEQ ID NO: 254

SSP$^{125}$TAQP$^{129}$APR; SEQ ID NO: 255

KSP$^{125}$TQAP$^{129}$APR; SEQ ID NO: 256

SSP$^{125}$TQAP$^{129}$APR; SEQ ID NO: 257

ASP$^{125}$TEIP$^{129}$APR; SEQ ID NO: 258

KSP$^{125}$HRDP$^{129}$TPR; SEQ ID NO: 259

KSP$^{125}$HRDP$^{129}$SPR; SEQ ID NO: 260

KSP$^{125}$HRDP$^{129}$TPA; SEQ ID NO: 261

KSP$^{125}$HRDP$^{129}$TPS; SEQ ID NO: 262

KSP$^{125}$HSDP$^{129}$TPA; SEQ ID NO: 263

KSP$^{125}$HADP$^{129}$TPS; SEQ ID NO: 264

KSP$^{125}$HADP$^{129}$TPA; SEQ ID NO: 265

Region 7(d): In these mutants, the wild-type RGP$^{134}$ARFLP$^{139}$LP (SEQ ID NO:218) is replaced with 1$_t$GP$^{134}$X$_n$O$_r$U$_s$2$_a$P$^{139}$B$_o$P wherein X, B, O, U, 1, 2 are independently selected from any uncharged amino acid, where O, 1 are independently selected from lysine (K) or arginine (R), and where at least one is T or S, and is a substrate for GalNAc transferase where GalNAc is added to at least T or S. The symbols t, n, r, s, a, o independently represent 0-3. Preferred mutations include:

RGP$^{134}$TSFLP$^{139}$LP; SEQ ID NO: 266

RGP$^{134}$TSGEP$^{139}$LP; SEQ ID NO: 267

RGP$^{134}$GSTAP$^{139}$LP; SEQ ID NO: 268

RGP$^{134}$ANTSP$^{139}$LP; SEQ ID NO: 269

RGP$^{134}$ATESP$^{139}$LP; SEQ ID NO: 270

RGP$^{134}$ATQTP$^{139}$LP; SEQ ID NO: 271

RGP$^{134}$ATQTP$^{139}$LP; SEQ ID NO: 272

RGP$^{134}$LTQTP$^{139}$LP; SEQ ID NO: 273

RGP$^{134}$TQFLP$^{139}$LP; SEQ ID NO: 274

RGP$^{134}$TSFLP$^{139}$LP; SEQ ID NO: 275

RGP$^{134}$VTSQP$^{139}$LP; SEQ ID NO: 276

SGP$^{134}$TSFLP$^{139}$LP; SEQ ID NO: 277

AGP$^{134}$TSGEP$^{139}$LP; SEQ ID NO: 278

SGP$^{134}$TSALP$^{139}$LP; SEQ ID NO: 279

Region 7(e): In these mutants, the wild-type RGP$^{134}$ARFLP$^{139}$LP (SEQ ID NO:219) is replaced with 1$_t$GP$^{134}$X$_n$O$_r$U$_s$2$_a$P$^{139}$B$_o$P wherein X, B, O, U, 1, 2 are independently selected from any uncharged amino acid, where O, 1 are independently selected from lysine (K) or arginine (R), and where at least one is T or S, and is a substrate for GalNAc transferase where GalNAc is added to at least T or S. The symbols t, n, r, s, a, o independently represent 0-3. Preferred mutations include:

RGP$^{134}$ARFLP$^{139}$TP; SEQ ID NO: 280

RGP$^{134}$ARFLP$^{139}$SP; SEQ ID NO: 281

RGP$^{134}$ASFLP$^{139}$TP; SEQ ID NO: 282

8. Region 8

In these mutants, the wild-type EPP$^{151}$GILAP$^{156}$Q (SEQ ID NO: 154) is replaced with B$_o$PP$^{151}$X$_n$O$_r$U$_s$2$_a$P$^{156}$1$_t$ wherein B, X, O, U, 2, 1 are independently selected from any uncharged amino acid, and where at least one is T or S, and is a substrate for GalNAc transferase where GalNAc is added to at least T or S. The symbols o, n, r, s, a, t independently represent 0-3. Preferred mutations include:

TPP$^{151}$GILAP$^{156}$Q; SEQ ID NO: 283

SPP$^{151}$GILAP$^{156}$Q; SEQ ID NO: 284

EPP$^{151}$TILAP$^{156}$Q; SEQ ID NO: 285

EPP$^{151}$TTLAP$^{156}$Q; SEQ ID NO: 286

EPP$^{151}$TQLAP$^{156}$Q; SEQ ID NO: 287

EPP$^{151}$TQGAP$^{156}$Q; SEQ ID NO: 288

EPP$^{151}$TSGEP$^{156}$Q; SEQ ID NO: 289

EPP$^{151}$GSTAP$^{156}$Q; SEQ ID NO: 290

EPP$^{151}$TTAVP$^{156}$Q; SEQ ID NO: 291

EPP$^{151}$GNTSP$^{156}$Q; SEQ ID NO: 292

EPP$^{151}$GTESP$^{156}$Q; SEQ ID NO: 293

EPP$^{151}$GTETP$^{156}$Q; SEQ ID NO: 294

EPP$^{151}$VTSQP$^{156}$Q; SEQ ID NO: 295

EPP$^{151}$AVQTP$^{156}$Q; SEQ ID NO: 296

EPP$^{151}$LTQTP$^{156}$Q; SEQ ID NO: 297

EPP$^{151}$VTSQP$^{156}$Q; SEQ ID NO: 298

EPP$^{151}$SSGAP$^{156}$Q; SEQ ID NO: 299

EPP$^{151}$TINTP$^{156}$Q; SEQ ID NO: 300

EPP$^{151}$TTNSP$^{156}$Q; SEQ ID NO: 301

EPP$^{151}$TQAAP$^{156}$Q; SEQ ID NO: 302

EPP$^{151}$GILAP$^{156}$T; SEQ ID NO: 303

EPP$^{151}$GILAP$^{156}$S; SEQ ID NO: 304

9. Region 9

In these mutants, the wild-type DVGSSDP$^{166}$ (SEQ ID NO:155) is replaced with X$_n$O$_r$U$_s$2$_a$B$_o$Z$_m$P$^{166}$ wherein Z, X, B, O, U, 2 are independently selected from any uncharged amino acid, glutamic acid (E), or aspartic acid (D), and where at least one is T or S, and is a substrate for GalNAc transferase where GalNAc is added to at least T or S. The symbols n, r, s, a, o, m independently represent 0-3. Preferred mutations include:

SEQ ID NO: 305
$TVGSSDP^{166}$;

SEQ ID NO: 306
$DVGSSTP^{166}$;

SEQ ID NO: 307
$DVGTETP^{166}$;

SEQ ID NO: 308
$DAASAAP^{166}$;

SEQ ID NO: 309
$DAATAAP^{166}$;

-continued

SEQ ID NO: 310
$DVGTSDP^{166}$;

SEQ ID NO: 311
$DVATSDP^{166}$;

SEQ ID NO: 312
$TGDSSDP^{166}$;

SEQ ID NO: 313
$TDASGAP^{166}$;

SEQ ID NO: 314
$DVGTSGP^{166}$;

10. Region 10

In these mutants, the wild-type $LSMVGP^{172}$ (SEQ ID NO:156) is replaced with $X_nO_rU_s2_aB_oP^{172}$ wherein B, O, U, 2 are independently selected from any uncharged amino acid, glutamic acid (E), or aspartic acid (D), where at least X is selected as either T or S, and is a substrate for GalNAc transferase where GalNAc is added to at least T or S. The symbols n, r, s, a, o independently represent 0-3. Preferred mutations include:

SEQ ID NO: 315
TSMVGP;

SEQ ID NO: 316
TSGVGP;

SEQ ID NO: 317
TSGAMP;

SEQ ID NO: 318
TQGAMP;

SEQ ID NO: 319
TSMVGP;

SEQ ID NO: 320
TQGAMP;

11. Region 1

In these mutants, the wild-type $SQGRSP^{178}SYAS$ (SEQ ID NO: 157) is subdivided into two regions; Region 11(a) $SQGRSP^{178}$ (SEQ ID NO:321); and the carboxy terminal Region 11(b) $RSP^{178}SYAS$ (SEQ ID NO:322). Mutations in each region are considered separately, below.

Region 11(a): In these mutants, the wild-type $SQGRSP^{178}$ (SEQ ID NO:321) is replaced with $X_nO_rU_s2_aB_oP^{178}$ wherein B, O, U, 2 are independently selected from any uncharged amino acid, glutamic acid (E), or aspartic acid (D), where at least X is selected as either T or S, and is a substrate for GalNAc transferase where GalNAc is added to at least T or S. The symbols n, r, s, a, o independently represent 0-3. Preferred mutations include:

SEQ ID NO: 323
$SQGASP^{178}$;

SEQ ID NO: 324
$TQGASP^{178}$;

SEQ ID NO: 325
$TQGAMP^{178}$;

SEQ ID NO: 326
$TQGAMp^{178}$;

Region 11(b): In these mutants, the wild-type carboxy terminal $RSP^{178}$ SYAS (SEQ ID NO:322) is replaced with ZSP$^{178}$X$_n$O$_r$U$_s$1B$_o$23 wherein Z, X, B, O, U, 1, 2, 3 are independently selected from any uncharged amino acid, glutamic acid (E), or aspartic acid (D), where at least X is selected as either T or S, where Z may be independently selected as arginine (R) or lysine (K), and is a substrate for GalNAc transferase where GalNAc is added to at least T or S. The symbols n, r, s, o independently represent 0-3. Preferred mutations include:

| | |
|---|---|
| ASP$^{178}$SYAS; | SEQ ID NO: 327 |
| RSP$^{178}$TSAVAA; | SEQ ID NO: 328 |
| ASP$^{178}$TSAVAA; | SEQ ID NO: 329 |
| ASP$^{178}$SSGAPPPS; | SEQ ID NO: 330 |
| ASP$^{178}$SSGAPP; | SEQ ID NO: 331 |
| ASP$^{178}$SSGAP; | SEQ ID NO: 332 |
| RSP$^{178}$SSGAPPPS; | SEQ ID NO: 333 |
| ASP$^{178}$TINT; | SEQ ID NO: 334 |
| ASP$^{178}$TSVS; | SEQ ID NO: 335 |
| ASP$^{178}$TQAF; | SEQ ID NO: 336 |
| ASP$^{178}$TINTP; | SEQ ID NO: 337 |

Example 4

Soluble Expression of FGF-20 and FGF-21 in *E. coli*

Therapeutic proteins are commonly expressed in *E. coli* as inactive, insoluble inclusion bodies. Following inclusion body purification, soluble therapeutics are obtained by a protein refolding reaction. This refolding process is typically enhanced by the inclusion of compounds that facilitate the reshuffling of disulfide bonds.

The *E. coli* cytoplasm, the site of the protein expression and inclusion body formation, is a chemically reducing environment that inhibits the formation of disulfide bonds. A strain that has a less reducing, more oxidizing cytoplasm would theoretically permit disulfide bond formation, facilitating the expression of therapeutic proteins in a soluble form.

Experimental:

Therapeutic proteins tested were human FGF-20 and FGF-21. The FGF-21 construct lacked its N-terminal signal sequence. Genes encoding these therapeutic proteins were cloned into up to four different vector backbones (Vector #1, Vector #2, Vector #3, and pET24a) as indicated in Table 8. These constructs were tested in one or two of four different bacterial strains (W3110, BL21DE3, *E. coli*$_{(trxb,gor,supp)}$-2, and *E. coli*$_{(trxb,gor,supp)}$-2 DE3) as indicated in Table 8.

For protein expression, an overnight small scale culture was used to inoculate a 100 mL culture of prewarmed martone LB containing 50 µg/mL kanamycin. The culture was incubated at 37 C with shaking, and monitored for OD$_{620}$. When the OD$_{620}$ reached 0.4-0.6, the cultures were split and transferred to a 37° C. or 20° C. shaking incubator for 15-20 minutes. IPTG was then added to 0.1-1.0 mM final concentration, and shaking incubation was continued for 1.5 hours up to overnight. Cells were harvested by centrifugation at 4° C., 7000×g for 15 mins in a Sorvall RC3C+.

For whole cell extract analysis of protein expression, cells from a 150 µL aliquot of the induced cultures were collected by centrifugation and lysed in 1×PBS/0.1% SDS. Following heating with 100 mM DTT and 1× protein sample buffer, samples were resolved by SDS-PAGE, and stained with Coomassie fluorescent orange.

For the analysis of protein solubility, bacterial cell pellets from 50-100 mL of induced cultures were resuspended using ~30 mL of lysis buffer (eg 1×PBS, 5 mM EDTA), and lysed by mechanical disruption with three passes through a microfluidizer. Small samples were taken and insoluble material was pelleted by centrifugation for 10 minutes at top speed at 4° C. in a microcentrifuge. Following the spin, the supernatant was separated from the pellet, and both were analyzed by SDS-PAGE and protein staining. Western blot analysis with antibodies specific for the therapeutic proteins was also carried out to verify the identity of the observed soluble proteins.

Results:

FGF-20

Vectors bearing FGF-20 were transformed into different bacterial strains as indicated in Table 8. 50-100 mL induction cultures, varying by temperature, aeration (rpm), IPTG concentration, and time, were analyzed by whole cell extract (WCE) SDS-PAGE. As shown in FIG. 1a, moderate expression was observed in Vector #2, Vector #3, and pET24a vectors, but not in Vector #1. Expression was observed as soon as 1.5 hours after induction, and greater levels of expression were at 37° C. than 20° C.

Figure 1B:
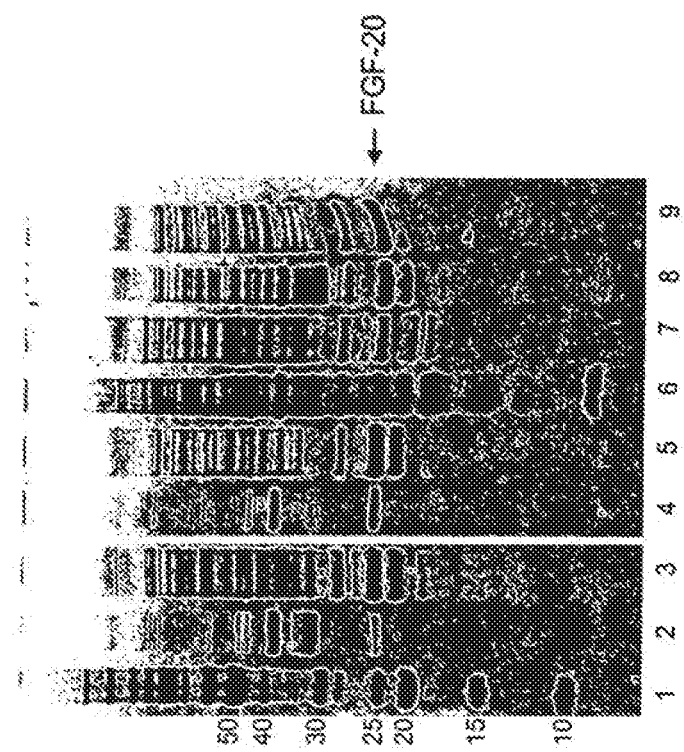
FIG. 1B displays results of an SDS-PAGE analysis of human FGF-20 solubility at varied temperature and *E. Coli* strains, lane 1: molecular weight marker (sized in kDa). Even numbers represent pellet and odd numbers represent supernatant. Induction temperatures used: lanes 2-3: 20° C.: lanes 4-5: 30° C.; lanes 6-7: 37° C.; lanes 8-9: 37° C. Strain used: lanes 6-7, BL21(DE3); lanes 2-5 and 8-9, *E. Coli*$_{(trxb,gor,supp)}$(DE3). Vector #4 was employed.

To determine whether FGF-20 was expressed as a soluble protein, induced cell pellets of BL21DE3 and *E. coli*$_{(trxb,gor,supp)}$-2DE3 strains bearing pET24a FGF-20 were lysed, centrifuged, and analyzed by SDS-PAGE. As shown in FIG. 1b, the majority of FGF-20 was soluble in the *E. coli*$_{(trxb,gor,supp)}$-2 DE3 cells when grown at 20° C. Growth at 37° C. yielded approximately equal amount of soluble and insoluble protein in both BL21 DE3 and *E. coli*$_{(trxb,gor,supp)}$-2 DE3 cells.

FGF-21

Figure 1C:
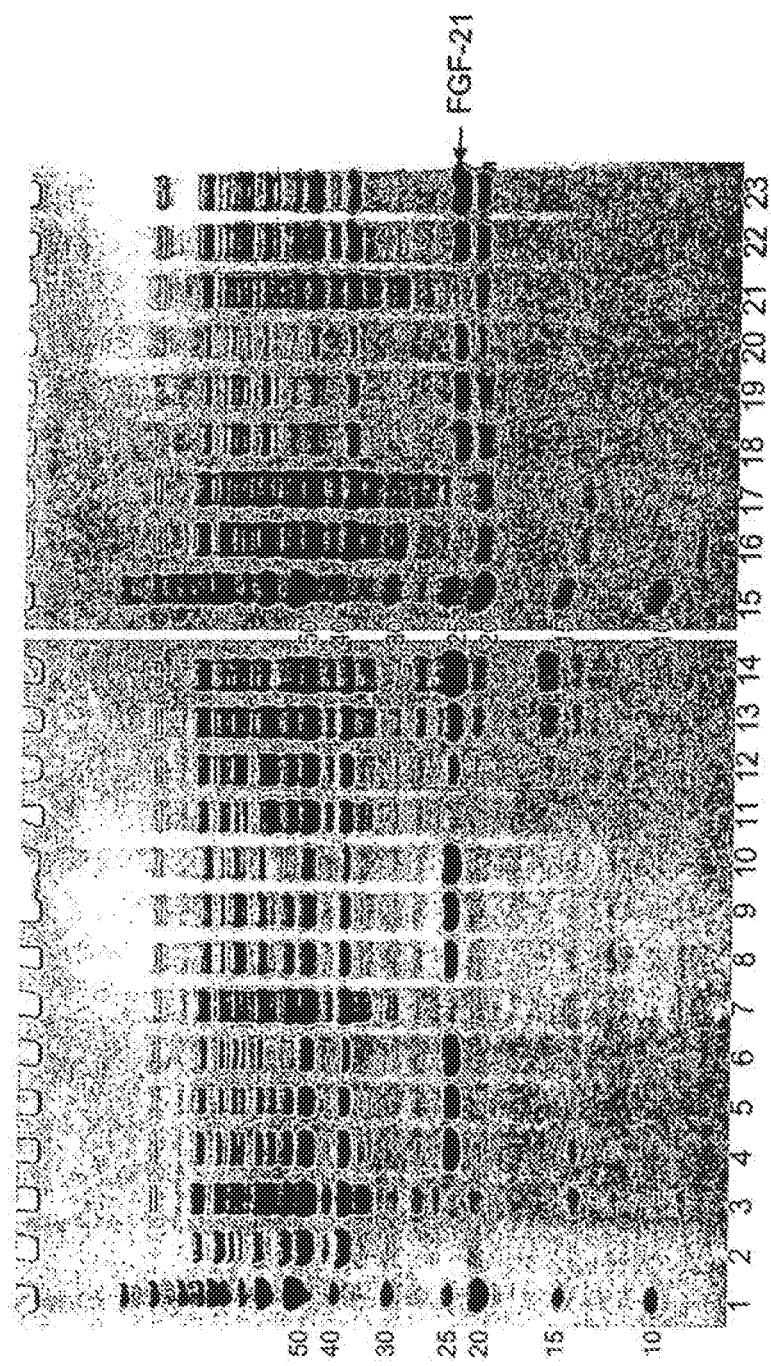
FIG. 1C displays results of an SDS-PAGE analysis of human FGF-21 induction at varied temperature, time, vector and *E. Coli* strains: lane 1 and 15: molecular weight marker (sized in kDa), lane 2 no induction; (induction temperature); lanes 3-10 and 16-20: 37° C., lanes 11-14 and 21-23: 20° C. Strains used: lanes 3-5 and 7-9 and 11-13, W3110; lanes 6, 10, and 14 BL21(DE3); lanes 16-19 and 21-23, *E. Coli*$_{(trxb,gor,supp)}$; lane 20, *E. Coli*$_{(trxb,gor,supp)}$(DE3). Vectors used: lanes 3, 7, 11, 17, 21 are vector #1; lanes 4, 8, 12, 18, 22 are vector #2; lanes 5, 9, 13, 19 and 23 are vector #3; lanes 6, 10, 14, and 20 are vector #4.

Vectors bearing FGF-21 were transformed into different bacterial strains as indicated in Table 8. 100 mL induction cultures, varying by temperature and time, were analyzed by WCE SDS-PAGE. As shown in FIG. 1c, expression was observed in Vector #2, Vector #3, and pET24a vectors, but not in Vector #1. Expression was observed as soon as 1.5 hours after induction. As rFGF-21 was observed to resolve by SDS-PAGE approximately 3-5 kDa larger than the expected ~19.7 kDa, the identity of the induced band was confirmed by Western blot (FIG. 1c).

Figure 1D:
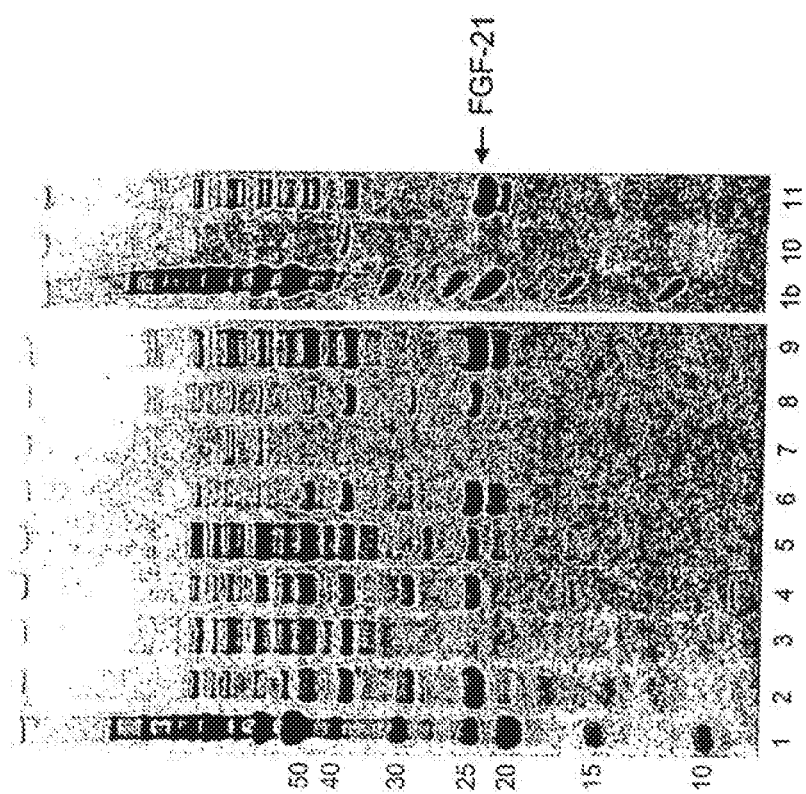
FIG. 1D displays results of an SDS-PAGE analysis of human FGF-21 solubility at varied temperature and *E. Coli* strains, lane 1+1b:molecular weight marker (sized in kDa). Even numbers represent pellet and odd numbers represent supernatant. Induction temperature used: lanes 2-3 and 6-7: 37° C.; lanes 4-5 and 8-9: 20° C.; lanes 11-12: 18° C. Strain used: lanes 2-5, W3110; lanes 6-12, *E. Coli*$_{(trxb,gor,supp)}$. Vector #3 was employed.

To determine whether FGF-21 was expressed as a soluble protein, induced cell pellets of W3110 and *E. coli*$_{(trxb,gor,supp)}$2 strains bearing Vector #3 FGF-21 were lysed, centrifuged, and analyzed by SDS-PAGE. As shown in FIG. 1d, the majority of FGF-21 was soluble only in the *E. coli*$_{(trxb,gor,supp)}$2 cells when induced at 20° C. Induction in *E. coli*$_{(trxb,gor,supp)}$-2 cells at 37° C., or in W3110 cells at either temperature yielded predominantly insoluble protein.

This study demonstrated a method for expressing the therapeutic proteins FGF-20 and FGF-21 in bacteria as soluble proteins. The expression technique using $E.\ coli_{(trxb,gor,supp)}$-2 described here should be applicable for the soluble expression of other therapeutic proteins.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in their entirety for all purposes.

What is claimed is:

1. A method of treating FGF-21 deficiency in a patient, comprising administering an effective amount of a Fibroblast Growth Factor-21 (FGF-21) conjugate to the patient, wherein the FGF-21 conjugate comprises a mutant FGF-21 peptide and a modifying group, wherein the mutant FGF-21 peptide comprises SEQ ID NO: 146 except for the presence of at least one O-linked or N-linked glycosylation site not present in SEQ ID NO: 146, wherein the mutant FGF-21 peptide comprises at least one amino acid sequence selected from the group consisting of SEQ ID NOs: 161-187, 189-214, 220-250, 252-271, 273-318, and 327-360, wherein the O-linked glycosylation site is a serine or threonine residue and the N-linked glycosylation site is an asparagine, and wherein the O-linked or N-linked glycosylation site is present at a site within one or more of SEQ ID NOs: 161-187, 189-214, 220-250, 252-271, 273-318, and 327-360, wherein said modifying group is covalently attached to said peptide at a preselected glycosyl or amino acid residue of said peptide via an intact glycosyl linking group, wherein said modifying group is not a naturally occurring saccharide moiety, and wherein the FGF-21 conjugate retains a biological activity of SEQ ID NO: 146, thereby treating the FGF-21 deficiency in the patient.

2. The method of claim 1, wherein said FGF-21 peptide is at least 95% homologous to the amino acid sequence of SEQ I) NO 146.

3. The method of claim 1, wherein said modifying group is covalently attached at said preselected glycosyl residue.

4. The method of claim 3, wherein said modifying group is a non-glycosidic modifying group.

5. The method of claim 4, wherein said non-glycosidic modifying group is a linear PEG or a branched PEG.

6. The method of claim 1, wherein said glycosyl linking group has a structure according to the following formula:

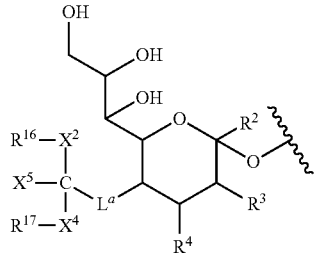

wherein $R^2$ is H, $CH_2OR^7$, $COOR^7$ or $OR^7$, wherein $R^7$ represents H, substituted or unsubstituted alkyl, or substituted or unsubstituted heteroalkyl;

$R^3$ and $R^4$ are members independently selected from the group consisting of H, substituted or unsubstituted alkyl, $OR^8$, and $NHC(O)R^9$, wherein $R^8$ and $R^9$ are independently selected from the group consisting of H, substituted or unsubstituted alkyl, substituted or unsubstituted heteroalkyl, and sialic acid;

$L^a$ is a linker selected from the group consisting of a bond, substituted or unsubstituted alkyl, and substituted or unsubstituted heteroalkyl;

$R^{16}$ and $R^{17}$ are independently selected polymeric arms;

$X^2$ and $X^4$ are independently selected linkage fragments joining polymeric moieties $R^{16}$ and $R^{17}$ to C; and $X^5$ is a non-reactive group.

7. The method of claim 1, wherein said glycosyl linking group has a structure according to the following formula:

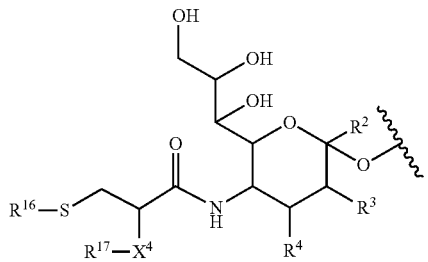

wherein $R^2$ is H, $CH_2OR^7$, $COOR^7$ or $OR^7$, wherein $R^7$ represents H, substituted or unsubstituted alkyl, or substituted or unsubstituted heteroalkyl;

$R^3$ and $R^4$ are members independently selected from the group consisting of H, substituted or unsubstituted alkyl, $OR^8$, and $NHC(O)R^9$, wherein $R^8$ and $R^9$ are independently selected from the group consisting of H, substituted or unsubstituted alkyl, substituted or unsubstituted heteroalkyl, and sialic acid;

$R^{16}$ and $R^{17}$ are independently selected polymeric arms; and $X^4$ is a linkage fragment joining polymeric moiety $R^{17}$ to C.

8. The method of claim 1, wherein said modifying group is selected from the group consisting of water-soluble polymers, therapeutic moieties, diagnostic moieties, targeting moieties, and biomolecules.

* * * * *

UNITED STATES PATENT AND TRADEMARK OFFICE
CERTIFICATE OF CORRECTION

PATENT NO. : 10,874,714 B2  Page 1 of 1
APPLICATION NO. : 14/954696
DATED : December 29, 2020
INVENTOR(S) : Shawn DeFrees It is certified that error appears in the above-identified patent and that said Letters Patent is hereby corrected as shown below:

In the Claims

In Claim 2, Column 249, Line 45, please replace "SEQ I) NO 146" with - SEQ ID NO: 146 -

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*